US012565492B2

(12) United States Patent
La

(10) Patent No.: US 12,565,492 B2
(45) Date of Patent: Mar. 3, 2026

(54) ANAPLASTIC LYMPHOMA KINASE (ALK) DEGRADERS AND USES THEREOF

(71) Applicant: Triana Biomedicines, Inc., Lexington, MA (US)

(72) Inventor: Daniel La, Lexington, MA (US)

(73) Assignee: Triana Biomedicines, Inc., Lexington, MA (US)

( * ) Notice: Subject to any disclaimer, the term of this patent is extended or adjusted under 35 U.S.C. 154(b) by 0 days.

(21) Appl. No.: 19/357,447

(22) Filed: Oct. 14, 2025

(65) Prior Publication Data

US 2026/0042752 A1 Feb. 12, 2026

Related U.S. Application Data

(63) Continuation of application No. PCT/US2025/041205, filed on Aug. 8, 2025.

(60) Provisional application No. 63/757,500, filed on Feb. 12, 2025, provisional application No. 63/723,238, filed on Nov. 21, 2024, provisional application No. 63/681,229, filed on Aug. 9, 2024.

(51) Int. Cl.
*C07D 413/14* (2006.01)
*A61K 31/454* (2006.01)

(52) U.S. Cl.
CPC .......... *C07D 413/14* (2013.01); *A61K 31/454* (2013.01)

(58) Field of Classification Search
CPC ............................ C07D 413/14; A61K 31/454
See application file for complete search history.

(56) References Cited

U.S. PATENT DOCUMENTS

| | | | |
|---|---|---|---|
| 9,108,978 | B2 | 8/2015 | Abell et al. |
| 11,485,726 | B2 | 11/2022 | Shu |
| 11,970,486 | B2 | 4/2024 | Le Bourdonnec et al. |
| 2011/0196150 | A1 | 8/2011 | Man et al. |
| 2019/0192668 | A1 | 6/2019 | Mainolfi et al. |
| 2024/0300938 | A1 | 9/2024 | Le Bourdonnec et al. |
| 2024/0400546 | A1 | 12/2024 | Le Bourdonnec et al. |

FOREIGN PATENT DOCUMENTS

| | | | |
|---|---|---|---|
| CN | 111848599 | A | 10/2020 |
| CN | 114507235 | A | 5/2022 |
| CN | 117720517 | A | 3/2024 |
| CN | 117924264 | A | 4/2024 |
| CN | 118184639 | A | 6/2024 |
| CN | 118206558 | A | 6/2024 |
| CN | 118217287 | A | 6/2024 |
| CN | 118255780 | A | 6/2024 |
| CN | 118271316 | A | 7/2024 |
| CN | 118290446 | A | 7/2024 |
| CN | 118359589 | A | 7/2024 |
| CN | 118834218 | A | 10/2024 |
| CN | 118852145 | A | 10/2024 |
| CN | 118852213 | A | 10/2024 |
| CN | 119306706 | A | 1/2025 |
| WO | 2004/014370 | A2 | 2/2004 |
| WO | 2008/039489 | A2 | 4/2008 |
| WO | 2010/053732 | A1 | 5/2010 |
| WO | 2011/060392 | A1 | 5/2011 |
| WO | 2012/018668 | A1 | 2/2012 |
| WO | 2013/040647 | A1 | 3/2013 |
| WO | 2014/110558 | A1 | 7/2014 |
| WO | 2014/179661 | A1 | 11/2014 |
| WO | 2015/066515 | A1 | 5/2015 |
| WO | 2015/177110 | A1 | 11/2015 |
| WO | 2017/197051 | A1 | 11/2017 |
| WO | 2018/064356 | A1 | 4/2018 |
| WO | 2018/081167 | A1 | 5/2018 |
| WO | 2018/160356 | A1 | 9/2018 |
| WO | 2019/018795 | A1 | 1/2019 |
| WO | 2019/038717 | A1 | 2/2019 |
| WO | 2019/060693 | A1 | 3/2019 |
| WO | 2019/060742 | A1 | 3/2019 |
| WO | 2019/079569 | A1 | 4/2019 |
| WO | 2019/084157 | A1 | 5/2019 |
| WO | 2019/099868 | A2 | 5/2019 |
| WO | 2019/209948 | A1 | 10/2019 |
| WO | 2020/113233 | A1 | 6/2020 |
| WO | 2020/115200 | A1 | 6/2020 |
| WO | 2020/173440 | A1 | 9/2020 |

(Continued)

OTHER PUBLICATIONS

International Search Report and Written Opinion for Application No. PCT/US2025/041205, dated Nov. 12, 2025, 13 pages.

(Continued)

*Primary Examiner* — Jean P Cornet

(74) *Attorney, Agent, or Firm* — McCarter & English LLP; Michael J. DeGrazia

(57) ABSTRACT

Provided are compounds of the structural Formula (I):

(I)

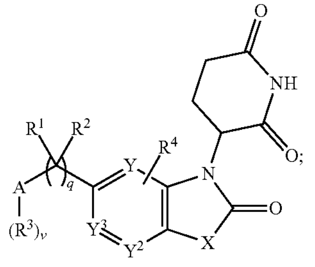

and pharmaceutically acceptable salts and compositions thereof, which are useful for treating a variety of conditions associated with ALK.

4 Claims, No Drawings

(56) References Cited

FOREIGN PATENT DOCUMENTS

| | | | |
|---|---|---|---|
| WO | 2020/200291 | A1 | 10/2020 |
| WO | 2020/251971 | A1 | 12/2020 |
| WO | 2021/009306 | A1 | 1/2021 |
| WO | 2021/124172 | A1 | 6/2021 |
| WO | 2021/127586 | A1 | 6/2021 |
| WO | 2021/170109 | A1 | 9/2021 |
| WO | 2021/173995 | A2 | 9/2021 |
| WO | 2021/188948 | A1 | 9/2021 |
| WO | 2022/012622 | A1 | 1/2022 |
| WO | 2022/012623 | A1 | 1/2022 |
| WO | 2022/029573 | A1 | 2/2022 |
| WO | 2022/033548 | A1 | 2/2022 |
| WO | 2022/058878 | A1 | 3/2022 |
| WO | 2022/143856 | A1 | 7/2022 |
| WO | 2022/171123 | A1 | 8/2022 |
| WO | 2022/216573 | A1 | 10/2022 |
| WO | 2022/228556 | A1 | 11/2022 |
| WO | 2023/274347 | A1 | 1/2023 |
| WO | 2023/283610 | A1 | 1/2023 |
| WO | 2023/019166 | A1 | 2/2023 |
| WO | 2023/023537 | A1 | 2/2023 |
| WO | 2023/049790 | A2 | 3/2023 |
| WO | 2023/059792 | A1 | 4/2023 |
| WO | 2023/072270 | A1 | 5/2023 |
| WO | 2023/098656 | A1 | 6/2023 |
| WO | 2023/125907 | A1 | 7/2023 |
| WO | 2023/125908 | A1 | 7/2023 |
| WO | 2023/138607 | A1 | 7/2023 |
| WO | 2023/139199 | A1 | 7/2023 |
| WO | 2023/183540 | A1 | 9/2023 |
| WO | 2023/208165 | A1 | 11/2023 |
| WO | 2023/232133 | A1 | 12/2023 |
| WO | 2023/237049 | A1 | 12/2023 |
| WO | 2023/244817 | A1 | 12/2023 |
| WO | 2023/249970 | A1 | 12/2023 |
| WO | 2023/250029 | A1 | 12/2023 |
| WO | 2024/012570 | A1 | 1/2024 |
| WO | 2024/019103 | A1 | 1/2024 |
| WO | 2024/039901 | A2 | 2/2024 |
| WO | 2024/050078 | A1 | 3/2024 |
| WO | 2024/054832 | A1 | 3/2024 |
| WO | 2024/056005 | A1 | 3/2024 |
| WO | 2024/059525 | A2 | 3/2024 |
| WO | 2024/102849 | A1 | 5/2024 |
| WO | 2024/118960 | A1 | 6/2024 |
| WO | 2024/118966 | A1 | 6/2024 |
| WO | 2024/149349 | A1 | 7/2024 |
| WO | 2024/151547 | A1 | 7/2024 |
| WO | 2024/167999 | A1 | 8/2024 |
| WO | 2024/192146 | A2 | 9/2024 |
| WO | 2024/193464 | A1 | 9/2024 |
| WO | 2024/209044 | A1 | 10/2024 |
| WO | 2024/217481 | A1 | 10/2024 |
| WO | 2024/220843 | A1 | 10/2024 |
| WO | 2024/222614 | A1 | 10/2024 |
| WO | 2024/233846 | A1 | 11/2024 |
| WO | 2024/259216 | A1 | 12/2024 |
| WO | 2024/261257 | A1 | 12/2024 |
| WO | 2024/264017 | A2 | 12/2024 |
| WO | 2025/016457 | A1 | 1/2025 |
| WO | 2025/043225 | A2 | 2/2025 |
| WO | 2025/049820 | A1 | 3/2025 |
| WO | 2025/049994 | A1 | 3/2025 |
| WO | 2025/062330 | A1 | 3/2025 |
| WO | 2025/076285 | A1 | 4/2025 |
| WO | 2025/207821 | A1 | 10/2025 |

OTHER PUBLICATIONS

Actis et al., Evaluation of Cereblon-Directing Warheads for the Development of Orally Bioavailable PROTACs. J Med Chem. Feb. 13, 2025;68(3):3591-3611.

Eagon et al., Identification of Plasmodium falciparum falcilysin inhibitors by a virtual screen. Bioorg Med Chem Lett. Nov. 15, 2021;52:128394, 4 pages.

Liu et al., Design, synthesis and biological evaluation of novel quinazolinone derivatives as CRBN E3 ligase modulators. Eur J Med Chem. Feb. 5, 2023;247:115016, 12 pages.

Moloney et al., Synthesis and cannabinoid activity of 1-substituted-indole-3-oxadiazole derivatives: novel agonists for the CB1 receptor. Eur J Med Chem. Mar. 2008;43(3):513-39.

Segura-Cabrera et al., Integrative computational protocol for the discovery of inhibitors of the Helicobacter pylori nickel response regulator (NikR). J Mol Model. Dec. 2011;17(12):3075-84.

Tieu et al., Heterocyclic acyl-phosphate bioisostere-based inhibitors of *Staphylococcus aureus* biotin protein ligase. Bioorg Med Chem Lett. Oct. 1, 2014;24(19):4689-4693.

Xu et al., Molecular similarity guided optimization of novel Nrf2 activators with 1,2,4-oxadiazole core. Bioorg Med Chem. Aug. 15, 2016;24(16):3540-7.

ANAPLASTIC LYMPHOMA KINASE (ALK) DEGRADERS AND USES THEREOF

RELATED APPLICATIONS

This application is a continuation of International Application No. PCT/US2025/041205, filed Aug. 8, 2025, which, in turn, claims the benefit of priority to U.S. Provisional Application No. 63/681,229, filed Aug. 9, 2024, U.S. Provisional Application No. 63/723,238, filed Nov. 21, 2024, and U.S. Provisional Application No. 63/757,500, filed Feb. 12, 2025, the entire contents of each of which are incorporated herein by reference.

BACKGROUND

Anaplastic Lymphoma Kinase (ALK) is a receptor tyrosine kinase whose expression and function in normal organisms is limited to the developing nervous system, and whose activity is regulated by extracellular ligand binding. In certain cancers including subsets of lung cancer, T-cell lymphoma, and neuroblastoma, ALK is rendered ligand-independent by activating mutations or fusion events that cause uncontrolled proliferation, survival, and metastatic spread. In approximately 5% of non-small cell lung cancer (NSCLC), ALK is involved in fusions, the most common of which involve coding sequences from the Echinoderm Microtubule Associated Like 4 (EML4) gene, creating EML4-ALK oncogenic fusions. Given the prevalence of ALK fusion events in NSCLC, multiple generations of ALK tyrosine kinase inhibitors (TKI) are approved by the FDA for treatment of ALK positive NSCLC. While highly efficacious, durable response to these drugs is limited by selection of ALK resistance mutations that prevent drug binding. Removing oncogenic ALK protein via targeted protein degradation presents an alternative therapeutic option for treating ALK positive cancers.

Currently disclosed degraders of ALK use a bivalent approach that requires binding to the enzymatic active site and would be subject to known TKI resistance mutations. However, a monovalent ALK molecular glue degrader that recruits an E3 ligase via sites distal to the sites involved in inhibitor binding has the potential to expand the treatment options for ALK positive cancers by addressing both wild-type and all clinically relevant resistance alleles. Further, an ALK molecular glue degrader that acts independently of kinase inhibition can be combined with approved TKI drugs to improve efficacy and tolerability.

SUMMARY

Provided herein are compounds having the Formula I.

(I)

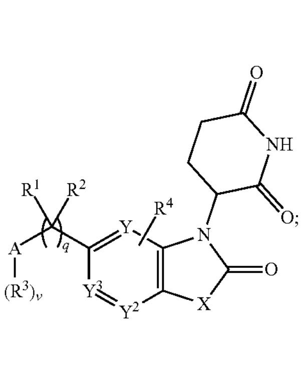

and pharmaceutically acceptable salts and compositions thereof, wherein A, $R^1$, $R^2$, $R^3$, $R^4$, q, v, Y, $Y^1$, $Y^2$, and X are as described herein. In one aspect, the described compounds of Formula I and pharmaceutically acceptable salts thereof modulate ALK (e.g., as degraders of ALK), and are useful in a variety of therapeutic applications such as, for example, in treating cancer.

Pharmaceutical compositions comprising the described compounds and pharmaceutically acceptable salts of the described compounds, as well as methods for their preparation are also included.

DETAILED DESCRIPTION

1. General Description of Compounds

In a first embodiment, provided herein is a compound of Formula I.

(I)

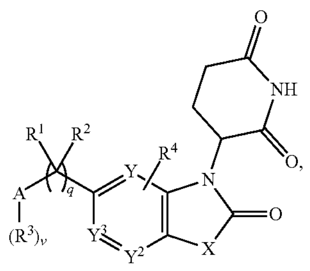

or a pharmaceutically acceptable salt thereof, wherein

X is O, $NR^V$ or $CR^VR^{V1}$;

$R^V$ and $R^{V1}$ are each independently hydrogen or $(C_1\text{-}C_4)$alkyl;

Y, $Y^1$, and $Y^2$ are each independently is N or CH;

Y is N or CH;

$R^1$ and $R^2$ are each independently hydrogen or $(C_1\text{-}C_4)$alkyl; or $R^1$ and $R^2$ taken together form a $(C_3\text{-}C_6)$cycloalkyl optionally substituted with 1 to 3 groups selected from $R^A$;

$R^A$ is selected from cyano, halo, $(C_1\text{-}C_4)$alkyl, halo$(C_1\text{-}C_4)$alkyl, $(C_1\text{-}C_4)$alkoxy, and halo$(C_1\text{-}C_4)$alkoxy;

A is an optionally substituted heterocyclyl or optionally substituted heteroaryl;

$R^3$ is $(C_1\text{-}C_4)$alkyl, aryl, heterocyclyl, or heteroaryl, wherein each of said aryl, heterocyclyl, and heteroaryl are optionally substituted with 1 to 4 groups selected from $R^B$;

$R^4$ is hydrogen, halo, $(C_1\text{-}C_4)$alkyl, halo$(C_1\text{-}C_4)$alkyl, $(C_1\text{-}C_4)$alkoxy, or halo$(C_1\text{-}C_4)$alkoxy;

$R^B$ is selected from halo, $(C_1\text{-}C_4)$alkyl, halo$(C_1\text{-}C_4)$alkyl, $(C_1\text{-}C_4)$alkoxy, halo$(C_1\text{-}C_4)$alkoxy, hydroxy, $(C_1\text{-}C_4)$alkyleneOH, $(C_1\text{-}C_4)$alkylene$(C_1\text{-}C_4)$alkoxy, —$(C_1\text{-}C_4)$alkyleneNR$^X$R$^Y$, cyano, oxo, —$(C_1\text{-}C_4)$alkoxyNR$^X$R$^Y$, —$(C_1\text{-}C_4)$alkyleneC(O)OR$^X$, —$(C_1\text{-}C_4)$alkoxyC(O)OR$^X$, —$(C_1\text{-}C_4)$alkyleneC(O)R$^X$, —$(C_1\text{-}C_4)$alkoxyC(O)R$^X$, —$(C_1\text{-}C_4)$alkyleneheterocyclyl, —$(C_1\text{-}C_4)$alkyleneheteroaryl, —$(C_1\text{-}C_4)$alkoxyheterocyclyl, —$(C_1\text{-}C_4)$alkoxyheteroaryl, —$(C_1\text{-}C_4)$alkylenecycloalkyl, —$(C_1\text{-}C_4)$alkoxycycloalkyl, —$(C_1\text{-}C_4)$alkylenephenyl, —$(C_1\text{-}C_4)$alkoxyphenyl —NR$^X$$(C_1\text{-}C_4)$alkyleneheteroaryl, —NR$^X$$(C_1\text{-}C_4)$alkyleneheterocyclyl, —NR$^X$$(C_1\text{-}C_4)$alkylenecycloalkyl, cycloalkyl, heteroaryl, heterocyclyl, —NR$^X$R$^Y$, —NR$^X$C(O)R$^Y$, —NR$^X$C(O)

$OR^Y$, $-NR^X(C_1-C_4)alkyleneC(O)NR^XR^Z$, $-NR^XC(O)NR^XR^Z$, $-(C_1-C_4)alkyleneNR^XC(O)R^Y$, $-(C_1-C_4)alkyleneNR^XC(O)OR^Y$, $-(C_1-C_4)alkyleneNR^X(C_1-C_4)alkyleneC(O)NR^XR^Z$, $-(C_1-C_4)alkyleneNR^XC(O)NR^XR^Z$, $-(C_1-C_4)alkoxyNR^XC(O)R^Y$, $-(C_1-C_4)alkoxyNR^XC(O)OR^Y$, $-(C_1-C_4)alkoxyNR^X(C_1-C_4)alkyleneC(O)NR^XR^Z$, $-(C_1-C_4)alkoxyNR^XC(O)NR^XR^Z$, $-S(C_1-C_4)alkyl$, —O(heteroaryl), —O(heterocyclyl), —O(cycloalkyl), $-C(O)NR^XR^Y-(C_1-C_4)alkyleneC(O)NR^XR^Y$, $-(C_1-C_4)alkoxyC(O)NR^XR^Y$, $-C(O)R^X$, and $-C(O)OR^X$, wherein each of said cycloalkyl, phenyl, heteroaryl, and heterocyclyl recited alone, or recited as being part of a larger group, are optionally substituted with 1 to 3 groups selected from $R^C$;

$R^C$ is selected from $(C_1-C_4)$alkyl, halo$(C_1-C_4)$alkyl, $(C_1-C_4)$alkoxy, halo$(C_1-C_4)$alkoxy cyano, oxo, hydroxy, $-C(O)R^X$, $-C(O)OR^X$, $-C(O)NR^XR^Y$, $-NR^XC(O)R^Y$, $-NR^XR^Y$, $-NR^XC(O)OR^Y$;

$R^X$, $R^Y$, and $R^Z$ are each independently selected from hydrogen, $(C_1-C_4)$alkyl, halo$(C_1-C_4)$alkyl, phenyl, benzyl, $(C_3-C_6)$cycloalkyl, 4- to 6-membered heterocyclyl, and 5- to 7-membered heteroaryl;

v is 0, 1, or 2; and q is 1, 2, or 3.

2. Definitions

Unless otherwise defined, all technical and scientific terms used herein have the same meaning as commonly understood by one of ordinary skill in the art to which this disclosure pertains. The terminology used in the description is for describing particular embodiments only and is not intended to be limiting of the disclosure.

As used in the structure herein a hyphen (-) or squiggly line "∿∿" indicates the point of attachment of the particular depicted structure or substituent group to the appropriate atom(s) in the remainder of the molecule. For example, $-[(C_1-C_6)alkyl]$heteroaryl means that the point of attachment for this group occurs on the $(C_1-C_6)$alkyl.

The terms "halo" and "halogen" refer to an atom selected from fluorine (fluoro, —F), chlorine (chloro, —Cl), bromine (bromo, —Br), and iodine (iodo, —I).

The term "alkyl" when used alone or as part of a larger moiety, such as "haloalkyl", and the like, means a saturated straight-chain or branched monovalent hydrocarbon radical.

"Alkoxy" means an alkyl radical attached through an oxygen linking atom, represented by —O-alkyl. For example, "$(C_1-C_4)$alkoxy" includes methoxy, ethoxy, proproxy, and butoxy.

The term "haloalkyl" includes mono, poly, and perhaloalkyl groups where the halogens are independently selected from fluorine, chlorine, bromine, and iodine.

"Haloalkoxy" is a haloalkyl group which is attached to another moiety via an oxygen atom such as, e.g., $-OCHF_2$ or $-OCF_3$.

As used herein, the term "alkylene" refers to divalent aliphatic hydrocarbyl groups, for example, having from 1 to 4 carbon atoms that are either straight-chained or branched. This term includes, by way of example, methylene ($-CH_2-$), ethylene ($-CH_2CH_2-$), n-propylene ($-CH_2CH_2CH_2-$), iso-propylene ($-CH_2CH(CH_3)-$), and the like.

The term oxo means the group =O.

The term "aryl" when used alone or as part of a substituent group also refers to a mono- or bicyclic-aromatic hydrocarbon ring structure having 6 or 10 carbon atoms in the ring, wherein one or more of the carbon atoms in the ring is optionally substituted. The term "aryl" also includes a mono- or bicyclic-aromatic hydrocarbon ring structure having 6 or 10 carbon atoms in the ring. Examples of aryl groups include phenyl and naphthyl.

The term "heteroaryl" used alone or as part of a larger moiety refers to, unless otherwise specified, a 5- to 12-membered aromatic radical containing 1-4 heteroatoms selected from N, O, and S. A heteroaryl group may be mono- or bi-cyclic. Monocyclic heteroaryl includes, for example, thienyl, furanyl, pyrrolyl, imidazolyl, pyrazolyl, triazolyl, tetrazolyl, oxazolyl, isoxazolyl, triazinyl, tetrazinyl, oxadiazolyl, thiazolyl, isothiazolyl, thiadiazolyl, pyridyl, pyridazinyl, pyrimidinyl, pyrazinyl, etc. Bi-cyclic heteroaryls include groups in which a monocyclic heteroaryl ring is fused to one or more aryl or heteroaryl rings. Nonlimiting examples include indolyl, imidazopyridinyl, benzooxazolyl, benzooxodiazolyl, indazolyl, benzimidazolyl, benzthiazolyl, quinolinyl, quinazolinyl, quinoxalinyl, pyrrolopyridinyl, pyrrolopyrimidinyl, pyrazolopyridinyl, thienopyridinyl, thienopyrimidinyl, indolizinyl, purinyl, naphthyridinyl, and pteridinyl. It will be understood that when specified, optional substituents on a heteroaryl group may be present on any substitutable position.

The term "heterocyclyl" means, unless otherwise specified, a 5- to 12-membered saturated or partially unsaturated heterocyclic ring containing 1 to 4 heteroatoms independently selected from N, O, and S. It can be monocyclic, bicyclic (e.g., a bridged, fused, or spiro bicyclic ring), or tricyclic. A heterocyclyl ring can be attached to its pendant group at any heteroatom or carbon atom that results in a stable structure. Examples of such saturated or partially unsaturated heterocyclic radicals include, without limitation, tetrahydrofuranyl, tetrahydrothienyl, terahydropyranyl, pyrrolidinyl, pyridinonyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, oxetanyl, azetidinyl and tetrahydropyrimidinyl. A heterocyclyl group may be mono- or bicyclic. The term "heterocyclyl" also includes, e.g., unsaturated heterocyclic radicals fused to another unsaturated heterocyclic radical or aryl or heteroaryl ring, such as for example, tetrahydronaphthyridine, indolinone, dihydropyrrolotriazole, imidazopyrimidine, quinolinone, dioxaspirodecane. It will also be understood that when specified, optional substituents on a heterocyclyl group may be present on any substitutable position.

The term "spiro" refers to two rings that shares one ring atom (e.g., carbon).

The term "fused" refers to two rings that share two adjacent ring atoms with one another.

The term "bridged" refers to two rings that share three ring atoms with one another.

The terms "cycloalkyl", used alone or as part of a larger moiety, refers to a saturated cyclic aliphatic monocyclic or bicyclic ring system, as described herein, having from, unless otherwise specified, 3 to 10 carbon ring atoms. Monocyclic cycloalkyl groups include, without limitation, cyclopropyl, cyclobutyl, cyclopentyl, cyclopentenyl, cyclohexyl, cyclohexenyl, cycloheptyl, cycloheptenyl, and cyclooctyl. It will be understood that when specified, optional substituents on a cycloalkyl may be present on any substitutable position.

It is to be understood that if an aryl, heteroaryl, cycloalkyl, or heterocyclyl moiety may be bonded or otherwise attached to a designated moiety through differing ring atoms (i.e., shown or described without denotation of a specific point of attachment), then all possible points are intended, whether through a carbon atom or, for example, a trivalent nitrogen atom. For example, the term "pyridinyl" means 2-, 3- or 4-pyridinyl, the term "thiophenyl" means 2- or 3-thiophenyl, and so forth.

The term "optionally substituted," as used herein to describe a chemical moiety defined herein, means that the moiety may, but is not required to be, substituted with one or more suitable functional groups or other substituents as provided herein.

As used herein, the term "substituted" means that an atom or group of atoms has replaced hydrogen as the substituent attached to another group.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of 20% or ±10%, including+5%, +1%, and ±0.1% from the specified value, as such variations are appropriate to perform the disclosed methods.

Compounds having one or more chiral centers can exist in various stereoisomeric forms. Stereoisomers are compounds that differ only in their spatial arrangement. Stereoisomers include all diastereomeric, enantiomeric, and epimeric forms as well as racemates and mixtures thereof. A "geometric isomer" refers to isomers that differ in the orientation of substituent group in relationship to a carbon-carbon double bond, a cycloalkyl ring, or a bridged bicyclic system. Atoms (other than H) on each side of a carbon-carbon double bond may be in an E (substituents are on opposite sides of the carbon-carbon double bond) or Z (substituents are oriented on the same side) configuration. "Cis" refers to substituents oriented on the same side of the ring, whereas "trans" refers to substituents oriented on opposite sides of the ring.

When the stereochemical configuration at a chiral center in a compound having one or more chiral centers is depicted by its chemical name (e.g., where the configuration is indicated in the chemical name by "R" or "S") or structure (e.g., the configuration is indicated by "wedge" bonds), the enrichment of the indicated configuration relative to the opposite configuration is greater than 50%, 60%, 70%, 80%, 90%, 99% or 99.9%. "Enrichment of the indicated configuration relative to the opposite configuration" is a mole percent and is determined by dividing the number of compounds with the indicated stereochemical configuration at the chiral center(s) by the total number of all of the compounds with the same or opposite stereochemical configuration in a mixture.

When a geometric isomer is depicted by name or structure, the enrichment of the indicated isomer relative to the opposite isomer is greater than 50%, 60%, 70%, 80%, 90%, 99% or 99.9%. "Enrichment of the indicated isomer relative to the opposite isomer" is a mole percent and is determined by dividing the number of compounds with the indicated geometrical configuration by the total number of all of the compounds with the same or opposite geometrical configuration in a mixture.

When a disclosed compound is named or depicted by structure without indicating stereochemistry, it is understood that the name or the structure encompasses one of the possible stereoisomers or geometric isomers free of the others, or a mixture of the encompassed stereoisomers or geometric isomers.

It will be understood that certain compounds described herein may exists in tautomeric forms. Such forms are included as part of the present disclosure. Thus, when a compound herein is represented by a structural formula or designated by a chemical name, all tautomeric forms which may exist for the compound are encompassed by the structural formula.

In certain aspects, the present disclosure also includes isotopically-labelled and/or isotopically-enriched forms of the described compounds. For example, in some aspects, one or more atoms of a described compound may be replaced by an isotope of the same element. Exemplary isotopes that can be incorporated into compounds described herein include isotopes of hydrogen, carbon, nitrogen, oxygen, sulfur, chlorine, such as $^{2}H$, $^{3}H$, $^{11}C$, $^{13}C$, $^{14}C$ $^{13}N$, $^{15}O$, $^{17}O$, $^{35}s$, $^{18}F$, and $^{36}Cl$. As used herein, each instance of enrichment, substitution, or replacement of an atom with corresponding isotope of that atom encompasses isotopic enrichment levels of one of about: 50%, 60%, 70%, 80%, 90%, 95%, 96%, 97%, 98%, 99%, 99.5%, 99.6%, 99.7% 99.8%, 99.9%, or 100%, or a range between any two of the preceding percentages. Isotopically-labeled compounds of the present disclosure can generally be prepared by standard methods and techniques known to those skilled in the art or by procedures similar to those described in the accompanying Examples substituting appropriate isotopically-labeled reagents in place of the corresponding non-labeled reagent.

The terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The term "inhibit," "inhibition" or "inhibiting" includes a decrease in the baseline activity of a biological activity or process.

As used herein, the terms "treatment," "treat," and "treating" refer to reversing, alleviating, delaying the onset of, or inhibiting the progress of a disease or disorder, or one or more symptoms thereof, as described herein. In some aspects, treatment may be administered after one or more symptoms have developed, i.e., therapeutic treatment. In other aspects, treatment may be administered in the absence of symptoms. For example, treatment may be administered to a susceptible individual prior to the onset of symptoms (e.g., in light of a history of symptoms and/or in light of exposure to a particular organism, or other susceptibility factors), i.e., prophylactic treatment. Treatment may also be continued after symptoms have resolved, for example to delay their recurrence.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

For use in medicines, the salts of the compounds described herein refer to non-toxic "pharmaceutically acceptable salts." Pharmaceutically acceptable salt forms include pharmaceutically acceptable acidic/anionic or basic/cationic salts. Suitable pharmaceutically acceptable acid addition salts of the compounds described herein include e.g., salts of inorganic acids (such as hydrochloric acid, hydrobromic, phosphoric, nitric, and sulfuric acids) and of organic acids (such as, acetic acid, benzenesulfonic, benzoic, methanesulfonic, and p-toluenesulfonic acids). Compounds of the present teachings with acidic groups such as carboxylic acids can form pharmaceutically acceptable salts with pharmaceutically acceptable base(s). Suitable pharmaceutically acceptable basic salts include e.g., ammonium salts, alkali metal salts (such as sodium and potassium salts) and alkaline earth metal salts (such as magnesium and calcium salts). Compounds with a quaternary ammonium group also contain a counteranion such as chloride, bromide, siodide, acetate, perchlorate and the like. Other examples of such salts include hydrochlorides, hydrobromides, sulfates, methanesulfonates, nitrates, benzoates and salts with amino acids such as glutamic acid.

The term "effective amount" or "therapeutically effective amount" refers to an amount of a compound described herein that is sufficient to achieve the desired therapeutic effect (such as treatment of a condition recited herein) under the conditions of administration.

3. Compounds

As part of a second embodiment, the compound of Formula I is of the structural Formula $I^z$ or $I^{zz}$:

($I^z$)

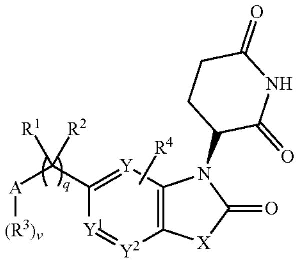

or ($I^{zz}$)

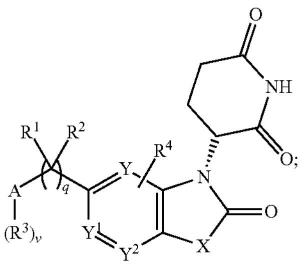

or a pharmaceutically acceptable salt thereof, wherein the remaining variables are as described above for Formula I.

As part of a third embodiment, $Y^1$, $Y^2$, and $Y^3$ in the compound of Formula I, $I^z$, or $I^{zz}$, or a pharmaceutically acceptable salt thereof, are each CH; or one of $Y^1$, $Y^2$, and $Y^3$ is N and the remainder are CH, wherein the remaining variables are as described above for Formula I.

As part of a fourth embodiment, the compound of Formula I is of the structural Formula I':

(I')

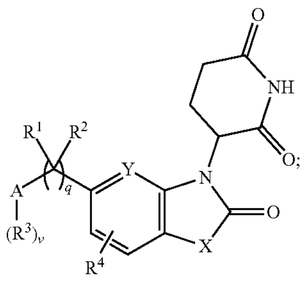

or a pharmaceutically acceptable salt thereof, wherein the remaining variables are as described above for Formula I. Alternatively, as part of a fourth embodiment, the compound of Formula I is of the structural $I^x$ or $I^{xx}$:

($I^x$)

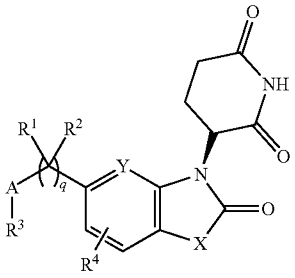

or ($I^{xx}$)

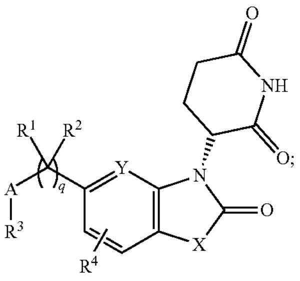

or a pharmaceutically acceptable salt thereof, wherein the remaining variables are as described above for Formula I.

As part of a fifth embodiment, A in the compound of Formula I, I', $I^z$, $I^{zz}$, $I^x$, or $I^{xx}$, or a pharmaceutically acceptable salt thereof, is selected from an optionally substituted oxadiazolyl, an optionally substituted thiadiazolyl, an optionally substituted triazolyl, an optionally substituted tetrazoyl, and an optionally substituted imidazolyl, wherein the remaining variables are as described above for Formula I. Alternatively, as part of a fifth embodiment, A in the compound of Formula I, I', $I^z$, $I^{zz}$, $I^x$, or $I^{xx}$, or a pharmaceutically acceptable salt thereof, is selected from oxadiazolyl, thiadiazolyl, triazolyl, tetrazoyl, and imidazolyl, wherein the remaining variables are as described above for Formula I. In another alternative, as part of a fifth embodiment, A in the compound of Formula I, I', $I^z$, $I^{zx}$, $I^x$, or $I^{xx}$, or a pharmaceutically acceptable salt thereof, is oxadiazolyl, wherein the remaining variables are as described above for Formula I.

As part of a sixth embodiment, the compound of Formula I is of the Formula Ia, Ib, or Ic:

(Ia)

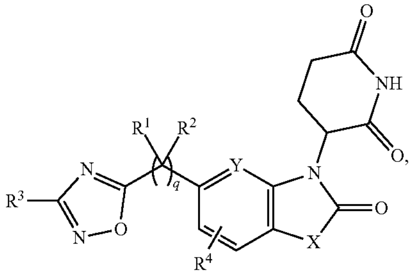

(Ib)

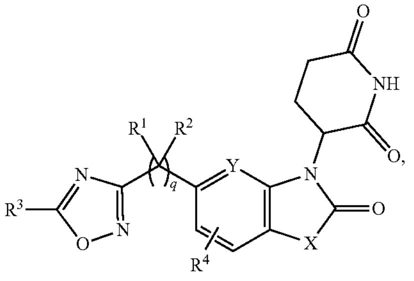

or (Ic)

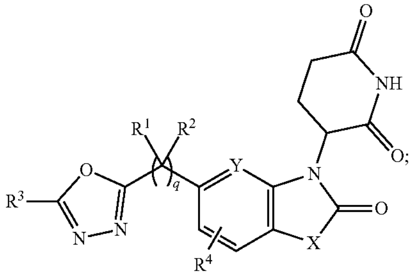

or a pharmaceutically acceptable salt thereof, wherein the variables are as described above for Formula I or the fifth embodiment. Alternatively, as part of a sixth embodiment, the compound is of the Formula Ia', Ia", Ib', Ib", Ic', or Ic":

(Ia')

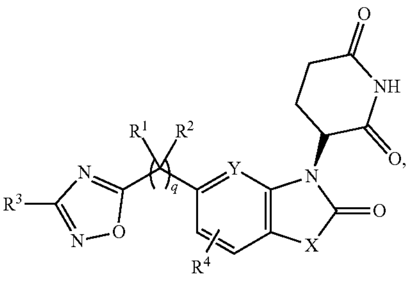

-continued (Ia")

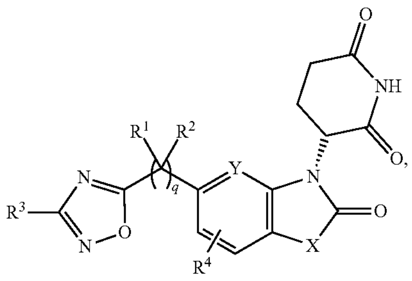

(Ib')

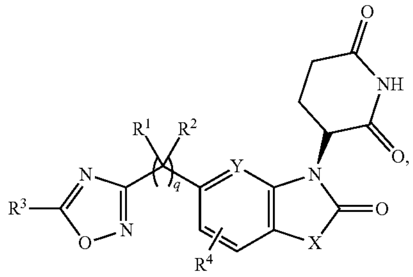

(Ib")

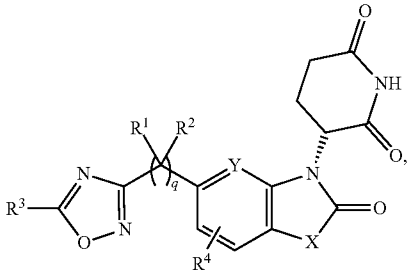

or (Ic')

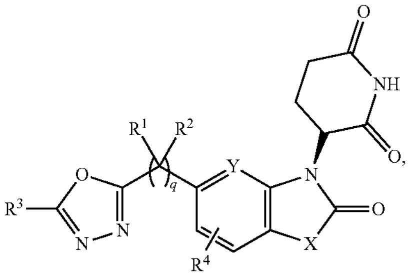

or (Ic")

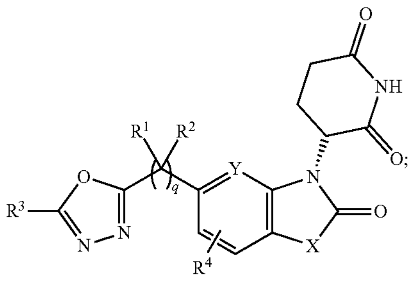

or a pharmaceutically acceptable salt thereof, wherein the variables are as described above for Formula I or the fifth embodiment. In another alternative, as part of a sixth embodiment, the compound is of the Formula Ia:

(Ia)

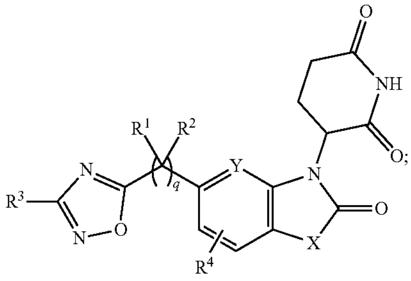

or a pharmaceutically acceptable salt thereof, wherein the variables are as described above for Formula I or the fifth embodiment. In another alternative, as part of a sixth embodiment, the compound is of the Formula Ia' or Ia".

(Ia')

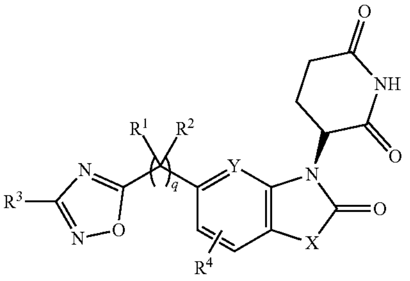

or (Ia")

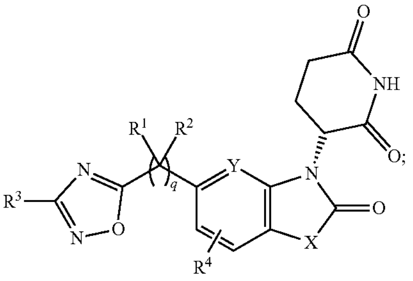

or a pharmaceutically acceptable salt thereof, wherein the variables are as described above for Formula I or the fifth embodiment.

As part of a seventh embodiment, Y in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is CH, wherein the variables are as described above for Formula I or the fifth embodiment.

As part of an eighth embodiment, $R^4$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is hydrogen, $(C_1-C_4)$alkyl, or halo, wherein the variables are as described above for Formula I or any of the fifth or seventh embodiments. Alternatively, as part of an eighth embodiment, $R^4$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is hydrogen, methyl, chloro, or fluoro, wherein the variables are as described above for Formula I or any of the fifth or seventh embodiments. In another alternative, as part of an eighth embodiment, $R^4$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is hydrogen or fluoro, wherein the variables are as described above for Formula I or any of the fifth or seventh embodiments. In yet another alternative, as part of an eighth embodiment, $R^4$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is hydrogen or fluoro, wherein the variables are as described above for Formula I or any of the fifth or seventh embodiments.

As part of a ninth embodiment, X in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is O, wherein the variables are as described above for Formula I or any of the fifth, seventh, or eighth embodiments.

As part of a tenth embodiment, q in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is 1, wherein the variables are as described above for Formula I or any of the fifth and seventh to ninth embodiments.

As part of an eleventh embodiment, $R^1$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is hydrogen or $(C_1-C_4)$alkyl, wherein the variables are as described above for Formula I or any of the fifth and seventh to tenth embodiments. Alternatively, as part of an eleventh embodiment, $R^1$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is hydrogen or methyl, wherein the variables are as described above for Formula I or any of the fifth and seventh to tenth embodiments. In another alternative, as part of an eleventh embodiment, $R^1$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is hydrogen, wherein the variables are as described above for Formula I or any of the fifth and seventh to tenth embodiments.

As part of a twelfth embodiment, $R^2$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is hydrogen, wherein the variables are as described above for Formula I or any of the fifth and seventh to eleventh embodiments.

As part of a thirteenth embodiment, $R^3$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is $(C_1-C_4)$alkyl, aryl, heterocyclyl, or heteroaryl, wherein each of said aryl, heterocyclyl, and heteroaryl are optionally substituted with 1 to 4 groups selected from $R^B$, wherein the variables are as described above for Formula I or any of the fifth and seventh to twelfth embodiments. Alternatively, as part of a thirteenth embodiment, $R^3$ in the compound of Formula I, I', $I^z$, $I^{zz}$, $I^x I^{xx}$, Ia, Ib, Ic, Ia', Ia", Ib', Ib", Ic', or Ic", or a pharmaceutically acceptable salt thereof, is $(C_1-C_4)$ alkyl, phenyl, heterocyclyl, or heteroaryl, wherein each of said phenyl, heterocyclyl, and heteroaryl are optionally substituted with 1 to 4 groups selected from $R^B$, wherein the variables are as described above for Formula I or any of the fifth and seventh to twelfth embodiments. In another alternative, as part of a thirteenth embodiment, $R^3$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is $(C_1-C_4)$alkyl, aryl, or heteroaryl, each of which are optionally substituted with 1 to 4 groups selected from $R^B$, wherein the variables are as described above for Formula I or any of the fifth and seventh to twelfth embodiments. In yet another alternative, as part of a thirteenth embodiment, $R^3$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is $(C_1-C_4)$alkyl, phenyl, or heteroaryl, each of which are optionally substituted with 1 to 4 groups selected from $R^B$, wherein the variables are as described above for Formula I or any of the fifth and seventh to twelfth embodiments. In yet another alternative, as part of a thirteenth embodiment, $R^3$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is $(C_1\text{-}C_4)$alkyl, phenyl, napthyl, or heteroaryl, each of which are optionally substituted with 1 to 4 groups selected from $R^B$, wherein the variables are as described above for Formula I or any of the fifth and seventh to twelfth embodiments. In yet another alternative, as part of a thirteenth embodiment, $R^3$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is $(C_1\text{-}C_4)$alkyl, phenyl, napthyl, or 5- to 9-membered heteroaryl, wherein said phenyl and 5- to 9-membered heteroaryl are optionally substituted with 1 to 4 groups selected from $R^B$, wherein the variables are as described above for Formula I or any of the fifth and seventh to twelfth embodiments. In yet another alternative, as part of a thirteenth embodiment, $R^3$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is $(C_1\text{-}C_4)$alkyl, phenyl, or 5- to 6-membered heteroaryl, wherein said phenyl and 5- to 6-membered heteroaryl are optionally substituted with 1 to 4 groups selected from $R^B$, wherein the variables are as described above for Formula I or any of the fifth and seventh to twelfth embodiments. In yet another alternative, as part of a thirteenth embodiment, $R^3$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is $(C_1\text{-}C_4)$alkyl, phenyl, napthyl, isoquinolinyl, thiazolyl, oxazolyl, pyrimidinyl, pyrazinyl, pyridazinyl, pyridinyl, imidazolyl, naphthyridinyl, benzooxazolyl, indolizinyl, or benzothiazolyl, wherein said phenyl, napthyl, isoquinolinyl, thiazolyl, oxazolyl, pyrimidinyl, pyrazinyl, pyridazinyl, pyridinyl, imidazolyl, naphthyridinyl, benzooxazolyl, indolizinyl, and benzothiazolyl are optionally substituted with 1 to 4 groups selected from $R^B$, wherein the variables are as described above for Formula I or any of the fifth and seventh to twelfth embodiments. In yet another alternative, as part of a thirteenth embodiment, $R^3$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is $(C_1\text{-}C_4)$alkyl, phenyl, napthyl, isoquinolinyl, thiazolyl, oxazolyl, pyrimidinyl, pyrazinyl, pyridazinyl, imidazolyl, or benzothiazolyl, wherein said phenyl, napthyl, isoquinolinyl, thiazolyl, oxazolyl, pyrimidinyl, pyrazinyl, pyridazinyl, imidazolyl, and benzothiazolyl are optionally substituted with 1 to 4 groups selected from $R^B$, wherein the variables are as described above for Formula I or any of the fifth and seventh to twelfth embodiments. In yet another alternative, as part of a thirteenth embodiment, $R^3$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is $(C_1\text{-}C_4)$alkyl, phenyl, or pyridinyl, wherein said phenyl and pyridinyl are each optionally substituted with 1 to 4 groups selected from $R^B$, wherein the variables are as described above for Formula I or any of the fifth and seventh to twelfth embodiments.

As part of a fourteenth embodiment, $R^B$ in the compound of Formula I, I', $I^z$, $I^z$, $I^{zz}$, $I^{xx}$, Ia, Ib, Ic, Ia', Ia", Ib', Ib", Ic', or Ic", or a pharmaceutically acceptable salt thereof, is $(C_1\text{-}C_4)$alkyl, halo$(C_1\text{-}C_4)$alkyl, $(C_1\text{-}C_4)$alkoxy, halo$(C_1\text{-}C_4)$alkoxy, halo, $(C_1\text{-}C_4)$alkyleneOH, —$NR^XR^Y$, 5- to 6-membered heteroaryl, 5- to 6-membered heterocyclyl, or 4- to 6-membered cycloalkyl, wherein said 5- to 6-membered heteroaryl, 5- to 6-membered heterocyclyl, or 4- to 6-membered cycloalkyl are each optionally substituted with 1 to 3 groups selected from $R^C$, wherein the variables are as described above for Formula I or any of the fifth and seventh to thirteenth embodiments. Alternatively, as part of a fourteenth embodiment, $R^B$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is $(C_1\text{-}C_4)$alkyl, halo$(C_1\text{-}C_4)$alkyl, $(C_1\text{-}C_4)$alkoxy, halo, $(C_1\text{-}C_4)$alkyleneOH, —$NR^XR^Y$, 5- to 6-membered heteroaryl, 5- to 6-membered heterocyclyl, or 4- to 6-membered cycloalkyl, wherein said 5- to 6-membered heteroaryl, 5- to 6-membered heterocyclyl, or 4- to 6-membered cycloalkyl are each optionally substituted with 1 to 3 groups selected from $R^C$, wherein the variables are as described above for Formula I or any of the fifth and seventh to thirteenth embodiments. In another alternative, as part of a fourteenth embodiment, $R^B$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is $(C_1\text{-}C_4)$alkyl, halo$(C_1\text{-}C_4)$alkyl, $(C_1\text{-}C_4)$alkoxy, halo$(C_1\text{-}C_4)$alkoxy, halo, $(C_1\text{-}C_4)$alkyleneOH, —$NR^XR^Y$, cyclopropyl, pyridinyl, pyrimidinyl, pyrazinyl, thiazolyl, pyridazinyl, or dihydropyridinyl, wherein said cyclopropyl, pyridinyl, pyrimidinyl, pyrazinyl, thiazolyl, pyridazinyl, and dihydropyridinyl are each optionally substituted with 1 to 3 groups selected from $R^C$, wherein the variables are as described above for Formula I or any of the fifth and seventh to thirteenth embodiments. In yet another alternative, as part of a fourteenth embodiment, $R^B$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is $(C_1\text{-}C_4)$alkyl, halo$(C_1\text{-}C_4)$alkyl, $(C_1\text{-}C_4)$alkoxy, halo, $(C_1\text{-}C_4)$alkyleneOH, —$NR^XR^Y$, cyclopropyl, pyridinyl, pyrimidinyl, pyrazinyl, pyridazinyl, or dihydropyridinyl, wherein said cyclopropyl, pyridinyl, pyrimidinyl, pyrazinyl, pyridazinyl, and dihydropyridinyl are each optionally substituted with 1 to 3 groups selected from $R^C$, wherein the variables are as described above for Formula I or any of the fifth and seventh to thirteenth embodiments. In yet another alternative, as as part of a fourteenth embodiment, $R^B$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is $(C_1\text{-}C_4)$alkyl or 5- to 6-membered heteroaryl, wherein the variables are as described above for Formula I or any of the fifth and seventh to thirteenth embodiments. In yet another alternative, as part of a fourteenth embodiment, $R^B$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is $(C_1\text{-}C_4)$alkyl, pyrimidinyl, or pyrazinyl, wherein the variables are as described above for Formula I or any of the fifth and seventh to thirteenth embodiments.

As part of a fifteenth embodiment, $R^C$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is $(C_1\text{-}C_4)$alkyl, $(C_1\text{-}C_4)$alkoxy, —$C(O)OR^X$, —$C(O)NR^XR^Y$, —$NR^XC(O)R^Y$, or oxo, wherein the variables are as described above for Formula I or any of the fifth and seventh to fourteenth embodiments. Alternatively, as part of a fifteenth embodiment, $R^C$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is —$C(O)OR^X$, —$C(O)NR^XR^Y$, —$NR^XC(O)R^Y$, or oxo, wherein the variables are as described above for Formula I or any of the fifth and seventh to fourteenth embodiments. In another alternative, as part of a fifteenth embodiment, $R^C$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is selected from $(C_1\text{-}C_4)$alkyl, halo$(C_1\text{-}C_4)$alkyl, $(C_1\text{-}C_4)$alkoxy, halo$(C_1\text{-}C_4)$alkoxy cyano, oxo, and hydroxy, wherein the variables are as described above for Formula I or any of the fifth and seventh to fourteenth embodiments.

As part of a sixteenth embodiment, $R^X$ and $R^Y$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, are each independently selected from hydrogen and $(C_1\text{-}C_4)$alkyl, wherein the variables are as described above for Formula I or any of the fifth and seventh to fifteenth embodiments.

As part of a seventeenth embodiment, $R^3$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is $CH_3$,

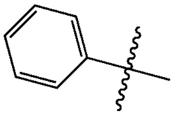, 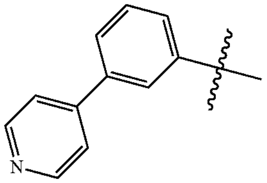,

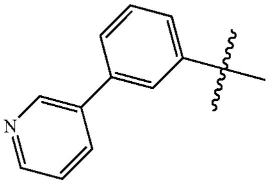, 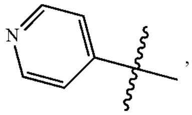,

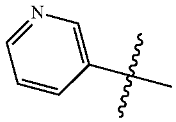, 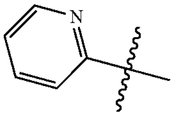,

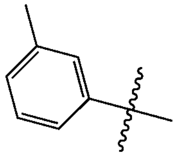, 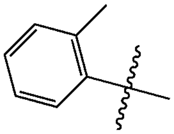,

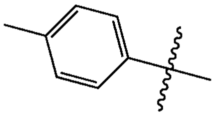, 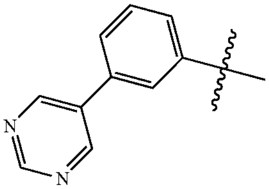,

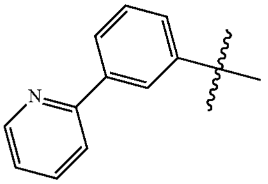, 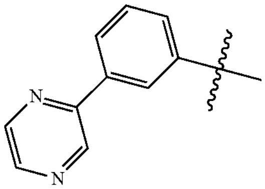,

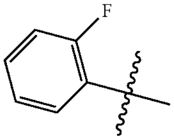, 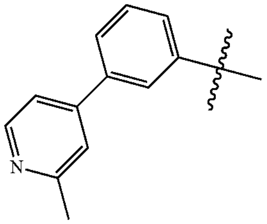,

-continued

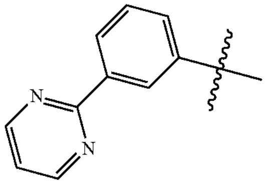, 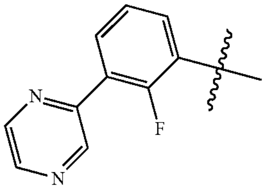,

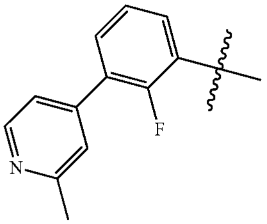, 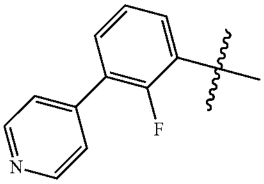,

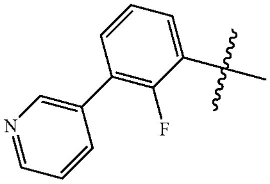, 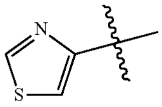,

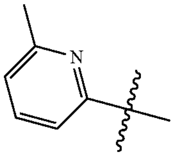, 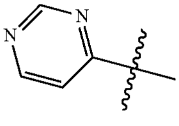,

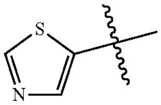, 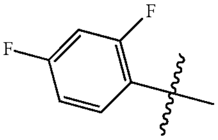,

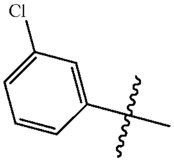, 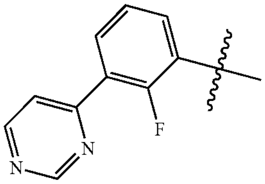,

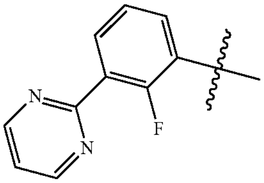, 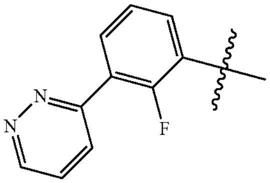,

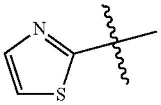, 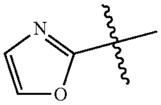,

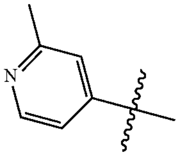, 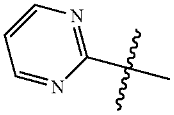,

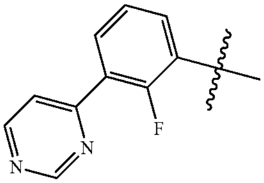, 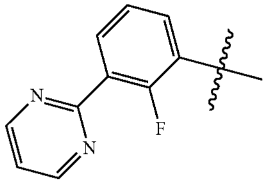,

-continued
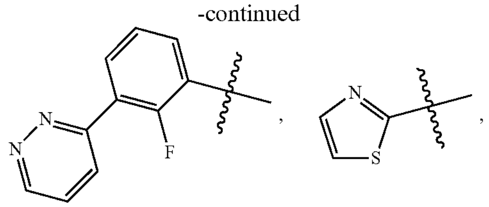
, ,
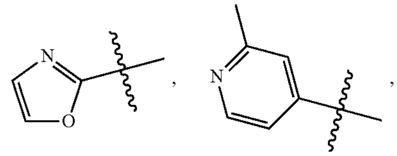
, ,
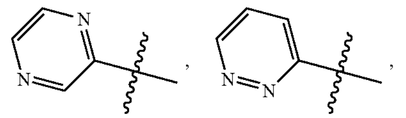
, ,
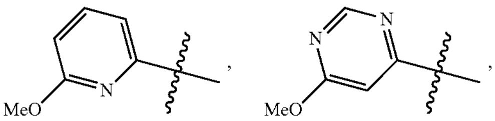
, ,
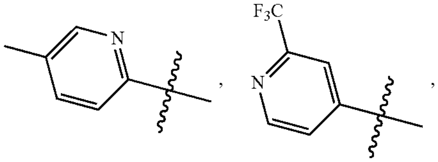
, ,
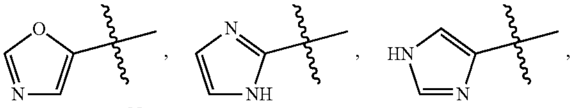
, , ,
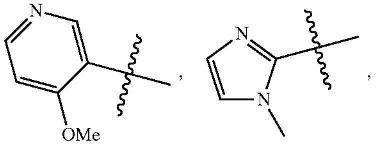
, ,
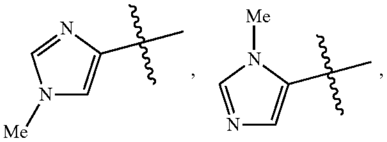
, ,
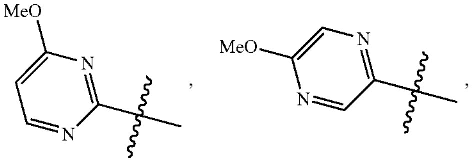
, ,
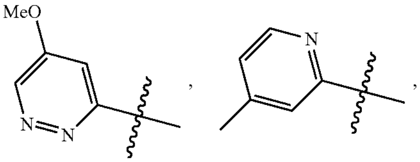
, ,
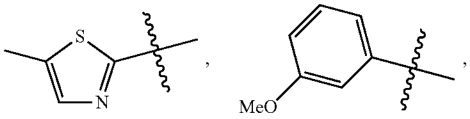
, ,
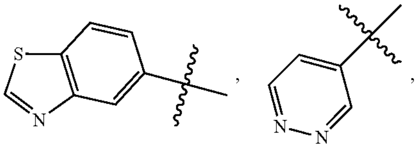
, ,
-continued
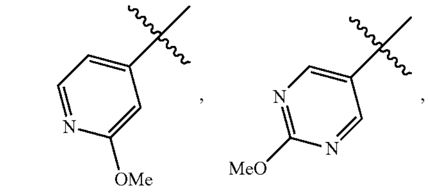
, ,
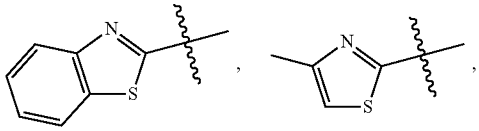
, ,
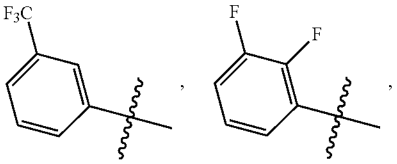
, ,
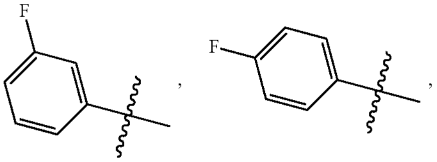
, ,
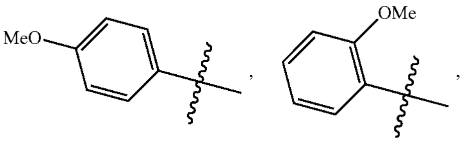
, ,
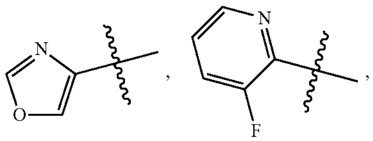
, ,
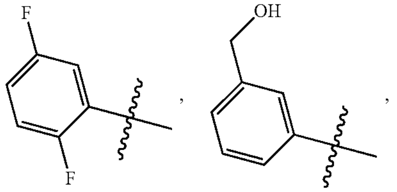
, ,
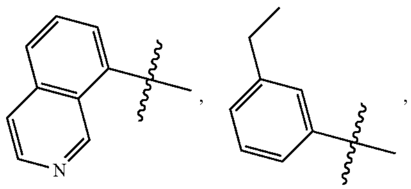
, ,
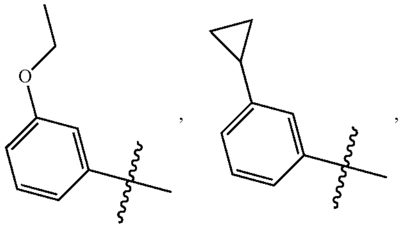
, ,
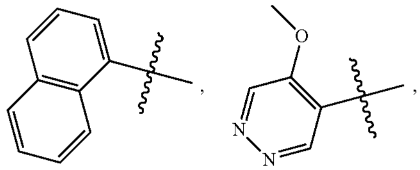
, , -continued
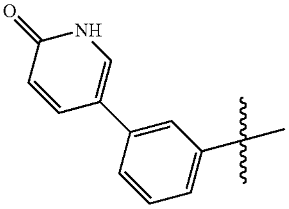
,
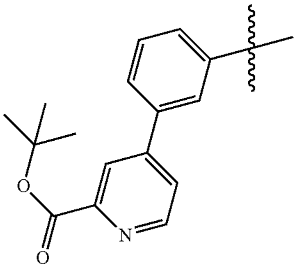
,
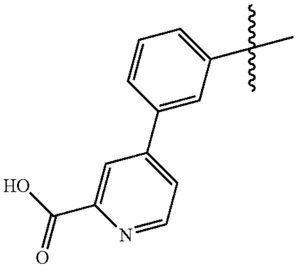
,
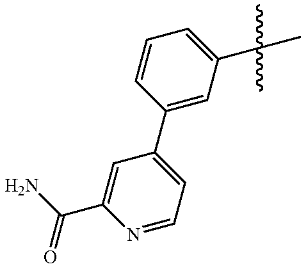
,
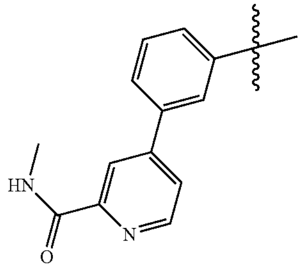
,
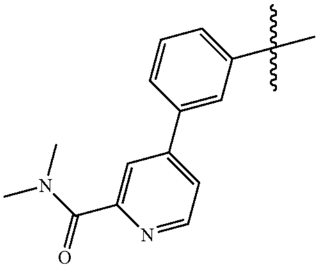
,
-continued
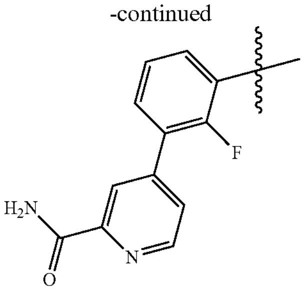
,
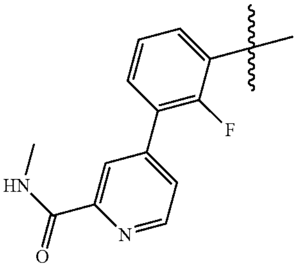
,
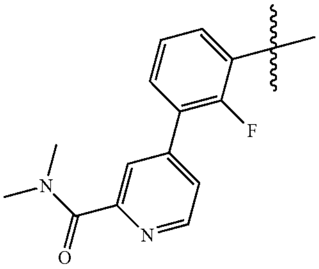
,
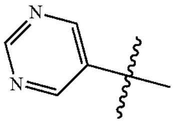
,
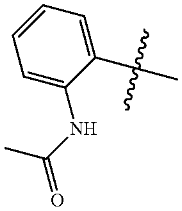
,
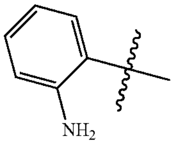
,
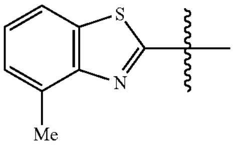
,
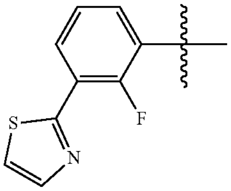
,
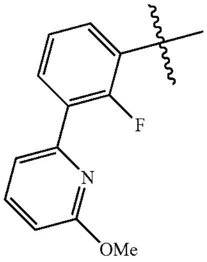
,
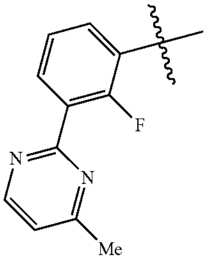
,
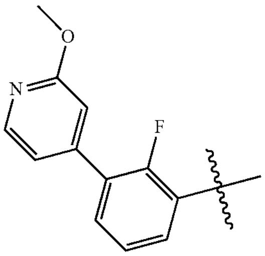
,
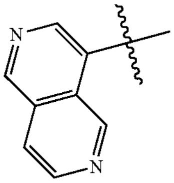
, -continued
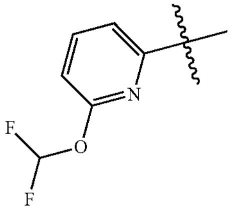, 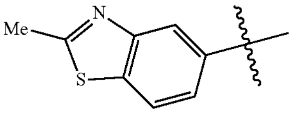,
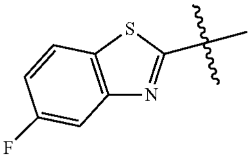, 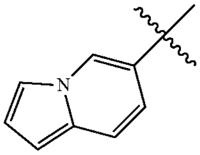,
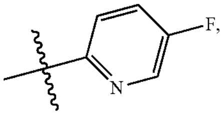 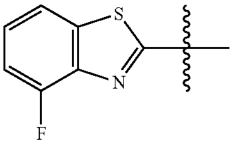,
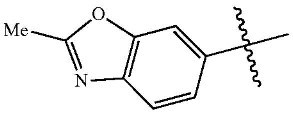, 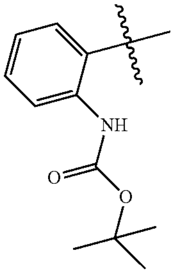, or
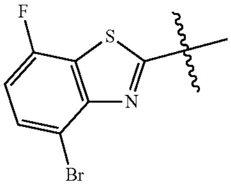,
wherein the variables are as described above for Formula I or any of the fifth and seventh to twelfth embodiments. Alternatively, as part of a seventeenth embodiment, $R^3$ in the compound of Formula I, I', $I^z$, $I^{zz}$, $I^x$, $I^{xx}$, Ib, Ic, Ia', Ia", Ib', Ib", Ic', or Ic", or a pharmaceutically acceptable salt thereof, is $CH_3$,
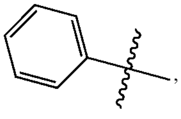, 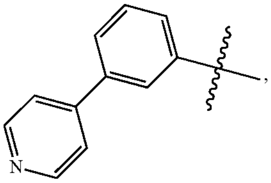,
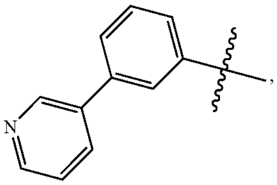, 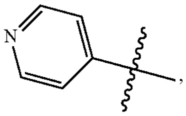,
-continued
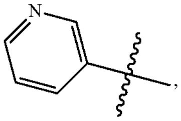, 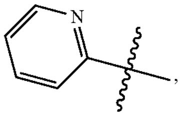, 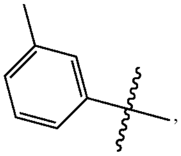,
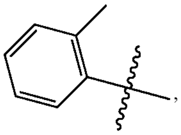, 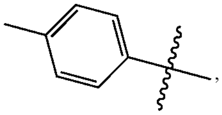,
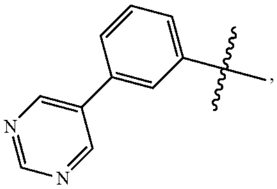, 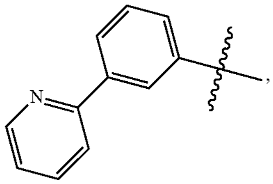,
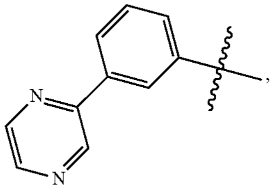, 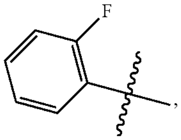,
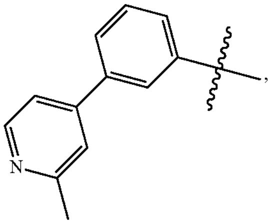, 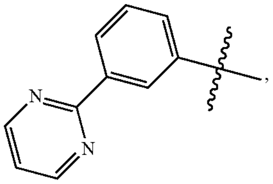,
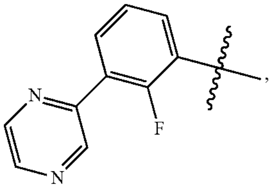, 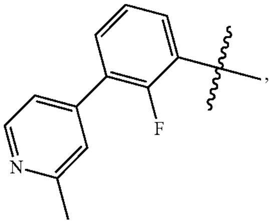,
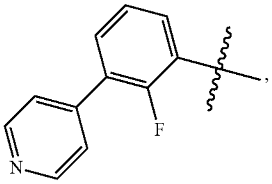, 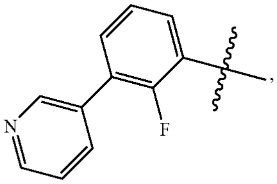,
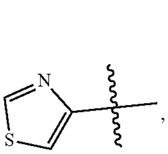, 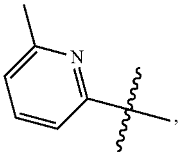, 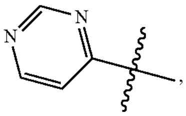,
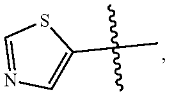, 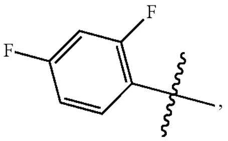, -continued
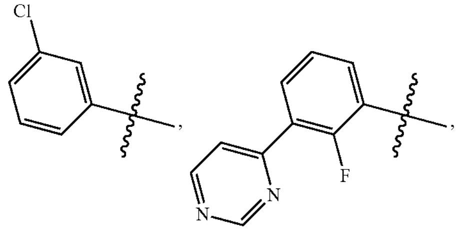
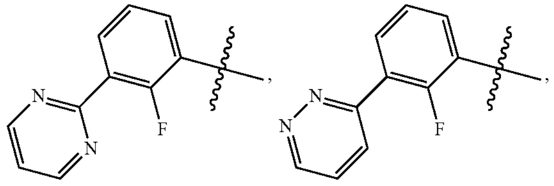
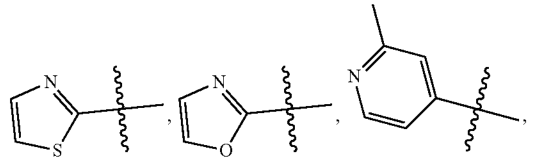
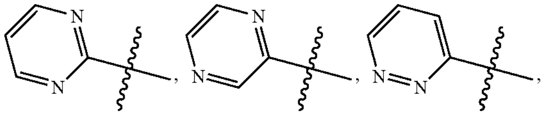
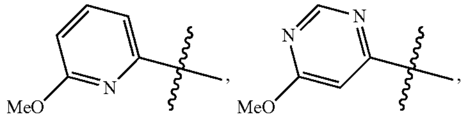
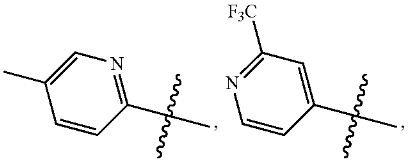
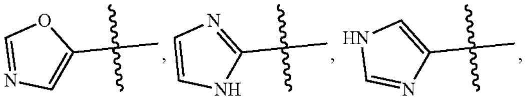
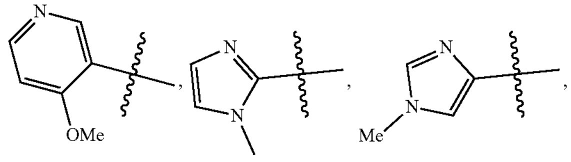
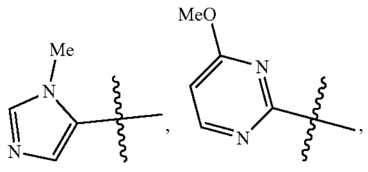
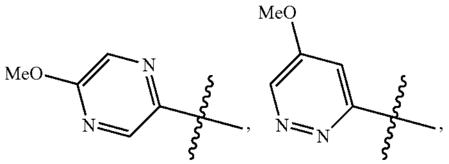
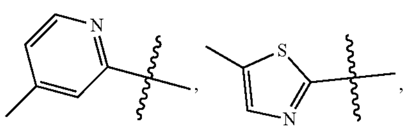
-continued
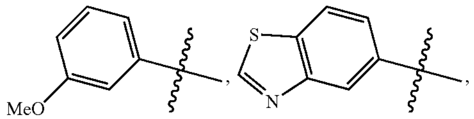
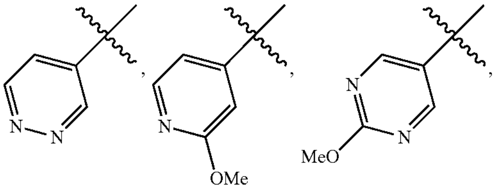
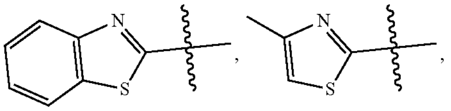
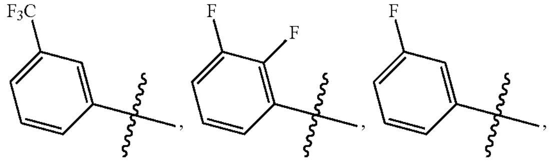
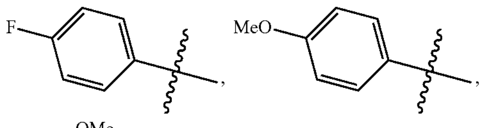
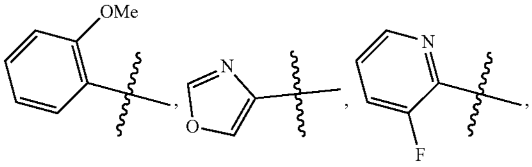
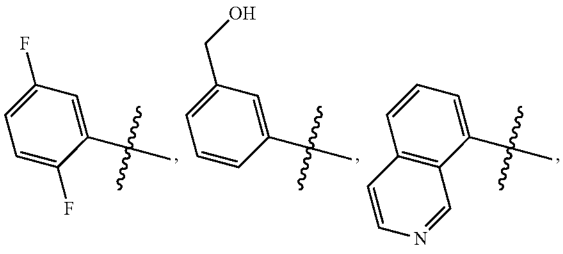
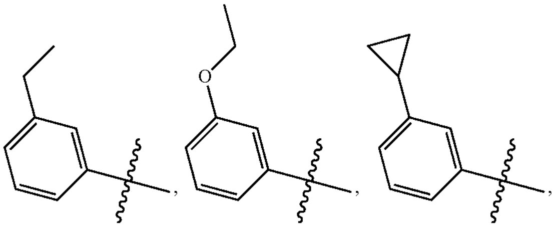
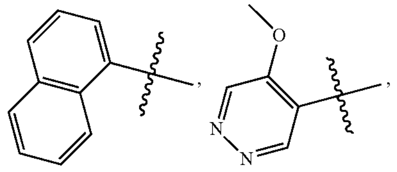
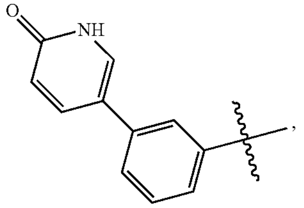

-continued
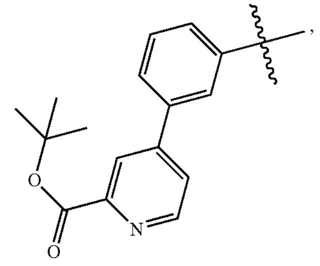
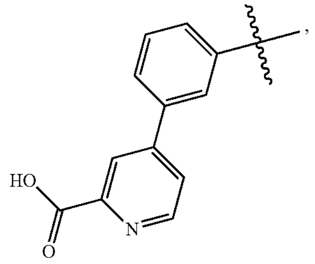
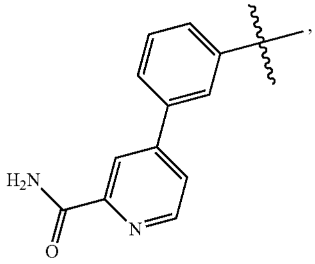
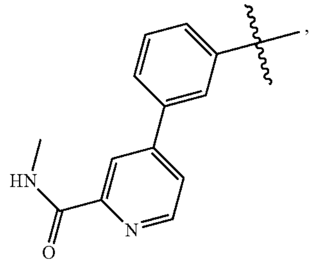
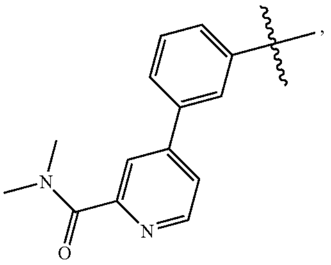
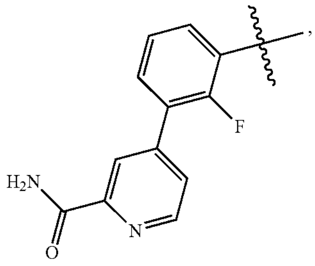
-continued
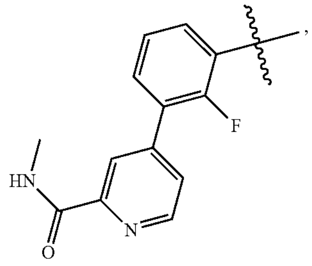
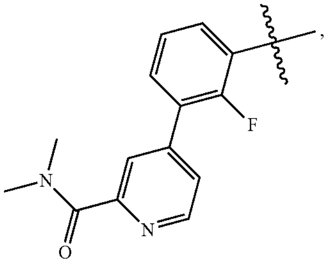
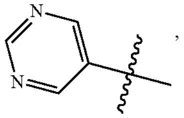
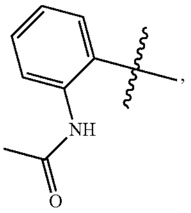
or
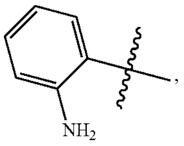
wherein the variables are as described above for Formula I or any of the fifth and seventh to twelfth embodiments. In another alternative, as part of a seventeenth embodiment, $R^3$ in the compound of Formula I, I', $I^z$, $I^{zz}$, $I^x$, $I^{xx}$, Ia, Ib, Ic, Ia', Ia", Ib', Ib", Ic', or Ic", or a pharmaceutically acceptable salt thereof, is $CH_3$,
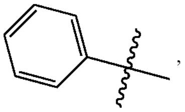
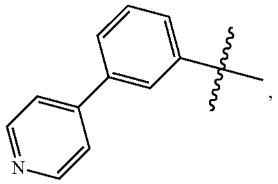
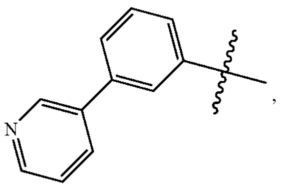
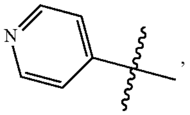
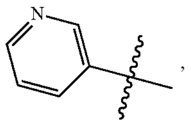
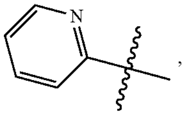
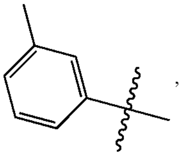
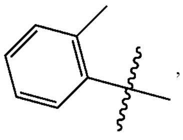

-continued

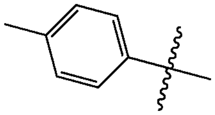,

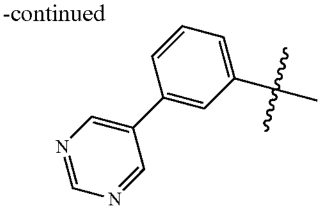,

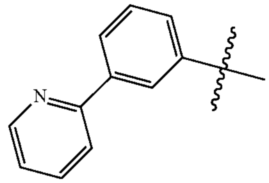,

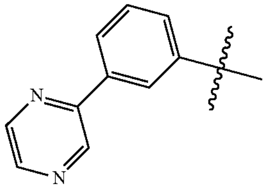, or

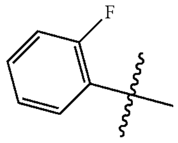, wherein the variables are as described above for Formula I or any of the fifth and seventh to twelfth embodiments.

Additional compounds are described and exemplified herein, and are included in the present disclosure. Pharmaceutically acceptable salts thereof as well as the neutral forms of such compounds are included.

4. Uses, Formulation and Administration

The compounds and compositions described herein are generally useful for modulating the activity of anaplastic lymphoma kinase (ALK). In some aspects, the compounds, pharmaceutical acceptable salts, and pharmaceutical compositions described herein degrade ALK.

In some aspects, the compounds and pharmaceutical compositions described herein are useful in treating a disorder associated with ALK function. Thus, provided herein are methods of treating a disorder associated with ALK function, comprising administering to a subject in need thereof, a therapeutically effective amount of a compound described herein, or a pharmaceutically acceptable salt thereof, or a pharmaceutical composition comprising a disclosed compound or pharmaceutically acceptable salt thereof.

Also provided is the use of a compound described herein, or a pharmaceutically acceptable salt thereof, or a pharmaceutical composition comprising a disclosed compound or pharmaceutically acceptable salt thereof, for the manufacture of a medicament for treating a disorder associated with ALK function. Also provided is a compound described herein, or a pharmaceutically acceptable salt thereof, or a pharmaceutical composition comprising a disclosed compound or pharmaceutically acceptable salt thereof, for use in treating a disorder associated with ALK.

In one aspect, the disorder associated with ALK is a proliferative disease such as cancer. Representative examples of cancers include adrenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (non-melanoma), biliary cancer, extrahepatic bile duct cancer, intrahepatic bile duct cancer, bladder cancer, urinary bladder cancer, brain cancer (e.g., gliomas and glioblastomas such as brain stem glioma, gestational trophoblastic tumor glioma, cerebellar astrocytoma, cerebral astrocytoma/malignant glioma, ependymoma, medulloblastoma, supratentorial primitive neuroectodermal tumors, visual pathway and hypothalamic glioma), breast cancer, bronchial adenomas/carcinoids, carcinoid tumor, nervous system cancer (e.g, central nervous system cancer, central nervous system lymphoma), cervical cancer, chronic myeloproliferative disorders, colorectal cancer (e.g, colon cancer, rectal cancer), polycythemia vera, lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g, stomach cancer, small intestine cancer, gastrointestinal carcinoid tumor, gastrointestinal stromal tumor (GIST)), germ cell tumor, ovarian germ cell tumor, head and neck cancer, Hodgkin's lymphoma, leukemia, lymphoma, multiple myeloma, hepatocellular carcinoma, hypopharyngeal cancer, intraocular melanoma, ocular cancer, islet cell tumors (endocrine pancreas), renal cancer (e.g, Wilm's Tumor, clear cell renal cell carcinoma), liver cancer, lung cancer (e.g, non-small cell lung cancer and small cell lung cancer), Waldenstrom's macroglobulinemia, melanoma, intraocular (eye) melanoma, merkel cell carcinoma, mesothelioma, metastatic squamous neck cancer with occult primary, multiple endocrine neoplasia (MEN), myelodysplastic syndromes, essential thrombocythemia, myelodysplastic/myeloproliferative diseases, nasopharyngeal cancer, neuroblastoma, oral cancer (e.g, mouth cancer, lip cancer, oral cavity cancer, tongue cancer, oropharyngeal cancer, throat cancer, laryngeal cancer), ovarian cancer (e.g, ovarian epithelial cancer, ovarian germ cell tumor, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma, pituitary tumor, plasma cell neoplasm, pleuropulmonary blastoma, prostate cancer, retinoblastoma rhabdomyosarcoma, salivary gland cancer, uterine cancer (e.g., endometrial uterine cancer, uterine sarcoma, uterine corpus cancer), squamous cell carcinoma, testicular cancer, thymoma, thymic carcinoma, thyroid cancer, transitional cell cancer of the renal pelvis and ureter and other urinary organs, urethral cancer, gestational trophoblastic tumor, vaginal cancer and vulvar cancer.

Sarcomas that may be treatable with compounds, pharmaceutically acceptable salts of the compounds and compostions comprising such as described herein include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue) and mesenchymous or mixed mesodermal tumor (mixed connective tissue types)

In some aspects, the cancer treated by the compounds, pharmaceutically acceptable salt thereof, and pharmaceutical compositions described herein is an ALK positive cancer.

In some aspects, the cancer treated by the compounds, pharmaceutically acceptable salt thereof, and pharmaceutical compositions described herein is selected from non-small cell lung cancer (NSCLC), large cell lymphoma (ALCL), or neuroblastomas.

In one aspect, the disorder associated with ALK is selected from a non-cancerous disorder such as inflammatory diseases and conditions, autoimmune diseases, neurodegenerative diseases, heart diseases, viral diseases, chronic and acute kidney diseases or injuries, metabolic diseases, and allergic and genetic diseases.

In certain aspects, a pharmaceutical composition described herein is formulated for administration to a patient in need of such composition. Pharmaceutical compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions are administered orally, intraperitoneally or intravenously. Sterile injectable forms of the pharmaceutical compositions described herein may be aqueous or oleaginous suspension. These suspensions may be formulated according to techniques known in the art using suitable dispersing or wetting agents and suspending agents.

In some aspects, the pharmaceutical compositions are administered orally.

A specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound described herein in the composition will also depend upon the particular compound in the pharmaceutical composition.

EXEMPLIFICATION

Compounds of the disclosure can be prepared by methods described in the General Schemes, procedures, and Examples set forth within, and by related methods known in the art.

Intermediates

Intermediate A-1: 5-((3-phenyl-1,2,4-oxadiazol-5-yl)methyl)benzo[d]oxazol-2(3H)-one Step 1: Methyl 2-(4-hydroxy-3-nitrophenyl)acetate

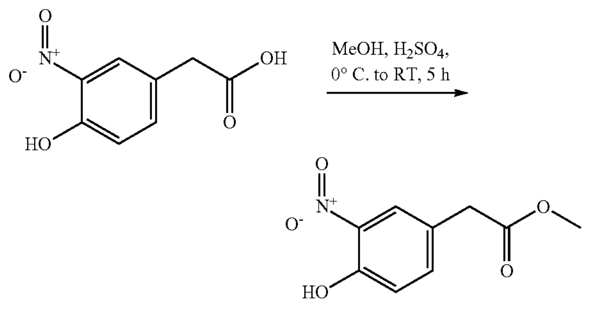

To a stirred solution of 2-(4-hydroxy-3-nitrophenyl)acetic acid (1 g, 5.1 mmol) in methanol (30 mL) was added sulfuric acid (0.54 mL, 10 mmol) at 0° C. The resulting reaction mixture was stirred at 0° C. for 5 min, warmed to room temperature and stirred for 5 h. After completion of the reaction, the reaction mixture was quenched with aq. sat. bicarbonate solution until pH~7 and extracted with ethyl acetate (3×60 mL). The combined organic layers were washed with brine solution (20 mL), dried over anhydrous sodium sulphate, filtered and the filtrate was concentrated under reduced pressure to afford methyl 2-(4-hydroxy-3-nitrophenyl)acetate (1.0 g, 93%) as a pale yellow solid. The obtained compound was used as such for the next step without further purification. MS (ESI) m/z 212.59 $[M+H]^+$.

Step 2: Methyl 2-(3-amino-4-hydroxyphenyl)acetate

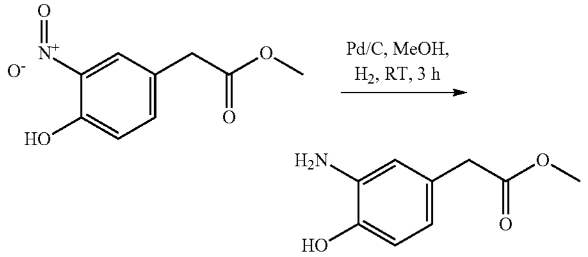

To a stirred solution of methyl 2-(4-hydroxy-3-nitrophenyl)acetate (1 g, 4.7 mmol) in MeOH (30 mL) was added palladium 10% on carbon (0.2 g, 1.9 mmol, 50% wet) under $N_2$ at room temperature. The resulting reaction mixture was stirred at room temperature for 3 h under $H_2$ atmosphere. After completion of the reaction, the reaction mixture was filtered through a Celite® pad; the pad was washed with methanol (10 mL), filtered and the filtrate was concentrated under reduced pressure to afford crude compound. The obtained crude compound was purified by silica gel (230-400 mesh) column chromatography and eluted by using 10-20% ethyl acetate in petroleum ether to afford methyl 2-(3-amino-4-hydroxyphenyl)acetate (1 g, 87%) as a pale yellow solid. MS (ESI) m/z 182.03 $[M+H]^+$.

Step 3: Methyl 2-(2-oxo-2,3-dihydrobenzo[d]oxazol-5-yl)acetate

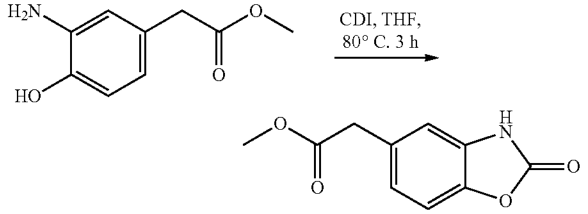

To a stirred solution of methyl 2-(3-amino-4-hydroxyphenyl)acetate (0.8 g, 4.4 mmol) in dry THF (8 mL) was added 1,1'-carbonyldiimidazole (0.72 g, 4.4 mmol) at room temperature. The resulting reaction mixture was stirred at 80° C. for 3 h. After completion of the reaction, the reaction mixture was quenched with water (10 mL) and extracted with ethyl acetate (3×20 mL). The combined organic layers were washed with brine solution (20 mL), dried over anhydrous sodium sulphate, filtered and the filtrate was concentrated under reduced pressure to afford crude compound. The obtained crude compound was purified by silica gel (230-400 mesh) column chromatography and eluted by using 20-30% ethyl acetate in petroleum ether to afford methyl 2-(2-oxo-2,3-dihydrobenzo[d]oxazol-5-yl)acetate (0.6 g, 65%) as an off-white solid. MS (ESI) m/z 208.55 $[M+H]^+$.

Step 4: 2-(2-Oxo-2,3-dihydrobenzo[d]oxazol-5-yl) acetic acid

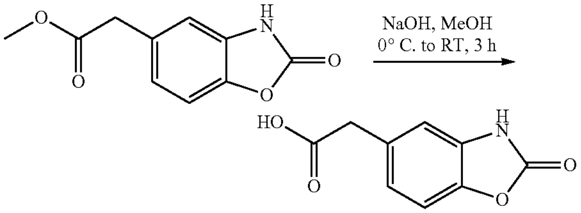

To a stirred solution of methyl 2-(2-oxo-2,3-dihydrobenzo[d]oxazol-5-yl)acetate (0.6 g, 2.9 mmol) in methanol (6 mL) was added NaOH (0.52 g, 13 mmol) dissolved in water (10 mL) at 0° C. The resulting reaction mixture was stirred at 0° C. for 5 min, warmed to room temperature and stirred for 3 h. After completion of the reaction, the reaction mixture was neutralized by 3N HCl until pH~2 and extracted with 10% MeOH in DCM (2×60 mL). The combined organic layers were dried over sodium sulphate, filtered and the filtrate was concentrated under reduced pressure to afford 2-(2-oxo-2,3-dihydrobenzo[d]oxazol-5-yl)acetic acid (0.5 g, 89%) as an off-white solid. The obtained compound was used as such for next step without further purification. MS (ESI) m/z 194.58 $[M+H]^+$.

Step 5: 5-((3-Phenyl-1,2,4-oxadiazol-5-yl)methyl) benzo[d]oxazol-2(3H)-one

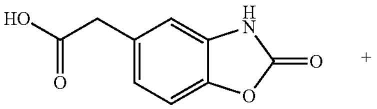

-continued

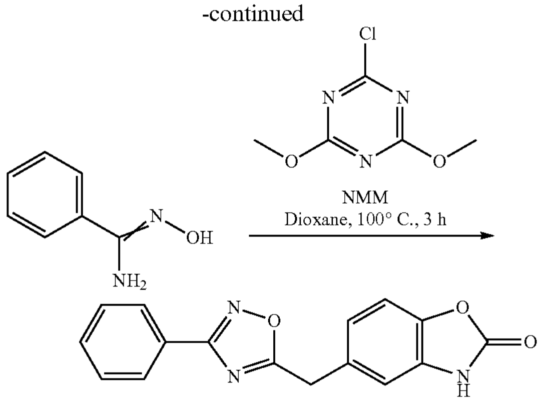

To a stirred solution of 2-chloro-4,6-dimethoxy-1,3,5-triazine (0.079 g, 0.45 mmol) in 1,4 dioxane (3 mL) was added 4-methylmorpholine (0.14 g, 1.4 mmol) at room temperature. The reaction mixture was stirred for 30 minutes followed by addition of 2-(2-oxo-2,3-dihydrobenzo[d]oxazol-5-yl)acetic acid (0.1 g, 0.45 mmol) at room temperature. The resulting reaction mixture was stirred for 40 minutes followed by addition of N-hydroxybenzimidamide (0.062 g, 0.45 mmol) at room temperature. The resulting reaction mixture was stirred at 100° C. for 3 h. After completion of the reaction, the reaction mixture was directly concentrated under reduced pressure to afford crude compound. The obtained crude compound was quenched with aq. sat. sodium carbonate solution (30 mL) and extracted with ethyl acetate (3×30 mL). The combined organic layers were washed with brine solution (20 mL), dried over anhydrous sodium sulphate, filtered and the filtrate was concentrated under reduced pressure to afford crude compound. The obtained crude compound was purified by silica gel (230-400 mesh) column chromatography and eluted by using 0 to 10% EtOAc in petroleum ether 5-((3-phenyl-1,2,4-oxadiazol-5-yl)methyl)benzo[d]oxazol-2(3H)-one (0.07 g, 46%) as a yellow solid. MS (ESI) m/z 294.61 $[M+H]^+$.

Intermediates below may be synthesized similarly to Intermediate A-1:

| Int. | Structure | $[M + H]^+$ | $^1H$ NMR |
| --- | --- | --- | --- |
| A-1 | 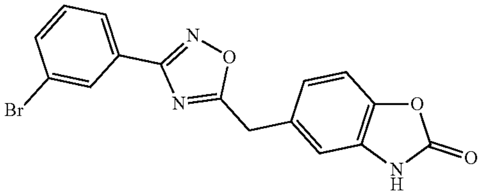 [SMILES: O=c1[nH]c2cc(Cc3nc(-c4cccc(Br)c4)no3)ccc2o1] | 372.51 | |
| A-2 | 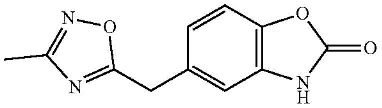 [SMILES: Cc1noc(Cc2ccc3oc(=O)[nH]c3c2)n1] | 232.06 | |
| A-3 | 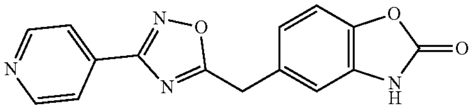 [SMILES: O=c1[nH]c2cc(Cc3nc(-c4ccncc4)no3)ccc2o1] | 295.10 | |

-continued
| Int. | Structure | [M + H]$^+$ | $^1$H NMR |
|---|---|---|---|
| A-4 | 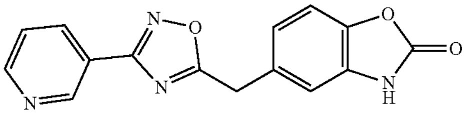 [SMILES: O=c1[nH]c2cc(Cc3nc(-c4cccnc4)no3)ccc2o1] | 295.10 | |
| A-5 | 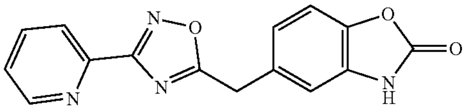 [SMILES: O=c1[nH]c2cc(Cc3nc(-c4ccccn4)no3)ccc2o1] | 295.71 | |
| A-6 | 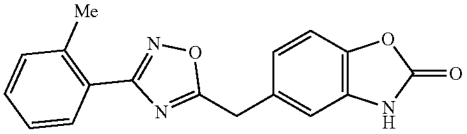 [SMILES: Cc1ccccc1-c1noc(Cc2ccc3oc(=O)[nH]c3c2)n1] | 308.08 | $^1$H NMR (400 MHz, DMSO-$d_6$) δ 11.21 (s, 1H), 7.87 (d, J = 7.6 Hz, 1H), 7.47-7.44 (m, 1H), 7.40-7.34 (m, 2H), 7.27 (d, J = 8.0 Hz, 1H), 7.16 (s, 1H), 7.12 (d, J = 8.4 Hz, 1H), 4.46 (s, 2H), 2.53 (s, 3H) |
| A-7 | 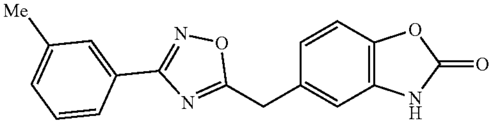 [SMILES: Cc1cccc(-c2noc(Cc3ccc4oc(=O)[nH]c4c3)n2)c1] | 306.37 | |
| A-8 | 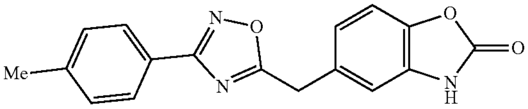 [SMILES: Cc1ccc(-c2noc(Cc3ccc4oc(=O)[nH]c4c3)n2)cc1] | 308.08 | $^1$H NMR (400 MHz, DMSO-$d_6$) δ 11.65 (br s, 1H), 7.86 (d, J = 8.0 Hz, 2H), 7.36 (d, J = 8.0 Hz, 2H), 7.27 (d, J = 8.0 Hz, 1H), 7.14 (br s, 1H), 7.10 (d, J = 8.0 Hz, 1H), 4.44 (s, 2H), 2.37 (s, 3H) |
| A-9 | 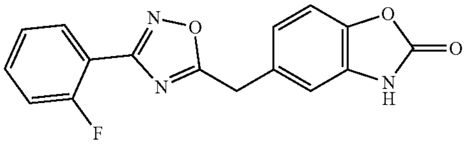 [SMILES: O=c1[nH]c2cc(Cc3nc(-c4ccccc4F)no3)ccc2o1] | 312.24 | $^1$H NMR (400 MHz, DMSO-$d_6$) δ 11.65 (s, 1H), 7.99-7.96 (m, 1H), 7.67 - 7.62 (m, 1H), 7.46-7.37 (m, 2H), 7.27 (d, J = 8.0 Hz, 1H), 7.15 (s, 1H), 7.11 (d, J = 8.4 Hz, 1H), 4.84 (s, 2H) |
| A-10 | 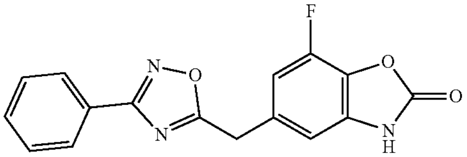 [SMILES: O=c1[nH]c2cc(Cc3nc(-c4ccccc4)no3)cc(F)c2o1] | 312.45 | $^1$H NMR (400 MHz, $CDCl_3$) δ 8.06 (d, J = 7.6 Hz, 2H), 7.52-7.45 (m, 3H), 6.96 (d, J = 10.0 Hz, 1H), 6.91 (s, 1H), 4.28 (s, 2H) |
| A-11 | 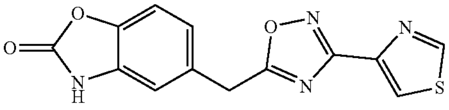 [SMILES: O=c1[nH]c2cc(Cc3nc(-c4cscn4)no3)ccc2o1] | 301.3 | $^1$H NMR (400 MHz, DMSO-$d_6$) δ 9.30 (d, J = 1.8 Hz, 1H), 8.47 (d, J = 1.8 Hz, 1H), 7.28 (d, J = 8.2 Hz, 1H), 7.15 (s, 1H), 7.11 (d, J = 8.2 Hz, 1H), 4.47 (s, 2H) |
| A-12 | 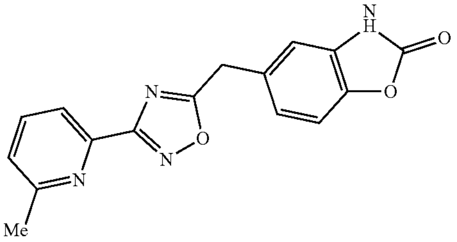 [SMILES: Cc1cccc(-c2noc(Cc3ccc4oc(=O)[nH]c4c3)n2)n1] | 309.3 | |
| A-13 | 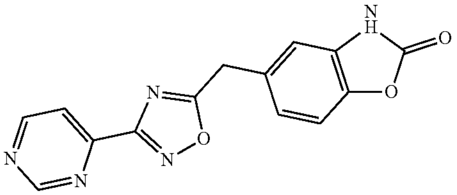 [SMILES: O=c1[nH]c2cc(Cc3nc(-c4ccncn4)no3)ccc2o1] | 296.3 | |

-continued
| Int. | Structure | $[M + H]^+$ | $^1H$ NMR |
|---|---|---|---|
| A-14 | 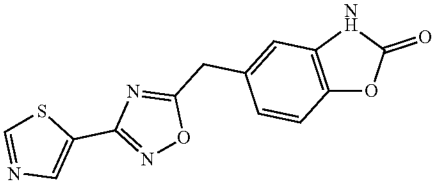 [SMILES: O=c1[nH]c2cc(Cc3nc(-c4cncs4)no3)ccc2o1] | 301.4 | |
| A-15 | 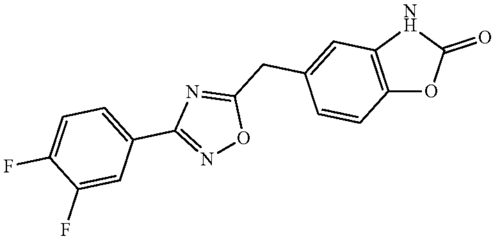 [SMILES: O=c1[nH]c2cc(Cc3nc(-c4ccc(F)c(F)c4)no3)ccc2o1] | 330.1 | $^1H$ NMR (400 MHz, DMSO-$d_6$) δ 11.64 (s, 1H), 7.99-7.92 (m, 1H), 7.88-7.82 (m, 1H), 7.69-7.59 (m, 1H), 7.27 (d, J = 8.2 Hz, 1H), 7.15 (d, J = 1.5 Hz, 1H), 7.13-7.08 (m, 1H), 4.47 (s, 2H) |
| A-16 | 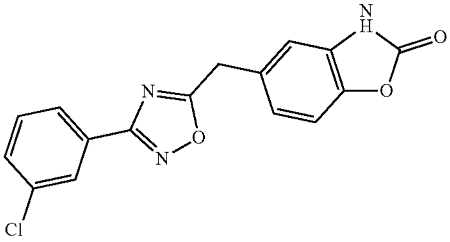 [SMILES: O=c1[nH]c2cc(Cc3nc(-c4cccc(Cl)c4)no3)ccc2o1] | 328.1 | $^1H$ NMR (400 MHz, DMSO) δ 11.65 (s, 1H), 7.97-7.92 (m, 2H), 7.72-7.64 (m, 1H), 7.62-7.56 (m, 1H), 7.27 (d, J = 8.2 Hz, 1H), 7.16 (d, J = 1.4 Hz, 1H), 7.11 (dd, J = 8.2, 1.7 Hz, 1H), 4.48 (s, 2H) |
| A-17 | 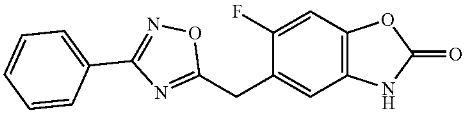 [SMILES: O=c1[nH]c2cc(Cc3nc(-c4ccccc4)no3)c(F)cc2o1] | 312.3 | |
| A-18 | 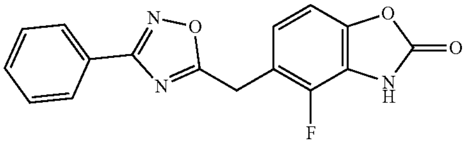 [SMILES: O=c1[nH]c2c(F)c(Cc3nc(-c4ccccc4)no3)ccc2o1] | 312.3 | |
| A-19 | 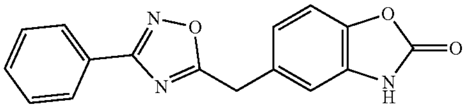 [SMILES: O=c1[nH]c2cc(Cc3nc(-c4ccccc4)no3)ccc2o1] | 295.2 | |
| A-20 | 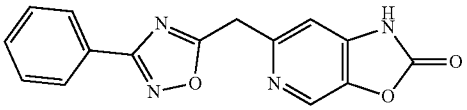 [SMILES: O=c1[nH]c2cc(Cc3nc(-c4ccccc4)no3)ncc2o1] | 295.3 | |
| A-21 | 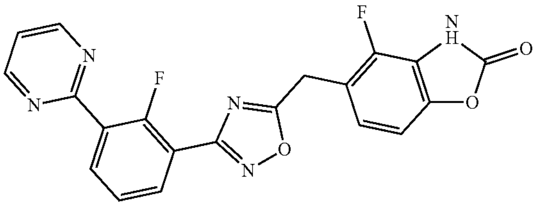 [SMILES: O=c1[nH]c2c(F)c(Cc3nc(-c4cccc(-c5ncccn5)c4F)no3)ccc2o1] | 408.3 | |

-continued

| Int. | Structure | [M + H]+ | 1H NMR |
|---|---|---|---|
| A-22 | 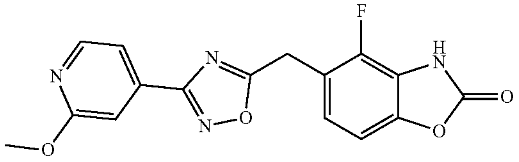 [SMILES: COc1cc(-c2noc(Cc3ccc4oc(=O)[nH]c4c3F)n2)ccn1] | 343.2 | |
| A-23 | 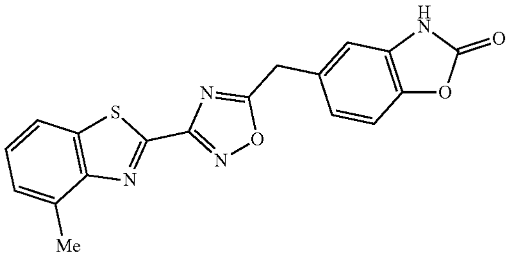 [SMILES: Cc1cccc2sc(-c3noc(Cc4ccc5oc(=O)[nH]c5c4)n3)nc12] | 365.3 | |
| A-24 | 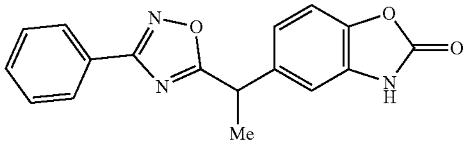 [SMILES: CC(c1ccc2oc(=O)[nH]c2c1)c1nc(-c2ccccc2)no1] | 308.4 | |

Intermediate B-1: 5-((3-(3-(pyridin-4-yl)phenyl)-1,2,4-oxadiazol-5-yl)methyl)benzo[d]oxazol-2(3H)-one

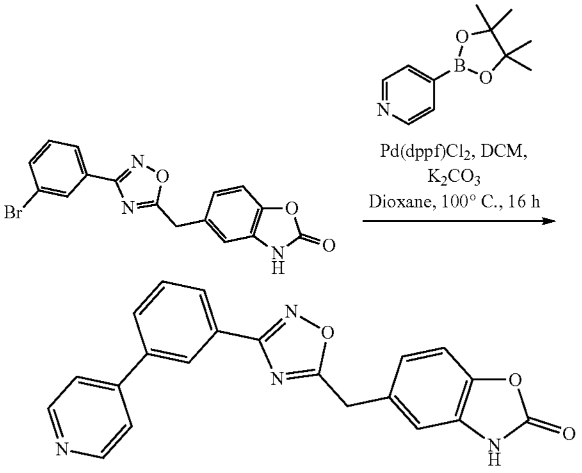

To a stirred solution of 5-((3-(3-bromophenyl)-1,2,4-oxadiazol-5-yl)methyl)benzo[d]oxazol-2(3H)-one (0.2 g, 0.54 mmol) in a mixture of 1,4 dioxane (6 mL) and water (2 mL) were added 4-(4,4,5,5-tetramethyl-1,3,2-dioxaborolan-2-yl) pyridine (0.17 g, 0.81 mmol) and potassium carbonate (0.22 g, 1.6 mmol) at room temperature. The resulting reaction mixture was purged with argon gas for 15 min and added 1,1'-bis(diphenylphosphino)ferrocene dichloropalladium-dichloromethane (0.044 g, 0.054 mmol) at room temperature. The reaction mixture was again purged with argon gas for another 3 min and heated to 100° C., then stirred for 16 h. After completion of the reaction, the reaction mixture was quenched with ice-cold water (30 mL) and extracted with ethyl acetate (3×60 mL). The combined organic layers were washed with brine solution (20 mL), dried over anhydrous sodium sulphate, filtered and the filtrate was concentrated under reduced pressure to afford crude compound. The obtained crude compound was purified by silica gel (230-400 mesh) column chromatography and eluted by using 10 to 15% EtOAc in petroleum ether to afford 5 5-((3-(3-(pyridin-4-yl)phenyl)-1,2,4-oxadiazol-5-yl)methyl)benzo[d]oxazol-2(3H)-one (0.15 g, 75%) as a yellow solid. MS (ESI) m/z 371.67 $[M+H]^+$.

Intermediates below may be synthesized similarly to Intermediate B-1:

| Int. | Structure | [M + H]+ | 1H NMR |
|---|---|---|---|
| B-1 | 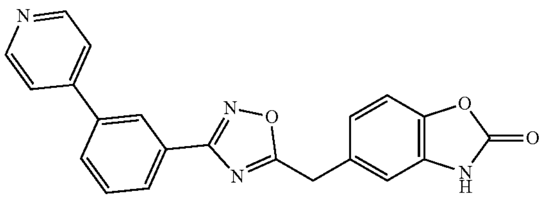 [SMILES: O=c1[nH]c2cc(Cc3nc(-c4cccc(-c5ccncc5)c4)no3)ccc2o1] | 371.09 | |

-continued
| Int. | Structure | $[M + H]^+$ | $^1H$ NMR |
|---|---|---|---|
| B-2 | 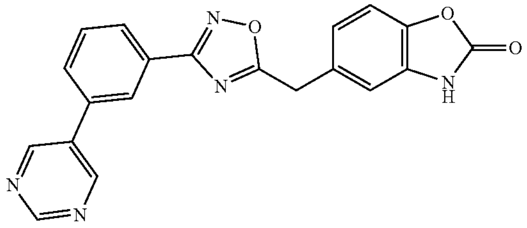 [SMILES: O=c1[nH]c2cc(Cc3nc(-c4cccc(-c5cncnc5)c4)no3)ccc2o1] | 372.05 | $^1H$ NMR (400 MHz, DMSO-$d_6$) δ 11.66 (s, 1H), 9.24 (s, 1H), 9.19 (s, 2H), 8.30 (br s, 1H), 8.08 (d, J = 8.0 Hz, 1H), 8.02 (d, J = 8.0 Hz, 1H), 7.74 (t, J = 8.0 Hz, 1H), 7.28 (d, J = 8.4 Hz, 1H), 7.17 (s, 1H), 7.13 (d, J = 8.4 Hz, 1H), 4.50 (s, 2H) |
| B-3 | 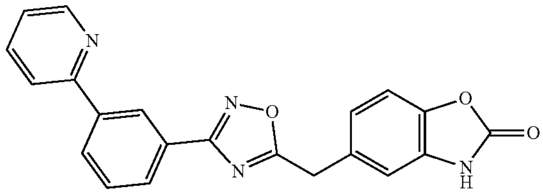 [SMILES: O=c1[nH]c2cc(Cc3nc(-c4cccc(-c5ccccn5)c4)no3)ccc2o1] | 371.67 | |
| B-4 | 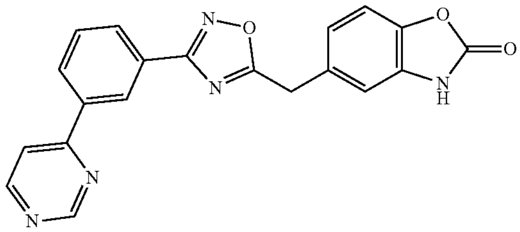 | 372.10 | |
| B-5 | 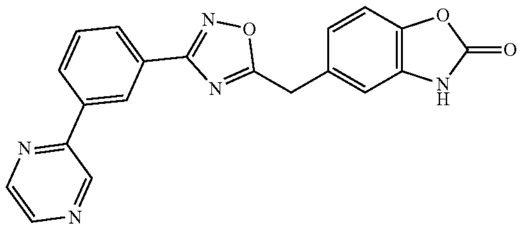 [SMILES: O=c1[nH]c2cc(Cc3nc(-c4cccc(-c5cnccn5)c4)no3)ccc2o1] | 372.05 | |
| B-6 | 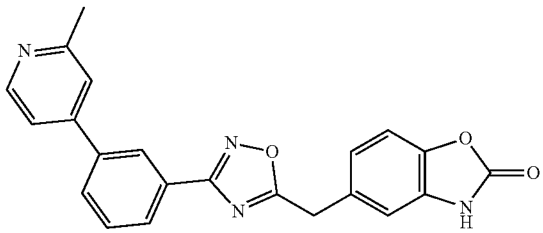 [SMILES: Cc1cc(-c2cccc(-c3noc(Cc4ccc5oc(=O)[nH]c5c4)n3)c2)ccn1] | 385.7 | |
| B-7 | 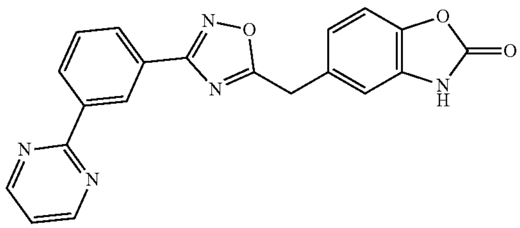 [SMILES: O=c1[nH]c2cc(Cc3nc(-c4cccc(-c5ncccn5)c4)no3)ccc2o1] | 372.05 | |

-continued
| Int. | Structure | [M + H]+ | $^1$H NMR |
|---|---|---|---|
| B-8 | 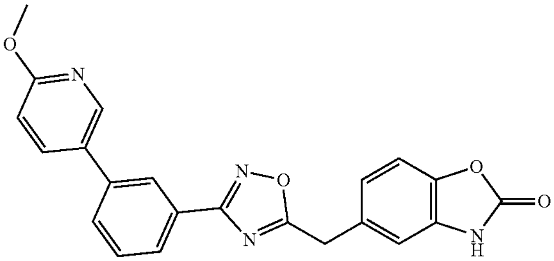 [SMILES: COc1ccc(-c2cccc(-c3noc(Cc4ccc5oc(=O)[nH]c5c4)n3)c2)cn1] | 401.12 | |
| B-9 | 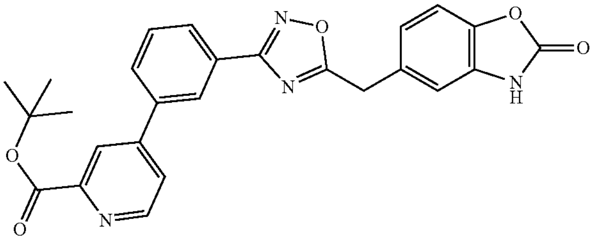 [SMILES: CC(C)(C)OC(=O)c1cc(-c2cccc(-c3noc(Cc4ccc5oc(=O)[nH]c5c4)n3)c2)ccn1] | 469.19 | $^1$H NMR (400 MHz, $CDCl_3$) δ 8.90-8.78 (m, 1H), 8.39-8.32 (m, 1H), 8.19-8.12 (m, 1H), 7.86-7.61 (m, 2H), 7.58-7.41 (m, 1H), 7.22-7.11 (m, 1H), 4.33 (s, 1H), 3.66 (s, 1H), 1.68-1.64 (m, 7H), 1.28-1.23 (m, 6H) |
| B-10 | 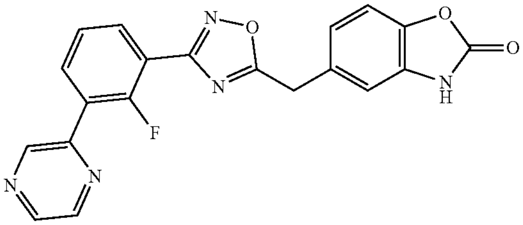 [SMILES: O=c1[nH]c2cc(Cc3nc(-c4cccc(-c5cnccn5)c4F)no3)ccc2o1] | 390.12 | |
| B-11 | 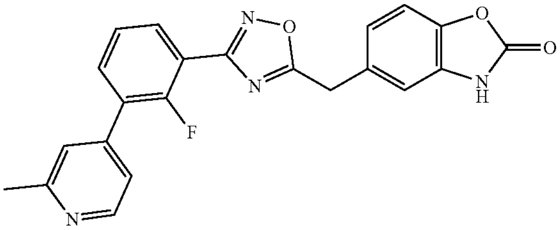 [SMILES: Cc1cc(-c2cccc(-c3noc(Cc4ccc5oc(=O)[nH]c5c4)n3)c2F)ccn1] | 403.71 | |
| B-12 | 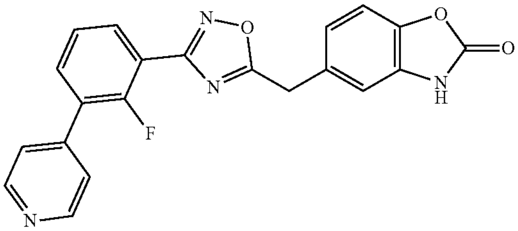 [SMILES: O=c1[nH]c2cc(Cc3nc(-c4cccc(-c5ccncc5)c4F)no3)ccc2o1] | 389.56 | |
| B-13 | 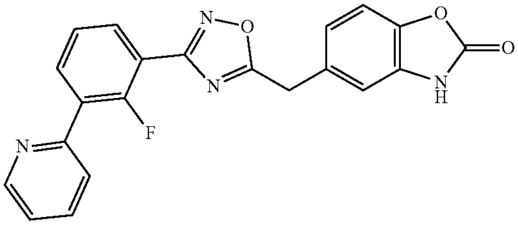 [SMILES: O=c1[nH]c2cc(Cc3nc(-c4cccc(-c5ccccn5)c4F)no3)ccc2o1] | 389.15 | |

Intermediate C-1: 3-(2-Oxo-5-((3-(3-(pyridazin-4-yl)phenyl)-1,2,4-oxadiazol-5-yl)methyl)benzo[d]oxazol-3(2H)-yl)piperidine-2,6-dione

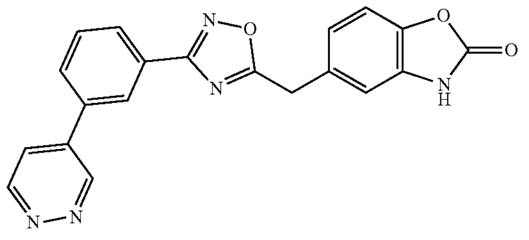 [SMILES: O=c1[nH]c2cc(Cc3nc(-c4cccc(-c5ccnnc5)c4)no3)ccc2o1]

5-((3-(3-(4,4,5,5-Tetramethyl-1,3,2-dioxaborolan-2-yl)phenyl)-1,2,4-oxadiazol-5-yl)methyl)benzo[d]oxazol-2(3H)-one (2)

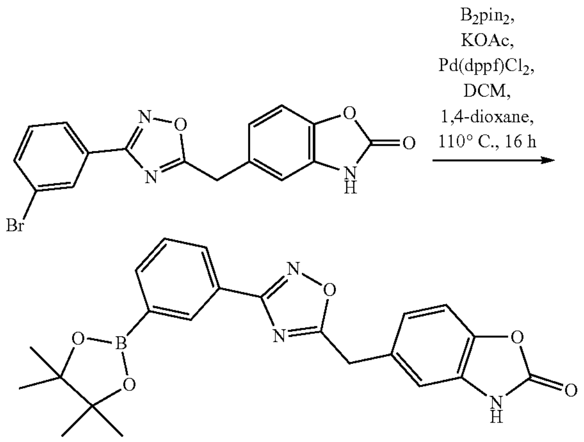

To a stirred solution of 5-((3-(3-bromo-2-fluorophenyl)-1,2,4-oxadiazol-5-yl)methyl)benzo[d]oxazol-2(3H)-one (1.5 g, 4.03 mmol) in a mixture of 1,4 dioxane (50 mL) at room temperature, were added bis(pinacolato)diboron (3.07 g, 12 mmol) and potassium acetate (1.19 g, 12.1 mmol). The resulting reaction mixture was purged with argon gas for 15 min. To this mixture, $Pd(dppf)Cl_2$ DCM (0.33 g, 0.403 mmol) was added and the reaction mixture was again purged with argon gas for another 3 min and stirred at 110° C. for 16 h. After completion of the reaction, the reaction mixture was quenched with ice-cold water (50 mL) and extracted with ethyl acetate (3×70 mL). The combined organic layers were washed with brine solution (30 mL), dried over anhydrous sodium sulphate, filtered and the filtrate was concentrated under reduced pressure to afford crude compound. The crude compound was purified by (230-400 silica gel) column chromatography and eluted by using 60-70% ethyl acetate in petroleum ether to afford 5-((3-(3-(4,4,5,5-tetramethyl-1,3,2-dioxaborolan-2-yl)phenyl)-1,2,4-oxadiazol-5-yl)methyl)benzo[d]oxazol-2(3H)-one (2) (1.2 g, 71%) as an off white solid. MS (ESI) m/z 420.58 $[M+H]^+$.

5-((3-(3-(Pyridazin-4-yl)phenyl)-1,2,4-oxadiazol-5-yl)methyl)benzo[d]oxazol-2(3H)-one (4)

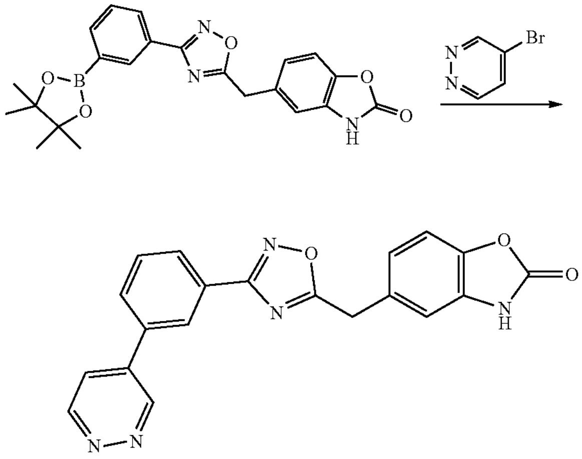

To a stirred solution of 5-((3-(3-(4,4,5,5-tetramethyl-1,3,2-dioxaborolan-2-yl)phenyl)-1,2,4-oxadiazol-5-yl)methyl)benzo[d]oxazol-2(3H)-one (0.3 g, 0.72 mmol) in a mixture of 1,4-dioxane (3 mL) and water (0.6 mL) at room temperature, 4-bromopyridazine (0.228 g, 1.43 mmol) and potassium carbonate (0.247 g, 1.79 mmol) were added and the resulting reaction mixture was purged with argon gas for 15 min. To this mixture, Amphos Pd G3 (0.051 g, 0.072 mmol) was added and the reaction mixture was again purged with argon gas for another 3 min and stirred at 80° C. for 3 h. After completion of the reaction, the reaction mixture was quenched with ice-cold water (20 mL) and extracted with ethyl acetate (2×30 mL). The combined organic layers were combined and washed with brine solution (20 mL), dried over anhydrous sodium sulphate, filtered and the filtrate was concentrated under reduced pressure to afford crude compound. The crude compound was purified over silica gel column chromatography and eluted by using 40-50% ethyl acetate in petroleum ether to afford 5-((3-(3-(pyridazin-4-yl)phenyl)-1,2,4-oxadiazol-5-yl)methyl)benzo[d]oxazol-2(3H)-one (0.15 g, 56%) as yellow solid. MS (ESI) m/z 290.10 $[M+H]^+$ Intermediate D: 2-(3-(2,6-dioxopiperidin-3-yl)-2-oxo-2,3-dihydrobenzo[d]oxazol-5-yl)acetic acid

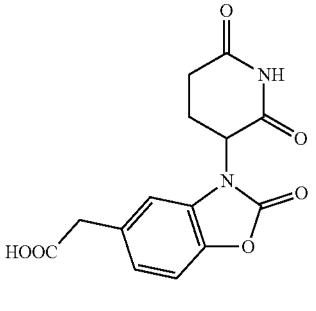 [SMILES: O=C(O)Cc1ccc2oc(=O)n(C3CCC(=O)NC3=O)c2c1]

Step 1. 3-(5-bromo-2-oxobenzo[d]oxazol-3(2H)-yl) piperidine-2,6-dione

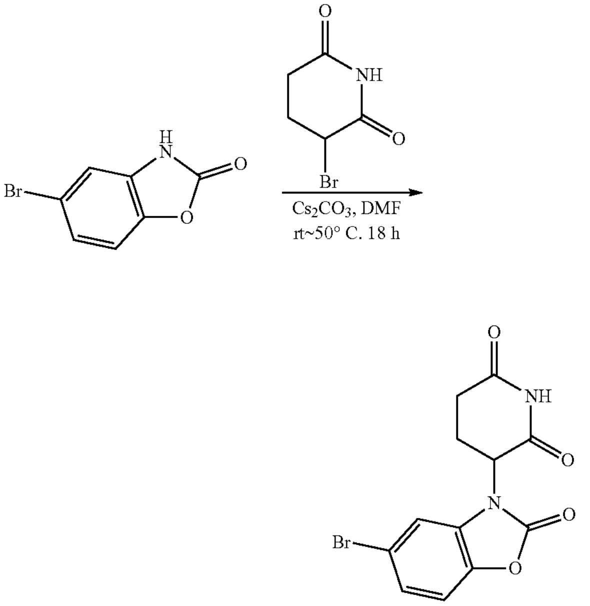 [SMILES: O=c1[nH]c2cc(Br)ccc2o1 ; O=C1CCC(Br)C(=O)N1 ; O=C1CCC(n2c(=O)oc3ccc(Br)cc32)C(=O)N1]

To a solution of 5-bromobenzo[d]oxazol-2(3H)-one (1 g, 4.67 mmol) in DMF (10 mL) was added $Cs_2CO_3$ (3.04 g, 9.35 mmol). The mixture was stirred at room temperature for 30 min and then 3-bromopiperidine-2,6-dione (1.79 g, 9.35 mmol) was added. The reaction was stirred at room temperature for 30 mins, then raised to 50° C. and stirred for 16 hrs. The resulting mixture was cooled to room temperature and poured into water (100 mL). The precipitate was filtered and collected to give 3-(5-bromo-2-oxobenzo[d]oxazol-3(2H)-yl)piperidine-2,6-dione (700 mg, 2.15 mmol, 46.1%). LCMS (m/z): [M]+ calcd: 323.97, found: 325.2. $^1H$ NMR (400 MHz, DMSO) δ 11.21 (s, 1H), 7.63 (s, 1H), 7.36 (q, J=8.5 Hz, 2H), 5.38 (dd, J=12.8, 5.2 Hz, 1H), 2.90-2.81 (m, 1H), 2.75-2.62 (m, 2H), 2.22-2.08 (m, 1H).

Step 2. (E)-3-(5-(2-ethoxyvinyl)-2-oxobenzo[d]oxazol-3(2H)-yl)piperidine-2,6-dione

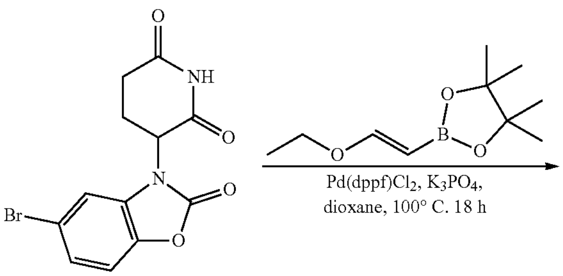

-continued

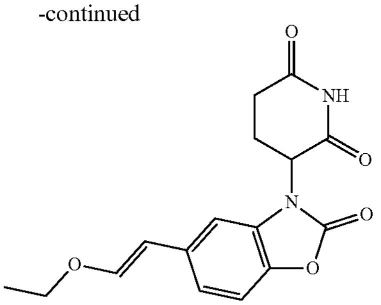

To a solution of 3-(5-bromo-2-oxobenzo[d]oxazol-3(2H)-yl)piperidine-2,6-dione (300 mg, 0.92 mmol) in dioxane (10 mL) and $H_2O$ (2 mL) were added (E)-2-(2-ethoxyvinyl)-4,4,5,5-tetramethyl-1,3,2-dioxaborolane (183 mg, 0.92 mmol), $K_3PO_4$ (392 mg, 1.85 mmol) and $Pd(dppf)Cl_2$ (67.5 mg, 0.09 mmol). The mixture was heated to 100° C. and stirred for 16 hrs under $N_2$. The mixture was concentrated in vacuo and purified by column chromatography (petroleum ether:ethyl acetate=50~60%) to get (E)-3-(5-(2-ethoxyvinyl)-2-oxobenzo[d]oxazol-3(2H)-yl)piperidine-2,6-dione (150 mg, 0.47 mmol, 51.4%). LCMS (m/z): $[M]^+$ calcd: 316.11, found: 317.3. $^1H$ NMR (400 MHz, DMSO) δ 11.20 (s, 1H), 7.30-7.16 (m, 3H), 7.03 (dd, J=8.4, 1.5 Hz, 1H), 5.85 (d, J=13.0 Hz, 1H), 5.34 (dd, J=12.9, 5.3 Hz, 1H), 3.96-3.83 (m, 2H), 2.96-2.84 (m, 1H), 2.80-2.63 (m, 2H), 2.23-2.10 (m, 1H), 1.26 (t, J=7.0 Hz, 3H).

Step 3. 2-(3-(2,6-dioxopiperidin-3-yl)-2-oxo-2,3-dihydrobenzo[d]oxazol-5-yl)acetaldehyde

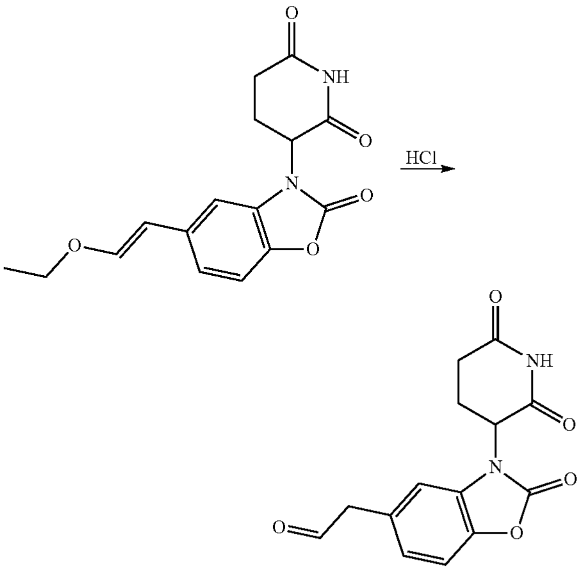

To a solution of (E)-3-(5-(2-ethoxyvinyl)-2-oxobenzo[d]oxazol-3(2H)-yl)piperidine-2,6-dione (100 mg, 0.32 mmol) in acetonitrile (2 mL) was added hydrogen chloride (0.63 mL, 0.63 mmol). The mixture was heated to 60° C. and stirred for 1 hr. The mixture was concentrated in vacuo to get a crude product of 2-(3-(2,6-dioxopiperidin-3-yl)-2-oxo-2,3-dihydrobenzo[d]oxazol-5-yl)acetaldehyde (90 mg, 0.31 mmol, 98.7%). The product was used in the next step without further purification. LCMS (m/z): $[M]^+$ calcd: 288.07, found: 289.3.

Step 4. 2-(3-(2,6-dioxopiperidin-3-yl)-2-oxo-2,3-dihydrobenzo[d]oxazol-5-yl)acetic acid

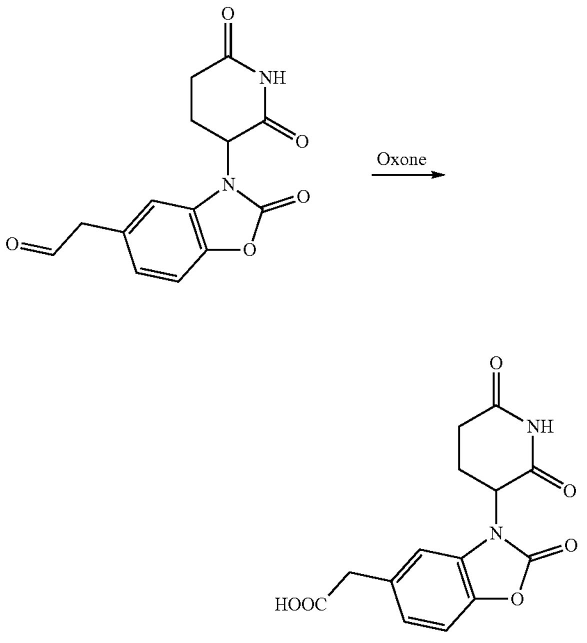

To a solution of 2-(3-(2,6-dioxopiperidin-3-yl)-2-oxo-2,3-dihydrobenzo[d]oxazol-5-yl)acetaldehyde (90 mg, 0.31 mmol) in DMF (2 mL) was added oxone (216 mg, 0.62 mmol). The mixture was stirred at room temperature for 16 hrs. The mixture was concentrated in vacuo and purified by column chromatography (DCM:MeOH=5% to 10%) to get 2-(3-(2,6-dioxopiperidin-3-yl)-2-oxo-2,3-dihydrobenzo[d]oxazol-5-yl)acetic acid (50 mg, 0.16 mmol, 52.6%). LCMS (m/z): [M]+ calcd: 304.07, found: 305.3. $^1$H NMR (400 MHz, DMSO) δ 11.20 (s, 1H), 7.32 (d, J=8.2 Hz, 1H), 7.21 (s, 1H), 7.05 (dd, J=8.2, 1.5 Hz, 1H), 5.37 (dd, J=12.9, 5.2 Hz, 1H), 2.93-2.83 (m, 1H), 2.74-2.62 (m, 2H), 2.15 (dd, J=10.3, 5.3 Hz, 1H).

Intermediate E-1: Step 4. 5-((5-phenyl-1,2,4-oxadiazol-3-yl)methyl)benzo[d]oxazol-2(3H)-one

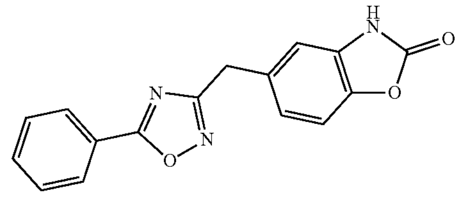 [SMILES: O=c1[nH]c2cc(Cc3noc(-c4ccccc4)n3)ccc2o1]

Step 1: 2-(3-amino-4-hydroxyphenyl)acetonitrile

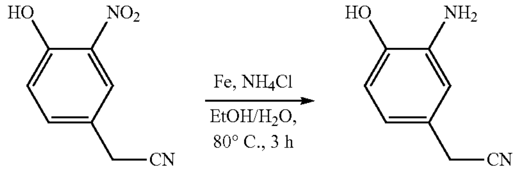 [SMILES: N#CCc1ccc(O)c([N+](=O)[O-])c1 ; N#CCc1ccc(O)c(N)c1]

To a mixture of 2-(4-hydroxy-3-nitrophenyl)acetonitrile (500 mg, 2.81 mmol) in EtOH/$H_2O$ (20 mL) were added Fe (784 mg, 14 mmol) and $NH_4Cl$ (2250 mg, 42.1 mmol). The mixture was stirred at 80° C. under $N_2$ for 2 h. The mixture was concentrated in vacuo. The residue was purified by FCC (silica gel, 5~20% EA in PE) to give 2-(3-amino-4-hydroxyphenyl)acetonitrile (328 mg, 2.21 mmol, 79%) as a brown solid. LCMS (m/z): $[M]^+$ calcd: 148.06, found: 149.2. $^1$H NMR (400 MHz, DMSO-$d_6$) δ 9.06 (s, 1H), 6.60 (d, J=7.9 Hz, 1H), 6.54 (d, J=2.2 Hz, 1H), 6.32 (dd, J=7.9, 2.2 Hz, 1H), 4.65 (s, 2H), 3.74 (s, 2H).

Step 2: 2-(2-oxo-2,3-dihydrobenzo[d]oxazol-5-yl)acetonitrile

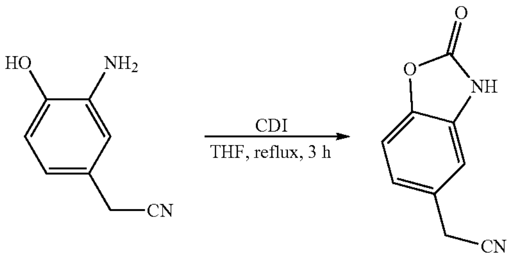 [SMILES: N#CCc1ccc(O)c(N)c1 ; "CDI" ; N#CCc1ccc2oc(=O)[nH]c2c1]

To the mixture of 2-(3-amino-4-hydroxyphenyl)acetonitrile (270 mg, 1.82 mmol) in THF (5 mL) was added CDI (443 mg, 2.73 mmol). The mixture was stirred at 70° C. under $N_2$ for 2 h. The mixture was concentrated in vacuo. The residue was purified by FCC (silica gel, 0~20% EA in PE) to give 2-(2-oxo-2,3-dihydrobenzo[d]oxazol-5-yl)acetonitrile (300 mg, 1.72 mmol, 95%) as a white solid. LCMS (m/z): [M]+ calcd: 174.04, found: 175.2. $^1$H NMR (400 MHz, DMSO-$d_6$) δ 11.71 (s, 1H), 7.29 (d, J=8.1 Hz, 1H), 7.08 (s, 1H), 7.06 (dd, J=8.1, 1.8 Hz, 1H), 4.04 (s, 2H).

Step 3. N-hydroxy-2-(2-oxo-2,3-dihydrobenzo[d]oxazol-5-yl)acetimidamide

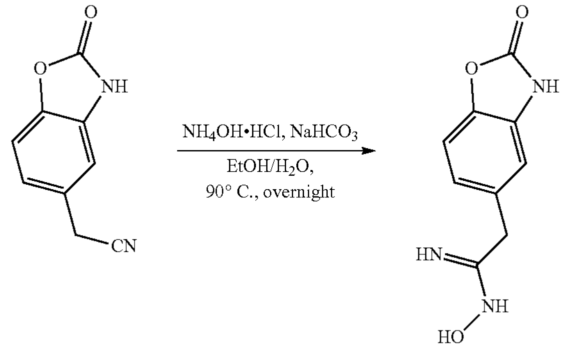 [SMILES: N#CCc1ccc2oc(=O)[nH]c2c1 ; N=C(Cc1ccc2oc(=O)[nH]c2c1)NO]

To a mixture of 2-(2-oxo-2,3-dihydrobenzo[d]oxazol-5-yl)acetonitrile (203 mg, 1.17 mmol) in $EtOH/H_2O$ (1.75 mL) were added $NH_2OH{\cdot}HCl$ (77 mg, 2.33 mmol) and $NaHCO_3$ (196 mg, 2.33 mmol). The mixture was stirred at 90° C. under $N_2$ for 2 h. The mixture was poured into water and extracted with EA. The organic phase was dried with $Na_2SO_4$, filtered and concentrated in vacuo to give N-hydroxy-2-(2-oxo-2,3-dihydrobenzo[d]oxazol-5-yl)acetimidamide (175 mg, 0.84 mmol, 72%) as a white solid. LCMS (m/z): $[M]^+$ calcd: 207.06, found: 208.2. $^1$H NMR (400 MHz, DMSO-$d_6$) δ 11.56 (s, 1H), 8.88 (s, 1H), 7.17 (d, J=8.2 Hz, 1H), 7.00 (d, J=1.6 Hz, 1H), 6.97 (dd, J=8.2, 1.7 Hz, 1H), 5.39 (s, 2H), 3.33 (s, 2H).

Step 4. 5-((5-phenyl-1,2,4-oxadiazol-3-yl)methyl)benzo[d]oxazol-2(3H)-one

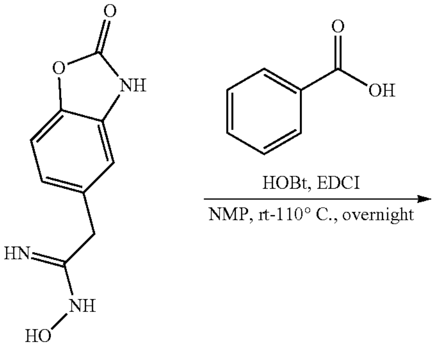

-continued

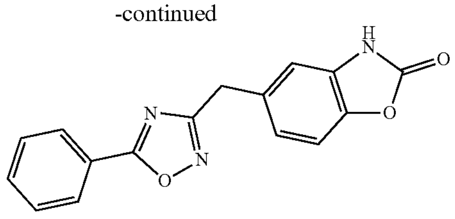

To a mixture of 5-[2-azanylidene-2-(hydroxyamino)ethyl]-2,3-dihydrobenzo[2,1-d][1,3]oxazol-2-one (127 mg, 0.61 mmol) and benzoic acid (90 mg, 0.74 mmol) in NMP (2 mL) were added EDCI (176 mg, 0.92 mmol) and HOBt (99 mg, 0.74 mmol). The mixture was stirred at rt under $N_2$ for 1 h and heated at 110° C. overnight. The mixture was quenched with water (10 mL), and extracted with EA (20 mL*3). The organic phase was washed with brine (20 mL*3), dried over $Na_2SO_4$, filtered, and concentrated in vacuo. The residue was purified by FCC (silica gel, 0~50% EA in PE) to give 5-((5-phenyl-1,2,4-oxadiazol-3-yl)methyl)benzo[d]oxazol-2(3H)-one (113 mg, 0.39 mmol, 62.86%) as a white solid. LCMS (m/z): $[M]^+$ calcd: 293.08, found: 294.2. $^1$H NMR (400 MHz, DMSO-$d_6$) δ 11.60 (s, 1H), 8.08 (d, J=7.2 Hz, 2H), 7.74-7.67 (m, 1H), 7.63 (d, J=7.8 Hz, 2H), 7.24 (d, J=8.1 Hz, 1H), 7.08 (d, J=12.4 Hz, 2H), 4.20 (s, 2H).

Intermediates below may be synthesized similarly to Intermediate E-1:

| Int. | Structure | $[M + H]^+$ | $^1$H NMR |
|---|---|---|---|
| E-2 | 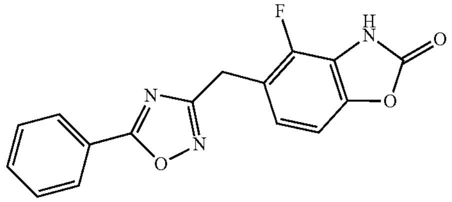 [SMILES: O=c1[nH]c2c(F)c(Cc3noc(-c4ccccc4)n3)ccc2o1] | 312.1 | |

Intermediate F: 8-methoxynaphthalen-1-amine

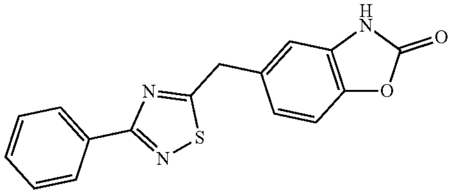 [SMILES: O=c1[nH]c2cc(Cc3nc(-c4ccccc4)ns3)ccc2o1]

Step 1: Preparation of 2-(4-hydroxy-3-nitrophenyl)acetonitrile

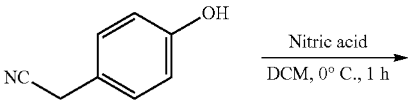

-continued

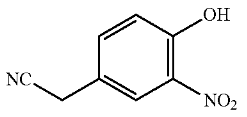

To a mixture of 2-(4-hydroxyphenyl)acetonitrile (10 g, 75.10 mmol) in DCM (200 mL) was added nitric acid (4.73 g, 73.60 mmol). The mixture was stirred at 0° C. under $N_2$ for 1 h. The reaction was quenched with water (20 mL) and extracted with DCM (200 mL*3). The organic layer was washed with aq. $NaHCO_3$. The organic phase was dried over $Na_2SO_4$, filtered, and concentrated in vacuo to give 2-(4-hydroxy-3-nitrophenyl)acetonitrile (11 g, 61.75 mmol, 82%) as a yellow solid. LCMS (m/z): $[M]^-$ calcd: 178.04, found: 177.2.

Step 2: Preparation of 2-nitro-4-((3-phenyl-1,2,4-thiadiazol-5-yl)methyl)phenol

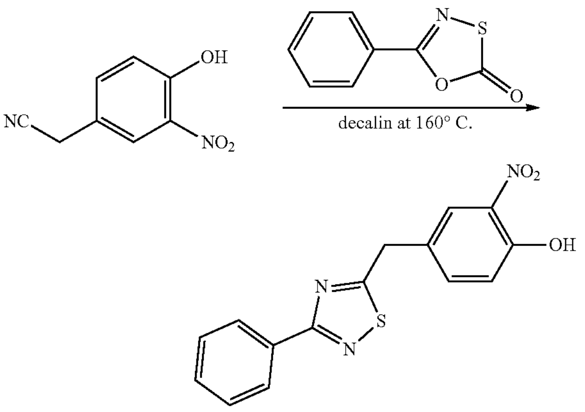

To a mixture of 2-(4-hydroxy-3-nitrophenyl)acetonitrile (11 g, 61.75 mmol) in decalin (60 mL) was added 5-phenyl-1,3,4-oxathiazol-2-one (11.06 g, 61.75 mmol). The mixture was stirred at 160° C. under $N_2$ for 18 h. The mixture was purified by FCC (silica gel, 10% EA in PE) to give 2-nitro-4-((3-phenyl-1,2,4-thiadiazol-5-yl)methyl)phenol (500 mg, 1.60 mmol, 3%) as a brown oil. LCMS (m/z): $[M]^+$ calcd: 313.15, found: 314.2.

Step 3: Preparation of 2-amino-4-((3-phenyl-1,2,4-thiadiazol-5-yl)methyl)phenol

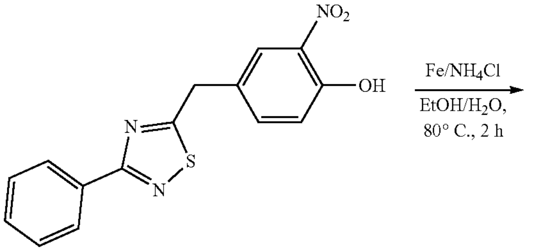

-continued

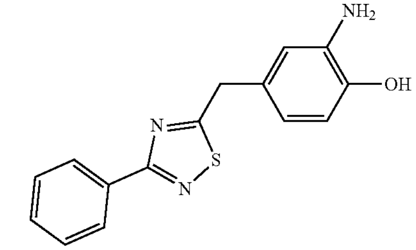

To a mixture of 2-nitro-4-((3-phenyl-1,2,4-thiadiazol-5-yl)methyl)phenol (400 mg, 1.28 mmol) and ammonium chloride (1024 mg, 19.15 mmol) in EtOH/$H_2O$ (8 mL) was added iron powder (356 mg, 6.38 mmol). The mixture was stirred at 80° C. under $N_2$ for 2 h. The mixture was filtered and the filtrate was concentrated under vacuum to give 2-amino-4-((3-phenyl-1,2,4-thiadiazol-5-yl)methyl)phenol (300 mg, 1.06 mmol, 83%) as a brown solid, which was used in the next step without further purification. LCMS (m/z): $[M]^+$ calcd: 283.08, found: 284.2.

Step 4: Preparation of 8-methoxynaphthalen-1-amine

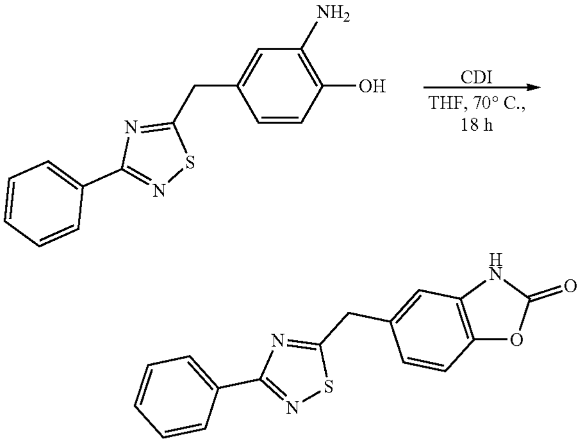

To a mixture of 2-amino-4-((3-phenyl-1,2,4-thiadiazol-5-yl)methyl)phenol (300 mg, 1.06 mmol) in THF (1 mL) was added 1,1'-carbonyldiimidazole (206 mg, 1.27 mmol). The mixture was stirred at 70° C. under $N_2$ for 1 h. The resulting mixture was purified by FCC (silica gel, 0~33% EA in PE) to give 5-((3-phenyl-1,2,4-thiadiazol-5-yl)methyl)benzo[d]oxazol-2(3H)-one (270 mg, 0.87 mmol, 82%) as a brown solid. LCMS (m/z): $[M]^+$ calcd: 309.06, found: 310.0.

Intermediate G: 5-((5-phenyl-1,3,4-thiadiazol-2-yl)methyl) benzo[d]oxazol-2(3H)-one

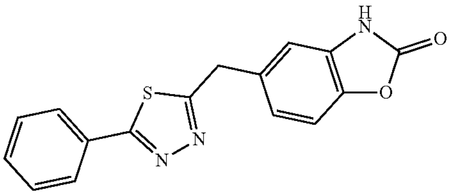 [SMILES: O=c1[nH]c2cc(Cc3nnc(-c4ccccc4)s3)ccc2o1]

Step 1: N'-(2-(2-oxo-2,3-dihydrobenzo[d]oxazol-5-yl) acetyl) benzo hydrazide

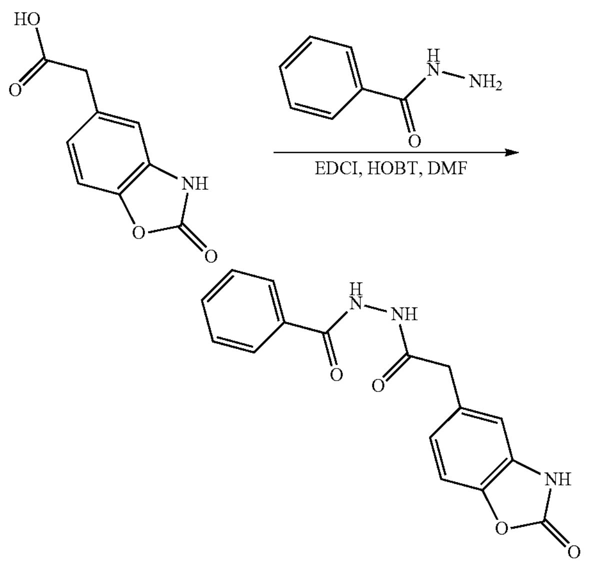

To the mixture of 2-(2-oxo-2,3-dihydrobenzo[d]oxazol-5-yl) acetic acid (1 g, 5.18 mmol), EDCI (1.19 g, 6.21 mmol), HOBt (0.84 g, 6.21 mmol) in DMF (25 mL) was added benzo hydrazide (0.78 g, 5.69 mmol). The mixture was stirred at 25° C. under $N_2$ for 2 h. The mixture was quenched with ice and $H_2O$ (100 mL), filtered and dried to give N'-(2-(2-oxo-2,3-dihydrobenzo[d]oxazol-5-yl) acetyl) benzo hydrazide (1.5 g, 4.82 mmol, yield: 93.07%) as a white solid. LCMS (m/z): $[M]^+$ calcd, 311.09; found, 312.3.

Step 2: 5-((5-phenyl-1,3,4-thiadiazol-2-yl) methyl) benzo[d]oxazol-2(3H)-one

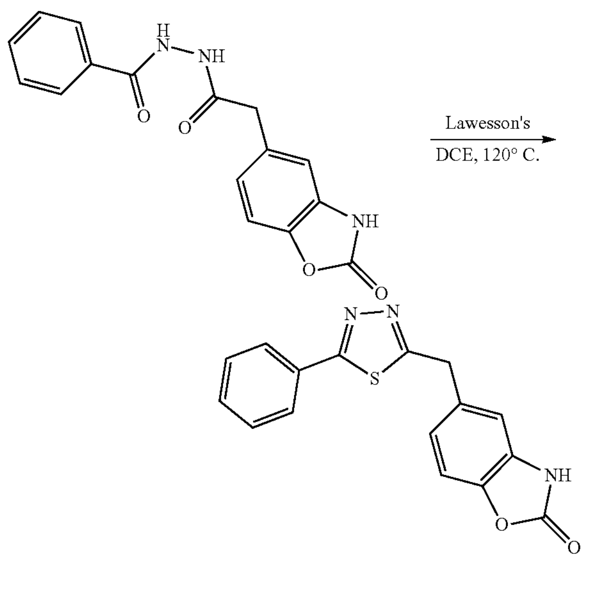

To the mixture of N'-(2-(2-oxo-2,3-dihydrobenzo[d]oxazol-5-yl) acetyl) benzo hydrazide (400 mg, 1.28 mmol) in DCE (10 mL) was added 2,4-bis(4-methoxyphenyl)-2,4-dithioxo-2λ5,4λ5-1,3,2,4-dithiadiphosphetane (1040 mg, 2.57 mmol). The mixture was stirred at 120° C. under $N_2$ for 8 h. The mixture was quenched with $H_2O$ (50 mL), extracted with EA (20 mL*3). The organic phase was dried over $Na_2SO_4$, filtered and concentrated in vacuo. The residue was purified by column chromatography ($SiO_2$, DCM/MeOH=20:1) to give 5-((5-phenyl-1,3,4-thiadiazol-2-yl) methyl) benzo[d]oxazol-2(3H)-one (220 mg, 0.71 mmol, yield: 55.35%) as a yellow solid. LCMS (m/z): $[M]^+$ calcd, 309.06; found, 310.3.

Intermediate H: 4-fluoro-5-((4-phenyl-1H-1,2,3-triazol-1-yl)methyl)benzo[d]oxazol-2(3H)-one

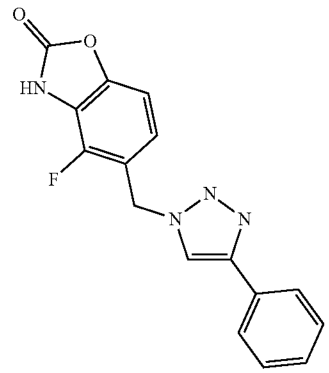 [SMILES: O=c1[nH]c2c(F)c(CN3C=C(c4ccccc4)NN3)ccc2o1]

Step 1: Preparation of 4-fluoro-5-(hydroxymethyl) benzo[d]oxazol-2(3H)-one

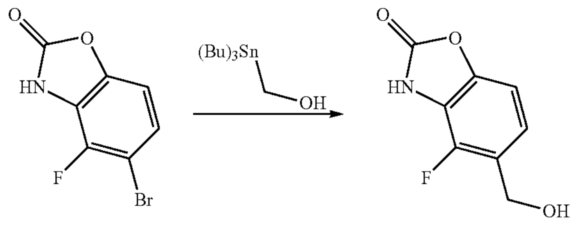

To the mixture of 5-bromo-4-fluoro-2,3-dihydrobenzo[d][1,3]oxazol-2-one (5 g, 21.55 mmol), (tributylstannyl) methanol (6.92 g, 21.55 mmol) in dioxane (5 mL) was added XPhos Pd G2 (169.35 mg, 0.22 mmol). The mixture was stirred at 80° C. under $N_2$ for 18 h. LCMS: SM consumed, DP found. The mixture was quenched with KF and filtered, extracted with EA (20 mL*3). The organic phase was dried over $Na_2SO_4$, filtered and concentrated in vacuo. The residue was purified by beating (5% DCM in PE) to give 4-fluoro-5-(hydroxymethyl)benzo[d]oxazol-2(3H)-one (2.9 g, 15.84 mmol, 73.48%) as white solid. LCMS (m/z): [M]+ calcd: 183.14, found: 184.1.

Step 2: Preparation of 5-(azidomethyl)-4-fluorobenzo[d]oxazol-2(3H)-one

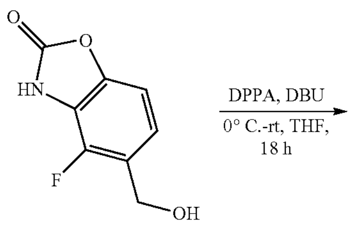

To the mixture of 4-fluoro-5-(hydroxymethyl)benzo[d]oxazol-2(3H)-one (500 mg, 2.73 mmol), diphenylphosphoryl azide (1127.03 mg, 4.10 mmol) in toluene (10 mL) was added 3,4,5,7,8,9,10,10a-octahydropyrido[1,2-a][1,4]diazepine (623.47 mg, 4.10 mmol) at 0° C. The mixture was stirred at 25° C. under $N_2$ for 18 h. LCMS: SM consumed, DP found. The mixture was quenched with water (10 mL), extracted with EA (10 mL*3). The organic phase was dried over $Na_2SO_4$, filtered and concentrated in vacuo. The residue was purified by FCC (silica gel, 0~33% EA in PE) to give 5-(azidomethyl)-4-fluorobenzo[d]oxazol-2(3H)-one as white solid. LCMS (m/z): [M+ calcd: 208.15, found: 209.3.

Step 3: Preparation of 4-fluoro-5-((4-phenyl-1H-1,2,3-triazol-1-yl)methyl)benzo[d]oxazol-2(3H)-one

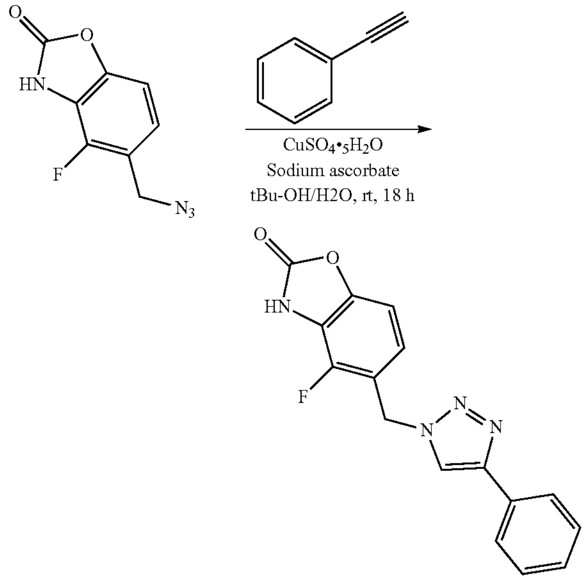

To the mixture of 5-(azidomethyl)-4-fluorobenzo[d]oxazol-2(3H)-one (100 mg, 0.48 mmol), sodium (2R)-2-[(1S)-1,2-dihydroxyethyl]-4-hydroxy-5-oxo-2,5-dihydrofuran-3-olate (76.14 mg, 0.38 mmol), ethynylbenzene (49.07 mg, 0.48 mmol) in t-BuOH/$H_2O$ (2.5 mL) was added. Copper(II) sulfate pentahydrate (30.67 mg, 0.19 mmol). The mixture was stirred at 25° C. under $N_2$ for 18 h. LCMS: SM consumed, DP found. The mixture was quenched with water (10 mL), extracted with EA (10 mL*3). The organic phase was dried over $Na_2SO_4$, filtered and concentrated in vacuo. The residue was purified by FCC (silica gel, 0~33% EA in PE) to give 4-fluoro-5-((4-phenyl-1H-1,2,3-triazol-1-yl)methyl)benzo[d]oxazol-2(3H)-one (0.39 mmol, 80.50%) as white solid. LCMS (m/z): [M]+ calcd: 310.29, found: 311.1.

Intermediate I: 5-((4-phenyloxazol-2-yl)methyl)benzo[d]oxazol-2(3H)-one

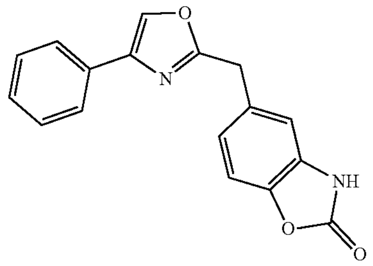 [SMILES: O=c1[nH]c2cc(Cc3nc(-c4ccccc4)co3)ccc2o1]

Step 1: Methyl 2-(2-oxo-2,3-dihydrobenzo[d]oxazol-5-yl)acetate

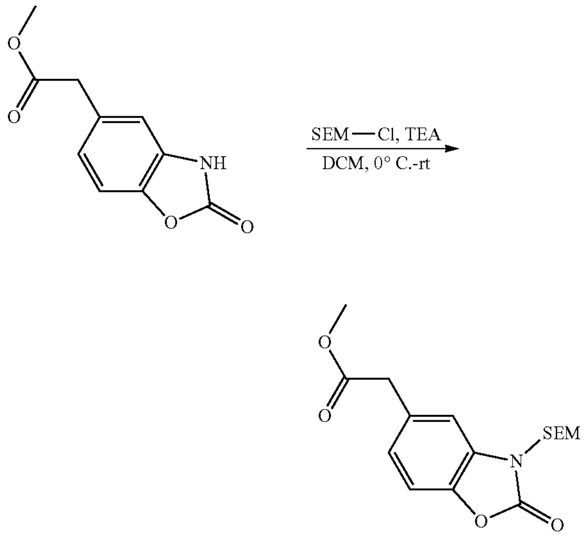

To the mixture of methyl 2-(2-oxo-2,3-dihydrobenzo[d]oxazol-5-yl)acetate (2.00 g, 9.65 mmol) in DCM (20 mL) was added SEM-Cl (3.42 mL, 19.31 mmol) and TEA (4.01 mL, 28.96 mmol) at 0° C. under $N_2$. The mixture was stirred at rt under $N_2$ over the weekend. The mixture was quenched with $H_2O$ (20 mL), extracted with EA (40 mL*3). The organic phase was dried over $Na_2SO_4$, filtered and concentrated in vacuo. The residue was purified by column chromatography ($SiO_2$, PE:EA=10:1-5:1-2:1) to give methyl 2-(2-oxo-3-((2-(trimethylsilyl)ethoxy)methyl)-2,3-dihydrobenzo[d]oxazol-5-yl)acetate (2.80 g, 8.30 mmol, 85.96%) as white oil. LCMS (m/z): [M]+ calcd: 337.45, found: 338.0. $^1$H NMR (400 MHz, $CDCl_3$) δ 7.16 (d, J=8.2 Hz, 1H), 7.10 (s, 1H), 7.05 (dd, J=8.2, 1.5 Hz, 1H), 5.26 (s, 2H), 3.70 (s, 3H), 3.67-3.60 (m, 4H), 0.98-0.90 (m, 2H), −0.02 (s, 9H).

Step 2: 2-(2-oxo-3-((2-(trimethylsilyl)ethoxy)methyl)-2,3-dihydrobenzo[d]oxazol-5-yl)acetic acid

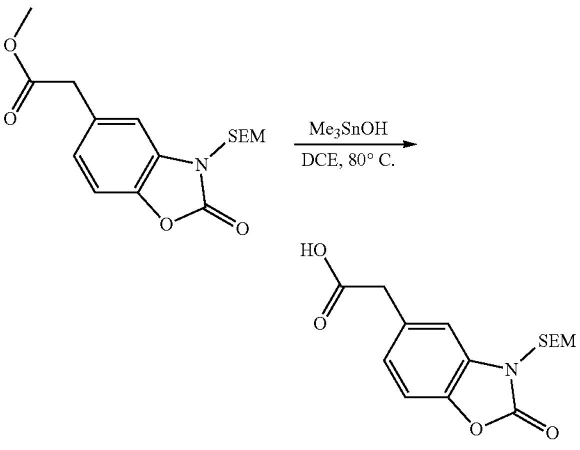

To the mixture of methyl 2-(2-oxo-3-((2-(trimethylsilyl)ethoxy)methyl)-2,3-dihydrobenzo[d]oxazol-5-yl)acetate (1.50 g, 4.45 mmol) in DCE (20 mL) was added $Me_3SnOH$ (1.61 g, 8.89 mmol) at 0° C. The mixture was stirred at 80° C. under $N_2$ for 4 h. The mixture was quenched with water (20 mL), extracted with EA (40 mL*3). The organic phase was dried over $Na_2SO_4$, filtered and concentrated on vacuo. The residue was purified by column chromatography ($SiO_2$, PE:EA=10:1-5:1-2:1) to give 2-(2-oxo-3-((2-(trimethylsilyl)ethoxy)methyl)-2,3-dihydrobenzo[d]oxazol-5-yl)acetic acid (1.30 g, 4.02 mmol, 90.43%) as white oil. LCMS (m/z): [M]+ calcd: 323.42, found: 324.30.

Step 3: 2-oxo-2-phenylethyl 2-(2-oxo-3-((2-(trimethylsilyl)ethoxy)methyl)-2,3-dihydrobenzo[d]oxazol-5-yl)acetate

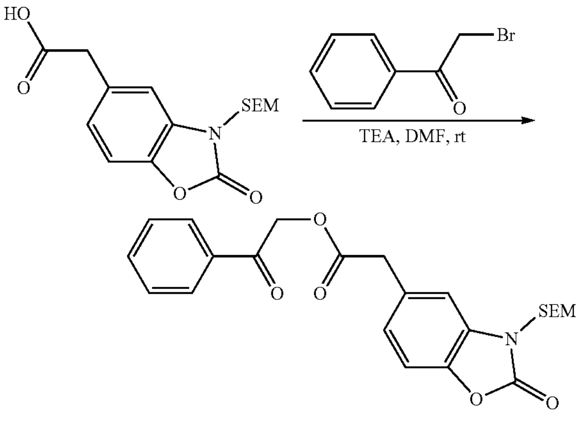

To the mixture of 2-bromo-1-phenylethan-1-one (800 mg, 4.02 mmol) and 2-(2-oxo-3-((2-(trimethylsilyl)ethoxy)methyl)-2,3-dihydrobenzo[d]oxazol-5-yl)acetic acid (1.30 g, 4.02 mmol) in DMF (10 mL) were added TEA (813.40 mg, 8.04 mmol). The mixture was stirred at rt under $N_2$ for 2 h. The mixture was quenched with water (20 mL), extracted with EA (40 mL*3). The organic phase was dried over $Na_2SO_4$, filtered and concentrated on vacuo. The residue was purified by column chromatography ($SiO_2$, PE:EA=10:1-8:1-5:1) to give 2-oxo-2-phenylethyl 2-(2-oxo-3-((2-(trimethylsilyl)ethoxy)methyl)-2,3-dihydrobenzo[d]oxazol-5-yl)acetate (1.50 g, 3.40 mmol, 84.52%) as white oil. LCMS (m/z): [M]+ calcd: 441.56, found: 442.30.

Step 4: 5-((4-phenyloxazol-2-yl)methyl)-3-((2-(trimethylsilyl)ethoxy)methyl)benzo[d]oxazol-2(3H)-one

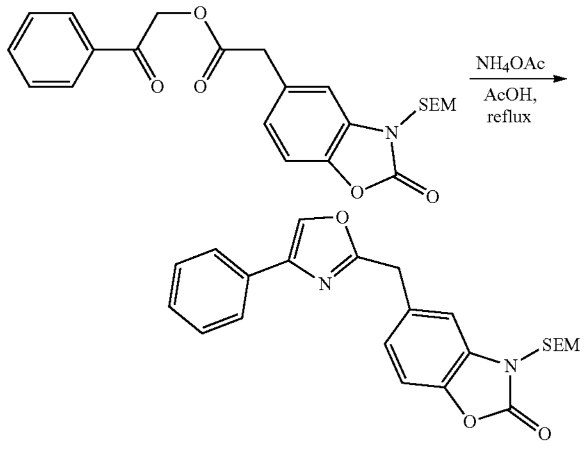

To the mixture of 2-oxo-2-phenylethyl 2-(2-oxo-3-((2-(trimethylsilyl)ethoxy)methyl)-2,3-dihydrobenzo[d]oxazol-5-yl)acetate (1.50 g, 3.40 mmol) in AcOH (10 mL) were added $NH_4OAc$ (523.69 mg, 6.79 mmol). The mixture was stirred at 120° C. under $N_2$ for 8 h. The mixture was concentrated on vacuo. The residue was quenched with water (20 mL), extracted with EA (40 mL*3). The organic phase was dried over $Na_2SO_4$, filtered and concentrated on vacuo. The residue was purified by column chromatography ($SiO_2$, PE:EA=10:1-7:1-4:1) to give 5-((4-phenyloxazol-2-yl)methyl)-3-((2-(trimethylsilyl)ethoxy)methyl)benzo[d]oxazol-2(3H)-one (800 mg, 1.89 mmol, 55.73%) as yellow oil. LCMS (m/z): [M]+ calcd: 422.56, found: 423.4.

Step 5: 5-((4-phenyloxazol-2-yl)methyl)benzo[d]oxazol-2(3H)-one

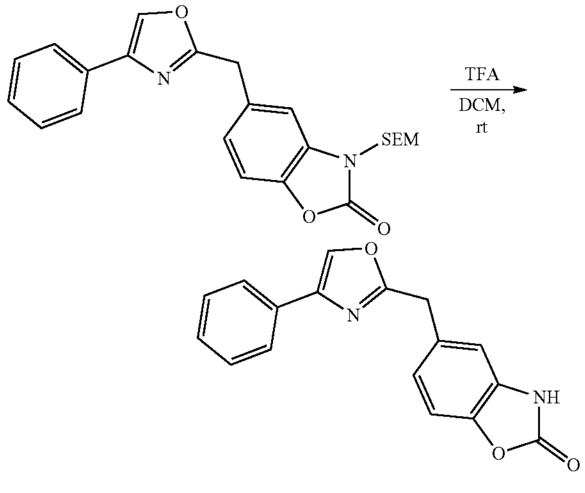

To the mixture of 5-((4-phenyloxazol-2-yl)methyl)-3-((2-(trimethylsilyl)ethoxy)methyl)benzo[d]oxazol-2(3H)-one (400 mg, 0.95 mmol) in DCM (4 mL) was added TFA (2 mL). The mixture was stirred at rt for 30 min. The mixture was concentrated on vacuo to give 5-((4-phenyloxazol-2-yl)methyl)benzo[d]oxazol-2(3H)-one (270 mg, 0.92 mmol, 97.58%) as yellow solid. LCMS (m/z): [M]+ calcd: 292.29, found: 293.20.

Intermediate J: 4-fluoro-5-((5-phenyl-2H-tetrazol-2-yl)methyl)benzo[d]oxazol-2(3H)-one

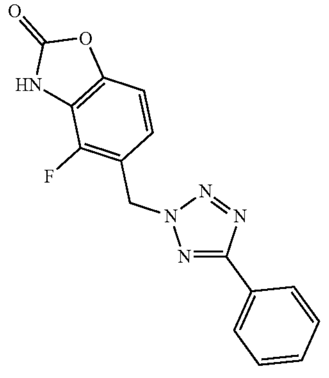 [SMILES: O=c1[nH]c2c(F)c(Cn3nnc(-c4ccccc4)n3)ccc2o1]

Step 1: 4-fluoro-5-((5-phenyl-2H-tetrazol-2-yl)methyl)benzo[d]oxazol-2(3H)-one

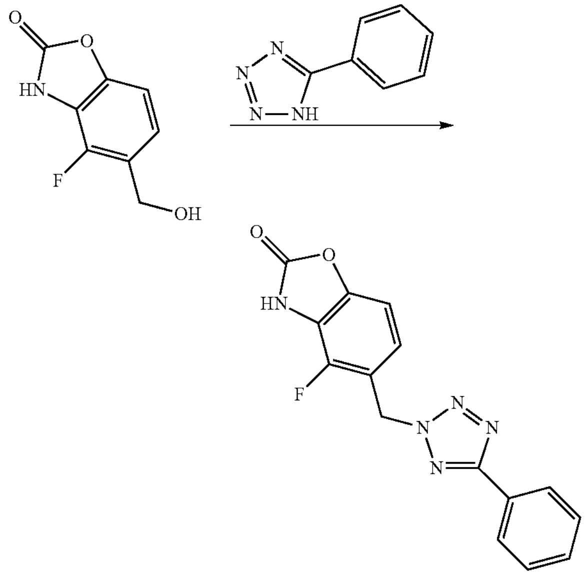

To the mixture of 4-fluoro-5-(hydroxymethyl)benzo[d]oxazol-2(3H)-one (500 mg, 2.73 mmol), triphenylphosphane (1432.21 mg, 5.46 mmol), 5-phenyl-3H-1,2,3,4-tetraazole (399.02 mg, 2.73 mmol) in THF (10 mL) was added diisopropyl azodicarboxylate (1104.14 mg, 5.46 mmol) at 0° C. The mixture was stirred at 25° C. under $N_2$ for uh. LCMS: SM consumed, DP found. The mixture was concentrated in vacuo. The residue was purified by FCC (silica gel, 0~5% EA in DCM) to give 4-fluoro-5-((5-phenyl-2H-tetrazol-2-yl)methyl)benzo[d]oxazol-2(3H)-one (1.93 mmol, 70.60%) as white solid. LCMS (m/z): [M]+ calcd: 311.28, found: 312.1.

Intermediate H: 5-((3-phenylisoxazol-5-yl)methyl)benzo[d]oxazol-2(3H)-one

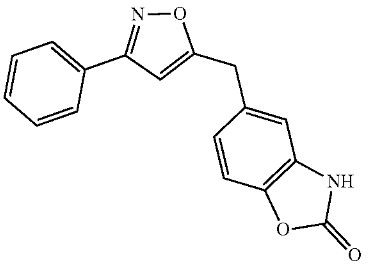 [SMILES: O=c1[nH]c2cc(Cc3cc(-c4ccccc4)no3)ccc2o1]

Step 1: (E)-5-(2-ethoxyvinyl)-3-(4-methoxybenzyl)benzo[d]oxazol-2(3H)-one

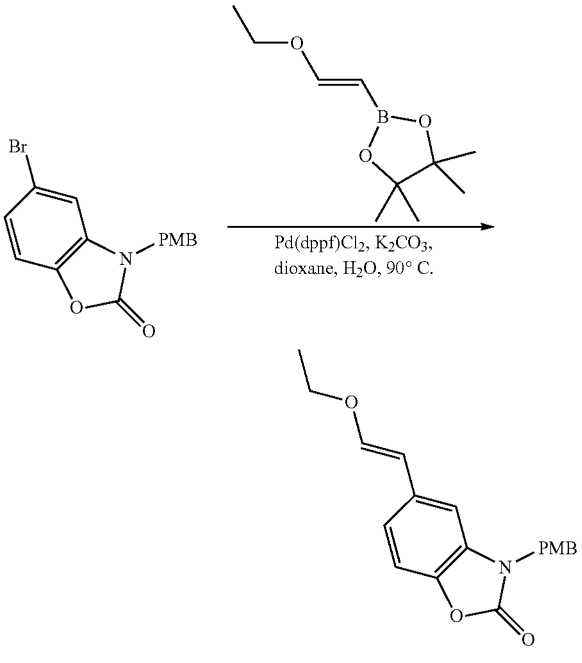

To a mixture of 5-bromo-3-(4-methoxybenzyl)benzo[d]oxazol-2(3H)-one (5.8 g, 17.42 mmol), (E)-2-(2-ethoxyvinyl)-4,4,5,5-tetramethyl-1,3,2-dioxaborolane (5.49 g, 27.87 mmol), $K_2CO_3$ (7.2 g, 52.26 mmol) in dioxane/$H_2O$ (100 mL, 8:1) were added Pd(dppf)$Cl_2$ (1.27 g, 1.74 mmol). The reaction was stirred at 90° C. for 16 h. Removal of solvent, the residue was purified by flash column chromatography (silica gel, 0~2% EA in DCM) and triturated with 80 mL (PE:DCM=3:1) to afford (E)-5-(2-ethoxyvinyl)-3-(4-methoxybenzyl)benzo[d]oxazol-2(3H)-one (4.2 g, 12.92 mmol, 74.1%) as a solid. LCMS (m/z): $[M]^+$ calcd, 325.13; found, 326.3.

Step 2: 2-(3-(4-methoxybenzyl)-2-oxo-2,3-dihydrobenzo[d]oxazol-5-yl)acetaldehyde

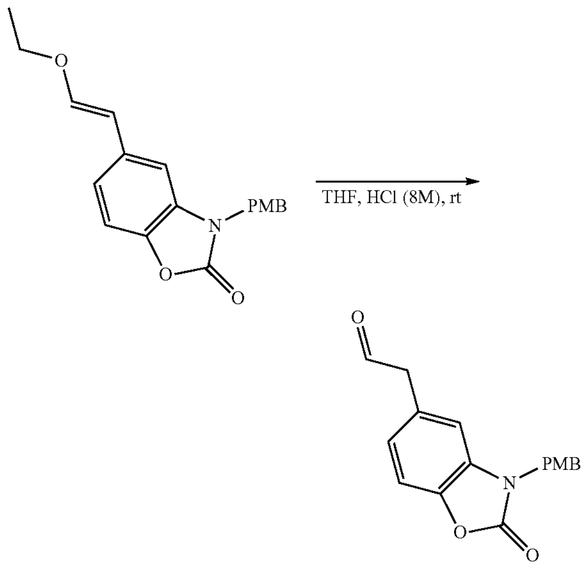

To a mixture of (E)-5-(2-ethoxyvinyl)-3-(4-methoxybenzyl)benzo[d]oxazol-2(3H)-one (4.2 g, 12.92 mmol) in THF (40 mL) was added HCl (15 mL, 8 M in $H_2O$). The reaction was stirred at rt for 6 h. The reaction was diluted with $H_2O$ and EA, the organic layer was washed with brine, dried over $Na_2SO_4$, filtered and concentrated to afford 2-(3-(4-methoxybenzyl)-2-oxo-2,3-dihydrobenzo[d]oxazol-5-yl)acetaldehyde (3.9 g, crude) as an oil. LCMS (m/z): $[M]^+$ calcd, 297.10; found, 298.3.

Step 3: 3-(4-methoxybenzyl)-5-(prop-2-yn-1-yl)benzo[d]oxazol-2(3H)-one

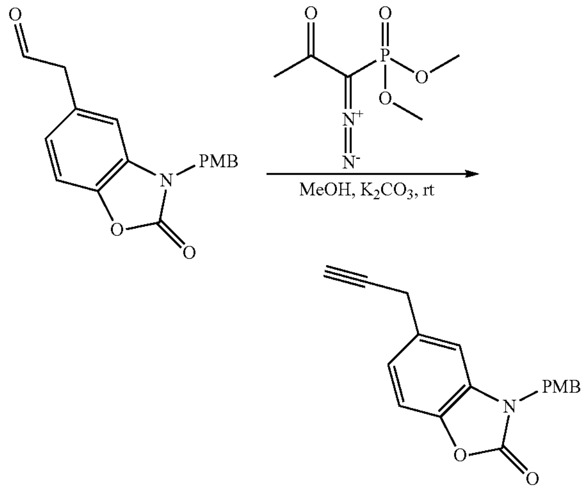

To a mixture of 2-(3-(4-methoxybenzyl)-2-oxo-2,3-dihydrobenzo[d]oxazol-5-yl)acetaldehyde (3.9 g, crude), $K_2CO_3$ (4.5 g, 32.61 mmol) in MeOH (40 mL) were added dimethyl (1-diazo-2-oxopropyl)phosphonate (5.1 g, 26.56 mmol). The reaction was stirred at rt for 4 h. Removal of solvent, the residue was purified by flash column chromatography (silica gel, 0-12% EA in PE) to afford 3-(4-methoxybenzyl)-5-(prop-2-yn-1-yl)benzo[d]oxazol-2(3H)-one (1.5 g, 5.12 mmol) as a white solid. LCMS (m/z): $[M]^+$ calcd, 293.11; found, 294.3.

Step 4: 3-(4-methoxybenzyl)-5-((3-phenylisoxazol-5-yl)methyl)benzo[d]oxazol-2(3H)-one

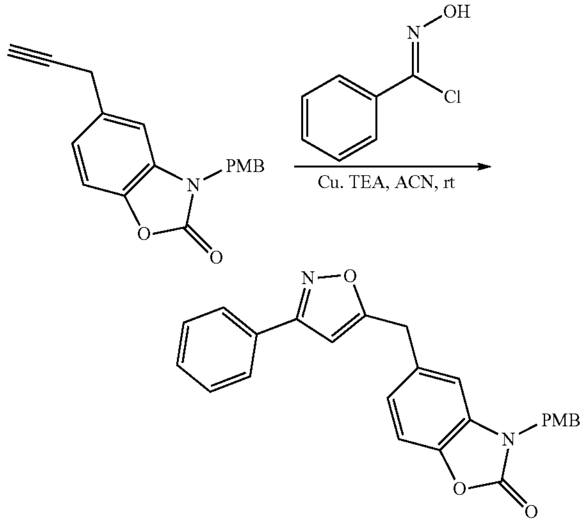

To a mixture of 3-(4-methoxybenzyl)-5-(prop-2-yn-1-yl)benzo[d]oxazol-2(3H)-one (700 mg, 2.38 mmol), Cu (20 mg, 0.36 mmol), (Z)—N-hydroxybenzimidoyl chloride (516 mg, 3.33 mmol) in ACN (10 mL) were added TEA (337 mg, 3.33 mmol). The reaction was stirred at rt for 4 h. Removal of solvent, the residue was purified by flash column chromatography (silica gel, 0~20% EA in PE) to afford 3-(4-methoxybenzyl)-5-((3-phenylisoxazol-5-yl)methyl)benzo[d]oxazol-2(3H)-one (690 mg, 87% purity) as a yellow solid. LCMS (m/z): $[M]^+$ calcd, 412.14; found, 413.4.

Step 5: 5-((3-phenylisoxazol-5-yl)methyl)benzo[d]oxazol-2(3H)-one

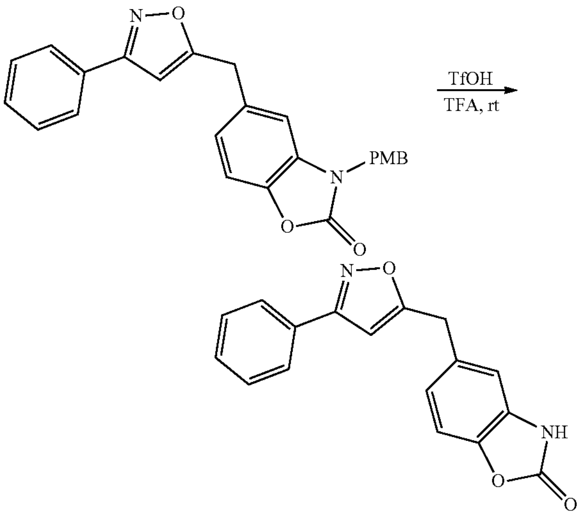

To a mixture of 3-(4-methoxybenzyl)-5-((3-phenylisoxazol-5-yl)methyl)benzo[d]oxazol-2(3H)-one (690 mg, 87% purity) in TFA (5 mL) was added TsOH (0.5 mL). The reaction was stirred at rt for 16 h. The reaction was concentrated and diluted with $NaHCO_3$ (aq.) and EA, the aqueous layer was extracted with EtOAc twice, the combined organic layers were washed with brine, dried over $Na_2SO_4$, filtered and concentrated. The residue was purified by flash column chromatography (silica gel, 0~40% EA in PE) and triturated with 30 mL (PE:EA=3:1) to afford 5-((3-phenylisoxazol-5-yl)methyl)benzo[d]oxazol-2(3H)-one (280 mg, 0.96 mmol) as a yellow solid. LCMS (m/z): $[M]^+$ calcd, 292.08; found, 293.3.

Intermediate I: 3-(4-fluoro-2-oxo-5-((2-phenyl-2H-1,2,3-triazol-4-yl)methyl)benzo[d]oxazol-3(2H)-yl) piperidine-2,6-dione

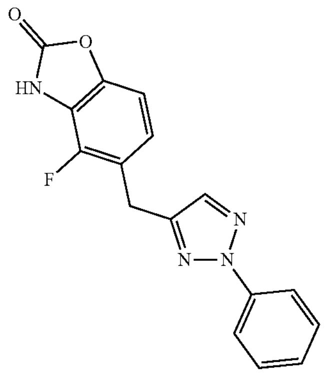 [SMILES: O=c1[nH]c2c(F)c(Cc3cnn(-c4ccccc4)n3)ccc2o1]

Step 1: Methyl 2-phenyl-2H-1,2,3-triazole-4-carboxylate

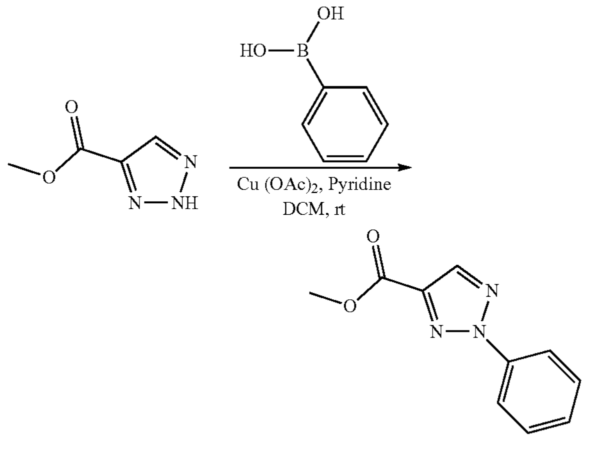

To the mixture of methyl 2H-1,2,3-triazole-4-carboxylate (5 g, 39.3 mmol) in DCM (80 mL) was added phenylboronic acid (9.59 g, 78.68 mmol), $Cu(OAc)_2$ (15.7 g, 78.7 mmol) and pyridine (6.22 g, 78.7 mmol). The mixture was stirred at room temperature under $N_2$ overnight. The mixture was quenched with $H_2O$ (50 mL), extracted with EA (100 mL*3). The organic phase was dried over $Na_2SO_4$, filtered and concentrated in vacuo. The residue was purified by column chromatography ($SiO_2$, PE:EA=1:0-20:1-15:1) to give methyl 2-phenyl-2H-1,2,3-triazole-4-carboxylate (1.7 g, 8.37 mmol, 21%) as white oil. LCMS (m/z): [M]+ calcd: 203.20, found: 204.30.

Step 2: Preparation of (2-phenyl-2H-1,2,3-triazol-4-yl)methanol

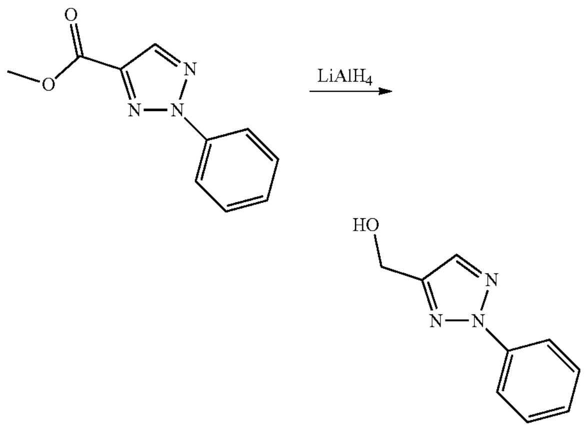

To the mixture of methyl 2-phenyl-2H-1,2,3-triazole-4-carboxylate (1.8 g, 8.86 mmol) in THF (25 mL) was added $LiAlH_4$ (672 mg, 17.7 mmol) at 0° C. under $N_2$. The mixture was stirred at 0° C. under $N_2$ for 30 min. The mixture was quenched with water (1 mL), 30% NaOH (1 mL) and water (3 mL). The mixture was filtered and concentrated on vacuo to give (2-phenyl-2H-1,2,3-triazol-4-yl)methanol (1.5 g, 8.56 mmol, 96.66%) as yellow oil. LCMS (m/z): [M]+ calcd: 175.19, found: 176.40.

Step 3. Preparation of 4-(bromomethyl)-2-phenyl-2H-1,2,3-triazole

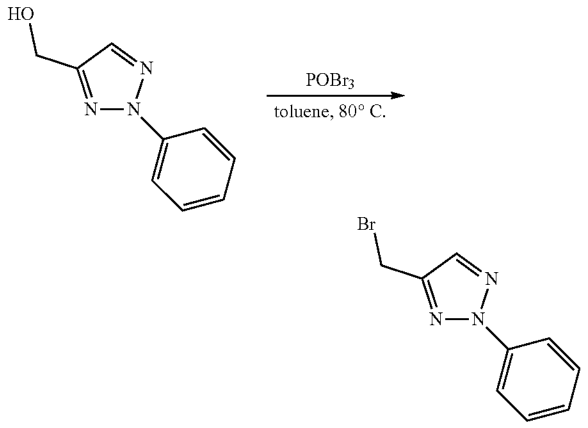

To the mixture of (2-phenyl-2H-1,2,3-triazol-4-yl)methanol (1.50 g, 8.56 mmol) in toluene (20 mL) were added $POBr_3$ (2.95 g, 10.27 mmol) at 0° C. The mixture was stirred at 80° C. under $N_2$ overnight. The mixture was quenched with sat. $NaHCO_3$ (20 mL), extracted with EA (40 mL*3). The organic phase was dried over $Na_2SO_4$, filtered and concentrated on vacuo. The residue was purified by column chromatography ($SiO_2$, PE:DCM=10:1-7:1-5:1) to give 4-(bromomethyl)-2-phenyl-2H-1,2,3-triazole (1 g, 4.20 mmol, 49.05%) as white oil. LCMS (m/z): [M]+ calcd: 238.09, found: 238.30.

Step 4: Preparation of 4-fluoro-5-((2-phenyl-2H-1,2,3-triazol-4-yl)methyl)-3-((2-(trimethylsilyl)ethoxy)methyl)benzo[d]oxazol-2(3H)-one

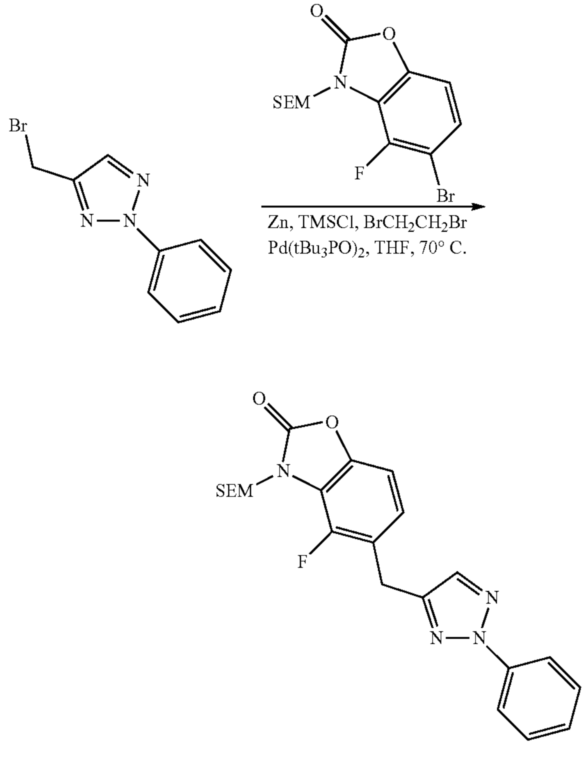

To the mixture of Zn (433 mg, 6.62 mmol) in THF (5 mL) were added 1,2-dibromoethane (0.03 mL, 0.33 mmol). The mixture was stirred at 80° C. under $N_2$ for 2 h. TMSCl (35.99 mg, 0.33 mmol) was added to the mixture. The mixture was stirred at 50° C. under $N_2$ until obvious delamination occurred. 4-(bromomethyl)-2-phenyl-2H-1,2,3-triazole (394 mg, 1.66 mmol) was added to the mixture. The mixture was stirred at 45° C. under $N_2$ for 30 min. Then the mixture was cooled to room temperature. Added the supernatant liquor to the mixture of 5-bromo-4-fluoro-3-((2-(trimethylsilyl)ethoxy)methyl)benzo[d]oxazol-2(3H)-one (300 mg, 0.83 mmol) and $Pd(tBu_3P)_2$ (42.32 mg, 0.08 mmol). The mixture was stirred at 70° C. for 2 h. The mixture was quenched with water (20 mL), extracted with EA (40 mL*3). The organic phase was dried over $Na_2SO_4$, filtered and concentrated on vacuo. The residue was purified by column chromatography ($SiO_2$, PE:DCM=1:1-1:2-0:1) to give 4-fluoro-5-((2-phenyl-2H-1,2,3-triazol-4-yl)methyl)-3-((2-(trimethylsilyl)ethoxy)methyl)benzo[d]oxazol-2(3H)-one (150 mg, 0.34 mmol, 41%) as white oil. LCMS (m/z): [M]+ calcd: 440.55, found: 441.30. $^1H$ NMR (400 MHz, $CDCl_3$) δ 8.02 (dd, J=8.6, 1.0 Hz, 2H), 7.58 (s, 1H), 7.47 (dd, J=10.8, 5.1 Hz, 2H), 7.33 (t, J=7.4 Hz, 1H), 7.09-7.03 (m, 1H), 6.99 (d, J=8.3 Hz, 1H), 5.36 (s, 2H), 4.19 (d, J=0.9 Hz, 2H), 3.73-3.65 (m, 2H), 0.99-0.92 (m, 2H), −0.02-−0.06 (m, 9H).

Step 5. Preparation of 4-fluoro-5-((2-phenyl-2H-1,2,3-triazol-4-yl)methyl)benzo[d]oxazol-2(3H)-one

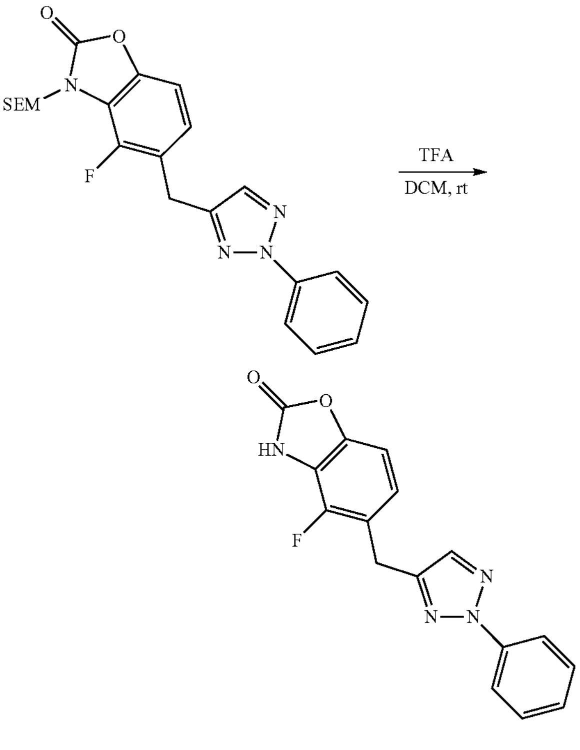

To the mixture of 4-fluoro-5-((2-phenyl-2H-1,2,3-triazol-4-yl)methyl)-3-((2-(trimethylsilyl)ethoxy)methyl)benzo[d]oxazol-2(3H)-one (150 mg, 0.34 mmol) in DCM (4 mL) was added TFA (2 mL). The mixture was stirred at rt for 3 h. The mixture was concentrated on vacuo to give 4-fluoro-5-((2-phenyl-2H-1,2,3-triazol-4-yl)methyl)benzo[d]oxazol-2(3H)-one (100 mg, 0.32 mmol, 96%) as yellow solid. LCMS (m/z): [M]+ calcd: 310.29, found: 311.30.

Intermediate J: 3-(4-fluoro-2-oxo-5-((2-phenyl-2H-tetrazol-5-yl) methyl) benzo[d]oxazol-3(2H)-yl) piperidine-2,6-dione

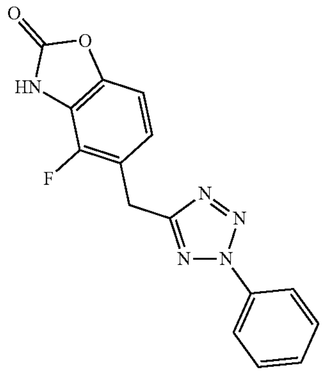 [SMILES: O=c1[nH]c2c(F)c(Cc3nnn(-c4ccccc4)n3)ccc2o1]

Step 1. tert-butyl 2-(4-fluoro-3-(4-methoxybenzyl)-2-oxo-2,3-dihydrobenzo[d]oxazol-5-yl) acetate

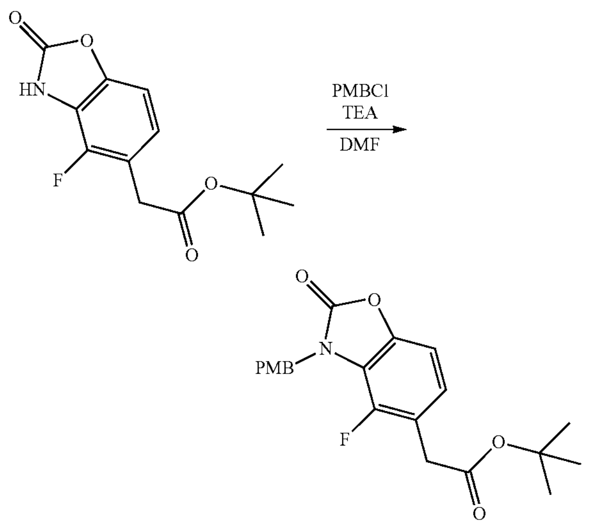

To the mixture of tert-butyl 2-(4-fluoro-2-oxo-2,3-dihydrobenzo[d]oxazol-5-yl) acetate (2 g, 7.48 mmol), $K_2CO_3$ (2.07 g, 14.97 mmol) in DMF (20 mL) was added PMBCl (1.76 g, 11.23 mmol) at 0° C. The mixture was stirred at rt under $N_2$ for 3 h. The mixture was quenched with $H_2O$ (100 ml), extracted with EA (30 ml^3). The organic phase was dried over $Na_2SO_4$, filtered and concentrated in vacuo. The residue was purified by column chromatography ($SiO_2$, PE:EA=9:1) to give tert-butyl 2-(4-fluoro-3-(4-methoxybenzyl)-2-oxo-2,3-dihydrobenzo[d]oxazol-5-yl) acetate (2.5 g, 6.45 mmol, yield: 86.23%) as a colorless oil. $^1$H NMR (400 MHz, Chloroform-d) δ 7.40-7.35 (m, 2H), 6.97-6.92 (m, 2H), 6.85 (d, J=8.7 Hz, 2H), 5.03 (s, 2H), 3.78 (s, 3H), 3.57 (s, 2H), 1.42 (s, 9H).

Step 2. 2-(4-fluoro-3-(4-methoxybenzyl)-2-oxo-2,3-dihydrobenzo[d]oxazol-5-yl) acetic acid

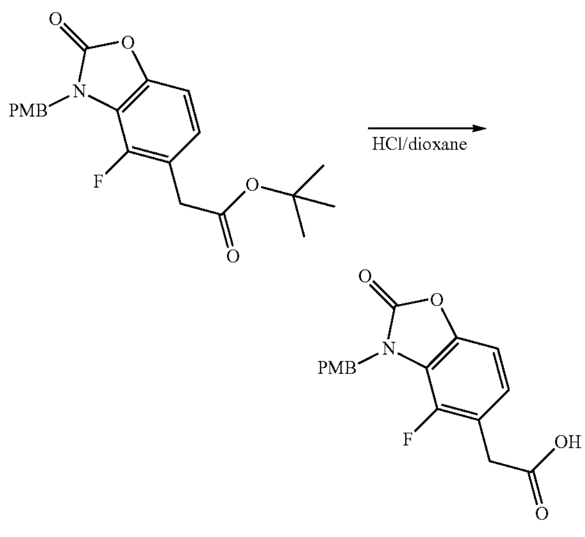

To the mixture of tert-butyl 2-(4-fluoro-3-(4-methoxybenzyl)-2-oxo-2,3-dihydrobenzo[d]oxazol-5-yl) acetate (2 g, 4.65 mmol) in HCl/dioxane (10 mL) was stirred at 25° C. under $N_2$ overnight. The mixture was concentrated to give 2-(4-fluoro-3-(4-methoxybenzyl)-2-oxo-2,3-dihydrobenzo[d]oxazol-5-yl) acetic acid (1.3 g, 3.92 mmol, yield: 84%) as a white solid. LCMS (m/z): $[M]^+$ calcd, 331.09; found, 332.3.

Step 3. 2-(4-fluoro-3-(4-methoxybenzyl)-2-oxo-2,3-dihydrobenzo[d]oxazol-5-yl) acetamide

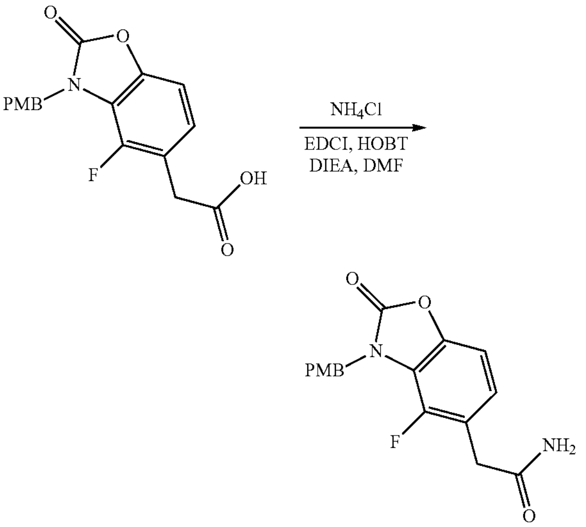

To the mixture of 2-(4-fluoro-3-(4-methoxybenzyl)-2-oxo-2,3-dihydrobenzo[d]oxazol-5-yl) acetic acid (1.3 g, 3.92 mmol), EDCI (0.90 g, 4.71 mmol), HOBt (0.64 g, 4.71 mmol) in DMF (20 mL) was added ammonium chloride (0.42 g, 7.85 mmol) and DIEA (1.52 g, 11.77 mmol). The mixture was stirred at 25° C. under $N_2$ for 2 h. The mixture was quenched with ice and $H_2O$ (100 mL), filtered and dried to give 2-(4-fluoro-3-(4-methoxybenzyl)-2-oxo-2,3-dihydrobenzo[d]oxazol-5-yl) acetamide (1.2 g, 3.63 mmol, yield: 93%) as a white solid. LCMS (m/z): $[M]^+$ calcd, 330.10; found, 331.3.

Step 4. 2-(4-fluoro-3-(4-methoxybenzyl)-2-oxo-2,3-dihydrobenzo[d]oxazol-5-yl) acetonitrile

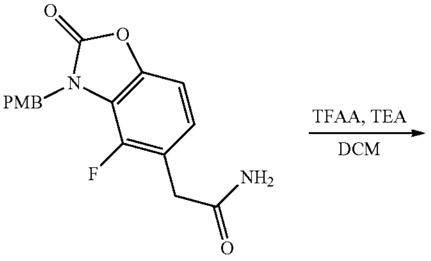

-continued

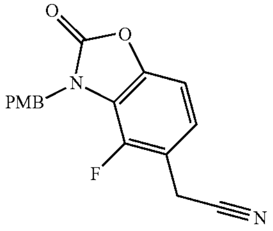

To a solution of 2-(4-fluoro-3-(4-methoxybenzyl)-2-oxo-2,3-dihydrobenzo[d]oxazol-5-yl) acetamide (1.2 g, 3.63 mmol) and TEA (0.22 mL, 1.57 mmol) in DCM (20 mL) was added TFAA (1.14 g, 5.45 mmol). The mixture was stirred at rt for 8 hrs. The reaction was quenched with $H_2O$ (100 ml), extracted with EA (30 ml^3). The organic phase was dried over $Na_2SO_4$, filtered and concentrated in vacuo. The residue was purified by flash chromatography (DCM/MeOH=20/1) to give 2-(4-fluoro-3-(4-methoxybenzyl)-2-oxo-2,3-dihydrobenzo[d]oxazol-5-yl) acetonitrile (1 g, 3.20 mmol, yield: 88%) as a white solid. LCMS (m/z): $[M]^+$ calcd, 312.09; found, 313.3.

Step 5. 5-((2H-tetrazol-5-yl) methyl)-4-fluoro-3-(4-methoxybenzyl) benzo[d]oxazol-2(3H)-one

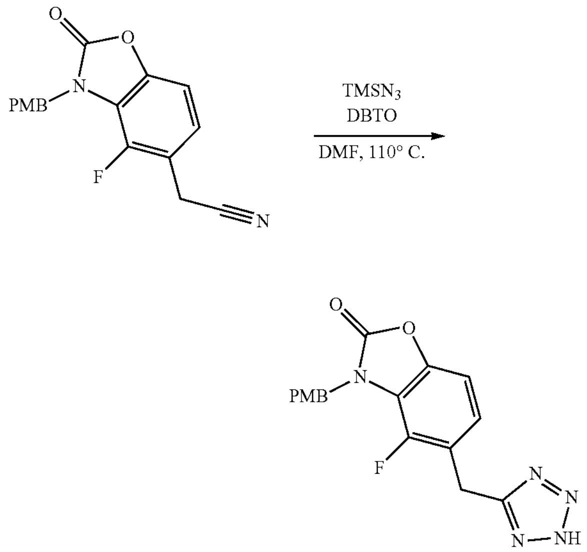

To a solution of 2-(4-fluoro-3-(4-methoxybenzyl)-2-oxo-2,3-dihydrobenzo[d]oxazol-5-yl) acetonitrile (1 g, 3.20 mmol) in DMF (10 mL) was added $TMSN_3$ (1.48 g, 12.81 mmol) and DBTO (0.37 g, 3.20 mmol). The mixture was stirred at 110° C. for 18 hrs. The mixture was quenched with $H_2O$ (100 ml), extracted with EA (30 ml^3). The organic phase was dried over $Na_2SO_4$, filtered and concentrated in vacuo. The residue was purified by column chromatography ($SiO_2$, DCM:MeOH=9:1) to give 5-((2H-tetrazol-5-yl) methyl)-4-fluoro-3-(4-methoxybenzyl) benzo[d]oxazol-2 (3H)-one (900 mg, 2.53 mmol, yield: 79%) as a white solid. LCMS (m/z): $[M]^+$ calcd, 355.11; found, 356.3.

Step 6. 4-fluoro-3-(4-methoxybenzyl)-5-((2-phenyl-2H-tetrazol-5-yl) methyl) benzo[d]oxazol-2(3H)-one

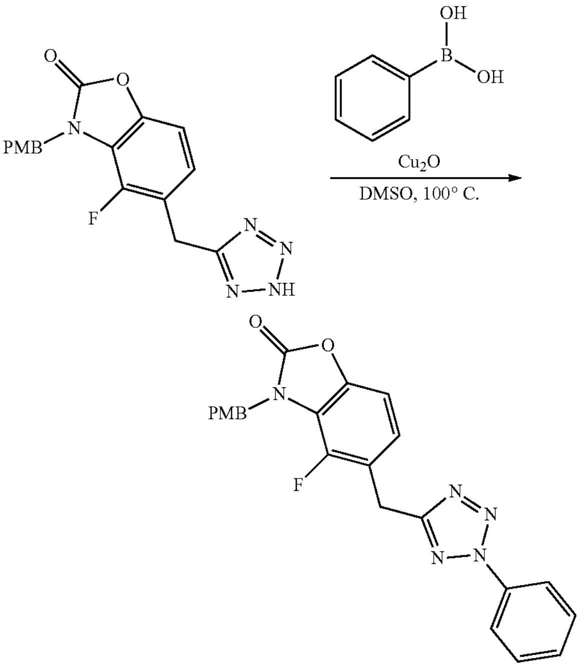

To a solution of 5-((2H-tetrazol-5-yl) methyl)-4-fluoro-3-(4-methoxybenzyl) benzo[d]oxazol-2(3H)-one (800 mg, 2.25 mmol) and phenylboronic acid (550 mg, 4.50 mmol) in DMSO (3 mL) was added $Cu_2O$ (33 mg, 0.23 mmol). The mixture was stirred at 110° C. for 6 hrs. The reaction was quenched with $H_2O$ (20 ml), extracted with EA (10 ml^3). The organic phase was dried over $Na_2SO_4$, filtered and concentrated in vacuo. The residue was purified by flash chromatography (PE/EA=7/1) to give 4-fluoro-3-(4-methoxybenzyl)-5-((2-phenyl-2H-tetrazol-5-yl) methyl) benzo[d]oxazol-2(3H)-one (200 mg, 0.46 mmol, yield: 21%) as a yellow solid. LCMS (m/z): $[M]^+$ calcd 431.14; found, 432.4.

Step 7. 4-fluoro-5-((2-phenyl-2H-tetrazol-5-yl) methyl) benzo[d]oxazol-2(3H)-one

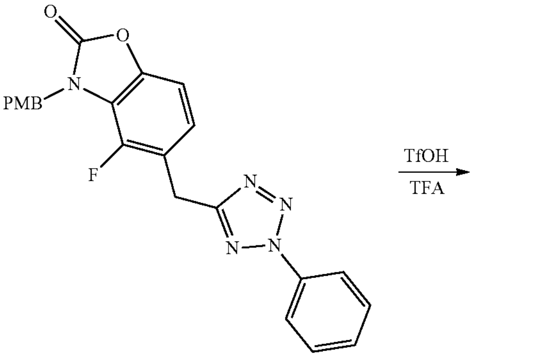

-continued

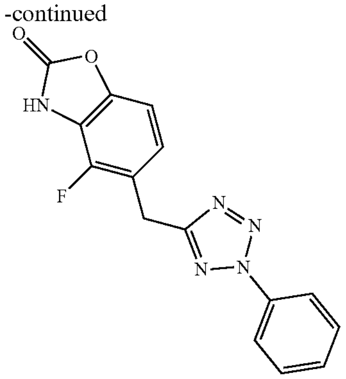

-continued

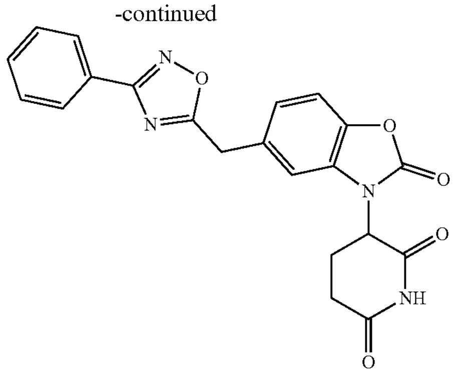

To a solution of 4-fluoro-3-(4-methoxybenzyl)-5-((2-phenyl-2H-tetrazol-5-yl) methyl) benzo[d]oxazol-2(3H)-one (230 mg, 0.70 mmol) in TFA (2 mL) was added TfOH (0.1 mL, 0.05 mmol). The mixture was stirred at rt for 8 hrs. The mixture was quenched with sat.$NaHCO_3$, extracted with EA (10 ml^3). The organic phase was dried over $Na_2SO_4$, filtered and concentrated in vacuo. The residue was purified by flash chromatography (PE/EA=3/1) to give 4-fluoro-5-((2-phenyl-2H-tetrazol-5-yl) methyl) benzo[d]oxazol-2(3H)-one (130 mg, 0.42 mmol, yield: 59%) as a yellow solid. LCMS (m/z): $[M]^+$ calcd: 311.08; found, 312.3.

EXAMPLES

General Method A

Compound 1: Preparation of 3-(2-Oxo-5-((3-phenyl-1,2,4-oxadiazol-5-yl)methyl)benzo[d]oxazol-3(2H)-yl)piperidine-2,6-dione

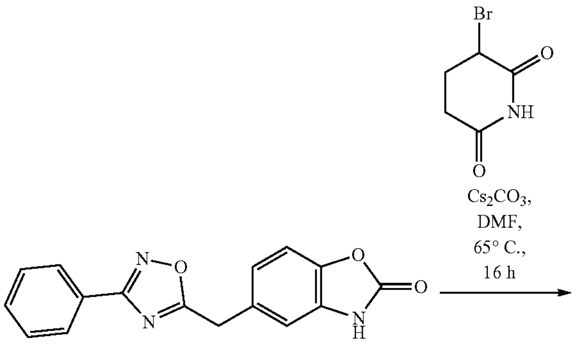

To a stirred solution of 5-((3-phenyl-1,2,4-oxadiazol-5-yl)methyl)benzo[d]oxazol-2(3H)-one (0.07 g, 0.24 mmol) in DMF (1 mL) were added 3-bromopiperidine-2,6-dione (0.23 g, 1.2 mmol) and cesium carbonate (0.23 g, 0.72 mmol) at room temperature. The resulting reaction mixture was stirred at 65° C. for 16 h. After completion of the reaction, the reaction mixture was quenched with ice-cold water (30 mL) and extracted with ethyl acetate (3×30 mL). The combined organic layers were dried over anhydrous sodium sulphate, filtered and the filtrate was concentrated under reduced pressure to afford crude compound. The obtained crude compound was purified by RP prep-HPLC [column/dimensions: X-bridge phenyl C18 (19×250) 5 μm, mobile phase (A): 10 mM ammonium acetate in water, mobile phase (B): acetonitrile, gradient (Time/% B): 0/30, 1/30, 10/45, 17/45, 17.1/1001, 17.1/30, 20/20. Flow rate: 16 ml/min, solubility: THF+ACN+water] and the fractions were concentrated under reduced pressure followed by lyophilization to afford 3-(2-oxo-5-((3-phenyl-1,2,4-oxadiazol-5-yl)methyl)benzo[d]oxazol-3(2H)-yl)piperidine-2,6-dione (0.011 g, 11%) as an off-white solid. MS (ESI) m/z 405.27 $[M+H]^+$. $^1H$ NMR (400 MHz, DMSO-$d_6$) δ 11.21 (s, 1H), 7.98 (dd, J=8.0, 1.6 Hz, 2H), 7.61-7.53 (m, 3H), 7.41 (s, 1H), 7.39 (s, 1H), 7.22 (dd, J=8.4, 1.6 Hz, 1H), 5.39 (d, J=13.2, 5.2 Hz, 1H), 4.46 (s, 2H), 2.93-2.80 (m, 1H), 2.74-2.67 (m, 2H), 2.20-2.16 (m, 1H).

Compounds below may be synthesized utilizing General Method A.

| Compound # | Structure | $[M + H]^+$ | $^1H$ NMR |
|---|---|---|---|
| 2 | 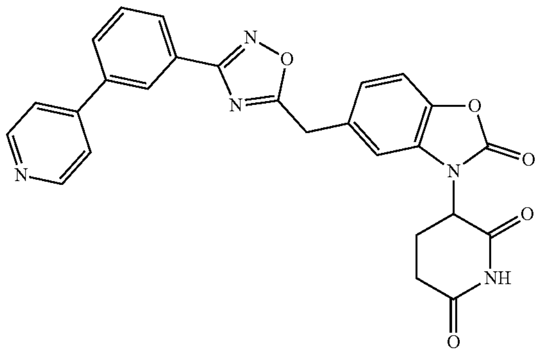 [SMILES: O=C1CCC(n2c(=O)oc3ccc(Cc4nc(-c5cccc(-c6ccncc6)c5)no4)cc32)C(=O)N1] | 482.31 | $^1H$ NMR (400 MHz, DMSO-$d_6$) δ 11.21 (s, 1H), 8.68 (dd, J = 4.4, 1.6 Hz, 2H), 8.30 (s, 1H), 8.07 (d, J = 7.6 Hz, 1H), 8.02 (d, J = 8.0 Hz, 1H), 7.77-7.70 (m, 3H), 7.41 (d, J = 8.0 Hz, 2H), 7.22 (dd, J = 8.4, 1.2 Hz, 1H), 5.39 (dd, J = 12.4, 5.2 Hz, 1H), 4.49 (s, 2H), 2.91-2.83 (m, 1H), 2.74-2.62 (m, 2H), 2.20-2.16 (m, 1H) |

-continued

| Compound # | Structure | [M + H]+ | $^{1}H$ NMR |
|---|---|---|---|
| 3 | 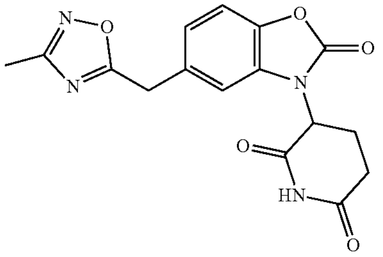 [SMILES: Cc1noc(Cc2ccc3oc(=O)n(C4CCC(=O)NC4=O)c3c2)n1] | 343.25 | $^{1}H$ NMR (400 MHz, DMSO-$d_6$) δ 11.22 (s, 1H), 7.37 (d, J = 8.4 Hz, 1H), 7.32 (d, J = 1.2 Hz, 1H), 7.14 (dd, J = 8.0, 2.4 Hz, 1H), 5.38 (dd, J = 12.8, 5.6 Hz, 1H), 4.32 (s, 2H), 2.93-2.84 (m, 1H), 2.70-2.63 (m, 2H), 2.29 (s, 3H), 2.19-2.12 (m, 1H) |
| 4 | 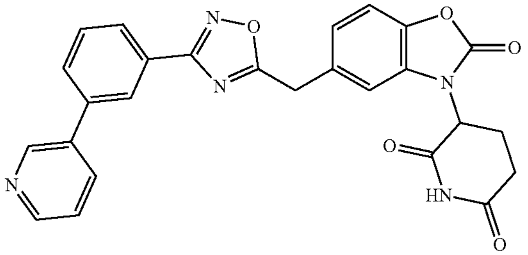 [SMILES: O=C1CCC(n2c(=O)oc3ccc(Cc4nc(-c5cccc(-c6cccnc6)c5)no4)cc32)C(=O)N1] | 482.31 | $^{1}H$ NMR (400 MHz, DMSO-$d_6$) δ 11.22 (s, 1H), 8.93 (d, J = 2.0 Hz, 1H), 8.63 (dd, J = 4.8, 1.6 Hz, 1H), 8.23 (s, 1H), 8.15-8.12 (m, 1H), 8.03 (d, J = 7.6 Hz, 1H), 7.95 (d, J = 8.0 Hz, 1H), 7.70 (d, J = 7.6 Hz, 1H), 7.53 (q, J = 4.8 Hz, 1H), 7.42-7.40 (m, 2H), 7.23 (dd, J = 8.4, 1.2 Hz, 1H), 5.40 (dd, J = 13.2, 4.8 Hz, 1H), 4.49 (s, 2H), 2.92-2.84 (m, 1H), 2.75-2.62 (m, 2H), 2.20-2.16 (m, 1H) |
| 5 | 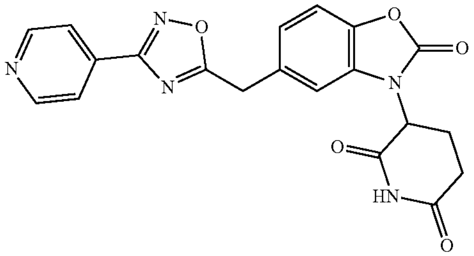 [SMILES: O=C1CCC(n2c(=O)oc3ccc(Cc4nc(-c5ccncc5)no4)cc32)C(=O)N1] | 406.30 | $^{1}H$ NMR (400 MHz, DMSO-$d_6$) δ 11.22 (s, 1H), 8.79 (dd, J = 4.8, 1.6 Hz, 2H), 7.90 (dd, J = 4.4, 1.6 Hz, 2H), 7.41 (s, 1H), 7.39 (s, 1H), 7.22 (dd, J = 8.0, 1.6 Hz, 1H), 5.39 (dd, J = 12.8, 5.6 Hz, 1H), 4.50 (s, 2H), 2.93-2.85 (m, 1H), 2.74-2.64 (m, 2H), 2.19-2.14 (m, 1H) |
| 6 | 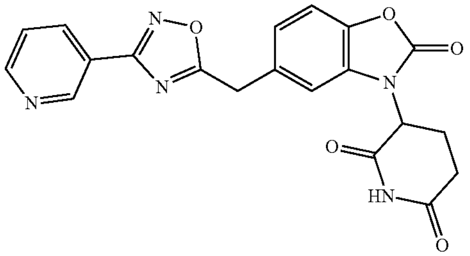 | 409.29 | $^{1}H$ NMR (400 MHz, DMSO-$d_6$) δ 11.28 (s, 1H), 9.13 (d, J = 1.6 Hz, 1H), 8.77 (dd, J = 4.8, 1.6 Hz, 1H), 8.34-8.31 (m, 1H), 7.60 (q, J = 4.8 Hz, 1H), 7.41 (s, 1H), 7.39 (s, 1H), 7.22 (dd, J = 8.4, 1.2 Hz, 1H), 5.39 (dd, J = 12.8, 5.2 Hz, 1H), 4.49 (s, 2H), 2.93-2.82 (m, 1H), 2.74-2.62 (m, 2H), 2.20-2.14 (m, 1H) |
| 7 | 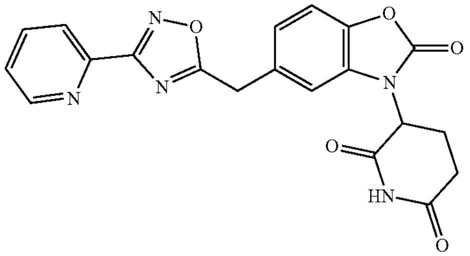 | 406.26 | $^{1}H$ NMR (400 MHz, DMSO-$d_6$) δ 11.21 (s, 1H), 8.74-8.73 (m, 1H), 8.04-7.98 (m, 2H), 7.61-7.57 (m, 1H), 7.42-7.39 (m, 2H), 7.23 (dd, J = 8.4, 1.6 Hz, 1H), 5.39 (dd, J = 12.8, 5.2 Hz, 1H), 4.48 (s, 2H), 2.93-2.85 (m, 1H), 2.74-2.67 (m, 2H), 2.20-2.07 (m, 1H). |

-continued

| Compound # | Structure | $[M + H]^+$ | $^1H$ NMR |
|---|---|---|---|
| 8 | 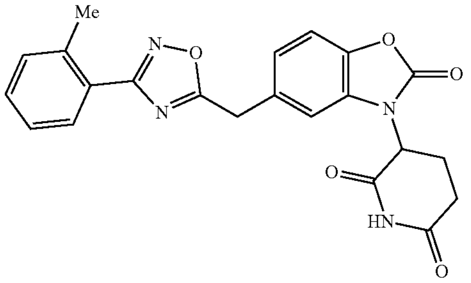 [SMILES: Cc1ccccc1-c1noc(Cc2ccc3oc(=O)n(C4CCC(=O)NC4=O)c3c2)n1] | 419.30 | $^1H$ NMR (400 MHz, DMSO-$d_6$) δ 11.21 (s, 1H), 7.87 (d, J = 7.6 Hz, 1H), 7.47-7.34 (m, 5H), 7.22 (dd, J = 9.6, 1.2 Hz, 1H), 5.40 (dd, J = 12.8, 5.2 Hz, 1H), 4.46 (s, 2H), 2.94-2.86 (m, 1H), 2.74-2.67 (m, 2H), 2.52 (s, 3H), 2.20-2.16 (m, 1H) |
| 9 | 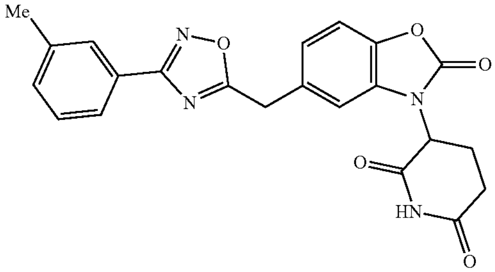 [SMILES: Cc1cccc(-c2noc(Cc3ccc4oc(=O)n(C5CCC(=O)NC5=O)c4c3)n2)c1] | 419.30 | $^1H$ NMR (400 MHz, DMSO-$d_6$) δ 11.21 (s, 1H), 7.78 (d, J = 6.8 Hz, 1H), 7.76 (s, 1H), 7.45-7.38 (m, 4H), 7.21 (dd, J = 8.0, 1.6 Hz, 1H), 5.39 (dd, J = 12.8, 5.2 Hz, 1H), 4.45 (s, 2H), 2.93-2.85 (m, 1H), 2.73-2.63 (m, 2H), 2.38 (s, 3H), 2.19-2.14 (m, 1H) |
| 10 | 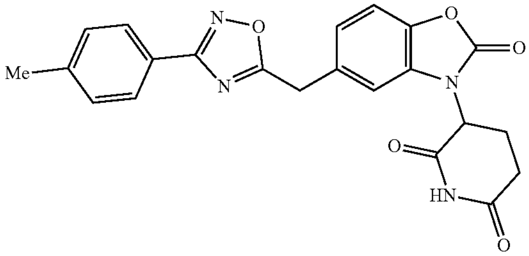 [SMILES: Cc1ccc(-c2noc(Cc3ccc4oc(=O)n(C5CCC(=O)NC5=O)c4c3)n2)cc1] | 419.26 | $^1H$ NMR (400 MHz, DMSO-$d_6$) δ 11.22 (s, 1H), 7.86 (d, J = 8.0 Hz, 2H), 7.41-7.35 (m, 4H), 7.21 (d, J = 8.0 Hz, 1H), 5.39 (dd, J = 12.4, 5.2 Hz, 1H), 4.44 (s, 2H), 2.93-2.85 (m, 1H), 2.74-2.63 (m, 2H), 2.37 (s, 3H), 2.20-2.17 (m, 1H). |
| 11 | 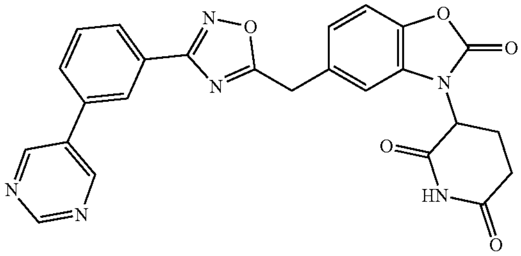 [SMILES: O=C1CCC(n2c(=O)oc3ccc(Cc4nc(-c5cccc(-c6cncnc6)c5)no4)cc32)C(=O)N1] | 483.32 | $^1H$ NMR (400 MHz, DMSO-$d_6$) δ 11.22 (s, 1H), 9.23 (s, 1H), 9.19 (s, 2H), 8.48 (br s, 1H), 8.30 (s, 1H), 8.08 (d, J = 8.0 Hz, 1H), 8.02 (d, J = 8.4 Hz, 1H), 7.74 (t, J = 8.0 Hz, 1H), 7.42-7.40 (m, 1H), 7.23 (dd, J = 8.4, 1.2 Hz, 1H), 5.40 (dd, J = 12.8, 5.2 Hz, 1H), 4.49 (s, 2H), 2.93-2.85 (m, 1H), 2.75-2.63 (m, 2H), 2.20-2.15 (m, 1H) |
| 12 | 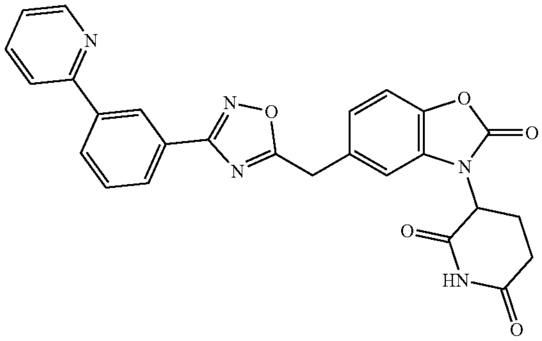 [SMILES: O=C1CCC(n2c(=O)oc3ccc(Cc4nc(-c5cccc(-c6ccccn6)c5)no4)cc32)C(=O)N1] | 482.31 | $^1H$ NMR (400 MHz, DMSO-$d_6$) δ 11.22 (s, 1H), 8.74 (t, J = 1.6 Hz, 1H), 8.72 (dd, J = 4.8, 0.8 Hz, 1H), 8.47 (br s, 1H), 8.27 (d, J = 8.0 Hz, 1H), 8.06-8.03 (m, 2H), 7.95-7.91 (m, 1H), 7.68 (t, J = 7.6 Hz, 1H), 7.43-7.40 (m, 2H), 7.24 (dd, J = 8.4, 1.6 Hz, 1H), 5.40 (dd, J = 13.2, 5.2 Hz, 1H), 4.49 (s, 2H), 2.93-2.84 (m, 1H), 2.75-2.67 (m, 2H), 2.20-2.18 (m, 1H). |

-continued

| Compound # | Structure | [M + H]$^+$ | $^1$H NMR |
|---|---|---|---|
| 13 | 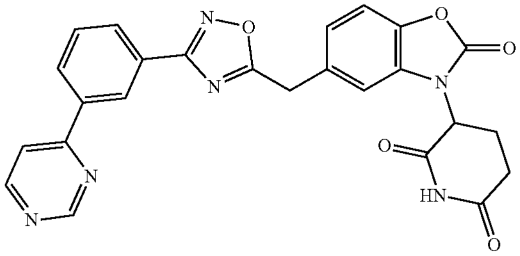 [SMILES: O=C1CCC(n2c(=O)oc3ccc(Cc4nc(-c5cccc(-c6ccncn6)c5)no4)cc32)C(=O)N1] | 483.28 | $^1$H NMR (400 MHz, DMSO-$d_6$) δ 11.22 (s, 1H), 9.31 (s, 1H), 8.92 (d, J = 5.6 Hz, 1H), 8.83 (s, 1H), 8.40 (d, J = 7.6 Hz, 1H), 8.19 (dd, J = 5.6, 1.2 Hz, 1H), 8.23 (d, J = 7.6 Hz, 1H), 7.75 (t, J = 8.0 Hz, 1H), 7.42 (s, 1H), 7.40 (s, 1H), 7.24 (d, J = 8.4 Hz, 1H), 5.40 (dd, J = 12.8, 5.2 Hz, 1H), 4.50 (s, 2H), 2.90-2.84 (m, 1H), 2.73-2.66 (m, 2H), 2.19-2.17 (m, 1H) |
| 14 | 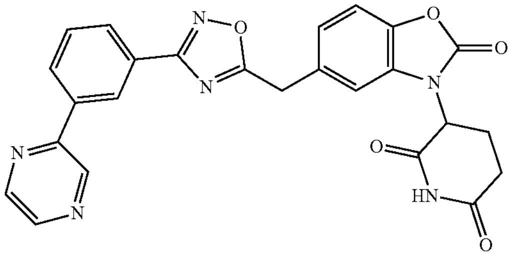 [SMILES: O=C1CCC(n2c(=O)oc3ccc(Cc4nc(-c5cccc(-c6cnccn6)c5)no4)cc32)C(=O)N1] | 483.32 | $^1$H NMR (400 MHz, DMSO-$d_6$) δ 11.22 (s, 1H), 9.35 (s, 1H), 8.76 (d, J = 8.8 Hz, 2H), 8.68 (d, J = 2.4 Hz, 1H), 8.36 (d, J = 8.0 Hz, 1H), 8.10 (d, J = 8.0 Hz, 1H), 7.73 (t, J = 7.6 Hz, 1H), 7.42 (s, 1H), 7.43 (s, 1H), 7.24 (d, J = 8.4 Hz, 1H), 5.40 (dd, J = 13.2, 4.8 Hz, 1H), 4.50 (s, 2H), 2.93-2.84 (m, 1H), 2.72-2.62 (m, 2H), 2.19-2.16 (m, 1H) |
| 15 | 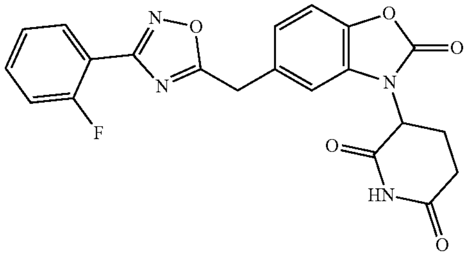 [SMILES: O=C1CCC(n2c(=O)oc3ccc(Cc4nc(-c5ccccc5F)no4)cc32)C(=O)N1] | 423.24 | $^1$H NMR (400 MHz, DMSO-$d_6$) δ 11.28 (s, 1H), 7.99-7.95 (m, 1H), 7.67-7.62 (m, 1H), 7.46-7.38 (m, 4H), 7.21 (d, J = 9.2 Hz, 1H), 5.39 (dd, J = 12.4, 5.6 Hz, 1H), 4.48 (s, 2H), 2.94-2.85 (m, 1H), 2.74-2.63 (m, 2H), 2.20-2.15 (m, 1H) |
| 16 | 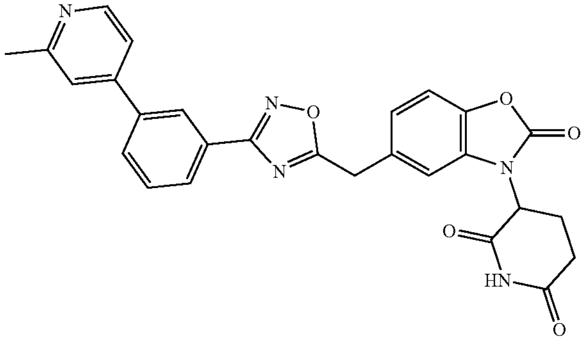 [SMILES: Cc1cc(-c2cccc(-c3noc(Cc4ccc5oc(=O)n(C6CCC(=O)NC6=O)c5c4)n3)c2)ccn1] | 496.31 | $^1$H-NMR (400 MHz, DMSO-$d_6$) δ 11.23 (s, 1H), 8.54 (d, J = 5.2 Hz, 2H), 8.29 (s, 1H), 8.06 (d, J = 8.0 Hz, 1H), 8.00 (d, J = 8.4 Hz, 1H), 7.69 (t, J = 7.8 Hz, 1H), 7.64 (s, 1H), 7.55 (dd, J = 0.6 Hz, 1H), 7.41 (d, J = 8.0 Hz, 1H), 7.22 (d, J = 1.2 Hz, 1H), 5.40 (dd, J = 12.8, 5.2 Hz, 1H), 4.50 (s, 2H), 2.94-2.90 (m, 1H), 2.75-2.74 (m, 1H), 2.72-2.63 (m, 1H), 2.56 (s, 3H), 2.19-2.17 (m, 1H) |
| 17 | 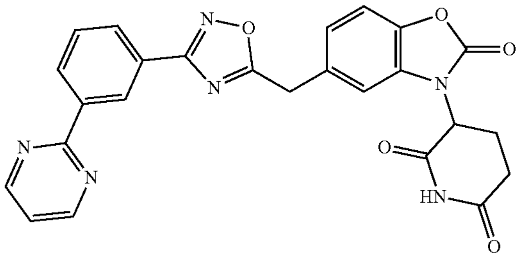 [SMILES: O=C1CCC(n2c(=O)oc3ccc(Cc4nc(-c5cccc(-c6ncccn6)c5)no4)cc32)C(=O)N1] | 481.27 | $^1$H NMR (400 MHz, DMSO-$d_6$) δ 11.21 (br s, 1H), 9.04 (s, 1H), 8.97 (d, J = 4.8 Hz, 2H), 8.59 (d, J = 8.0 Hz, 1H), 8.14 (d, J = 7.6 Hz, 1H), 7.73 (t, J = 8.0 Hz, 1H), 7.52 (t, J = 5.2 Hz, 1H), 7.42 (d, J = 8.0 Hz, 2H), 7.24 (d, J = 9.2 Hz, 1H), 5.39 (dd, J =13.2, 5.2 Hz, 1H), 4.50 (s, 2H), 2.92-2.84 (m, 1H), 2.76-2.63 (m, 2H), 2.19-2.16 (m, 1H) |

-continued

| Compound # | Structure | [M + H]+ | 1H NMR |
|---|---|---|---|
| 18 | 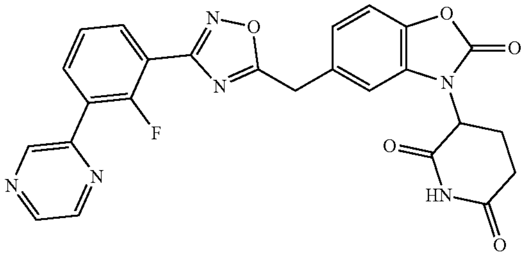 [SMILES: O=C1CCC(n2c(=O)oc3ccc(Cc4nc(-c5cccc(-c6cnccn6)c5F)no4)cc32)C(=O)N1] | 501.28 | $^{1}H$ NMR (400 MHz, DMSO-$d_6$) δ 11.22 (s, 1H), 9.09 (s, 1H), 8.83 (t, J = 2.4 Hz, 1H), 8.72 (d, J = 2.4 Hz, 1H), 8.13-8.09 (m, 2H), 7.58 (t, J = 8.0 Hz, 1H), 7.42 (s, 1H), 7.40 (s, 1H), 7.24 (dd, J = 8.4, 1.2 Hz, 1H), 5.40 (dd, J = 12.8, 5.2 Hz, 1H), 4.54 (s, 2H), 2.92-2.85 (m, 1H), 2.75-2.63 (m, 2H), 2.20-2.16 (m, 1H) |
| 19 | 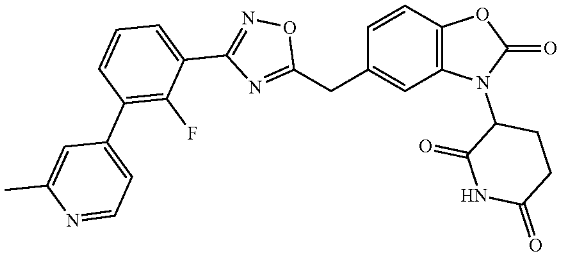 [SMILES: Cc1cc(-c2cccc(-c3noc(Cc4ccc5oc(=O)n(C6CCC(=O)NC6=O)c5c4)n3)c2F)ccn1] | 514.31 | $^{1}H$ NMR (400 MHz, DMSO-$d_6$) δ 11.22 (s, 1H), 8.56 (d, J = 5.2 Hz, 1H), 8.08-8.01 (m, 1H), 7.84-7.79 (m, 1H), 7.53 (d, J = 7.6 Hz, 1H), 7.50 (d, J = 4.8 Hz, 1H), 7.41 (d, J = 8.4 Hz, 3H), 7.22 (d, J = 8.4 Hz, 3H), 5.40 (dd, J = 12.8, 5.2 Hz, 1H), 4.50 (s, 2H), 2.91-2.84 (m, 1H), 2.72-2.61 (m, 2H), 2.58-2.55 (m, 1H), 2.19-2.12 (m, 1H) |
| 20 | 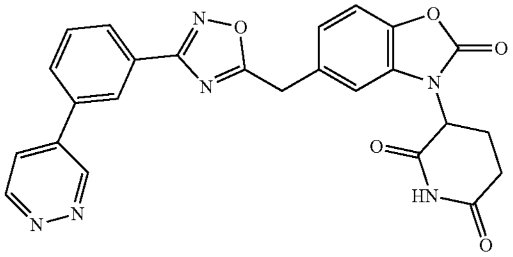 [SMILES: O=C1CCC(n2c(=O)oc3ccc(Cc4nc(-c5cccc(-c6ccnnc6)c5)no4)cc32)C(=O)N1] | 483.35 | $^{1}H$ NMR (400 MHz, DMSO-$d_6$) δ 11.28 (s, 1H), 9.67 (q, J = 1.2 Hz, 1H), 9.32 (dd, J = 5.6,1.2 Hz, 1H), 8.40 (t, J = 1.6 Hz, 1H), 8.13 (dd, J = 8.0, 1.2 Hz, 2H), 8.08 (dd, J = 5.6, 2.4 Hz, 1H), 7.77 (t, J = 7.6 Hz, 1H), 7.42-7.40 (m, 2H), 7.23 (dd, J = 8.4, 1.6 Hz, 1H), 5.16 (dd, J = 12.8, 5.2 Hz, 1H), 4.50 (s, 2H), 2.92-2.85 (m, 1H), 2.72-2.61 (m, 1H), 2.4-2.5 (m, 1H), 2.21-2.18 (m, 1H) |
| 21 | 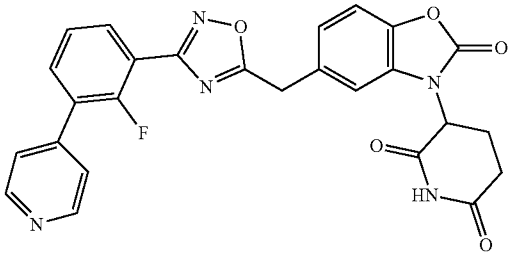 [SMILES: O=C1CCC(n2c(=O)oc3ccc(Cc4nc(-c5cccc(-c6ccncc6)c5F)no4)cc32)C(=O)N1] | 500.49 | $^{1}H$ NMR (400 MHz, DMSO-$d_6$) δ 11.28 (s, 1H), 8.71 (dd, J = 4.4, 1.6 Hz, 2H), 8.08-8.04 (m, 1H), 7.86-7.82 (m, 1H), 7.63 (d, J = 4.8 Hz, 2H), 7.54 (t, J = 7.6 Hz, 1H), 7.41 (d, J = 8.4 Hz, 2H), 7.23 (d, J = 9.6 Hz, 1H), 5.40 (dd, J = 12.8, 5.2 Hz, 1H), 4.50 (s, 2H), 2.93-2.85 (m, 1H), 2.74-2.62 (m, 2H), 2.21-2.13 (m, 1H) |
| 22 | 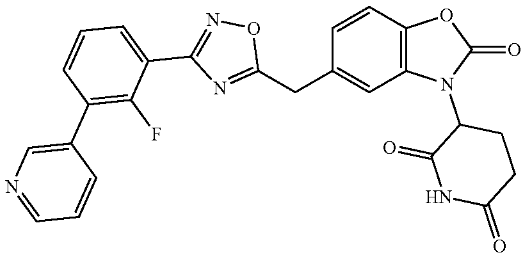 [SMILES: O=C1CCC(n2c(=O)oc3ccc(Cc4nc(-c5cccc(-c6cccnc6)c5F)no4)cc32)C(=O)N1] | 500.49 | $^{1}H$ NMR (400 MHz, DMSO-$d_6$) δ 11.28 (s, 1H), 8.79 (s, 1H), 8.65 (dd, J = 4.8, 1.6 Hz, 1H), 8.50-8.01 (m, 2H), 7.84-7.80 (m, 1H), 7.56-7.50 (m, 2H), 7.41 (d, J = 8.0 Hz, 2H), 7.23 (d, J = 9.6 Hz, 1H), 5.40 (dd, J = 12.8, 5.2 Hz, 1H), 4.50 (s, 2H), 2.96-2.82 (m, 1H), 2.76-2.62 (m, 2H), 2.21-2.12 (m, 1H) |

-continued

| Compound # | Structure | [M + H]+ | $^1$H NMR |
|---|---|---|---|
| 23 | 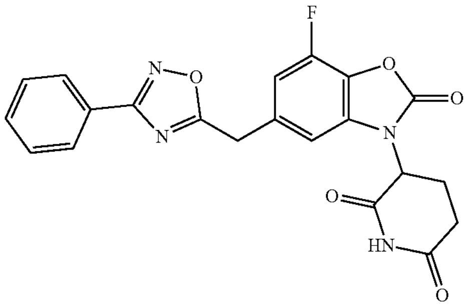 [SMILES: O=C1CCC(n2c(=O)oc3c(F)cc(Cc4nc(-c5ccccc5)no4)cc32)C(=O)N1] | 421.26 | $^1$H NMR (400 MHz, DMSO-$d_6$) δ 11.28 (s, 1H), 7.97 (dd, J = 7.6, 1.6 Hz, 2H), 7.59-7.52 (m, 3H), 7.28 (d, J = 2.4 Hz, 1H), 7.25 (s, 1H), 5.41 (dd, J = 12.8, 5.6 Hz, 1H), 4.48 (s, 2H), 2.93-2.84 (m, 1H), 2.71-2.62 (m, 2H), 2.21-2.12 (m, 1H) |
| 24 | 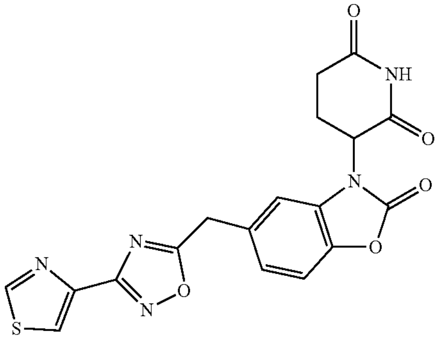 | 412.3 | $^1$H NMR (400 MHz, $CDCl_3$) δ 8.96 (d, J = 2.0 Hz, 1H), 8.31 (s, 1H), 8.14 (d, J = 2.0 Hz, 1H), 7.24 (d, J = 8.3 Hz, 1H), 7.18 (dd, J = 8.3, 1.5 Hz, 1H), 6.94 (d, J = 1.2 Hz, 1H), 5.03 (dd, J = 12.8, 5.4 Hz, 1H), 4.32 (s, 2H), 3.02-2.94 (m, 1H), 2.89-2.70 (m, 2H), 2.32 (ddd, J = 10.7, 7.4, 5.0 Hz, 1H) |
| 25 | 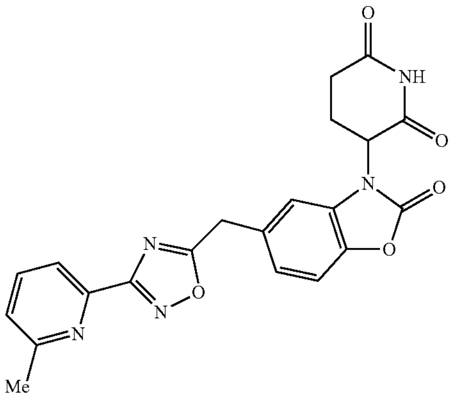 [SMILES: Cc1cccc(-c2noc(Cc3ccc4oc(=O)n(C5CCC(=O)NC5=O)c4c3)n2)n1] | 420.4 | $^1$H NMR (400 MHz, $CDCl_3$) δ 8.60 (s, 1H), 7.89 (d, J = 7.7 Hz, 1H), 7.72 (dd, J = 9.7, 5.8 Hz, 1H), 7.29 (t, J = 6.2 Hz, 1H), 7.23 (d, J = 8.2 Hz, 1H), 7.17 (dd, J = 8.3, 1.4 Hz, 1H), 6.96 (d, J = 1.3 Hz, 1H), 5.04 (dt, J = 18.8, 7.4 Hz, 1H), 4.34 (s, 2H), 3.02-2.90 (m, 1H), 2.78 (tdd, J = 26.1, 13.2, 4.7 Hz, 2H), 2.66 (s, 3H), 2.36 - 2.23 (m, 1H). |
| 26 | 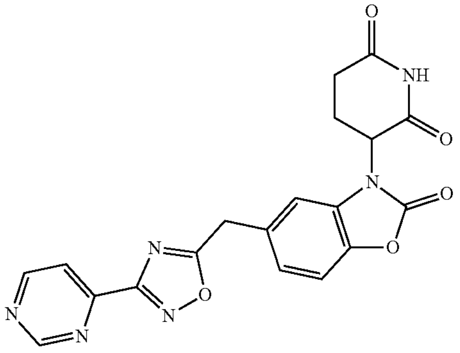 [SMILES: O=C1CCC(n2c(=O)oc3ccc(Cc4nc(-c5ccncn5)no4)cc32)C(=O)N1] | 407.4 | $^1$H NMR (400 MHz, DMSO) δ 11.22 (s, 1H), 9.39 (d, J = 1.4 Hz, 1H), 9.07 (d, J = 5.1 Hz, 1H), 8.08 (dd, J = 5.1, 1.4 Hz, 1H), 7.40 (dd, J = 7.7, 4.9 Hz, 2H), 7.23 (dd, J = 8.2, 1.7 Hz, 1H), 5.44-5.27 (m, 1H), 4.52 (s, 2H), 2.87 (d, J = 15.3 Hz, 1H), 2.67 (t, J = 11.8 Hz, 2H), 2.18 (d, J = 5.2 Hz, 1H) |

-continued
| Compound # | Structure | [M + H]+ | 1H NMR |
|---|---|---|---|
| 27 | 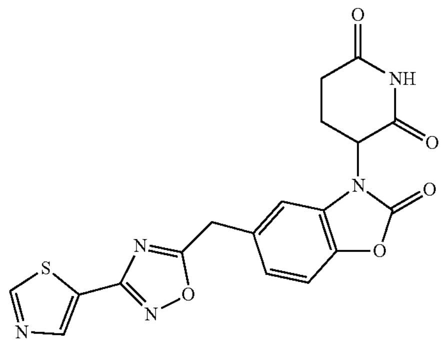 [SMILES: O=C1CCC(n2c(=O)oc3ccc(Cc4nc(-c5cncs5)no4)cc32)C(=O)N1] | 412.3 | 1H NMR (400 MHz, DMSO) δ 11.23 (s, 1H), 9.36 (s, 1H), 8.54 (s, 1H), 7.39 (dd, J = 10.5, 4.7 Hz, 2H), 7.21 (dd, J = 8.3, 1.5 Hz, 1H), 5.39 (dd, J = 12.9, 5.3 Hz, 1H), 4.47 (s, 2H), 2.96-2.79 (m, 1H), 2.73-2.60 (m, 2H), 2.25-2.13 (m, 1H) |
| 28 | 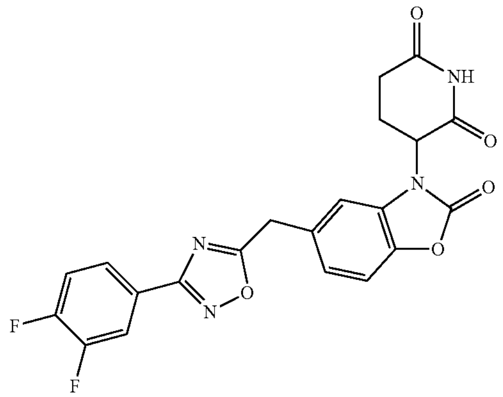 [SMILES: O=C1CCC(n2c(=O)oc3ccc(Cc4nc(-c5ccc(F)c(F)c5)no4)cc32)C(=O)N1] | 441.1 | 1H NMR (400 MHz, DMSO-$d_6$) δ 11.22 (s, 1H), 7.99-7.92 (m, 1H), 7.88-7.82 (m, 1H), 7.69-7.60 (m, 1H), 7.42-7.36 (m, 2H), 7.21 (dd, J = 8.3, 1.6 Hz, 1H), 5.38 (dd, J = 12.9, 5.3 Hz, 1H), 4.47 (s, 2H), 2.96-2.80 (m, 1H), 2.76-2.60 (m, 2H), 2.21-2.12 (m, 1H) |
| 29 | 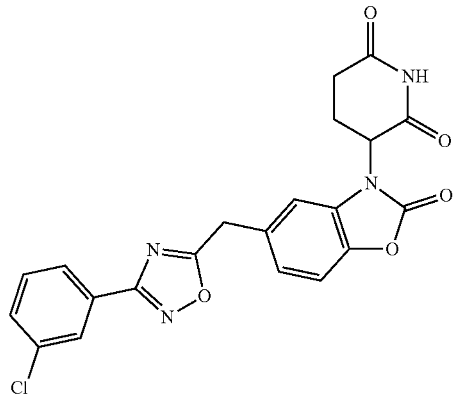 [SMILES: O=C1CCC(n2c(=O)oc3ccc(Cc4nc(-c5cccc(Cl)c5)no4)cc32)C(=O)N1] | 439.1 | 1H NMR (400 MHz, DMSO-$d_6$) δ 11.22 (s, 1H), 7.99-7.91 (m, 2H), 7.71-7.64 (m, 1H), 7.63-7.56 (m, 1H), 7.43-7.35 (m, 2H), 7.22 (dd, J = 8.3, 1.5 Hz, 1H), 5.39 (dd, J = 12.9, 5.2 Hz, 1H), 4.48 (s, 2H), 2.96-2.81 (m, 1H), 2.77-2.60 (m, 2H), 2.24-2.13 (m, 1H) |
| 30 | 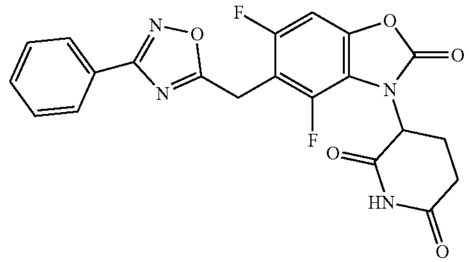 [SMILES: O=C1CCC(n2c(=O)oc3cc(F)c(Cc4nc(-c5ccccc5)no4)c(F)c32)C(=O)N1] | 423.4 | 1H NMR (400 MHz, $CDCl_3$) δ 8.14 (s, 1H), 8.06-8.01 (m, 2H), 7.49 (tdd, J = 7.7, 5.4, 2.1 Hz, 3H), 7.13 (d, J = 8.5 Hz, 1H), 6.89 (d, J = 5.9 Hz, 1H), 5.00 (dd, J = 12.9, 5.3 Hz, 1H), 4.33 (tt, J = 16.5, 8.3 Hz, 2H), 3.03 - 2.94 (m, 1H), 2.86-2.68 (m, 2H), 2.36-2.29 (m, 1H) |

-continued

| Compound # | Structure | $[M + H]^+$ | $^1H$ NMR |
|---|---|---|---|
| 31 | 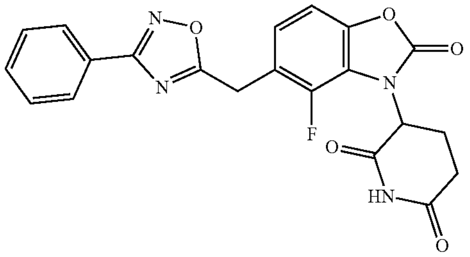 | 423.3 | $^1H$ NMR (400 MHz, $CDCl_3$) δ 8.05 (dt, J = 3.8, 2.2 Hz, 2H), 7.51-7.43 (m, 3H), 7.21-7.16 (m, 1H), 7.11 (d, J = 8.4 Hz, 1H), 5.21 (d, J = 8.3 Hz, 1H), 4.33 (dd, J = 43.6, 16.4 Hz, 2H), 2.97 (dd, J = 13.5, 2.4 Hz, 1H), 2.88-2.79 (m, 1H), 2.59 (s, 1H), 2.38 (ddd, J = 10.6, 5.4, 3.1 Hz, 1H) |
| 32 | 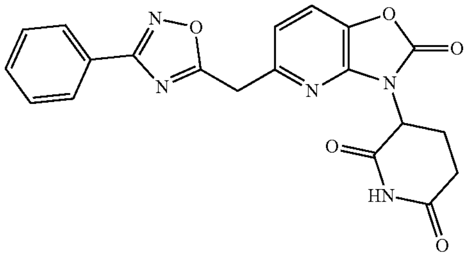 [SMILES: O=C1CCC(n2c(=O)oc3ccc(Cc4nc(-c5ccccc5)no4)nc32)C(=O)N1] | 406.3 | $^1H$ NMR (400 MHz, $CDCl_3$) δ 8.68 (d, J = 5.1 Hz, 1H), 8.53 (s, 1H), 8.15-8.03 (m, 1H), 7.86 (s, 1H), 7.65 (td, J = 7.6, 1.7 Hz, 1H), 7.60-7.52 (m, 1H), 7.40 (t, J = 7.8 Hz, 1H), 7.24 (s, 1H), 7.18 (dd, J = 8.3, 1.4 Hz, 1H), 6.96 (d, J = 1.2 Hz, 1H), 5.06 (dd, J = 12.8, 5.3 Hz, 1H), 4.34 (s, 2H), 3.15 (d, J = 10.5 Hz, 6H), 3.03-2.91 (m, 1H), 2.88-2.68 (m, 2H), 2.37-2.22 (m, 1H) |
| 33 | 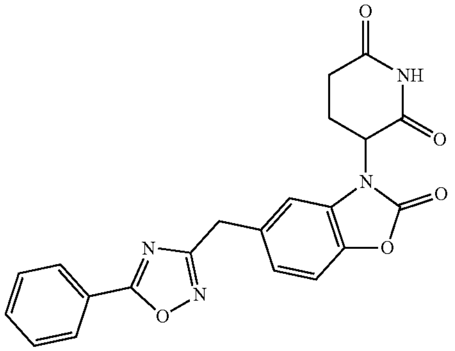 [SMILES: O=C1CCC(n2c(=O)oc3ccc(Cc4noc(-c5ccccc5)n4)cc32)C(=O)N1] | 405.1 | $^1H$ NMR (400 MHz, $DMSO-d_6$) δ 11.22 (s, 1H), 8.10-8.04 (m, 2H), 7.74-7.67 (m, 1H), 7.62 (t, J = 7.7 Hz, 2H), 7.37 (d, J = 8.2 Hz, 1H), 7.33 (d, J = 1.7 Hz, 1H), 7.16 (dd, J = 8.2, 1.7 Hz, 1H), 5.38 (dd, J = 12.7, 5.2 Hz, 1H), 4.21 (s, 2H), 2.88 (td, J = 14.1, 13.4, 5.7 Hz, 1H), 2.76-2.64 (m, 2H), 2.23-2.11 (m, 1H) |
| 95 | 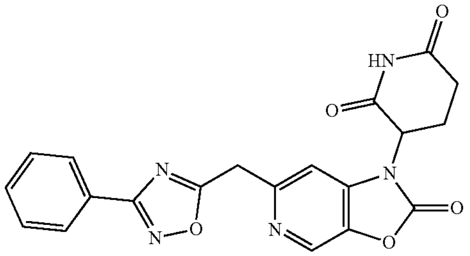 [SMILES: O=C1CCC(n2c(=O)oc3cnc(Cc4nc(-c5ccccc5)no4)cc32)C(=O)N1] | 406.3 | $^1HNMR$(400 MHz, $CDCl_3$) δ 8.48 (s, 1H), 8.29 (s, 1H), 8.05 (dd, J = 8.0, 1.6 Hz, 2H), 7.53-7.42 (m, 3H), 6.99 (s, 1H), 5.02 (dd, J = 13.0, 5.3 Hz, 1H), 4.51 (d, J = 1.6 Hz, 2H), 3.07-2.95 (m, 1H), 2.91-2.66 (m, 2H), 2.42-2.29 (m, 1H) |
| 96 | 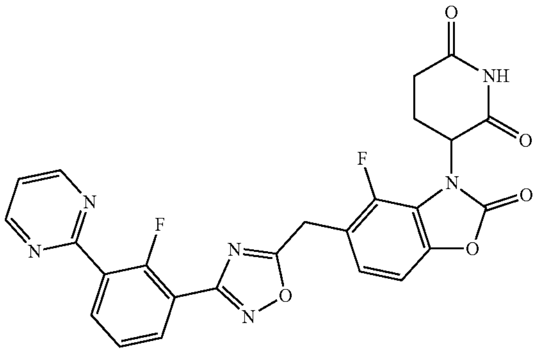 [SMILES: O=C1CCC(n2c(=O)oc3ccc(Cc4nc(-c5cccc(-c6ncccn6)c5F)no4)c(F)c32)C(=O)N1] | 519.4 | $^1H$ NMR (400 MHz, $DMSO-d_6$) δ 11.25 (s, 1H), 8.99 (d, J = 4.9 Hz, 2H), 8.23-8.14 (m, 1H), 8.09 (ddd, J = 8.0, 6.3, 1.9 Hz, 1H), 7.59-7.50 (m, 2H), 7.40-7.33 (m, 2H), 5.47 (s, 1H), 4.58 (s, 2H), 2.96 (s, 1H), 2.72-2.61 (m, 1H), 2.38-2.11 (m, 2H) |

-continued
| Compound # | Structure | $[M + H]^+$ | $^1H$ NMR |
|---|---|---|---|
| 97 | 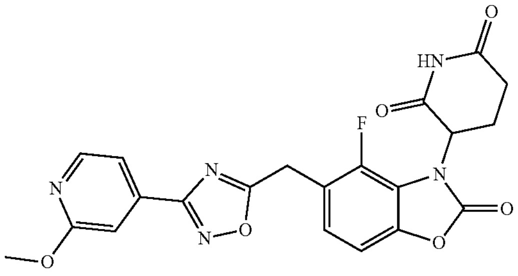 [SMILES: COc1cc(-c2noc(Cc3ccc4oc(=O)n(C5CCC(=O)NC5=O)c4c3F)n2)ccn1] | 454.1 | $^1H$ NMR (400 MHz, DMSO) δ 11.23 (s, 1H), 8.37 (d, J = 5.3 Hz, 1H), 7.48 (dd, J = 5.3, 1.2 Hz, 1H), 7.37-7.29 (m, 2H), 7.25 (s, 1H), 5.45 (s, 1H), 4.56 (s, 2H), 3.91 (s, 3H), 3.06-2.87 (m, 1H), 2.68-2.61 (m, 1H), 2.38-2.10 (m, 2H) |
| 98 | 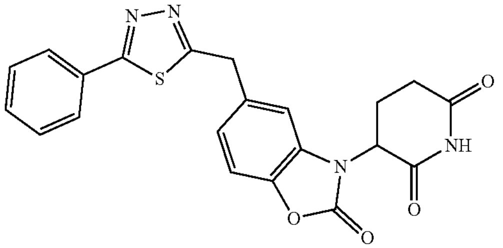 [SMILES: O=C1CCC(n2c(=O)oc3ccc(Cc4nnc(-c5ccccc5)s4)cc32)C(=O)N1] | 421.1 | $^1H$ NMR (400 MHz, DMSO-$d_6$) δ 11.21 (s, 1H), 7.92 (dt, J = 7.7, 1.7 Hz, 2H), 7.57-7.50 (m, 3H), 7.43-7.36 (m, 2H), 7.22 (dd, J = 8.2, 1.7 Hz, 1H), 5.39 (dd, J = 12.7, 5.2 Hz, 1H), 4.54 (s, 2H), 2.94-2.84 (m, 1H), 2.75-2.63 (m, 2H), 2.21-2.12 (m, 1H) |
| 99 | 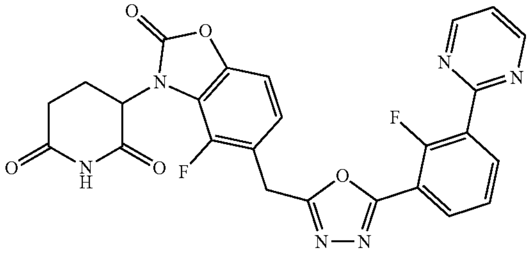 [SMILES: O=C1CCC(n2c(=O)oc3ccc(Cc4nnc(-c5cccc(-c6ncccn6)c5F)o4)c(F)c32)C(=O)N1] | 519.3 | $^1H$ NMR (400 MHz, DMSO) δ 11.25 (s, 1H), 9.00 (d, J = 4.9 Hz, 2H), 8.26-8.19 (m, 1H), 8.14-8.09 (m, 1H), 7.60-7.53 (m, 2H), 7.38-7.29 (m, 2H), 5.62-5.29 (m, 1H), 4.46 (s, 2H), 2.97 (s, 1H), 2.68-2.61 (m, 1H), 2.40-2.13 (m, 2H) |
| 100 | 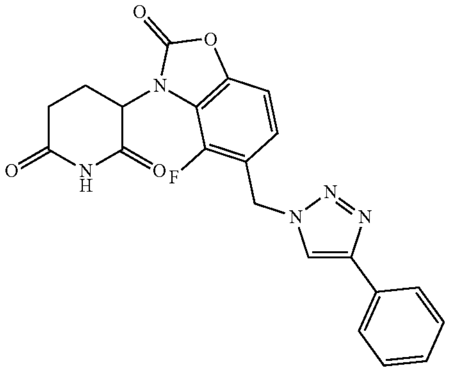 [SMILES: O=C1CCC(n2c(=O)oc3ccc(Cn4cc(-c5ccccc5)nn4)c(F)c32)C(=O)N1] | 422.3 | $^1H$ NMR (400 MHz, DMSO) δ 11.26 (s, 1H), 8.61 (s, 1H), 7.87-7.79 (m, 2H), 7.43 (t, J = 7.6 Hz, 2H), 7.39-7.26 (m, 3H), 5.72 (s, 2H), 5.46 (s, 1H), 2.96 (s, 1H), 2.72-2.62 (m, 1H), 2.27 (dd, J = 27.9, 22.5 Hz, 2H) |
| 101 | 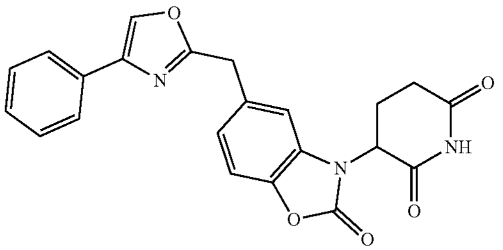 [SMILES: O=C1CCC(n2c(=O)oc3ccc(Cc4nc(-c5ccccc5)co4)cc32)C(=O)N1] | 404.3 | $^1H$ NMR (400 MHz, DMSO) δ 11.21 (s, 1H), 8.50 (s, 1H), 7.77-7.70 (m, 2H), 7.45-7.26 (m, 5H), 7.13 (dd, J = 8.3, 1.4 Hz, 1H), 5.39 (dd, J = 12.8, 5.2 Hz, 1H), 4.23 (s, 2H), 2.94-2.82 (m, 1H), 2.77-2.60 (m, 2H), 2.17 (dd, J = 10.7, 5.3 Hz, 1H) |

-continued
| Compound # | Structure | [M + H]+ | 1H NMR |
| --- | --- | --- | --- |
| 102 | 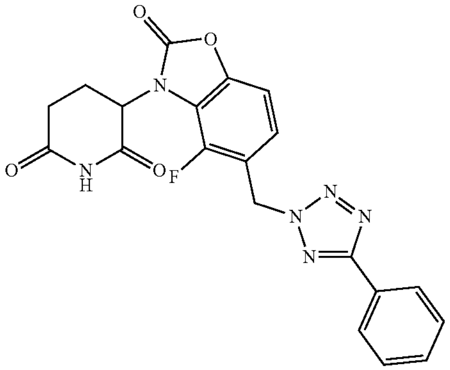 [SMILES: O=C1CCC(n2c(=O)oc3ccc(Cn4nnc(-c5ccccc5)n4)c(F)c32)C(=O)N1] | 423.3 | 1H NMR (400 MHz, DMSO) δ 11.25 (s, 1H), 8.02 (dd, J = 6.5, 3.1 Hz, 2H), 7.61-7.51 (m, 3H), 7.46-7.34 (m, 2H), 6.08 (s, 2H), 5.45 (s, 1H), 2.95 (s, 1H), 2.65 (d, J = 12.8 Hz, 1H), 2.30 (dd, J = 13.5, 7.5 Hz, 2H) |
| 103 | 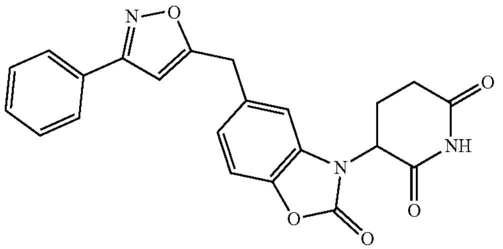 [SMILES: O=C1CCC(n2c(=O)oc3ccc(Cc4cc(-c5ccccc5)no4)cc32)C(=O)N1] | 404.3 | 1H NMR (400 MHz, DMSO) δ 11.22 (s, 1H), 7.87-7.78 (m, 2H), 7.52-7.45 (m, 3H), 7.38 (d, J = 8.2 Hz, 1H), 7.33 (d, J = 1.3 Hz, 1H), 7.14 (dd, J = 8.3, 1.5 Hz, 1H), 6.76 (s, 1H), 5.39 (dd, J = 12.9, 5.3 Hz, 1H), 4.23 (s, 2H), 2.95-2.82 (m, 1H), 2.76-2.62 (m, 2H), 2.18 (dd, J = 10.7, 5.2 Hz, 1H) |
| 104 | 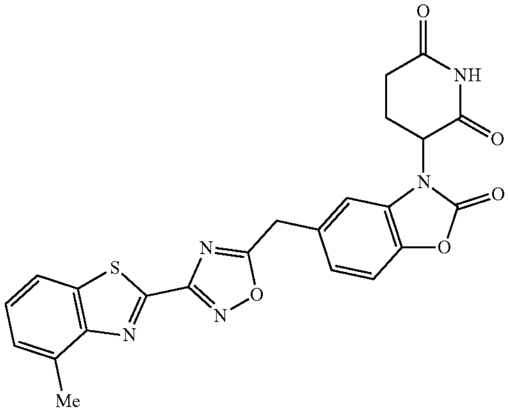 [SMILES: Cc1cccc2sc(-c3noc(Cc4ccc5oc(=O)n(C6CCC(=O)NC6=O)c5c4)n3)nc12] | 476.3 | 1H NMR (400 MHz, DMSO) δ 11.23 (s, 1H), 8.06 (d, J = 7.8 Hz, 1H), 7.57-7.35 (m, 4H), 7.25 (d, J = 8.5 Hz, 1H), 5.40 (dd, J = 12.8, 5.2 Hz, 1H), 4.55 (s, 2H), 2.96-2.83 (m, 1H), 2.77-2.60 (m, 5H), 2.24-2.13 (m, 1H). |
| 105 | 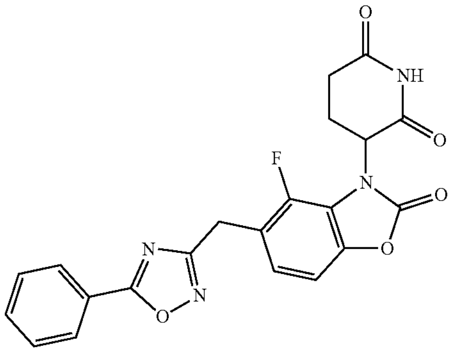 [SMILES: O=C1CCC(n2c(=O)oc3ccc(Cc4noc(-c5ccccc5)n4)c(F)c32)C(=O)N1] | 423.1 | 1H NMR (400 MHz, DMSO) δ 11.23 (s, 1H), 8.07 (d, J = 7.4 Hz, 2H), 7.70 (d, J = 7.5 Hz, 1H), 7.62 (t, J = 7.6 Hz, 2H), 7.29 (dd, J = 17.9, 7.7 Hz, 2H), 5.45 (s, 1H), 4.25 (s, 2H), 2.96 (s, 1H), 2.67 (s, 1H), 2.30 (d, J = 19.1 Hz, 2H). |

-continued

| Compound # | Structure | [M + H]+ | 1H NMR |
|---|---|---|---|
| 106 | 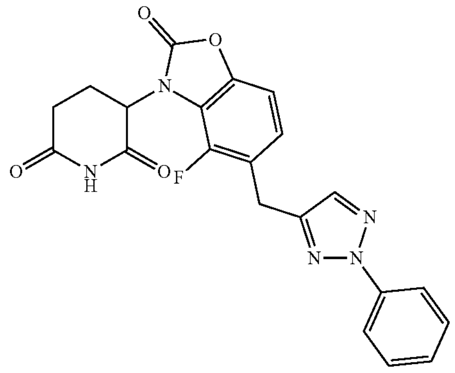 [SMILES: O=C1CCC(n2c(=O)oc3ccc(Cc4cnn(-c5ccccc5)n4)c(F)c32)C(=O)N1] | 422.2 | $^1$H NMR (400 MHz, DMSO) δ 11.25 (s, 1H), 7.95 (d, J = 8.0 Hz, 2H), 7.89 (s, 1H), 7.54 (t, J = 7.8 Hz, 2H), 7.39 (t, J = 7.4 Hz, 1H), 7.28 (d, J = 8.3 Hz, 1H), 7.21 (t, J = 7.6 Hz, 1H), 5.46 (s, 1H), 4.18 (s, 2H), 2.97 (s, 1H), 2.66 (d, J = 17.2 Hz, 1H), 2.28 (d, J = 4.1 Hz, 2H). |
| 107 | 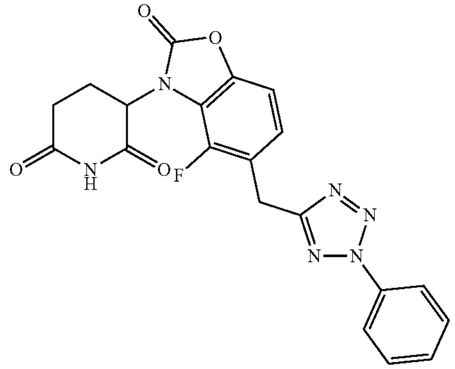 | 423.3 | $^1$H NMR (400 MHz, DMSO-$d_6$) δ 11.24 (s, 1H), 8.16-7.96 (m, 2H), 7.72-7.54 (m, 3H), 7.38-7.14 (m, 2H), 5.46 (s, 1H), 4.43 (s, 2H), 2.96 (s, 1H), 2.66 (d, J = 17.5 Hz, 1H), 2.41-2.09 (m, 2H). |

General Method B

Preparation of 3-(5-((3-(2-Fluoro-3-(pyrimidin-4-yl) phenyl)-1,2,4-oxadiazol-5-yl)methyl)-2-oxobenzo[d] oxazol-3(2H)-yl)piperidine-2,6-dione (Compound 34)

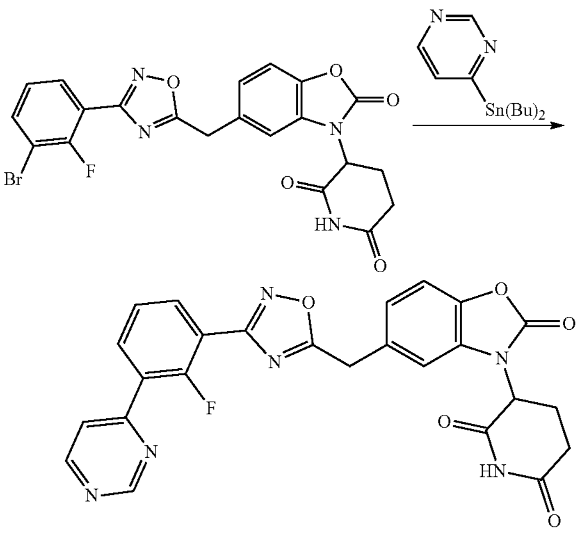

In sealed tube, to a stirred solution of 3-(5-((3-(3-bromo-2-fluorophenyl)-1,2,4-oxadiazol-5-yl)methyl)-2-oxobenzo[d]oxazol-3(2H)-yl)piperidine-2,6-dione (0.100 g, 0.199 mmol) in 1,4 dioxane (5 mL), was degassed with nitrogen for 15 min. Then 4-(tributylstannyl) pyrimidine (0.147 g, 0.399 mmol) and bis(tri-tert-butylphosphine)palladium(0) (0.01 g, 0.02 mmol) were added and the reaction mixture was stirred at 100° C. for 16 h. After completion of the reaction, the reaction mixture was quenched with water (5 mL) and extracted with EtOAc (3x5 mL). The combined organic layers were washed with brine solution (2x5 mL), dried over anhydrous sodium sulphate, filtered and concentrated under reduced pressure to afford crude compound. Thus, obtained crude compound was purified by flash column chromatography and RP prep-HPLC [column: X-bridge phenyl (10x250) 5 μm, mobile phase (A): 0.1% FA in water, mobile phase (B): 100% acetonitrile, gradient: 0/10, 1/10, 10/35, 14/35, 14.1/100, 16/100, 16.1/10, 19/10. Flow: 16 mL/min, solubility: acetonitrile+THF+water] and the obtained fractions were concentrated under reduced pressure followed by lyophilized to afford 3-(5-((3-(2-fluoro-3-(pyrimidin-4-yl)phenyl)-1,2,4-oxadiazol-5-yl) methyl)-2-oxobenzo[d]oxazol-3(2H)-yl)piperidine-2,6-dione (12 mg, 12%) as an off white solid. MS (LCMS) m/z 501.32 [M+H]$^+$. $^1$H NMR (400 MHz, DMSO-$d_6$) δ 11.22 (s, 1H), 9.35 (d, J=0.8 Hz, 1H), 8.95 (d, J=5.2 Hz, 1H), 8.25-8.21 (m, 1H), 8.17-8.14 (m, 1H), 7.98 (d, J=5.2 Hz, 1H), 7.58 (t, J=7.8 Hz, 1H), 7.43-7.40 (m, 2H), 7.24 (d, J=8.4 Hz, 1H), 5.37 (d, J=5.2 Hz, 1H), 4.51 (s, 2H), 2.91-2.86 (m, 1H), 2.74-2.71 (m, 1H), 2.68-2.65 (m, 1H), 2.22-2.21 (m, 1H)

Compounds below may be synthesized utilizing General Method B.

| Compound # | Structure | [M + H]$^+$ | $^1$H NMR |
|---|---|---|---|
| 35 | 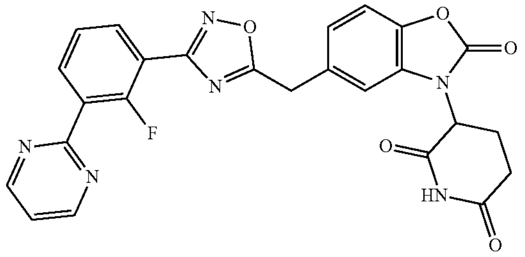 [SMILES: O=C1CCC(n2c(=O)oc3ccc(Cc4nc(-c5cccc(-c6ncccn6)c5F)no4)cc32)C(=O)N1] | 501.28 | $^1$H NMR (400 MHz, DMSO-$d_6$) δ 11.22 (s, 1H), 8.99 (d, J = 4.8 Hz, 1H), 8.49 (s, 1H), 8.19-8.15 (m, 1H), 8.13-8.09 (m, 1H), 7.58-7.51 (m, 2H), 7.41 (d, J = 8.0 Hz, 2H), 7.24 (t, J = 8.4 Hz, 1H), 5.40 (dd, J = 12.8, 5.2 Hz, 1H), 4.50 (s, 2H), 2.96-2.85 (m, 1H), 2.74-2.61 (m, 2H), 2.21-2.16 (m, 1H) |
| 36 | 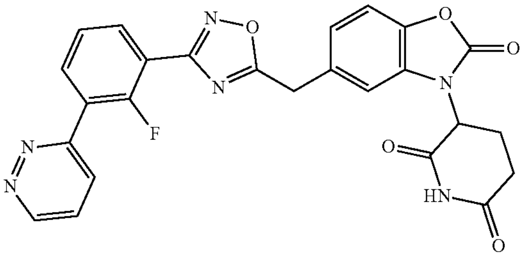 [SMILES: O=C1CCC(n2c(=O)oc3ccc(Cc4nc(-c5cccc(-c6cccnn6)c5F)no4)cc32)C(=O)N1] | 501.3 | $^1$H NMR (400 MHz, DMSO) δ 11.24 (s, 1H), 9.53 (d, J = 1.1 Hz, 1H), 9.38 (dd, J = 5.4, 1.1 Hz, 1H), 8.15-8.10 (m, 1H), 7.97 (td, J = 7.6, 1.6 Hz, 2H), 7.59 (t, J = 7.8 Hz, 1H), 7.42 (d, J = 8.0 Hz, 2H), 7.23 (dd, J = 8.4, 1.3 Hz, 1H), 5.40 (dd, J = 12.8, 5.2 Hz, 1H), 4.51 (s, 2H), 2.91 (td, J = 14.7, 9.3 Hz, 1H), 2.71 (dt, J = 27.3, 10.0 Hz, 2H), 2.23-2.14 (m, 1H) |
| 108 | 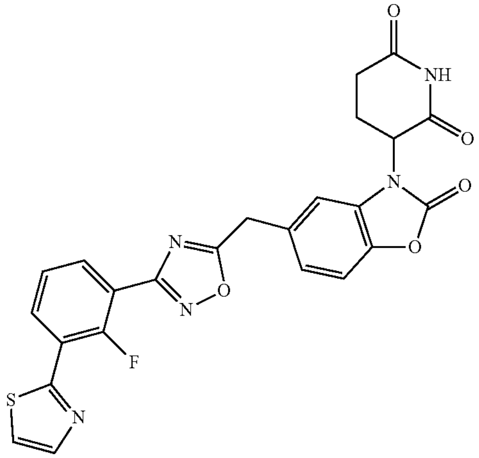 [SMILES: O=C1CCC(n2c(=O)oc3ccc(Cc4nc(-c5cccc(-c6nccs6)c5F)no4)cc32)C(=O)N1] | 506.1 | $^1$H NMR (400 MHz, DMSO) δ 11.23 (s, 1H), 8.51-8.41 (m, 1H), 8.12-8.05 (m, 2H), 8.01 (d, J = 3.2 Hz, 1H), 7.56 (t, J = 7.8 Hz, 1H), 7.45-7.38 (m, 2H), 7.24 (dd, J = 8.4, 1.5 Hz, 1H), 5.40 (dd, J = 12.9, 5.3 Hz, 1H), 4.52 (s, 2H), 2.91 (td, J = 14.6, 9.1 Hz, 1H), 2.71 (dt, J = 27.5, 10.1 Hz, 2H), 2.24-2.12 (m, 1H) |
| 109 | 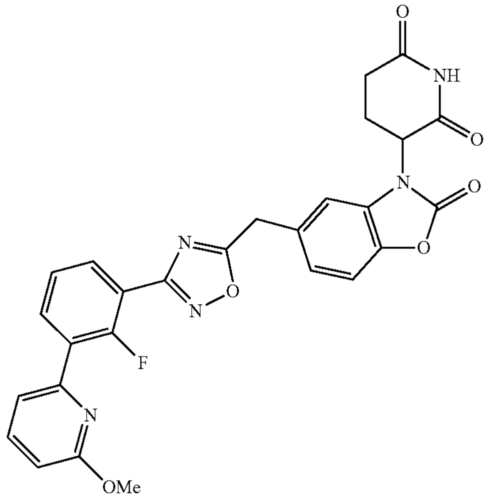 [SMILES: COc1cccc(-c2cccc(-c3noc(Cc4ccc5oc(=O)n(C6CCC(=O)NC6=O)c5c4)n3)c2F)n1] | 530.3 | $^1$H NMR (400 MHz, DMSO) δ 11.24 (s, 1H), 8.20 (td, J = 7.6, 1.8 Hz, 1H), 8.09-7.97 (m, 1H), 7.85 (dd, J = 8.2, 7.5 Hz, 1H), 7.52 (t, J = 7.8 Hz, 1H), 7.47 (dd, J = 7.4, 1.9 Hz, 1H), 7.42 (dd, J = 4.8, 3.3 Hz, 2H), 7.24 (dd, J = 8.3, 1.5 Hz, 1H), 6.89 (d, J = 8.2 Hz, 1H), 5.40 (dd, J = 12.9, 5.3 Hz, 1H), 4.51 (s, 2H), 3.94 (s, 3H), 2.99-2.82 (m, 1H), 2.77-2.59 (m, 2H), 2.25-2.12 (m, 1H) |

-continued

| Compound # | Structure | [M + H]$^+$ | $^1$H NMR |
|---|---|---|---|
| 110 | 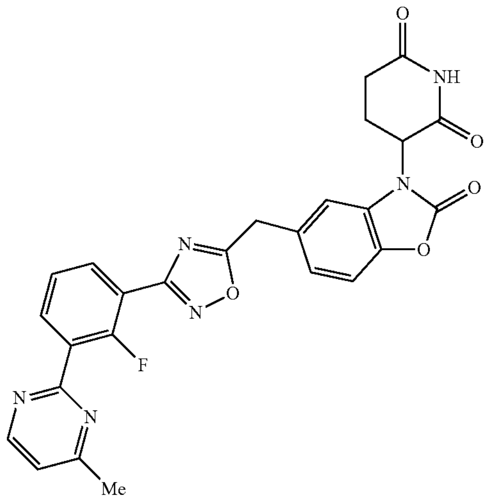 [SMILES: Cc1ccnc(-c2cccc(-c3noc(Cc4ccc5oc(=O)n(C6CCC(=O)NC6=O)c5c4)n3)c2F)n1] | 515.3 | $^1$H NMR (400 MHz, $CDCl_3$) δ 9.12 (s, 1H), 8.83 (s, 1H), 8.23 (s, 1H), 8.12 (t, J = 6.8 Hz, 1H), 7.41 (t, J = 7.6 Hz, 1H), 7.28 (d, J = 7.0 Hz, 1H), 7.23 (d, J = 8.5 Hz, 1H), 7.16 (d, J = 7.9 Hz, 2H), 5.11 (d, J = 7.8 Hz, 1H), 4.34 (q, J = 16.1 Hz, 2H), 2.96 (d, J = 16.6 Hz, 1H), 2.88 (d, J = 13.1 Hz, 1H), 2.83-2.74 (m, 1H), 2.70 (s, 3H), 2.33 (s, 1H) |
| 111 | 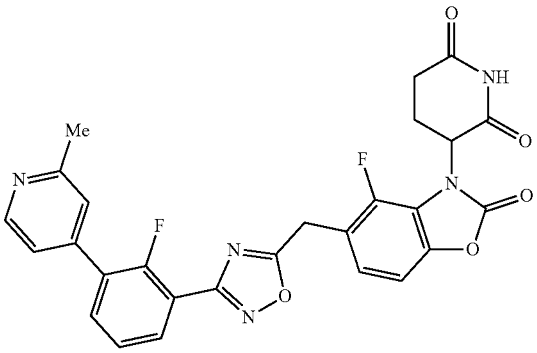 [SMILES: Cc1cc(-c2cccc(-c3noc(Cc4ccc5oc(=O)n(C6CCC(=O)NC6=O)c5c4F)n3)c2F)ccn1] | 532.2 | $^1$H NMR (400 MHz, $CDCl_3$) δ 8.60 (d, J = 5.2 Hz, 1H), 8.22 (s, 1H), 8.11-8.01 (m, 1H), 7.60 (td, J = 7.5, 1.7 Hz, 1H), 7.43-7.35 (m, 2H), 7.33 (d, J = 5.2 Hz, 1H), 7.22-7.16 (m, 1H), 7.12 (d, J = 8.4 Hz, 1H), 5.22 (d, J = 8.3 Hz, 1H), 4.37 (dd, J = 40.1, 16.3 Hz, 2H), 2.97 (d, J = 15.9 Hz, 1H), 2.89-2.79 (m, 1H), 2.64 (s, 3H), 2.42-2.33 (m, 2H) |
| 112 | 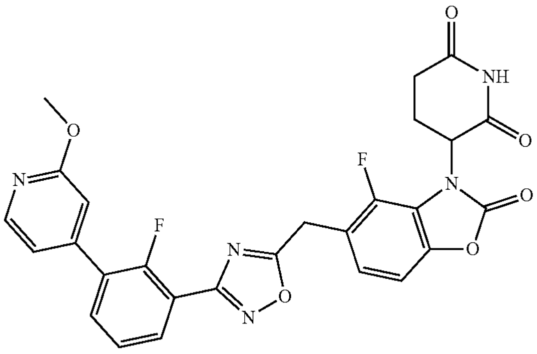 [SMILES: COc1cc(-c2cccc(-c3noc(Cc4ccc5oc(=O)n(C6CCC(=O)NC6=O)c5c4F)n3)c2F)ccn1] | 548.2 | $^1$H NMR (400 MHz, $CDCl_3$) δ 8.34 (s, 1H), 8.12 (dd, J = 15.2, 8.4 Hz, 2H), 7.63 (s, 1H), 7.41 (s, 1H), 7.26 (s, 1H), 7.22-7.17 (m, 1H), 7.12 (d, J = 8.3 Hz, 2H), 5.20 (s, 1H), 4.37 (dd, J = 38.4, 16.5 Hz, 2H), 4.17 (s, 3H), 2.97 (d, J = 15.6 Hz, 1H), 2.85 (dd, J = 22.3, 9.2 Hz, 1H), 2.47-2.31 (m, 2H) |
| 113 | 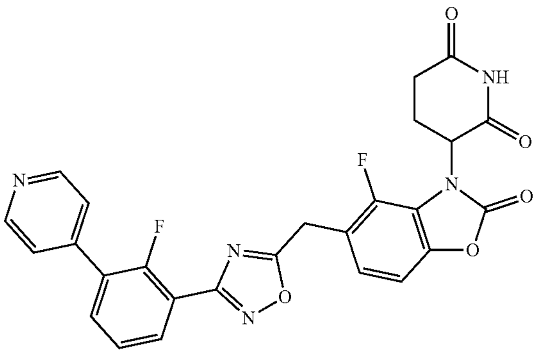 [SMILES: O=C1CCC(n2c(=O)oc3ccc(Cc4nc(-c5cccc(-c6ccncc6)c5F)no4)c(F)c32)C(=O)N1] | 518.3 | $^1$H NMR (400 MHz, $CDCl_3$) δ 8.71 (d, J = 4.2 Hz, 2H), 8.47 (s, 1H), 8.08 (t, J = 6.4 Hz, 1H), 7.61 (t, J = 6.8 Hz, 1H), 7.52 (d, J = 4.2 Hz, 2H), 7.39 (t, J = 7.7 Hz, 1H), 7.19 (t, J = 7.5 Hz, 1H), 7.12 (d, J = 8.3 Hz, 1H), 5.22 (d, J = 8.3 Hz, 1H), 4.37 (dd, J = 39.3, 16.4 Hz, 2H), 2.97 (d, J = 16.2 Hz, 1H), 2.83 (dd, J = 21.8, 8.9 Hz, 1H), 2.60 (s, 1H), 2.39 (d, J = 5.8 Hz, 1H) |

-continued

| Compound # | Structure | [M + H]$^+$ | $^1$H NMR |
|---|---|---|---|
| 114 | 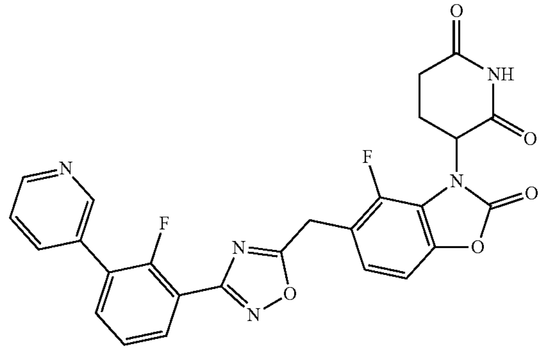 [SMILES: O=C1CCC(n2c(=O)oc3ccc(Cc4nc(-c5cccc(-c6cccnc6)c5F)no4)c(F)c32)C(=O)N1] | 518.4 | $^1$HNMR(400 MHz, CDCl3) δ 8.81 (s, 1H), 8.65 (dd,J = 4.8, 1.5 Hz, 1H), 8.18 (s, 1H), 8.09-8.01 (m, 1H), 7.93 (dd,J = 7.9, 1.8 Hz, 1H), 7.59 (td,J = 7.5, 1.7 Hz, 1H), 7.40 (dt,J = 15.4, 6.3 Hz, 2H), 7.23-7.16 (m, 1H), 7.12 (d,J = 8.4 Hz, 1H), 5.21 (d,J = 7.6 Hz, 1H), 4.37 (dd,J = 42.6, 16.4 Hz, 2H), 2.97 (d,J = 16.5 Hz, 1H), 2.90-2.74 (m, 1H), 2.61 (s, 1H), 2.47-2.31 (m, 1H) |

General Method C 3-(2-oxo-5-((3-(thiazol-2-yl)-1,2,4-oxadiazol-5-yl)methyl)benzo[d]oxazol-3(2H)-yl)piperidine-2,6-dione (Compound 37)

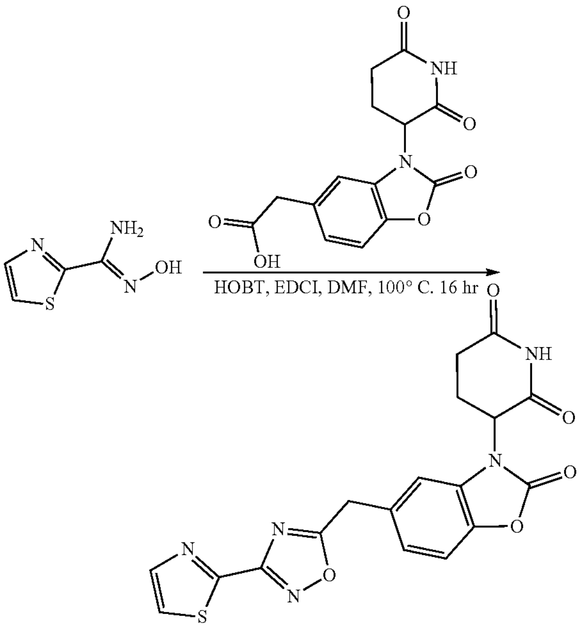

To a solution of (Z)—N'-hydroxythiazole-2-carboximidamide (40 mg, 0.13 mmol) in DMF (2 mL) were added HOBt (18 mg, 0.13 mmol), EDCI (38 mg, 0.20 mmol) and 2-(3-(2,6-dioxopiperidin-3-yl)-2-oxo-2,3-dihydrobenzo[d]oxazol-5-yl)acetic acid (19 mg, 0.13 mmol). The mixture was stirred at rt for 1 hrs and then stirred at 110° C. for 16 hrs. The reaction mixture was poured into water and extracted with EA. The organic phase was concentrated in vacuo and purified by FCC (DCM:MeOH=6%) to get crude product (30 mg) which was then purified by prep-HPLC (C18, Wave length: 220 nm/254 nm; phase A: $H_2O$ (FA 0.1%), phase B: MeCN 10%-95%; 17 min/20 min) to get 3-(2-oxo-5-((3-(thiazol-2-yl)-1,2,4-oxadiazol-5-yl)methyl)benzo[d]oxazol-3(2H)-yl)piperidine-2,6-dione (6.2 mg, 0.02 mmol, 11.5%). LCMS (m/z): [M]+ calcd: 411.06, found: 412.3. $^1$H NMR (400 MHz, $CDCl_3$) δ 8.22 (s, 1H), 8.06 (d, J=3.1 Hz, 1H), 7.59 (d, J=3.2 Hz, 1H), 7.24 (s, 1H), 7.19 (dd, J=8.3, 1.6 Hz, 1H), 6.97 (d, J=1.4 Hz, 1H), 5.02 (dd, J=12.7, 5.3 Hz, 1H), 4.34 (s, 2H), 3.06-2.93 (m, 1H), 2.90-2.71 (m, 2H), 2.39-2.27 (m, 1H).

Compounds below may be synthesized utilizing General Method C.

| Compound # | Structure | [M + H]$^+$ | $^1$H NMR |
|---|---|---|---|
| 38 | 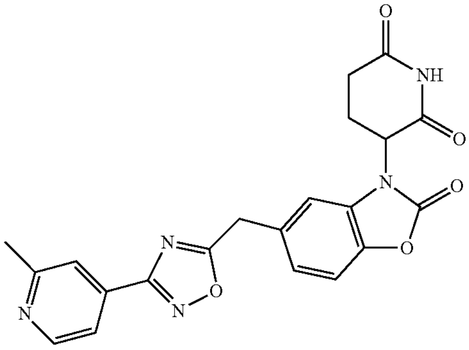 [SMILES: Cc1cc(-c2noc(Cc3ccc4oc(=O)n(C5CCC(=O)NC5=O)c4c3)n2)ccn1] | 420.2 | $^1$H NMR (400 MHz, $CDCl_3$) δ 8.65 (d, J = 5.1 Hz, 1H), 8.28 (s, 1H), 7.78 (s, 1H), 7.71 (d, J = 5.1 Hz, 1H), 7.25 (s, 1H), 7.19 (dd, J = 8.3, 1.5 Hz, 1H), 6.88 (d, J = 1.3 Hz, 1H), 5.04 (dd, J = 12.8, 5.3 Hz, 1H), 4.32 (s, 2H), 3.05-2.95 (m, 1H), 2.89-2.69 (m, 2H), 2.64 (s, 3H), 2.36-2.30 (m, 1H) |

-continued
| Compound # | Structure | [M + H]+ | 1H NMR |
|---|---|---|---|
| 39 | 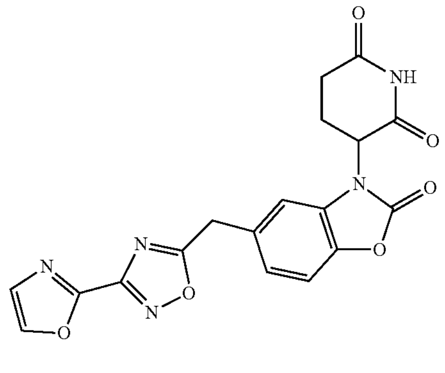 [SMILES: O=C1CCC(n2c(=O)oc3ccc(Cc4nc(-c5ncco5)no4)cc32)C(=O)N1] | 396.3 | 1H NMR (400 MHz, $CDCl_3$) δ 8.30 (s, 1H), 7.87 (d, J = 0.6 Hz, 1H), 7.42 (s, 1H), 7.23 (s, 1H), 7.20-7.15 (m, 1H), 6.97 (d, J = 1.5 Hz, 1H), 5.02 (dd, J = 12.8, 5.4 Hz, 1H), 4.35 (s, 2H), 3.06-2.95 (m, 1H), 2.79 (ddd, J = 17.0, 13.3, 6.5 Hz, 2H), 2.38-2.28 (m, 1H) |
| 40 | 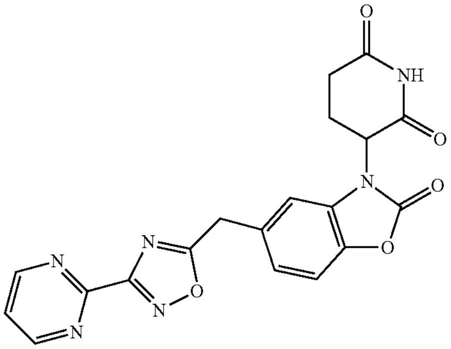 [SMILES: O=C1CCC(n2c(=O)oc3ccc(Cc4nc(-c5ncccn5)no4)cc32)C(=O)N1] | 407.0 | 1H NMR (400 MHz, DMSO) δ 11.23 (s, 1H), 9.01 (d, J = 4.9 Hz, 2H), 7.70 (t, J = 4.9 Hz, 1H), 7.41 (dd, J = 9.3, 4.8 Hz, 2H), 7.23 (dd, J = 8.3, 1.5 Hz, 1H), 5.39 (dd, J = 12.9, 5.2 Hz, 1H), 4.50 (s, 2H), 2.94-2.84 (m, 1H), 2.74-2.63 (m, 2H), 2.22-2.14 (m, 1H) |
| 41 | 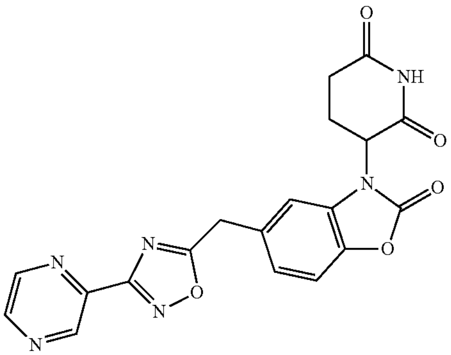 [SMILES: O=C1CCC(n2c(=O)oc3ccc(Cc4nc(-c5cnccn5)no4)cc32)C(=O)N1] | 407.3 | 1H NMR (400 MHz, $CDCl_3$) δ 9.35 (d, J = 1.4 Hz, 1H), 8.77-8.75 (m, 1H), 8.74 (d, J = 2.5 Hz, 1H), 8.18 (s, 1H), 7.25 (s, 1H), 7.22-7.18 (m, 1H), 6.95 (s, 1H), 5.02 (dd, J = 12.8, 5.3 Hz, 1H), 4.37 (s, 2H), 2.99 (d, J = 17.1 Hz, 1H), 2.90-2.73 (m, 2H), 2.33 (dd, J = 11.5, 6.1 Hz, 1H) |
| 42 | 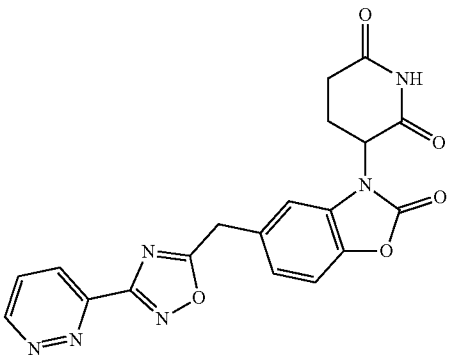 [SMILES: O=C1CCC(n2c(=O)oc3ccc(Cc4nc(-c5cccnn5)no4)cc32)C(=O)N1] | 407.3 | 1H NMR (400 MHz, CDCl3) δ 9.35 (dd, J = 5.0, 1.7 Hz, 1H), 8.36 (s, 1H), 8.23 (dd, J = 8.5, 1.7 Hz, 1H), 7.66 (dd, J = 8.5, 5.0 Hz, 1H), 7.24 (s, 1H), 7.22-7.18 (m, 1H), 7.04 (s, 1H), 5.04 (dd, J = 12.7, 5.4 Hz, 1H), 4.39 (s, 2H), 2.99 (d, J = 13.3 Hz, 1H), 2.89-2.74 (m, 2H), 2.38-2.29 (m, 1H) |

-continued
| Compound # | Structure | [M + H]+ | $^1$H NMR |
|---|---|---|---|
| 43 | 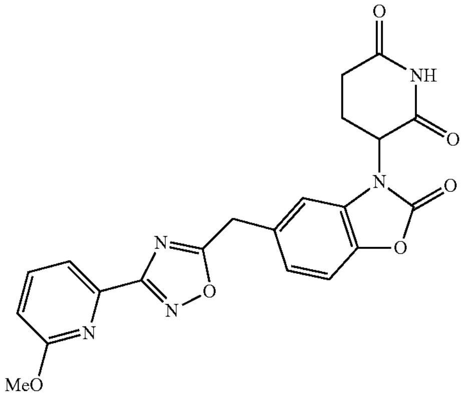 [SMILES: COc1cccc(-c2noc(Cc3ccc4oc(=O)n(C5CCC(=O)NC5=O)c4c3)n2)n1] | 436.4 | $^1$H NMR (400 MHz, $CDCl_3$) δ 8.14 (s, 1H), 7.73-7.68 (m, 1H), 7.66 (d, J = 6.8 Hz, 1H), 7.23 (s, 1H), 7.18 (d, J = 8.5 Hz, 1H), 6.90 (d, J = 7.7 Hz, 2H), 5.03 (dd, J = 12.8, 5.2 Hz, 1H), 4.34 (s, 2H), 4.04 (s, 3H), 2.98 (d, J = 15.7 Hz, 1H), 2.90-2.69 (m, 2H), 2.36-2.27 (m, 1H) |
| 44 | 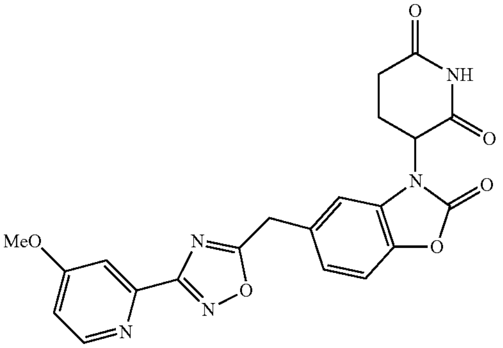 [SMILES: COc1ccnc(-c2noc(Cc3ccc4oc(=O)n(C5CCC(=O)NC5=O)c4c3)n2)c1] | 436.4 | $^1$H NMR (400 MHz, $CDCl_3$) δ 8.65 (d, J = 5.9 Hz, 1H), 8.28 (s, 1H), 7.67 (d, J = 2.3 Hz, 1H), 7.22 (d, J = 8.2 Hz, 1H), 7.16 (d, J = 8.1 Hz, 1H), 7.02 (d, J = 3.4 Hz, 1H), 5.22 (s, 1H), 4.35 (s, 2H), 3.98 (s, 3H), 2.95 (d, J = 5.7 Hz, 2H), 2.86-2.73 (m, 1H), 2.40-2.28 (m, 1H) |
| 45 | 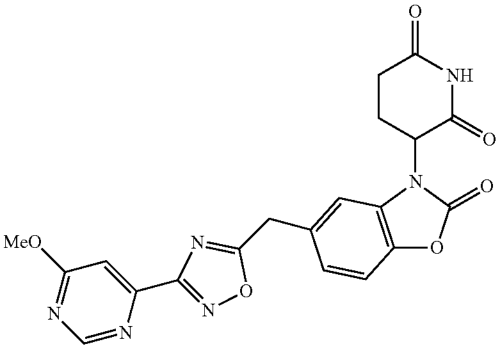 [SMILES: COc1cc(-c2noc(Cc3ccc4oc(=O)n(C5CCC(=O)NC5=O)c4c3)n2)ncn1] | 437.4 | $^1$H NMR (400 MHz, $CDCl_3$) δ 8.98 (s, 1H), 8.21 (s, 1H), 7.49 (d, J = 0.8 Hz, 1H), 7.24 (d, J = 8.3 Hz, 1H), 7.16 (dd, J = 8.2, 1.5 Hz, 1H), 7.06 (s, 1H), 5.13 (dd, J = 12.9, 5.4 Hz, 1H), 4.35 (s, 2H), 4.09 (s, 3H), 3.00-2.71 (m, 3H), 2.38-2.28 (m, 1H) |
| 46 | 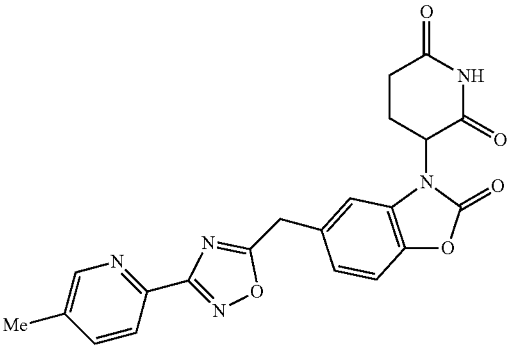 [SMILES: Cc1ccc(-c2noc(Cc3ccc4oc(=O)n(C5CCC(=O)NC5=O)c4c3)n2)nc1] | 420.5 | $^1$H NMR (400 MHz, DMSO) δ 11.23 (s, 1H), 8.57 (s, 1H), 7.93 (d, J = 8.0 Hz, 1H), 7.81 (dd, J = 8.0, 1.6 Hz, 1H), 7.40 (dd, J = 6.3, 4.9 Hz, 2H), 7.22 (dd, J = 8.3, 1.4 Hz, 1H), 5.39 (dd, J = 12.8, 5.2 Hz, 1H), 4.47 (s, 2H), 2.96-2.85 (m, 1H), 2.74-2.63 (m, 2H), 2.38 (s, 3H), 2.23-2.14 (m, 1H) |

-continued
| Compound # | Structure | [M + H]+ | 1H NMR |
|---|---|---|---|
| 47 | 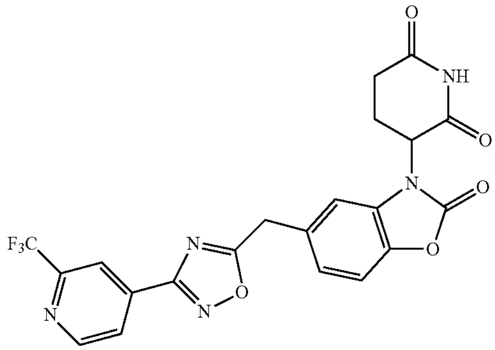 [SMILES: O=C1CCC(n2c(=O)oc3ccc(Cc4nc(-c5ccnc(C(F)(F)F)c5)no4)cc32)C(=O)N1] | 474.3 | 1H NMR (400 MHz, $CDCl_3$) δ 8.89 (d, J = 5.0 Hz, 1H), 8.31 (s, 1H), 8.16 (s, 1H), 8.12 (dd, J = 5.0, 1.0 Hz, 1H), 7.28 (s, 1H), 7.19 (dd, J = 8.3, 1.7 Hz, 1H), 6.88 (d, J = 1.4 Hz, 1H), 5.05 (dd, J = 12.9, 5.3 Hz, 1H), 4.35 (s, 2H), 3.06-2.96 (m, 1H), 2.79 (dtd, J = 38.2, 13.3, 8.6 Hz, 2H), 2.39-2.30 (m, 1H) |
| 48 | 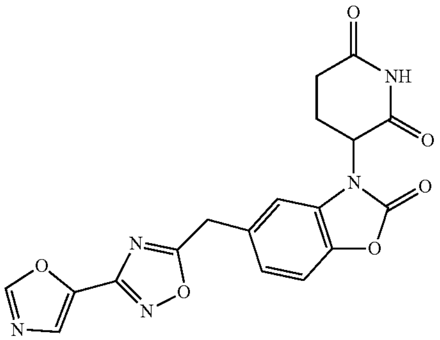 | 396.3 | 1H NMR (400 MHz, $CDCl_3$) δ 8.16 (s, 1H), 8.06 (s, 1H), 7.78 (s, 1H), 7.25 (s, 1H), 7.17 (dd, J = 8.3, 1.6 Hz, 1H), 6.87 (d, J = 1.5 Hz, 1H), 5.03 (dd, J = 12.9, 5.3 Hz, 1H), 4.31 (s, 2H), 3.04-2.96 (m, 1H), 2.89-2.70 (m, 2H), 2.36-2.29 (m, 1H |
| 49 | 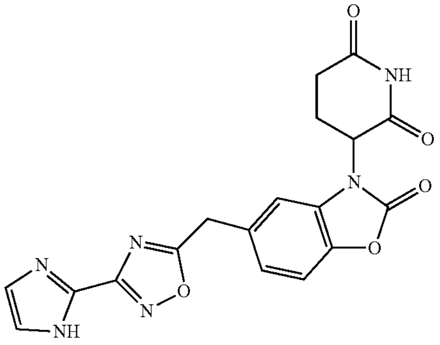 [SMILES: O=C1CCC(n2c(=O)oc3ccc(Cc4nc(-c5ncc[nH]5)no4)cc32)C(=O)N1] | 395.3 | 1H NMR (400 MHz, DMSO) δ 11.24 (s, 1H), 7.58 (s, 2H), 7.41 (dd, J = 11.1, 4.8 Hz, 2H), 7.21 (dd, J = 8.3, 1.5 Hz, 1H), 5.41 (dd, J = 13.0, 5.3 Hz, 1H), 4.53 (s, 2H), 2.93-2.86 (m, 1H), 2.69 (dd, J = 17.2, 9.9 Hz, 2H), 2.22-2.14 (m, 1H) |
| 50 | 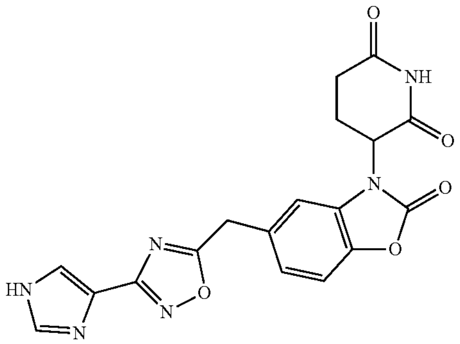 [SMILES: O=C1CCC(n2c(=O)oc3ccc(Cc4nc(-c5c[nH]cn5)no4)cc32)C(=O)N1] | 395.3 | 1H NMR (400 MHz, DMSO-d6) δ 11.23 (s, 1H), 8.78 (s, 1H), 8.18 (s, 1H), 7.41 (d, J = 8.2 Hz, 1H), 7.38 (s, 1H), 7.19 (d, J = 8.3 Hz, 1H), 5.40 (dd, J = 12.9, 5.3 Hz, 1H), 4.47 (s, 2H), 2.90 (dd, J = 11.0, 7.6 Hz, 1H), 2.69 (dd, J = 17.1, 9.7 Hz, 2H), 2.21-2.14 (m, 1H) |

-continued
| Compound # | Structure | $[M + H]^+$ | $^1$H NMR |
|---|---|---|---|
| 51 | 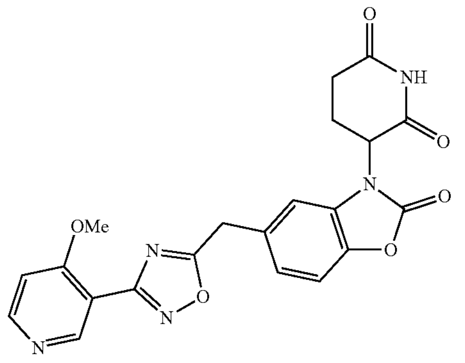 [SMILES: COc1ccncc1-c1noc(Cc2ccc3oc(=O)n(C4CCC(=O)NC4=O)c3c2)n1] | 436.3 | $^1$H NMR (400 MHz, DMSO-$d_6$) δ 11.22 (s, 1H), 8.82 (s, 1H), 8.61 (d, J = 5.9 Hz, 1H), 7.43-7.36 (m, 2H), 7.29 (d, J = 6.0 Hz, 1H), 7.21 (dd, J = 8.3, 1.6 Hz, 1H), 5.39 (dd, J = 12.8, 5.3 Hz, 1H), 4.47 (s, 2H), 3.94 (s, 3H), 2.87 (d, J = 15.6 Hz, 1H), 2.64 (s, 1H), 2.54 (s, 2H), 2.18 (dd, J = 11.0, 5.5 Hz, 1H) |
| 52 | 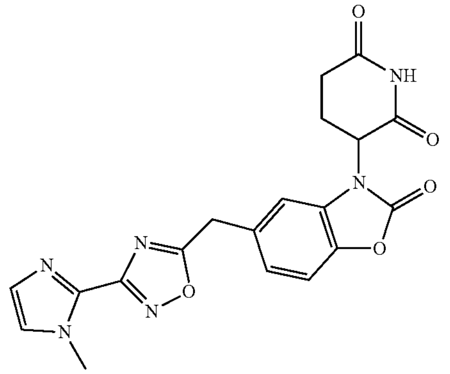 [SMILES: Cn1ccnc1-c1noc(Cc2ccc3oc(=O)n(C4CCC(=O)NC4=O)c3c2)n1] | 409.4 | $^1$H NMR (400 MHz, $CDCl_3$) δ 8.87 (s, 1H), 7.26-7.20 (m, 1H), 7.18-7.12 (m, 2H), 7.10-6.99 (m, 2H), 5.10-4.98 (m, 1H), 4.33-4.16 (m, 2H), 3.96 (s, 3H), 2.92-2.76 (m, 2H), 2.75-2.63 (m, 1H), 2.33-2.22 (m, 1H) |
| 53 | 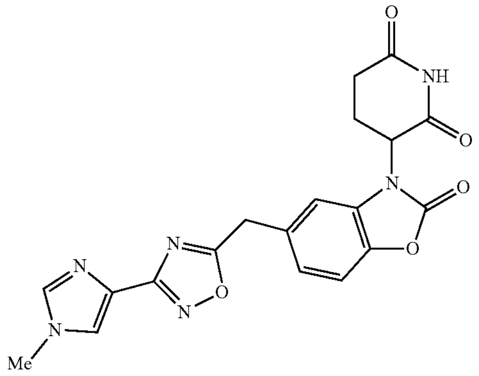 [SMILES: Cn1cnc(-c2noc(Cc3ccc4oc(=O)n(C5CCC(=O)NC5=O)c4c3)n2)c1] | 409.3 | $^1$H NMR (400 MHz, $CDCl_3$) δ 8.67 (s, 1H), 7.56 (d, J = 24.9 Hz, 2H), 7.21 (d, J = 8.1 Hz, 1H), 7.14 (d, J = 8.3 Hz, 1H), 7.06 (s, 1H), 5.04 (dd, J = 12.5, 5.5 Hz, 1H), 4.35-4.21 (m, 2H), 3.77 (s, 3H), 3.01-2.67 (m, 3H), 2.36-2.27 (m, 1H) |
| 54 | 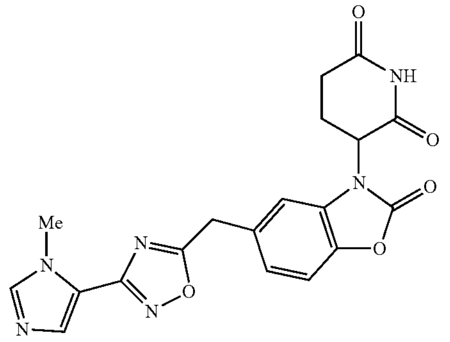 [SMILES: Cn1cncc1-c1noc(Cc2ccc3oc(=O)n(C4CCC(=O)NC4=O)c3c2)n1] | 409.3 | $^1$H NMR (400 MHz, $CDCl_3$) δ 8.14 (s, 1H), 7.78 (s, 1H), 7.71 (s, 1H), 7.24 (s, 1H), 7.17 (d, J = 8.2 Hz, 1H), 6.88 (d, J = 1.0 Hz, 1H), 5.03 (dd, J = 12.9, 5.5 Hz, 1H), 4.29 (s, 2H), 3.98 (s, 3H), 3.05-2.97 (m, 1H), 2.90-2.72 (m, 2H), 2.36-2.29 (m, 1H) |

-continued

| Compound # | Structure | [M + H]$^+$ | $^1$H NMR |
|---|---|---|---|
| 55 | 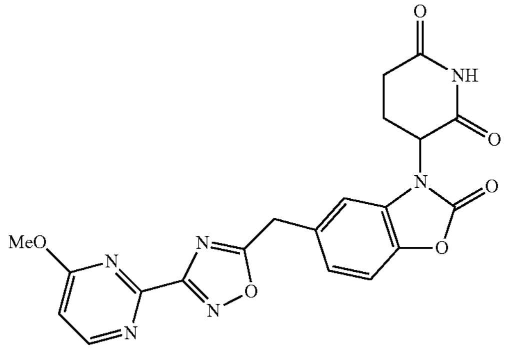 [SMILES: COc1ccnc(-c2noc(Cc3ccc4oc(=O)n(C5CCC(=O)NC5=O)c4c3)n2)n1] | 437.4 | $^1$H NMR (400 MHz, $CDCl_3$) δ 8.65 (d, J = 5.8 Hz, 1H), 8.22 (s, 1H), 7.23 (d, J = 8.2 Hz, 1H), 7.17 (d, J = 8.4 Hz, 1H), 7.10 (s, 1H), 6.91 (d, J = 5.8 Hz, 1H), 5.13 (dd, J = 12.8, 5.4 Hz, 1H), 4.38 (s, 2H), 4.14 (s, 3H), 3.01-2.73 (m, 3H), 2.37-2.27 (m, 1H) |
| 56 | 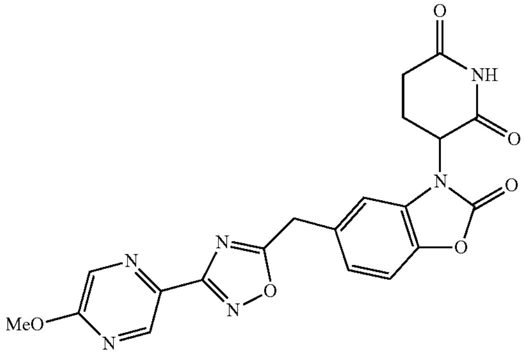 [SMILES: COc1cnc(-c2noc(Cc3ccc4oc(=O)n(C5CCC(=O)NC5=O)c4c3)n2)cn1] | 437.1 | $^1$H NMR (400 MHz, $CDCl_3$) δ 8.78 (d, J = 1.3 Hz, 1H), 8.27 (d, J = 1.3 Hz, 1H), 8.18 (s, 1H), 7.18 (d, J = 8.3 Hz, 1H), 7.12 (dd, J = 8.3, 1.4 Hz, 1H), 6.87 (d, J = 1.0 Hz, 1H), 4.95 (dd, J = 12.8, 5.3 Hz, 1H), 4.27 (s, 2H), 3.98 (s, 3H), 2.96-2.87 (m, 1H), 2.81-2.63 (m, 2H), 2.28-2.20 (m, 1H) |
| 57 | 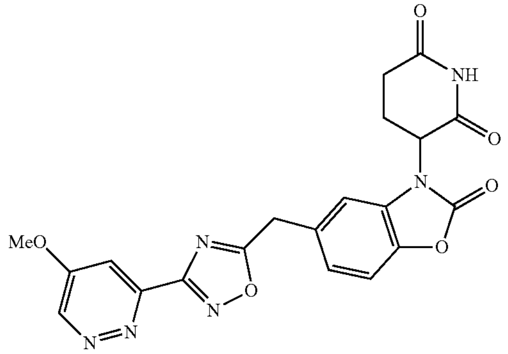 [SMILES: COc1cnnc(-c2noc(Cc3ccc4oc(=O)n(C5CCC(=O)NC5=O)c4c3)n2)c1] | 437.1 | $^1$H NMR (400 MHz, $CDCl_3$) δ 9.04 (d, J = 2.9 Hz, 1H), 8.48 (s, 1H), 7.69 (d, J = 2.9 Hz, 1H), 7.23 (d, J = 8.6 Hz, 1H), 7.19-7.15 (m, 2H), 5.17 (dd, J = 12.7, 5.4 Hz, 1H), 4.38 (s, 2H), 4.04 (s, 3H), 2.93 (dd, J = 21.4, 9.5 Hz, 2H), 2.87-2.72 (m, 1H), 2.33 (dd, J = 8.6, 4.5 Hz, 1H) |
| 58 | 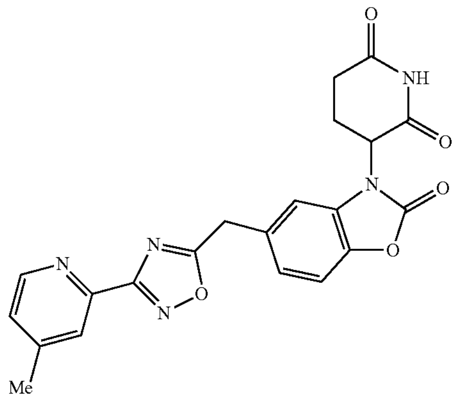 [SMILES: Cc1ccnc(-c2noc(Cc3ccc4oc(=O)n(C5CCC(=O)NC5=O)c4c3)n2)c1] | 420.4 | $^1$H NMR (400 MHz, $CDCl_3$) δ 8.68 (d, J = 5.1 Hz, 1H), 8.30 (s, 1H), 7.98 (s, 1H), 7.33 (d, J = 4.8 Hz, 1H), 7.23 (d, J = 8.2 Hz, 1H), 7.19-7.15 (m, 1H), 7.11 (s, 1H), 5.14 (dd, J = 12.4, 5.2 Hz, 1H), 4.35 (s, 2H), 2.93 (dd, J = 17.3, 5.2 Hz, 2H), 2.79 (m, J = 18.3, 13.3, 5.1 Hz, 1H), 2.48 (s, 3H), 2.36-2.29 (m, 1H) |

-continued

| Compound # | Structure | [M + H]$^+$ | $^1$H NMR |
| --- | --- | --- | --- |
| 59 | 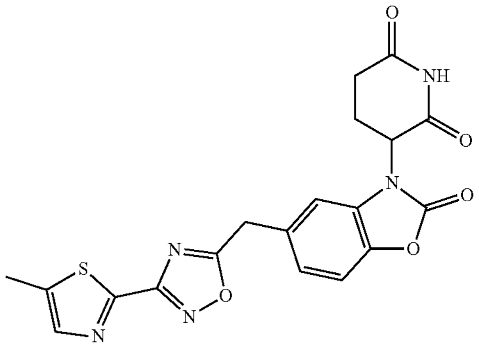 [SMILES: Cc1cnc(-c2noc(Cc3ccc4oc(=O)n(C5CCC(=O)NC5=O)c4c3)n2)s1] | 426.3 | $^1$H NMR (400 MHz, DMSO-$d_6$) δ 11.22 (s, 1H), 7.83 (d, J = 1.3 Hz, 1H), 7.41 (d, J = 8.3 Hz, 1H), 7.38 (d, J = 1.7 Hz, 1H), 7.21 (dd, J = 8.3, 1.7 Hz, 1H), 5.38 (dd, J = 12.8, 5.2 Hz, 1H), 4.48 (s, 2H), 2.97-2.82 (m, 1H), 2.74-2.64 (m, 2H), 2.55 (d, J = 1.2 Hz, 3H), 2.17 (dt, J = 10.4, 5.5 Hz, 1H) |
| 60 | 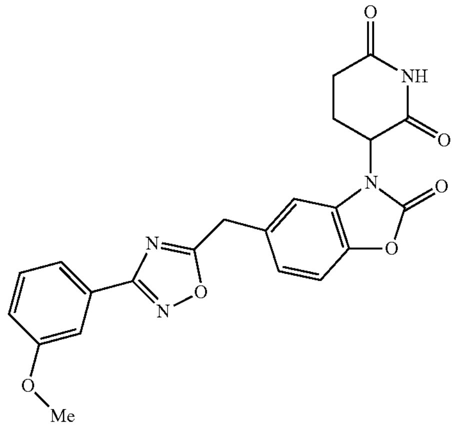 | 435.4 | $^1$H NMR (400 MHz, DMSO) δ 11.22 (s, 1H), 7.56 (dt, J = 7.7, 1.1 Hz, 1H), 7.50-7.44 (m, 2H), 7.40 (t, J = 5.3 Hz, 2H), 7.24-7.13 (m, 2H), 5.39 (dd, J = 12.9, 5.2 Hz, 1H), 4.47 (s, 2H), 3.82 (s, 3H), 2.95-2.83 (m, 1H), 2.75-2.62 (m, 2H), 2.22-2.14 (m, 1H) |
| 61 | 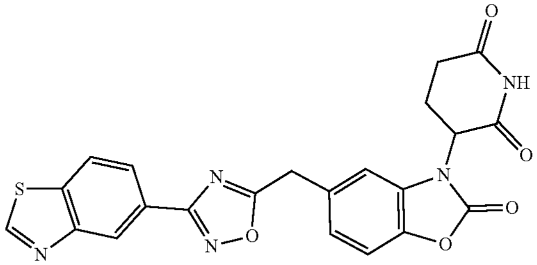 [SMILES: O=C1CCC(n2c(=O)oc3ccc(Cc4nc(-c5ccc6scnc6c5)no4)cc32)C(=O)N1] | 462.0 | $^1$H NMR (400 MHz, DMSO) δ 11.23 (s, 1H), 9.53 (s, 1H), 8.61 (d, J = 1.3 Hz, 1H), 8.37 (d, J = 8.4 Hz, 1H), 8.07 (dd, J = 8.4, 1.5 Hz, 1H), 7.42 (dd, J = 4.8, 3.4 Hz, 2H), 7.25 (dd, J = 8.3, 1.5 Hz, 1H), 5.40 (dd, J = 12.9, 5.3 Hz, 1H), 4.50 (s, 2H), 2.89 (dd, J = 12.2, 8.8 Hz, 1H), 2.68 (dd, J = 19.6, 9.6 Hz, 2H), 2.19 (dd, J = 10.6, 5.2 Hz, 1H |
| 62 | 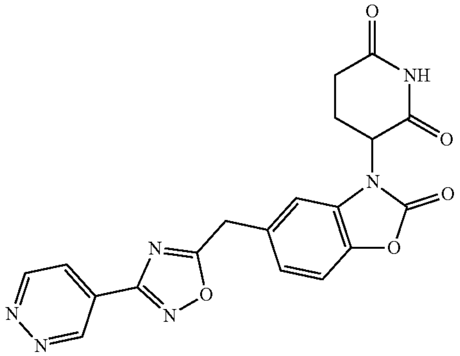 [SMILES: O=C1CCC(n2c(=O)oc3ccc(Cc4nc(-c5ccnnc5)no4)cc32)C(=O)N1] | 407.1 | $^1$H NMR (400 MHz, $CDCl_3$) δ 9.80 (dd, J = 2.1, 1.3 Hz, 1H), 9.39 (dd, J = 5.3, 1.2 Hz, 1H), 8.06 (dd, J = 5.3, 2.2 Hz, 1H), 7.28 (s, 1H), 7.19 (dd, J = 8.3, 1.6 Hz, 1H), 6.89 (d, J = 1.5 Hz, 1H), 5.05 (dd, J = 12.9, 5.2 Hz, 1H), 4.35 (s, 2H), 3.01 (d, J = 18.6 Hz, 1H), 2.91-2.69 (m, 2H), 2.38-2.31 (m, 1H) |

-continued
| Compound # | Structure | [M + H]$^+$ | $^1$H NMR |
|---|---|---|---|
| 63 | 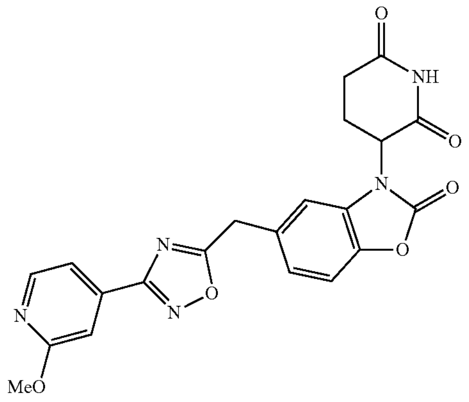 [SMILES: COc1cc(-c2noc(Cc3ccc4oc(=O)n(C5CCC(=O)NC5=O)c4c3)n2)ccn1] | 436.4 | $^1$H NMR (400 MHz, DMSO-$d_6$) δ 11.23 (s, 1H), 8.37 (d, J = 5.3 Hz, 1H), 7.49 (dd, J = 5.3, 1.4 Hz, 1H), 7.43-7.38 (m, 2H), 7.27 (t, J = 1.1 Hz, 1H), 7.22 (dd, J = 8.3, 1.7 Hz, 1H), 5.39 (dd, J = 12.9, 5.2 Hz, 1H), 4.50 (s, 2H), 3.91 (s, 3H), 2.94-2.84 (m, 1H), 2.75-2.64 (m, 2H), 2.22-2.15 (m, 1H) |
| 64 | 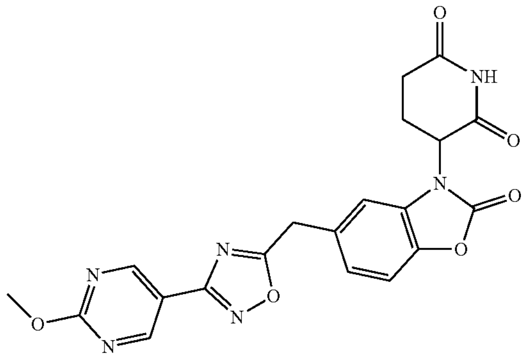 [SMILES: COc1ncc(-c2noc(Cc3ccc4oc(=O)n(C5CCC(=O)NC5=O)c4c3)n2)cn1] | 437.4 | $^1$H NMR (400 MHz, DMSO-$d_6$) δ 11.23 (s, 1H), 9.11 (s, 2H), 7.40 (d, J = 8.3 Hz, 1H), 7.39 (d, J = 1.7 Hz, 1H), 7.21 (dd, J = 8.2, 1.7 Hz, 1H), 5.39 (dd, J = 12.9, 5.2 Hz, 1H), 4.49 (s, 2H), 4.01 (s, 3H), 2.87 (d, J = 13.9 Hz, 1H), 2.79-2.66 (m, 2H), 2.18 (d, J = 5.5 Hz, 1H) |
| 65 | 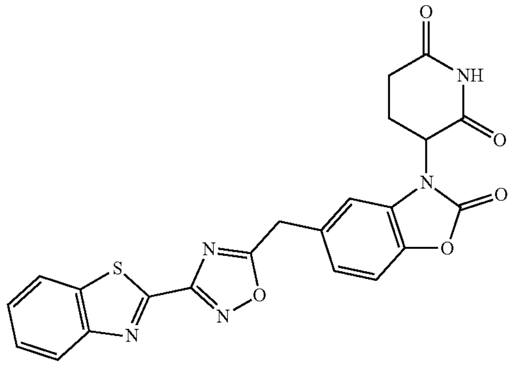 [SMILES: O=C1CCC(n2c(=O)oc3ccc(Cc4nc(-c5nc6ccccc6s5)no4)cc32)C(=O)N1] | 462.4 | $^1$H NMR (400 MHz, DMSO-$d_6$) δ 11.24 (s, 1H), 8.29-8.26 (m, 1H), 8.23-8.19 (m, 1H), 7.69-7.59 (m, 2H), 7.43 (d, J = 8.4 Hz, 2H), 7.26 (dd, J = 8.2, 1.7 Hz, 1H), 5.40 (dd, J = 12.8, 5.2 Hz, 1H), 4.55 (s, 2H), 2.98-2.84 (m, 1H), 2.77-2.64 (m, 2H), 2.23-2.15 (m, 1H) |
| 66 | 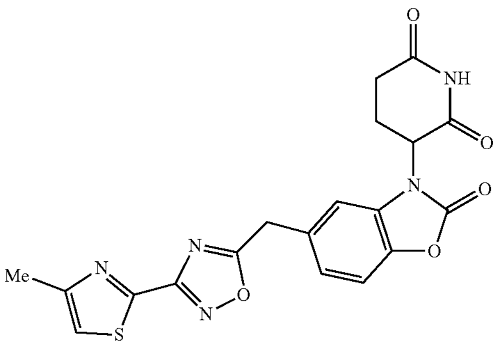 [SMILES: Cc1csc(-c2noc(Cc3ccc4oc(=O)n(C5CCC(=O)NC5=O)c4c3)n2)n1] | 426.1 | $^1$H NMR (400 MHz, $CDCl_3$) δ 8.35 (s, 1H), 7.23 (d, J = 8.3 Hz, 1H), 7.17 (d, J = 8.5 Hz, 1H), 7.14 (s, 1H), 6.97 (s, 1H), 5.03 (dd, J = 12.6, 5.2 Hz, 1H), 4.33 (s, 2H), 3.03-2.92 (m, 1H), 2.90-2.69 (m, 2H), 2.57 (s, 3H), 2.32 (dd, J = 7.8, 5.4 Hz, 1H) |

-continued
| Compound # | Structure | [M + H]+ | 1H NMR |
|---|---|---|---|
| 67 | 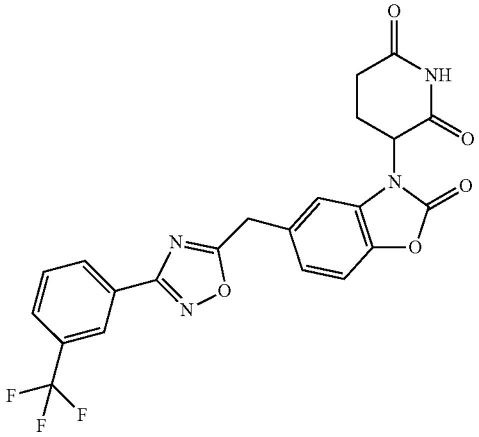 [SMILES: O=C1CCC(n2c(=O)oc3ccc(Cc4nc(-c5cccc(C(F)(F)F)c5)no4)cc32)C(=O)N1] | 473.1 | 1H NMR (400 MHz, $CDCl_3$) δ 8.33 (s, 1H), 8.24 (d, J = 7.8 Hz, 1H), 8.06 (s, 1H), 7.77 (d, J = 7.8 Hz, 1H), 7.62 (t, J = 7.8 Hz, 1H), 7.25 (s, 1H), 7.19 (dd, J = 8.3, 1.6 Hz, 1H), 6.90 (d, J = 1.4 Hz, 1H), 5.03 (dd, J = 12.8, 5.3 Hz, 1H), 4.32 (s, 2H), 3.00 (d, J = 16.0 Hz, 1H), 2.90-2.69 (m, 2H), 2.37-2.30 (m, 1H |
| 68 | 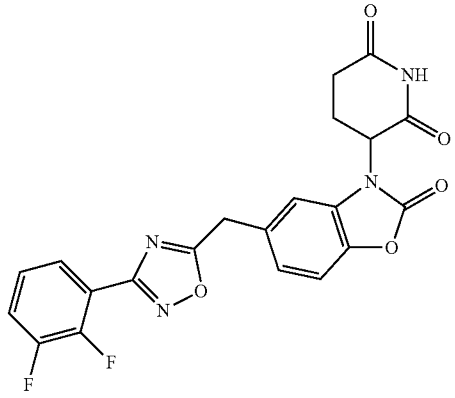 [SMILES: O=C1CCC(n2c(=O)oc3ccc(Cc4nc(-c5cccc(F)c5F)no4)cc32)C(=O)N1] | 441.0 | 1H NMR (400 MHz, DMSO) δ 11.24 (s, 1H), 7.79 (ddd, J = 7.7, 4.6, 1.5 Hz, 1H), 7.74-7.63 (m, 1H), 7.46-7.37 (m, 3H), 7.23 (dd, J = 8.4, 1.4 Hz, 1H), 5.40 (dd, J = 12.9, 5.3 Hz, 1H), 4.51 (s, 2H), 2.97-2.83 (m, 1H), 2.78-2.61 (m, 2H), 2.24-2.13 (m, 1H) |
| 69 | 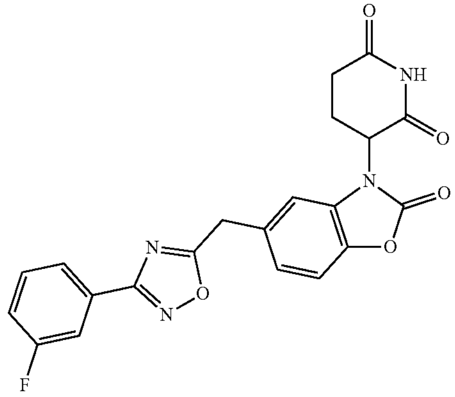 [SMILES: O=C1CCC(n2c(=O)oc3ccc(Cc4nc(-c5cccc(F)c5)no4)cc32)C(=O)N1] | 423.0 | 1H NMR (400 MHz, DMSO) δ 11.24 (s, 1H), 7.83 (d, J = 7.8 Hz, 1H), 7.72 (ddd, J = 9.6, 2.5, 1.5 Hz, 1H), 7.62 (td, J = 8.1, 5.9 Hz, 1H), 7.46 (td, J = 8.7, 2.6 Hz, 1H), 7.41 (d, J = 8.3 Hz, 2H), 7.22 (dd, J = 8.2, 1.6 Hz, 1H), 5.40 (dd, J = 12.9, 5.3 Hz, 1H), 4.48 (s, 2H), 2.97-2.83 (m, 1H), 2.77-2.61 (m, 2H), 2.24-2.13 (m, 1H) |
| 70 | 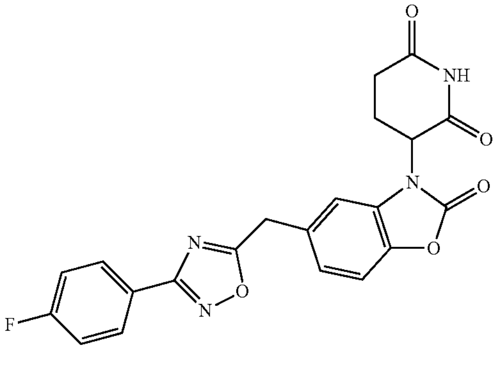 [SMILES: O=C1CCC(n2c(=O)oc3ccc(Cc4nc(-c5ccc(F)cc5)no4)cc32)C(=O)N1] | 423.1 | 1H NMR (400 MHz, DMSO) δ 11.23 (s, 1H), 8.06-7.99 (m, 2H), 7.43-7.37 (m, 4H), 7.21 (dd, J = 8.2, 1.5 Hz, 1H), 5.40 (dd, J = 12.9, 5.2 Hz, 1H), 4.47 (s, 2H), 2.89 (dd, J = 11.3, 7.7 Hz, 1H), 2.76-2.60 (m, 2H), 2.24-2.12 (m, 1H) |

-continued
| Compound # | Structure | [M + H]+ | 1H NMR |
|---|---|---|---|
| 71 | 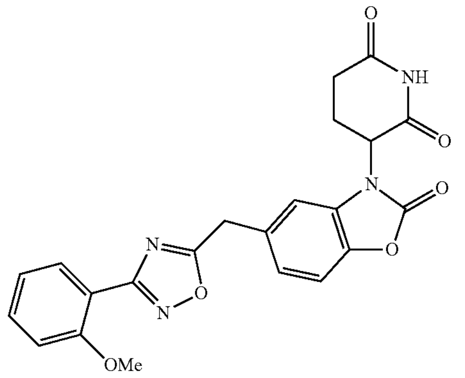 [SMILES: COc1ccccc1-c1noc(Cc2ccc3oc(=O)n(C4CCC(=O)NC4=O)c3c2)n1] | 434.3 | $^1$H NMR (400 MHz, DMSO) δ 11.22 (s, 1H), 7.78 (dd, J = 7.7, 1.7 Hz, 1H), 7.57-7.51 (m, 1H), 7.39 (t, J = 5.1 Hz, 2H), 7.23-7.17 (m, 2H), 7.09 (td, J = 7.6, 0.9 Hz, 1H), 5.39 (dd, J = 12.9, 5.2 Hz, 1H), 4.44 (s, 2H), 3.85 (s, 3H), 2.96-2.82 (m, 1H), 2.75-2.63 (m, 2H), 2.23-2.13 (m, 1H) |
| 72 | 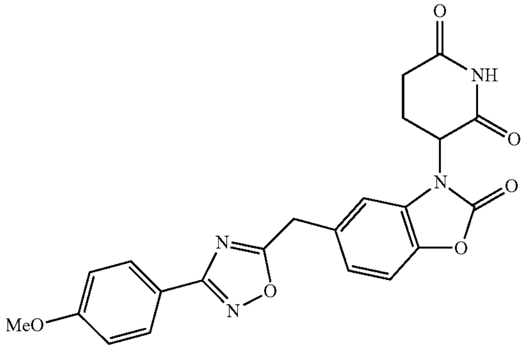 [SMILES: COc1ccc(-c2noc(Cc3ccc4oc(=O)n(C5CCC(=O)NC5=O)c4c3)n2)cc1] | 435.4 | $^1$H NMR (400 MHz, DMSO-$d_6$) δ 11.25 (s, 1H), 7.96-7.90 (m, 2H), 7.41 (d, J = 8.2 Hz, 2H), 7.21 (dd, J = 8.3, 1.7 Hz, 1H), 7.13-7.07 (m, 2H), 5.40 (dd, J = 12.8, 5.2 Hz, 1H), 4.44 (s, 2H), 3.83 (s, 3H), 2.96-2.84 (m, 1H), 2.78-2.64 (m, 2H), 2.24-2.15 (m, 1H) |
| 73 | 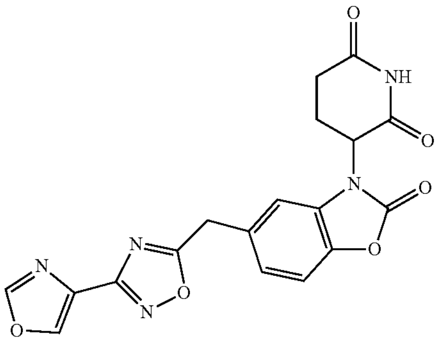 [SMILES: O=C1CCC(n2c(=O)oc3ccc(Cc4nc(-c5cocn5)no4)cc32)C(=O)N1] | 396.0 | $^1$H NMR (400 MHz, DMSO) δ 11.22 (s, 1H), 8.86 (s, 1H), 8.64 (s, 1H), 7.40 (d, J = 8.2 Hz, 1H), 7.36 (d, J = 1.3 Hz, 1H), 7.19 (dd, J = 8.3, 1.5 Hz, 1H), 5.38 (dd, J = 12.9, 5.2 Hz, 1H), 4.45 (s, 2H), 2.96-2.81 (m, 1H), 2.76-2.59 (m, 2H), 2.22-2.10 (m, 1H) |
| 74 | 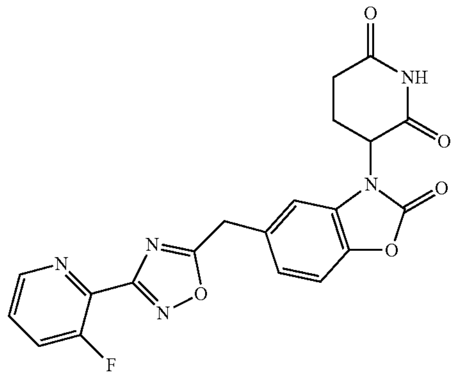 [SMILES: O=C1CCC(n2c(=O)oc3ccc(Cc4nc(-c5ncccc5F)no4)cc32)C(=O)N1] | 424.0 | $^1$H NMR (400 MHz, $CDCl_3$) δ 8.70 (d, J = 4.4 Hz, 1H), 8.14 (s, 1H), 7.72 (t, J = 9.1 Hz, 1H), 7.58 (m, J = 8.6, 4.4 Hz, 1H), 7.23 (d, J = 8.3 Hz, 1H), 7.18 (d, J = 8.3 Hz, 1H), 7.11 (s, 1H), 5.12 (dd, J = 12.7, 5.4 Hz, 1H), 4.39 (s, 2H), 3.03-2.71 (m, 3H), 2.32 (m, J = 13.2, 7.5, 4.1 Hz, 1H) |

-continued
| Compound # | Structure | [M + H]+ | 1H NMR |
|---|---|---|---|
| 75 | 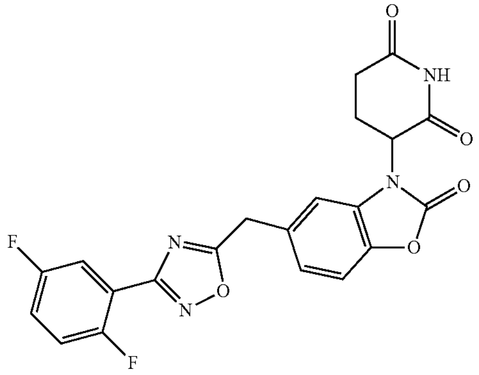 [SMILES: O=C1CCC(n2c(=O)oc3ccc(Cc4nc(-c5cc(F)ccc5F)no4)cc32)C(=O)N1] | 441.4 | 1H NMR (400 MHz, $CDCl_3$) δ 8.07 (s, 1H), 7.77-7.69 (m, 1H), 7.25 (s, 1H), 7.23-7.16 (m, 3H), 6.93 (d, J = 1.1 Hz, 1H), 5.04 (dd, J = 12.8, 5.2 Hz, 1H), 4.33 (s, 2H), 3.07-2.94 (m, 1H), 2.90-2.69 (m, 2H), 2.37-2.29 (m, 1H) |
| 76 | 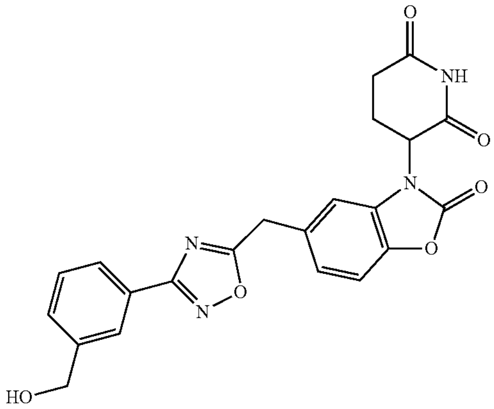 [SMILES: O=C1CCC(n2c(=O)oc3ccc(Cc4nc(-c5cccc(CO)c5)no4)cc32)C(=O)N1] | 435.1 | 1H NMR (400 MHz, DMSO-$d_6$) δ 11.22 (s, 1H), 7.96 (s, 1H), 7.87-7.81 (m, 1H), 7.52-7.47 (m, 2H), 7.42-7.37 (m, 2H), 7.21 (dd, J = 8.2, 1.6 Hz, 1H), 5.43-5.31 (m, 2H), 4.57 (d, J = 5.6 Hz, 2H), 4.46 (s, 2H), 2.94-2.82 (m, 1H), 2.73-2.62 (m, 2H), 2.22-2.13 (m, 1H) |
| 77 | 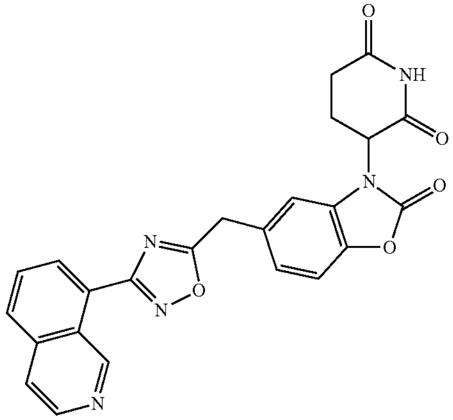 [SMILES: O=C1CCC(n2c(=O)oc3ccc(Cc4nc(-c5cccc6ccncc56)no4)cc32)C(=O)N1] | 456.3 | 1H NMR (400 MHz, DMSO-$d_6$) δ 11.28 (s, 1H), 10.09 (s, 1H), 8.65 (d, J = 5.6 Hz, 1H), 8.29 (dd, J = 7.3, 1.2 Hz, 1H), 8.23 (d, J = 8.3 Hz, 1H), 7.99 (d, J = 5.6 Hz, 1H), 7.94 (dd, J = 8.3, 7.2 Hz, 1H), 7.47 (d, J = 1.7 Hz, 1H), 7.43 (d, J = 8.3 Hz, 1H), 7.29 (dd, J = 8.2, 1.7 Hz, 1H), 5.41 (dd, J = 12.9, 5.2 Hz, 1H), 4.57 (s, 2H), 2.98-2.86 (m, 1H), 2.77-2.65 (m, 2H), 2.24-2.16 (m, 1H) |

-continued
| Compound # | Structure | [M + H]+ | 1H NMR |
|---|---|---|---|
| 78 | 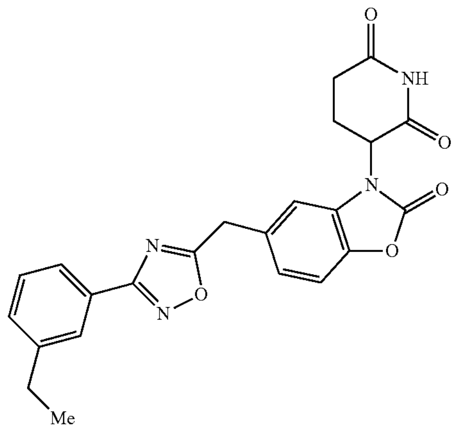 [SMILES: CCc1cccc(-c2noc(Cc3ccc4oc(=O)n(C5CCC(=O)NC5=O)c4c3)n2)c1] | 433.4 | 1H NMR (400 MHz, $CDCl_3$) δ 8.38 (s, 1H), 7.90-7.81 (m, 2H), 7.37 (dt, J = 15.5, 7.6 Hz, 2H), 7.24 (d, J = 8.3 Hz, 1H), 7.18 (dd, J = 8.3, 1.4 Hz, 1H), 6.92 (s, 1H), 5.03 (dd, J = 12.7, 5.3 Hz, 1H), 4.30 (s, 2H), 3.00-2.90 (m, 1H), 2.79 (ddd, J = 17.4, 13.4, 9.2 Hz, 2H), 2.73-2.68 (m, 2H), 2.30 (ddd, J = 12.8, 6.4, 4.0 Hz, 1H), 1.27 (t, J = 7.6 Hz, 3H) |
| 79 | 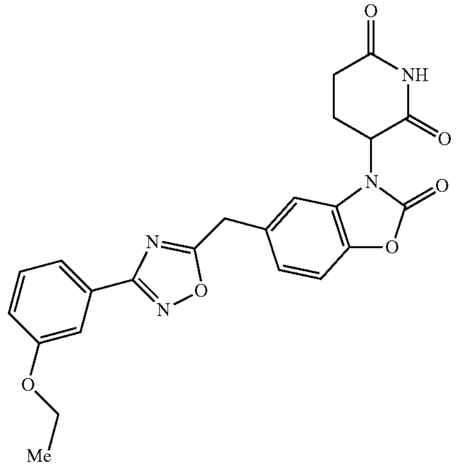 [SMILES: CCOc1cccc(-c2noc(Cc3ccc4oc(=O)n(C5CCC(=O)NC5=O)c4c3)n2)c1] | 449.4 | 1H NMR (400 MHz, $CDCl_3$) δ 8.16 (s, 1H), 7.62 (d, J = 7.7 Hz, 1H), 7.57 (d, J = 2.2 Hz, 1H), 7.37 (t, J = 8.0 Hz, 1H), 7.24 (s, 1H), 7.21-7.16 (m, 1H), 7.04 (dd, J = 8.3, 2.0 Hz, 1H), 6.94 (s, 1H), 5.03 (dd, J = 12.8, 5.3 Hz, 1H), 4.30 (s, 2H), 4.10 (q, J = 7.0 Hz, 2H), 3.00 (dd, J = 13.9, 2.9 Hz, 1H), 2.89-2.70 (m, 2H), 2.37-2.28 (m, 1H), 1.44 (t, J = 7.0 Hz, 3H) |
| 80 | 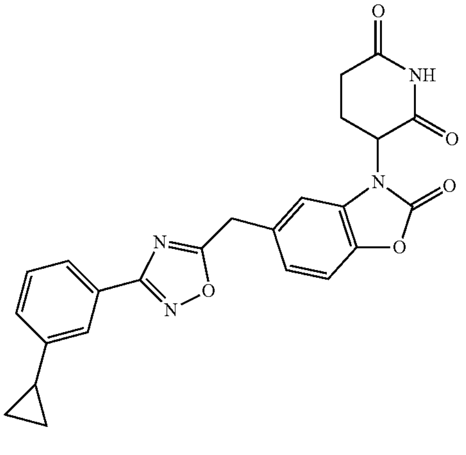 [SMILES: O=C1CCC(n2c(=O)oc3ccc(Cc4nc(-c5cccc(C6CC6)c5)no4)cc32)C(=O)N1] | 445.1 | 1H NMR (400 MHz, $CDCl_3$) δ 8.22 (s, 1H), 7.84-7.78 (m, 1H), 7.75 (d, J = 1.6 Hz, 1H), 7.35 (t, J = 7.7 Hz, 1H), 7.25 (d, J = 8.4 Hz, 1H), 7.22-7.17 (m, 2H), 6.90 (d, J = 1.3 Hz, 1H), 5.05-4.98 (m, 1H), 4.30 (s, 2H), 3.03-2.94 (m, 1H), 2.88-2.80 (m, 1H), 2.75 (dq, J = 13.3, 4.6 Hz, 1H), 2.31 (ddd, J = 12.9, 6.5, 4.0 Hz, 1H), 1.96 (td, J = 8.4, 4.2 Hz, 1H), 1.03-0.98 (m, 2H), 0.77-0.73 (m, 2H) |

-continued
| Compound # | Structure | [M + H]+ | 1H NMR |
|---|---|---|---|
| 81 | 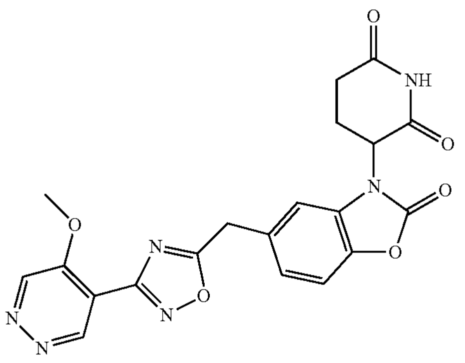 [SMILES: COc1cnncc1-c1noc(Cc2ccc3oc(=O)n(C4CCC(=O)NC4=O)c3c2)n1] | 437.3 | 1H NMR (400 MHz, DMSO) δ 11.23 (s, 1H), 8.87 (s, 1H), 7.97 (s, 1H), 7.44-7.34 (m, 2H), 7.17 (dd, J = 8.3, 1.4 Hz, 1H), 5.39 (dd, J = 12.9, 5.3 Hz, 1H), 4.43 (s, 2H), 3.95 (d, J = 5.3 Hz, 3H), 2.95-2.84 (m, 1H), 2.68 (dd, J = 17.3, 9.9 Hz, 2H), 2.18 (dd, J = 10.2, 5.0 Hz, 1H) |
| 82 | 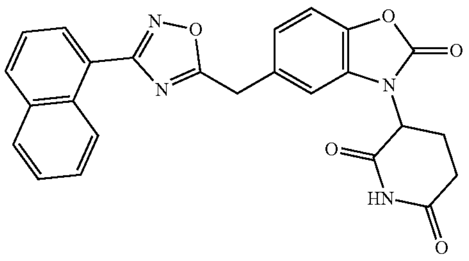 [SMILES: O=C1CCC(n2c(=O)oc3ccc(Cc4nc(-c5cccc6ccccc56)no4)cc32)C(=O)N1] | 455.3 | 1HNMR (400 MHz, DMSO) δ 11.24 (s, 1H), 8.77 (d, J = 8.3 Hz, 1H), 8.23-8.13 (m, 2H), 8.08 (d, J = 7.7 Hz, 1H), 7.72-7.62 (m, 3H), 7.48-7.34 (m, 2H), 7.27 (dd, J = 8.3, 1.1 Hz, 1H), 5.41 (dd, J = 12.9, 5.3 Hz, 1H), 4.54 (s, 2H), 2.97-2.84 (m, 1H), 2.71 (ddd, J = 20.1, 14.7, 8.2 Hz, 2H), 2.20 (dd, J = 10.8, 5.2 Hz, 1H) |
| 115 | 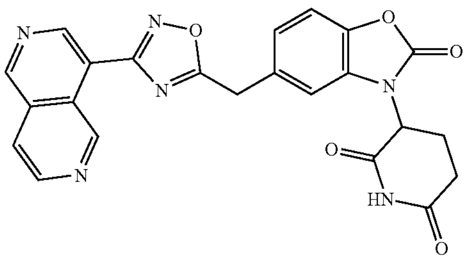 [SMILES: O=C1CCC(n2c(=O)oc3ccc(Cc4nc(-c5cncc6ccncc56)no4)cc32)C(=O)N1] | 457.2 | 1H NMR (400 MHz, DMSO-d6) δ 11.25 (s, 1H), 10.16 (s, 1H), 9.67 (d, J = 3.2 Hz, 1H), 9.25 (d, J = 3.0 Hz, 1H), 8.89 (dd, J = 5.5, 2.7 Hz, 1H), 8.23-8.14 (m, 1H), 7.47 (d, J = 1.2 Hz, 1H), 7.43 (d, J = 8.2 Hz, 1H), 7.29 (dd, J = 8.3, 1.3 Hz, 1H), 5.41 (dd, J = 12.9, 5.3 Hz, 1H), 4.59 (s, 2H), 2.94-2.85 (m, 1H), 2.77-2.65 (m, 2H), 2.20 (dd, J = 10.7, 5.2 Hz, 1H). |
| 116 | 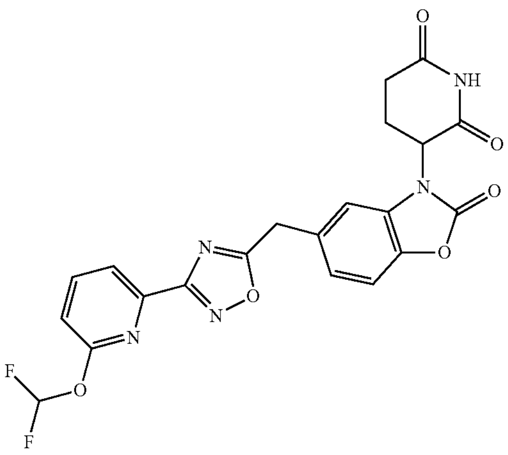 [SMILES: O=C1CCC(n2c(=O)oc3ccc(Cc4nc(-c5cccc(OC(F)F)n5)no4)cc32)C(=O)N1] | 472.1 | 1H NMR (400 MHz, DMSO-$d_6$) δ 11.23 (s, 1H), 8.13 (t, J = 7.9 Hz, 1H), 7.97-7.51 (m, 2H), 7.43-7.36 (m, 2H), 7.32 (d, J = 8.2 Hz, 1H), 7.21 (dd, J = 8.3, 1.7 Hz, 1H), 5.39 (dd, J = 12.8, 5.2 Hz, 1H), 4.50 (s, 2H), 2.97-2.84 (m, 1H), 2.77-2.61 (m, 2H), 2.24-2.14 (m, 1H) |

-continued

| Compound # | Structure | $[M + H]^+$ | $^1H$ NMR |
|---|---|---|---|
| 117 | 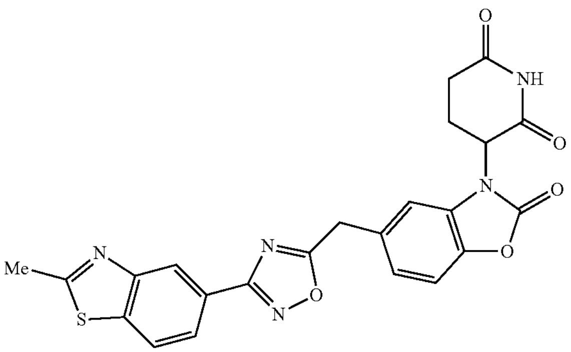 [SMILES: Cc1nc2cc(-c3noc(Cc4ccc5oc(=O)n(C6CCC(=O)NC6=O)c5c4)n3)ccc2s1] | 476.1 | $^1H$ NMR (400 MHz, DMSO-$d_6$) δ 11.23 (s, 1H), 8.44 (d, J = 1.6 Hz, 1H), 8.23 (d, J = 8.5 Hz, 1H), 7.99 (dd, J = 8.4, 1.7 Hz, 1H), 7.52-7.39 (m, 2H), 7.30-7.17 (m, 1H), 5.41 (dd, J = 12.7, 5.3 Hz, 1H), 4.50 (s, 2H), 2.95-2.87 (m, 1H), 2.85 (s, 3H), 2.68 (dd, J = 3.6, 1.8 Hz, 2H), 2.20 (dd, J = 9.6, 6.3 Hz, 1H) |
| 118 | 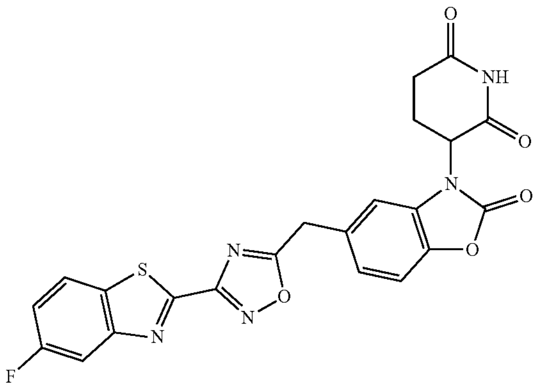 [SMILES: O=C1CCC(n2c(=O)oc3ccc(Cc4nc(-c5nc6cc(F)ccc6s5)no4)cc32)C(=O)N1] | 480.0 | $^1H$ NMR (400 MHz, DMSO) δ 11.23 (s, 1H), 8.32 (dd, J = 9.0, 5.3 Hz, 1H), 8.09 (dd, J = 9.6, 2.5 Hz, 1H), 7.55 (td, J = 9.1, 2.6 Hz, 1H), 7.45-7.39 (m, 2H), 7.25 (dd, J = 8.3, 1.4 Hz, 1H), 5.40 (dd, J = 12.8, 5.2 Hz, 1H), 4.55 (s, 2H), 2.96-2.84 (m, 1H), 2.74-2.64 (m, 2H), 2.23-2.15 (m, 1H) |
| 119 | 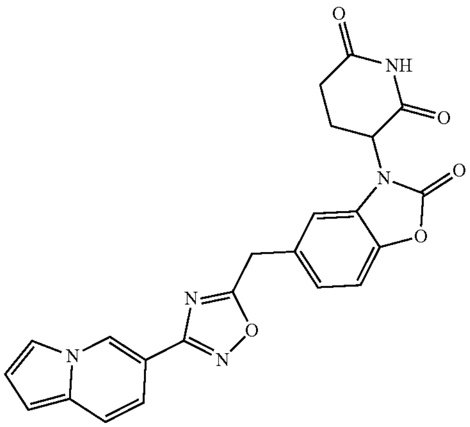 [SMILES: O=C1CCC(n2c(=O)oc3ccc(Cc4nc(-c5ccc6cccn6c5)no4)cc32)C(=O)N1] | 444.1 | $^1H$ NMR (400 MHz, DMSO-$d_6$) δ 11.23 (s, 1H), 9.01 (s, 1H), 7.78 (d, J = 2.6 Hz, 1H), 7.55 (d, J = 9.3 Hz, 1H), 7.42 (d, J = 8.3 Hz, 1H), 7.39 (d, J = 1.6 Hz, 1H), 7.21 (dd, J = 8.3, 1.6 Hz, 1H), 7.12 (dd, J = 9.3, 1.5 Hz, 1H), 6.84 (dd, J = 3.8, 2.7 Hz, 1H), 6.51 (d, J = 3.8 Hz, 1H), 5.39 (dd, J = 12.8, 5.2 Hz, 1H), 4.46 (s, 2H), 2.87 (d, J = 15.4 Hz, 1H), 2.77-2.65 (m, 2H), 2.19 (dd, J = 11.0, 5.4 Hz, 1H) |
| 120 | 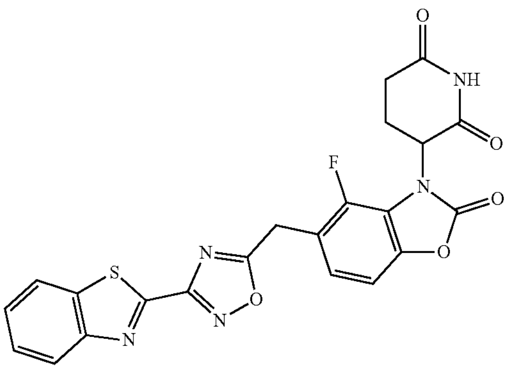 [SMILES: O=C1CCC(n2c(=O)oc3ccc(Cc4nc(-c5nc6ccccc6s5)no4)c(F)c32)C(=O)N1] | 480.3 | $^1H$ NMR (400 MHz, DMSO-$d_6$) δ 11.25 (s, 1H), 8.27 (dd, J = 7.8, 1.5 Hz, 1H), 8.21 (dd, J = 7.9, 1.5 Hz, 1H), 7.68-7.59 (m, 2H), 7.41-7.35 (m, 2H), 5.57-5.38 (m, 1H), 4.62 (s, 2H), 3.05-2.90 (m, 1H), 2.70-2.62 (m, 1H), 2.40-2.12 (m, 2H) |

-continued
| Compound # | Structure | [M + H]+ | $^1$H NMR |
|---|---|---|---|
| 121 | 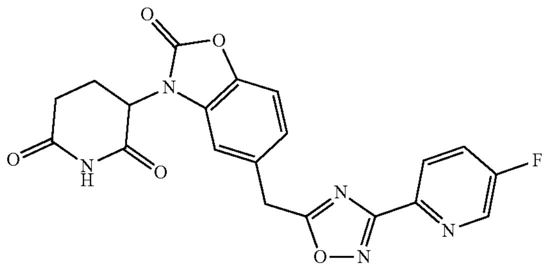 [SMILES: O=C1CCC(n2c(=O)oc3ccc(Cc4nc(-c5ccc(F)cn5)no4)cc32)C(=O)N1] | 424.3 | $^1$H NMR (400 MHz, DMSO) δ 11.22 (s, 1H), 8.76 (d, J = 2.9 Hz, 1H), 8.12 (dd, J = 8.8, 4.5 Hz, 1H), 7.93 (td, J = 8.7, 2.9 Hz, 1H), 7.40 (dd, J = 7.5, 4.8 Hz, 2H), 7.22 (dd, J = 8.3, 1.6 Hz, 1H), 5.39 (dd, J = 12.9, 5.3 Hz, 1H), 4.48 (s, 2H), 2.95-2.80 (m, 1H), 2.70 (dt, J = 26.8, 10.1 Hz, 2H), 2.24-2.12 (m, 1H) |
| 122 | 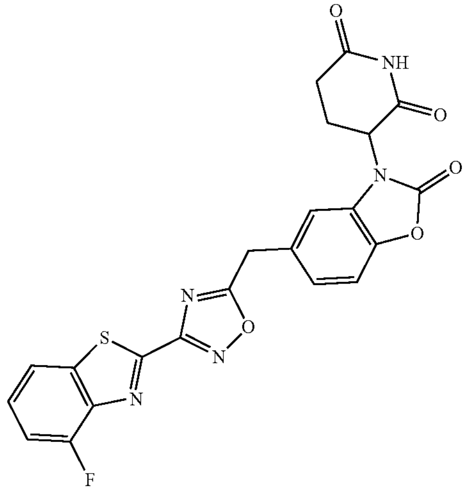 [SMILES: O=C1CCC(n2c(=O)oc3ccc(Cc4nc(-c5nc6c(F)cccc6s5)no4)cc32)C(=O)N1] | 480.1 | $^1$H NMR (400 MHz, DMSO-$d_6$) δ 11.23 (s, 1H), 8.10 (dd, J = 8.2, 1.0 Hz, 1H), 7.64 (td, J = 8.1, 4.8 Hz, 1H), 7.56-7.47 (m, 1H), 7.43 (d, J = 6.7 Hz, 1H), 7.42 (s, 1H), 7.26 (dd, J = 8.2, 1.7 Hz, 1H), 5.40 (dd, J = 12.7, 5.2 Hz, 1H), 4.56 (s, 2H), 2.97-2.83 (m, 1H), 2.77-2.64 (m, 2H), 2.18 (dt, J = 10.0, 5.5 Hz, 1H) |
| 123 | 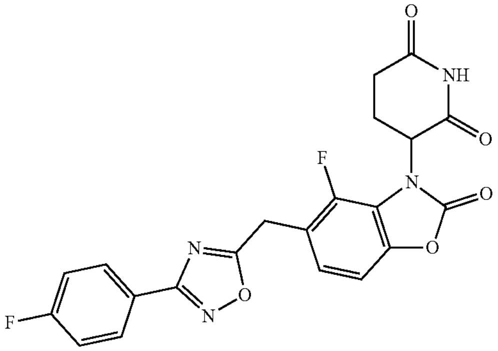 [SMILES: O=C1CCC(n2c(=O)oc3ccc(Cc4nc(-c5ccc(F)cc5)no4)c(F)c32)C(=O)N1] | 441.3 | $^1$H NMR (400 MHz, DMSO) δ 11.23 (s, 1H), 8.06-7.98 (m, 2H), 7.43-7.29 (m, 4H), 5.45 (s, 1H), 4.53 (s, 2H), 2.96 (s, 1H), 2.65 (d, J = 16.1 Hz, 1H), 2.35-2.14 (m, 2H). |
| 124 | 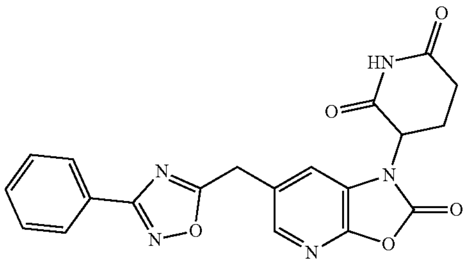 [SMILES: O=C1CCC(n2c(=O)oc3ncc(Cc4nc(-c5ccccc5)no4)cc32)C(=O)N1] | 406.2 | $^1$H NMR (400 MHz, DMSO-d6) δ 11.25 (s, 1H), 8.13 (d, J = 1.7 Hz, 1H), 7.97 (dd, J = 8.0, 1.6 Hz, 2H), 7.83 (d, J = 1.8 Hz, 1H), 7.61-7.54 (m, 3H), 5.44 (dd, J = 12.9, 5.3 Hz, 1H), 4.53 (s, 2H), 2.91-2.82 (m, 1H), 2.65 (d, J = 15.0 Hz, 2H), 2.21 (dd, J = 10.6, 5.2 Hz, 1H) |

-continued
| Compound # | Structure | [M + H]+ | 1H NMR |
|---|---|---|---|
| 125 | 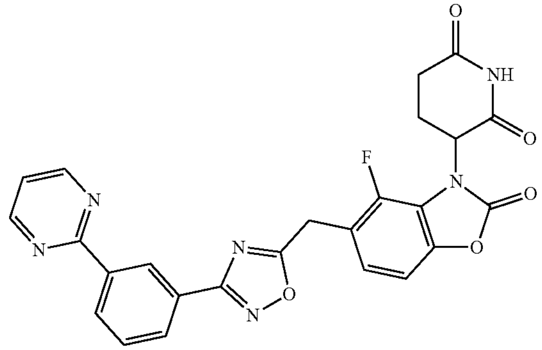 [SMILES: O=C1CCC(n2c(=O)oc3ccc(Cc4nc(-c5cccc(-c6ncccn6)c5)no4)c(F)c32)C(=O)N1] | 501.4 | 1H NMR (400 MHz, DMSO) δ 11.24 (s, 1H), 9.02 (s, 1H), 8.96 (d, J = 4.9 Hz, 2H), 8.59 (d, J = 8.0 Hz, 1H), 8.13 (d, J = 7.8 Hz, 1H), 7.72 (t, J = 7.8 Hz, 1H), 7.52 (t, J = 4.8 Hz, 1H), 7.37 (d, J = 2.0 Hz, 2H), 5.46 (s, 1H), 4.57 (s, 2H), 2.96 (s, 1H), 2.64 (d, J = 17.5 Hz, 1H), 2.38-2.16 (m, 2H) |
| 126 | 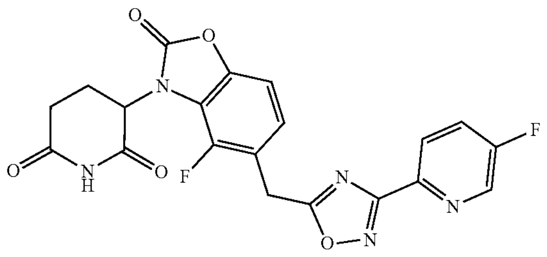 [SMILES: O=C1CCC(n2c(=O)oc3ccc(Cc4nc(-c5ccc(F)cn5)no4)c(F)c32)C(=O)N1] | 442.1 | 1H NMR (400 MHz, DMSO) δ 11.23 (s, 1H), 8.76 (d, J = 2.8 Hz, 1H), 8.11 (dd, J = 8.8, 4.4 Hz, 1H), 7.93 (td, J = 8.7, 2.9 Hz, 1H), 7.41-7.29 (m, 2H), 5.45 (s, 1H), 4.55 (s, 2H), 2.95 (s, 1H), 2.65 (d, J = 16.3 Hz, 1H), 2.36-2.11 (m, 2H) |
| 127 | 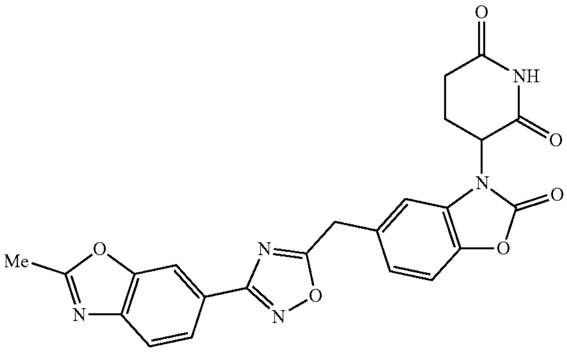 [SMILES: Cc1nc2ccc(-c3noc(Cc4ccc5oc(=O)n(C6CCC(=O)NC6=O)c5c4)n3)cc2o1] | 460.1 | 1H NMR (400 MHz, DMSO) δ 11.23 (s, 1H), 8.20 (d, J = 1.1 Hz, 1H), 7.98 (dd, J = 8.3, 1.5 Hz, 1H), 7.82 (d, J = 8.3 Hz, 1H), 7.42 (d, J = 8.3 Hz, 2H), 7.23 (dd, J = 8.2, 1.5 Hz, 1H), 5.40 (dd, J = 12.8, 5.2 Hz, 1H), 4.49 (s, 2H), 2.91 (td, J = 14.8,9.3 Hz, 1H), 2.76-2.63 (m, 5H), 2.18 (dt, J = 21.6, 8.5 Hz, 1H) |
| 128 | 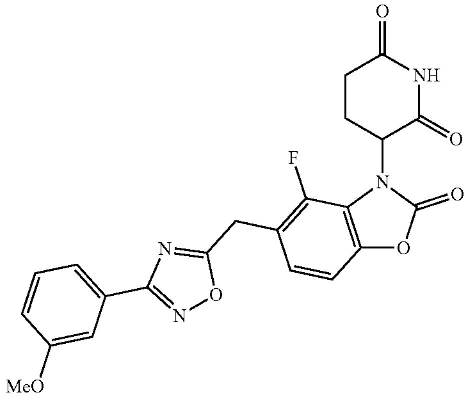 [SMILES: COc1cccc(-c2noc(Cc3ccc4oc(=O)n(C5CCC(=O)NC5=O)c4c3F)n2)c1] | 457.3 | 1H NMR (400 MHz, DMSO) δ 11.23 (s, 1H), 7.55 (d, J = 7.2 Hz, 1H), 7.51-7.41 (m, 2H), 7.35 (t, J = 7.4 Hz, 2H), 7.16 (d, J = 8.3 Hz, 1H), 5.45 (s, 1H), 4.53 (s, 2H), 3.82 (s, 3H), 2.96 (s, 1H), 2.65 (d, J = 17.1 Hz, 1H), 2.25 (t, J = 26.4 Hz, 2H) |

-continued
| Compound # | Structure | [M + H]+ | $^1$H NMR |
|---|---|---|---|
| 129 | 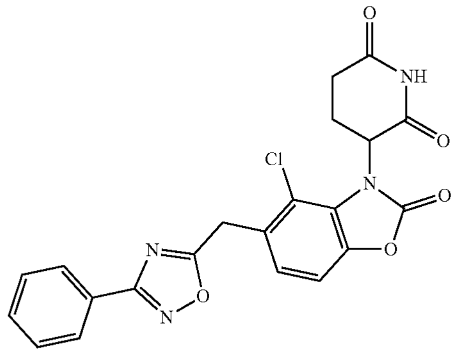 [SMILES: O=C1CCC(n2c(=O)oc3ccc(Cc4nc(-c5ccccc5)no4)c(Cl)c32)C(=O)N1] | 438.1 | $^1$H NMR (400 MHz, DMSO) δ 11.29 (d, J = 17.3 Hz, 1H), 8.05 (d, J = 7.8 Hz, 2H), 7.72-7.51 (m, 5H), 6.14-5.51 (m, 1H), 4.73 (d, J = 15.4 Hz, 2H), 3.15-2.92 (m, 1H), 2.80-2.63 (m, 2H), 2.44-2.33 (m, 1H) |
| 130 | 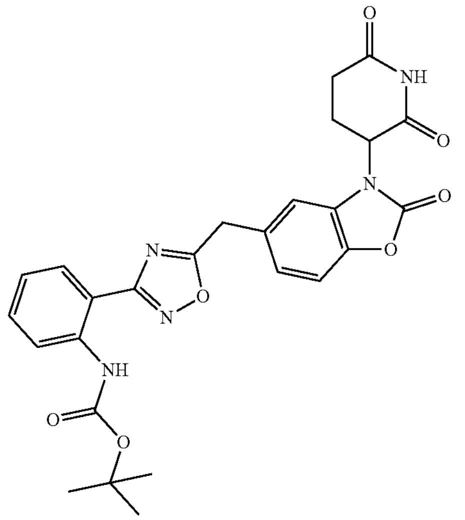 [SMILES: CC(C)(C)OC(=O)Nc1ccccc1-c1noc(Cc2ccc3oc(=O)n(C4CCC(=O)NC4=O)c3c2)n1] | 520.4 | 1HNMR(400 MHz, CDCl3) δ 9.31 (s, 1H), 8.38 (d, J = 8.4 Hz, 1H), 8.14 (s, 1H), 8.10 (dd, J = 7.9, 1.5 Hz, 1H), 7.47 (dd, J = 9.5, 5.0 Hz, 1H), 7.25 (s, 1H), 7.20 (dd, J = 8.3, 1.4 Hz, 1H), 7.10 (t, J = 7.2 Hz, 1H), 6.91 (d, J = 1.1 Hz, 1H), 5.04 (dd, J = 12.8, 5.3 Hz, 1H), 4.33 (s, 2H), 2.99 (d, J = 16.2 Hz, 1H), 2.90-2.69 (m, 2H), 2.37-2.29 (m, 1H), 1.53 (s, 9H |
| 131 | 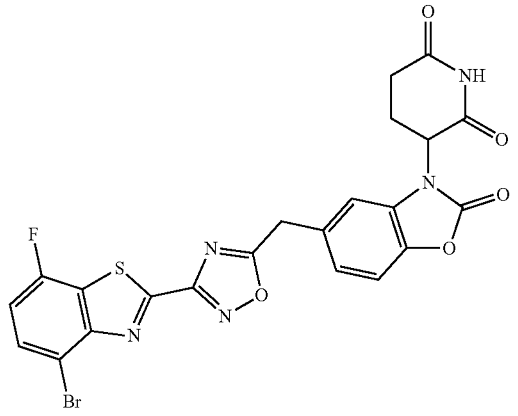 [SMILES: O=C1CCC(n2c(=O)oc3ccc(Cc4nc(-c5nc6c(Br)ccc(F)c6s5)no4)cc32)C(=O)N1] | 558.1 | $^1$H NMR (400 MHz, DMSO-$d_6$) δ 11.23 (s, 1H), 7.97 (dd, J = 8.6, 4.8 Hz, 1H), 7.53 (t, J = 8.9 Hz, 1H), 7.43 (d, J = 8.4 Hz, 2H), 7.26 (dd, J = 8.2, 1.7 Hz, 1H), 5.40 (dd, J = 12.8, 5.2 Hz, 1H), 4.58 (s, 2H), 2.97-2.84 (m, 1H), 2.76-2.62 (m, 2H), 2.23-2.15 (m, 1H). |
| 132 | 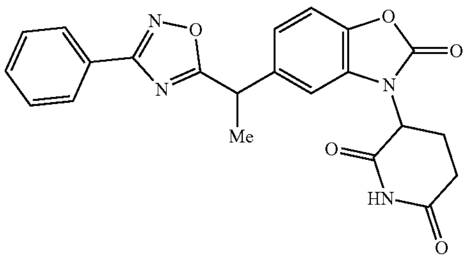 [SMILES: CC(c1ccc2oc(=O)n(C3CCC(=O)NC3=O)c2c1)c1nc(-c2ccccc2)no1] | 419.3 | $^1$H NMR (400 MHz, DMSO) δ 11.22 (d, J = 5.4 Hz, 1H), 8.06-7.93 (m, 2H), 7.63-7.52 (m, 3H), 7.39 (d, J = 8.4 Hz, 2H), 7.23-7.16 (m, 1H), 5.44-5.34 (m, 1H), 4.70 (q, J = 7.1 Hz, 1H), 2.95-2.81 (m, 1H), 2.79-2.63 (m, 2H), 2.23-2.12 (m, 1H), 1.81-1.68 (m, 3H). |

General Method E: 3-(2-oxo-5-((5-phenyl-1,3,4-oxadiazol-2-yl)methyl)benzo[d]oxazol-3(2H)-yl)piperidine-2,6-dione (Compound 83)

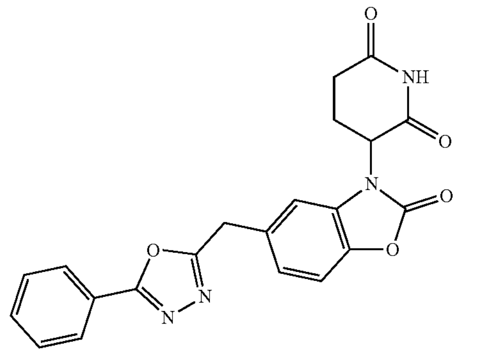

Step 1: Preparation of N'-(2-(3-(2,6-dioxopiperidin-3-yl)-2-oxo-2,3-dihydrobenzo[d]oxazol-5-yl)acetyl)benzohydrazide

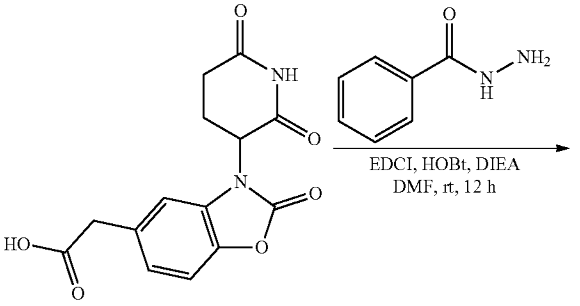

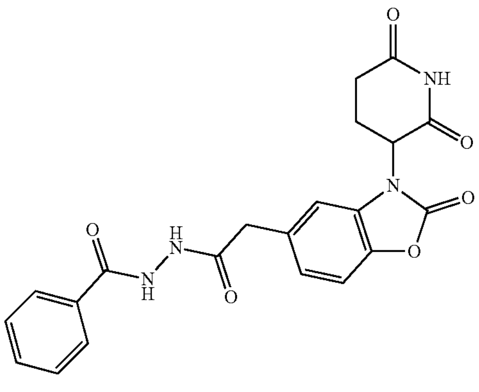

To a solution of 2-(3-(2,6-dioxopiperidin-3-yl)-2-oxo-2,3-dihydrobenzo[d]oxazol-5-yl)acetic acid (140 mg, 0.46 mmol) and benzohydrazide (68.9 mg, 0.51 mmol) in DMF (5.0 mL) were added HOBt (93.3 mg, 0.69 mmol), DIEA (178 mg, 1.38 mmol) and EDCI (132 mg, 0.69 mmol). The mixture was stirred at room temperature. for 12 hours. LCMS indicated the reaction was complete. The mixture was poured into $H_2O$ (20 mL) and extracted with EtOAc (20 mL×3). The combined organic phases were dried anhydrous $Na_2SO_4$, filtered and concentrated in vacuo. The residue was purified by flash column chromatography on silica gel (MeOH in DCM, 0~10%, V/V) to give to give N'-(2-(3-(2,6-dioxopiperidin-3-yl)-2-oxo-2,3-dihydrobenzo[d]oxazol-5-yl)acetyl)benzohydrazide (170.0 mg, 0.40 mmol, 87%) as a light yellow solid. LCMS (m/z): $[M]^+$ calcd: 422.12, found: 423.1 $^1H$ NMR (400 MHz, DMSO) δ 11.21 (s, 1H), 10.40 (s, 1H), 10.21 (s, 1H), 7.93-7.83 (m, 2H), 7.64-7.53 (m, 1H), 7.53-7.43 (m, 2H), 7.39-7.27 (m, 2H), 7.17-7.10 (m, 1H), 5.40 (dd, J=12.9, 5.3 Hz, 1H), 3.62-3.52 (m, 2H), 3.01-2.86 (m, 1H), 2.83-2.61 (m, 2H), 2.24-2.12 (m, 1H).

Step 2: 3-(2-oxo-5-((5-phenyl-1,3,4-oxadiazol-2-yl)methyl)benzo[d]oxazol-3(2H)-yl)piperidine-2,6-dione

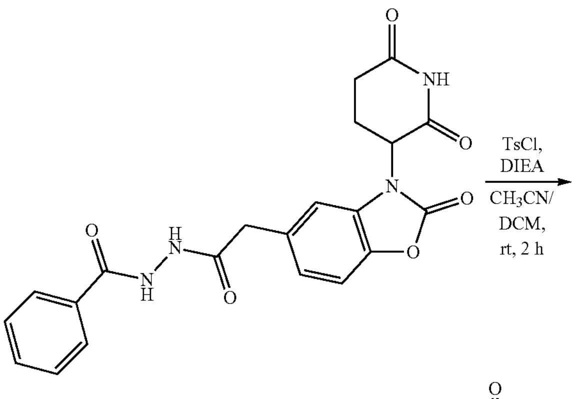

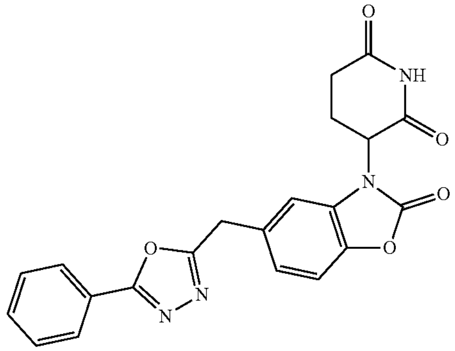 [SMILES: O=C1CCC(n2c(=O)oc3ccc(Cc4nnc(-c5ccccc5)o4)cc32)C(=O)N1]

To a solution of N'-(2-(3-(2,6-dioxopiperidin-3-yl)-2-oxo-2,3-dihydrobenzo[d]oxazol-5-yl)acetyl)benzohydrazide (140 mg, 0.33 mmol) in DCM (2.0 mL) and $CH_3CN$ (2.0 mL) were added DIEA (129 mg, 0.99 mmol) and tosyl chloride (126 mg, 0.66 mmol). The mixture was stirred at rt. for 2 hours. LCMS showed the reaction was completed. The resulting mixture was purified by prep-HPLC (C18, Wave length: 220 nm/254 nm; phase A: $H_2O$ (0.1% FA); phase B: MeCN 15%-95%, 12 min/20 min) to give 3-(2-oxo-5-((5-phenyl-1,3,4-oxadiazol-2-yl)methyl)benzo[d]oxazol-3(2H)-yl)piperidine-2,6-dione (25.0 mg, 0.06 mmol, 19%) as a light yellow solid. LCMS (m/z): $[M]^+$ calcd: 404.11, found: 405.1. $^1H$ NMR (400 MHz, DMSO-$d_6$) δ 11.22 (s, 1H), 7.98-7.91 (m, 2H), 7.65-7.55 (m, 3H), 7.42-7.35 (m, 2H), 7.20 (dd, J=8.2, 1.6 Hz, 1H), 5.39 (dd, J=12.9, 5.3 Hz, 1H), 4.39 (s, 2H), 2.96-2.82 (m, 1H), 2.76-2.60 (m, 2H), 2.22-2.13 (m, 1H).

Compounds below may be synthesized utilizing General Method E.

| Compound # | Structure | [M + H]$^+$ | $^1$H NMR |
|---|---|---|---|
| 133 | 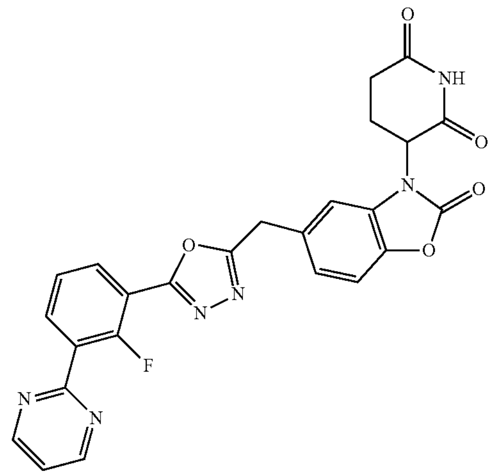 [SMILES: O=C1CCC(n2c(=O)oc3ccc(Cc4nnc(-c5cccc(-c6ncccn6)c5F)o4)cc32)C(=O)N1] | 501.1 | $^1$H NMR (400 MHz, DMSO) δ 11.22 (s, 1H), 8.99 (d, J = 4.9 Hz, 2H), 8.22 (td, J = 7.6, 1.8 Hz, 1H), 8.16-8.09 (m, 1H), 7.61-7.51 (m, 2H), 7.39 (dd, J = 7.3, 4.8 Hz, 2H), 7.21 (dd, J = 8.3, 1.5 Hz, 1H), 5.39 (dd, J = 13.0, 5.2 Hz, 1H), 4.43 (s, 2H), 2.95-2.81 (m, 1H), 2.77-2.62 (m, 2H), 2.18 (dd, J = 10.6, 5.1 Hz, 1H) |
| 134 | 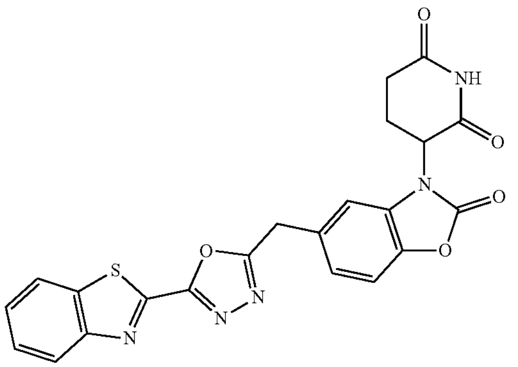 [SMILES: O=C1CCC(n2c(=O)oc3ccc(Cc4nnc(-c5nc6ccccc6s5)o4)cc32)C(=O)N1] | 462.1 | $^1$HNMR (400 MHz, DMSO) δ 11.23 (s, 1H), 8.32-8.26 (m, 1H), 8.24-8.17 (m, 1H), 7.74-7.57 (m, 2H), 7.41 (dd, J = 13.4, 4.8 Hz, 2H), 7.23 (dd, J = 8.3, 1.6 Hz, 1H), 5.40 (dd, J = 12.8, 5.2 Hz, 1H), 4.49 (s, 2H), 2.96-2.82 (m, 1H), 2.78-2.62 (m, 2H), 2.24-2.12 (m, 1H) |
| 135 | 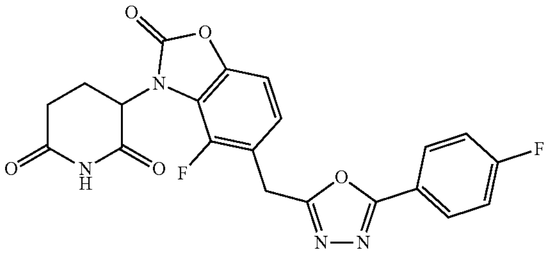 [SMILES: O=C1CCC(n2c(=O)oc3ccc(Cc4nnc(-c5ccc(F)cc5)o4)c(F)c32)C(=O)N1] | 441.3 | $^1$H NMR (400 MHz, DMSO) δ 11.25 (s, 1H), 8.00 (dd, J = 8.9, 5.3 Hz, 2H), 7.44 (t, J = 8.9, Hz, 2H), 7.32 (dd, J = 10.7, 7.4 Hz, 2H), 5.46 (s, 1H), 4.43 (s, 2H), 2.97 (s, 1H), 2.66 (d, J = 13.4 Hz, 1H), 2.31 (d, J = 15.7 Hz, 2H) |
| 136 | 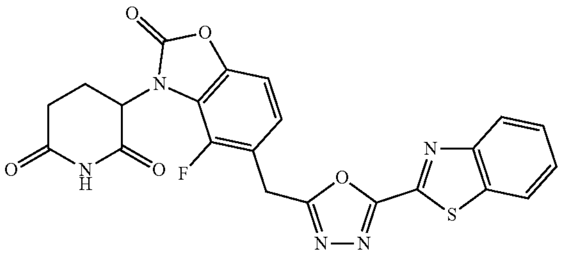 [SMILES: O=C1CCC(n2c(=O)oc3ccc(Cc4nnc(-c5nc6ccccc6s5)o4)c(F)c32)C(=O)N1] | 480.1 | $^1$H NMR (400 MHz, DMSO) δ 11.26 (s, 1H), 8.30 (dd, J = 7.2, 1.7 Hz, 1H), 8.24-8.18 (m, 1H), 7.66 (pd, J = 7.2, 1.4 Hz, 2H), 7.41-7.31 (m, 2H), 5.47 (s, 1H), 4.55 (s, 2H), 2.97 (s, 1H), 2.72-2.65 (m, 1H), 2.37-2.19 (m, 2H) |

-continued
| Compound # | Structure | [M + H]+ | 1H NMR |
|---|---|---|---|
| 137 | 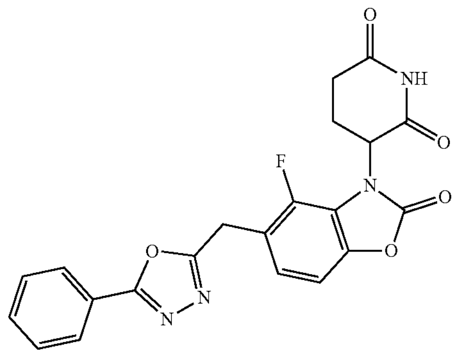 [SMILES: O=C1CCC(n2c(=O)oc3ccc(Cc4nnc(-c5ccccc5)o4)c(F)c32)C(=O)N1] | 423.3 | 1H NMR (400 MHz, DMSO) δ 11.24 (s, 1H), 8.00-7.89 (m, 2H), 7.65-7.56 (m, 3H), 7.37-7.26 (m, 2H), 5.65-5.25 (m, 1H), 4.44 (s, 2H), 3.10-2.83 (m, 1H), 2.73-2.59 (m, 1.5H), 2.35-2.27 (m, 1.5H) |
| 138 | 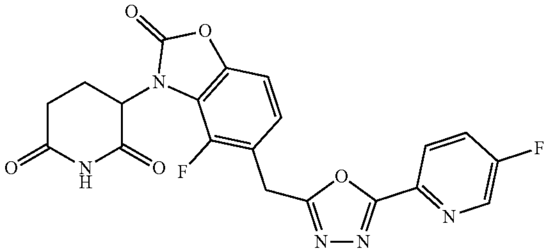 [SMILES: O=C1CCC(n2c(=O)oc3ccc(Cc4nnc(-c5ccc(F)cn5)o4)c(F)c32)C(=O)N1] | 442.3 | 1H NMR (400 MHz, DMSO-$d_6$) δ 11.25 (s, 1H), 8.77 (d, J = 2.9 Hz, 1H), 8.23 (dd, J = 8.8, 4.4 Hz, 1H), 7.98 (td, J = 8.7, 2.9 Hz, 1H), 7.37-7.27 (m, 2H), 5.46 (s, 1H), 4.47 (s, 2H), 3.05-2.91 (m, 1H), 2.69-2.61 (m, 1H), 2.37-2.12 (m, 2H) |
| 139 | 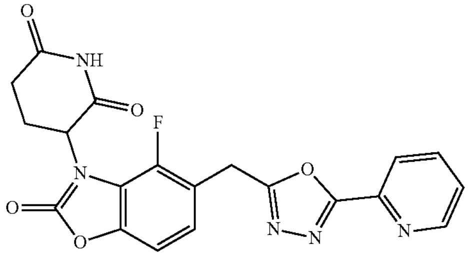 | 424.20 | 1H NMR (400 MHz, DMSO) δ 11.24 (s, 1H), 8.74 (d, J = 4.7 Hz, 1H), 8.14 (d, J = 7.9 Hz, 1H), 8.07-8.00 (m, 1H), 7.62 (ddd, J = 7.6, 4.8, 1.1 Hz, 1H), 7.38-7.25 (m, 2H), 5.46 (s, 1H), 4.48 (s, 2H), 3.05-2.88 (m, 1H), 2.65 (d, J = 16.6 Hz, 1H), 2.38-2.03 (m, 2H) |
| 140 | 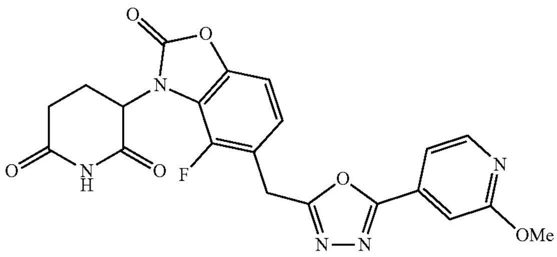 [SMILES: COc1cc(-c2nnc(Cc3ccc4oc(=O)n(C5CCC(=O)NC5=O)c4c3F)o2)ccn1] | 454.1 | 1H NMR (400 MHz, DMSO) δ 11.24 (s, 1H), 8.40 (d, J = 5.3 Hz, 1H), 7.47 (dd, J = 5.3, 1.3 Hz, 1H), 7.36-7.29 (m, 2H), 7.25 (s, 1H), 5.47 (s, 1H), 4.46 (s, 2H), 3.92 (s, 3H), 2.96 (s, 1H), 2.71-2.60 (m, 1H), 2.38-2.15 (m, 2H) |
| 141 | 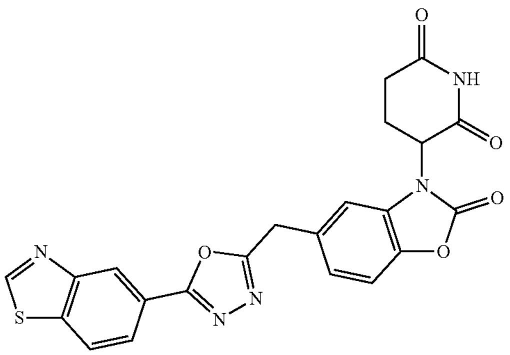 [SMILES: O=C1CCC(n2c(=O)oc3ccc(Cc4nnc(-c5ccc6scnc6c5)o4)cc32)C(=O)N1] | 462.3 | 1H NMR (400 MHz, DMSO) δ 11.22 (s, 1H), 9.55 (s, 1H), 8.58 (d, J = 1.4 Hz, 1H), 8.40 (d, J = 8.4 Hz, 1H), 8.06 (dd, J = 8.4, 1.6 Hz, 1H), 7.46-7.34 (m, 2H), 7.24 (d, J = 8.3 Hz, 1H), 5.40 (dd, J = 12.9, 5.1 Hz, 1H), 4.42 (s, 2H), 2.89 (t, J = 14.6 Hz, 1H), 2.77-2.63 (m, 2H), 2.23-2.15 (m, 1H) |

3-(2-Oxo-5-((3-(3-(6-oxo-1,6-dihydropyridin-3-yl)phenyl)-1,2,4-oxadiazol-5-yl)methyl)benzo[d]oxazol-3(2H)-yl)piperidine-2,6-dione (Compound 84)

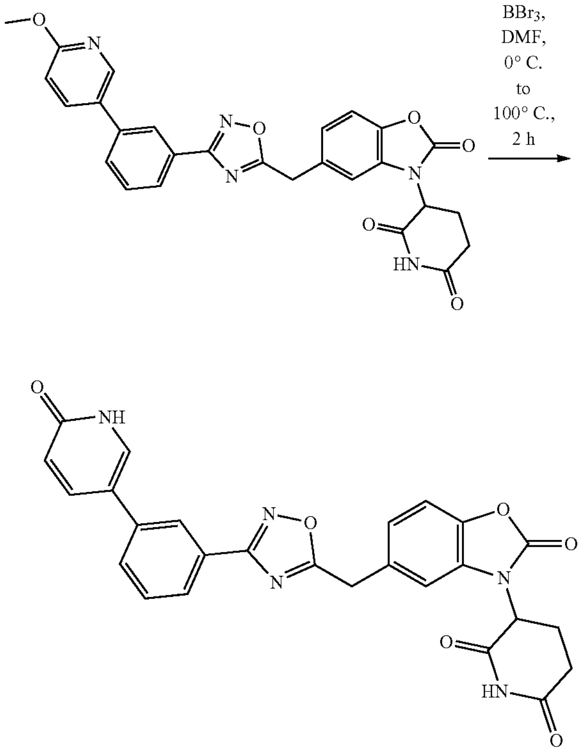

To a stirred solution of 3-(5-((3-(3-(6-methoxypyridin-3-yl)phenyl)-1,2,4-oxadiazol-5-yl)methyl)-2-oxobenzo[d]oxazol-3 (2H)-yl)piperidine-2,6-dione (0.120 g, 0.235 mmol) in DMF (2 mL) at 0° C., $BBr_3$ in DCM (2.4 mL) was added and the resulting reaction mixture stirred at 100° C. for 2 h. After completion of the reaction, the reaction mixture was quenched with ice-cold water (15 mL) and extracted with ethyl acetate (2×20 mL). The combined organic layers were washed with aq. sodium bicarbonate solution (10 mL) and brine solution (10 mL), dried over anhydrous sodium sulphate, filtered and the filtrate was concentrated under reduced pressure to afford crude compound. Thus obtained crude compound was purified by reverse phase prep-HPLC [column/dimensions: X-select (19×250), mobile phase (A): 0.1% FA in water, mobile phase (B): 100% acetonitrile, gradient (Time/% B): 0/15, 2/15, 10/50, 13/50, 13.10/100, 15/100, 16.10/15, 18/15. Flow rate: 17 ml/min, solubility: THF+ACN+water] and the fractions were concentrated under reduced pressure followed by lyophilized to afford 3-(2-oxo-5-((3-(3-(6-oxo-1,6-dihydropyridin-3-yl)phenyl)-1,2,4-oxadiazol-5-yl)methyl)benzo[d]oxazol-3(2H)-yl)piperidine-2,6-dione (0.068 g, 17%) as an off-white solid. MS (ESI) m/z 498.35 $[M+H]^+$. $^1H$ NMR (400 MHz, DMSO-$d_6$) δ 11.89 (s, 1H), 10.29 (s, 1H), 8.06 (s, 1H), 7.89-7.85 (m, 2H), 7.78 (d, J=9.2 Hz, 2H), 7.59 (t, J=8.0 Hz, 1H), 7.40 (d, J=8.4 Hz, 2H), 7.21 (d, J=8.4 Hz, 1H), 6.45 (d, J=9.6 Hz, 1H), 5.40 (dd, J=13.2, 5.2 Hz, 1H), 4.48 (s, 2H), 2.93-2.84 (m, 1H), 2.74-2.63 (m, 2H), 2.21-2.16 (m, 1H).

tert-Butyl 4-(3-(5-((3-(2,6-dioxopiperidin-3-yl)-2-oxo-2,3-dihydrobenzo[d]oxazol-5-yl)methyl)-1,2,4-oxadiazol-3-yl)phenyl)picolinate (Compound 85)

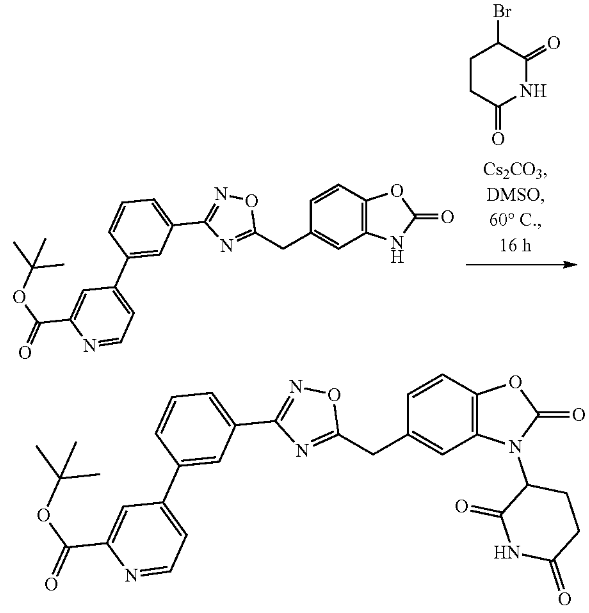

To a stirred solution of tert-butyl 4-(3-(5-((2-oxo-2,3-dihydrobenzo[d]oxazol-5-yl)methyl)-1,2,4-oxadiazol-3-yl)phenyl)picolinate (2 g, 4.25 mmol) in DMSO (20 mL) at room temperature, 3-bromopiperidine-2,6-dione (4.9 g, 25.5 mmol) and cesium carbonate (4.15 g, 12.7 mmol) were added and the resulting reaction mixture was stirred at 60° C. for 16 h. After completion of the reaction, the reaction mixture was quenched with ice-cold water (50 mL) and extracted with ethyl acetate (3×50 mL). The combined organic layer was dried over anhydrous sodium sulphate, filtered and the filtrate was concentrated under reduced pressure to afford crude compound. The crude compound was purified by davisil silica column chromatography and eluted by using 100% ethyl acetate in petroleum ether to afford tert-butyl 4-(3-(5-((3-(2,6-dioxopiperidin-3-yl)-2-oxo-2,3-dihydrobenzo[d]oxazol-5-yl)methyl)-1,2,4-oxadiazol-3-yl)phenyl)picolinate (1 g, 22%) as white solid. MS (ESI) m/z 580.16 $[M-H]^+$.

4-(3-(5-((3-(2,6-Dioxopiperidin-3-yl)-2-oxo-2,3-dihydrobenzo[d]oxazol-5-yl)methyl)-1,2,4-oxadiazol-3-yl)phenyl)picolinic acid (Compound 86)

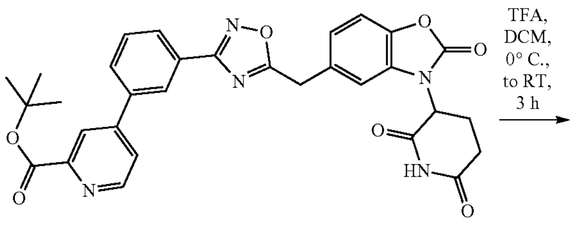

-continued

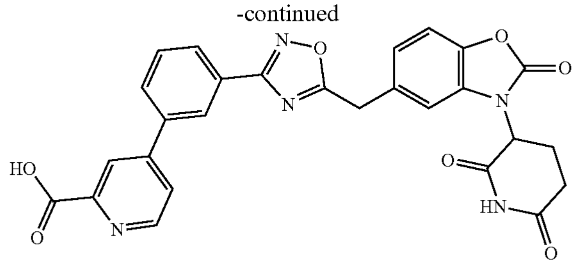

To a stirred solution of tert-butyl 4-(3-(5-((3-(2,6-dioxopiperidin-3-yl)-2-oxo-2,3-dihydrobenzo[d]oxazol-5-yl)methyl)-1,2,4-oxadiazol-3-yl)phenyl)picolinate (0.098 g, 0.169 mmol) in DCM (5 mL) at 0° C., trifluoroacetic acid (1 mL, 0.843 mmol) was added and the resulting reaction mixture was stirred at 0° C. for 5 min and then allowed to warm to room temperature and stirred for 3 h. After completion of the reaction, the reaction mixture was directly concentrated under reduced pressure and titurated with diethylether (20 mL) to afford crude compound. Thus obtained crude compound was purified by RP prep-HPLC [column/dimensions: X-select C18 (19×250×5 μm), mobile phase (A): 0.1% FA in water, mobile phase (B): acetonitrile, gradient (Time/% B): 0/25, 1/25, 10/55, 13/55, 13.1/100, 15/100, 15.1/25, 18/25. Flow rate: 16 ml/min, solubility: THF+ACN+water] and the fractions were concentrated under reduced pressure followed by lyophilized to afford 4-(3-(5-((3-(2,6-dioxopiperidin-3-yl)-2-oxo-2,3-dihydrobenzo[d]oxazol-5-yl)methyl)-1,2,4-oxadiazol-3-yl)phenyl)picolinic acid (0.035 g, 37%) as an white solid. MS (ESI) m/z 526.29 $[M+H]^+$. $^1$H NMR (400 MHz, DMSO-$d_6$) δ 13.57 (s, 1H), 11.22 (s, 1H), 8.81 (d, J=4.8 Hz, 1H), 8.33 (d, J=9.6 Hz, 2H), 8.10 (t, J=8.0 Hz, 2H), 8.03-7.98 (m, 1H), 7.75 (t, J=8.0 Hz, 1H), 7.41 (t, J=4.4 Hz, 2H), 7.23 (d, J=7.2 Hz, 1H), 5.40 (dd, J=12.8, 4.8 Hz, 1H), 4.51 (s, 2H), 2.94-2.82 (m, 1H), 2.72-2.61 (m, 2H), 2.21-2.14 (m, 1H).

General Method F 4-(3-(5-((3-(2,6-Dioxopiperidin-3-yl)-2-oxo-2,3-dihydrobenzo[d]oxazol-5-yl)methyl)-1,2,4-oxadiazol-3-yl)phenyl)picolinamide (Compound 87)

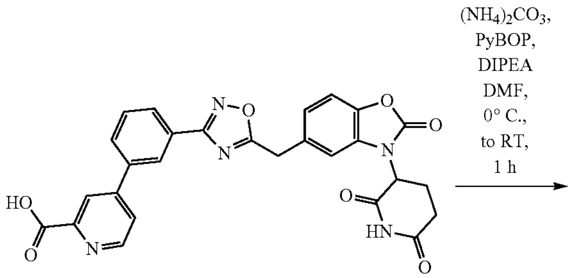

-continued

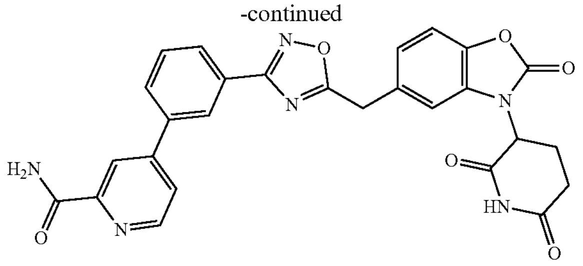

To a stirred solution of 4-(3-(5-((3-(2,6-dioxopiperidin-3-yl)-2-oxo-2,3-dihydrobenzo[d]oxazol-5-yl)methyl)-1,2,4-oxadiazol-3-yl)phenyl)picolinic acid (0.100 g, 0.190 mmol) in DMF (2 mL) at room temperature, N-diisopropylethylamine (0.2 mL, 0.952 mmol) and ammonium carbonate (0.183 g, 1.903 mmol) were added and the resulting reaction mixture was allowed to room temperature and stirred for 15 min. After cooling to 0° C., PyBOP (0.297 g, 0.571 mmol) was added and then the reaction mixture was allowed to warm to room temperature and stirred for 1 h. After completion of the reaction, the reaction mixture was quenched with water (10 mL) and extracted with ethyl acetate (2×20 mL). The combined organic layers were washed with brine solution (10 mL), dried over anhydrous sodium sulphate, filtered and the filtrate was concentrated under reduced pressure to afford crude compound. Thus obtained crude compound was purified by RP prep-HPLC [column/dimensions: X-select C18 (19×150) 5μ, mobile phase (A): 0.1% FA in water, mobile phase (B): acetonitrile, gradient (Time/% B): 0/20, 1/20, 10/50, 14/50, 14.1/100, 16/100, 16.1/20, 19/20. Flow rate: 17 ml/min, solubility: THF+ACN+water] and the fractions were concentrated under reduced pressure followed by lyophilized to afford 4-(3-(5-((3-(2,6-dioxopiperidin-3-yl)-2-oxo-2,3-dihydrobenzo[d]oxazol-5-yl)methyl)-1,2,4-oxadiazol-3-yl)phenyl)picolinamide (0.025 g, 23%) as a white solid. MS (ESI) m/z 525.49 $[M+H]^+$. $^1$H NMR (400 MHz, DMSO-$d_6$) δ 11.21 (s, 1H), 8.74 (d, J=4.8 Hz, 1H), 8.35 (s, 1H), 8.33 (d, J=1.2 Hz, 1H), 8.22 (s, 1H), 8.10 (t, J=7.6 Hz, 2H), 7.98 (dd, J=4.8, 2.0 Hz, 1H), 7.79-7.73 (m, 2H), 7.43-7.39 (m, 2H), 7.24 (dd, J=8.0, 1.2 Hz, 1H), 5.40 (dd, J=12.8, 5.2 Hz, 1H), 4.51 (s, 2H), 2.93-2.84 (m, 1H), 2.76-2.63 (m, 2H), 1.82-1.74 (m, 1H).

Compounds below may be synthesized utilizing General Method F

| Compound # | Structure | $[M + H]^+$ | $^1$H NMR |
|---|---|---|---|
| 88 | 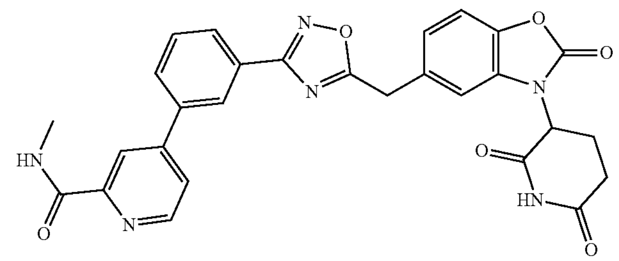 [SMILES: CNC(=O)c1cc(-c2cccc(-c3noc(Cc4ccc5oc(=O)n(C6CCC(=O)NC6=O)c5c4)n3)c2)ccn1] | 539.48 | $^1$H NMR (400 MHz, DMSO-$d_6$) δ 11.22 (s, 1H), 8.86 (q, J = 4.8 Hz, 1H), 8.74 (d, J = 5.2 Hz, 1H), 8.35 (s, 1H), 8.31 (d, J = 1.2 Hz, 1H), 8.10 (t, J = 8.0 Hz, 2H), 7.99 (dd, J = 5.2, 2.0 Hz, 1H), 7.75 (t, J = 7.6 Hz, 1H), 7.43-7.38 (m, 2H), 7.24 (dd, J = 8.4, 1.2 Hz, 1H), 5.40 (dd, J = 13.2, 5.2 Hz, 1H), 4.51 (s, 2H), 2.94-2.71 (m, 4H), 2.69-2.63 (m, 2H), 2.21-2.14 (m, 1H) |

-continued

| Compound # | Structure | [M + H]$^+$ | $^1$H NMR |
|---|---|---|---|
| 89 | 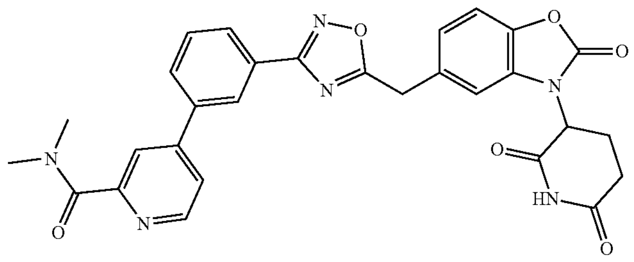 [SMILES: CN(C)C(=O)c1cc(-c2cccc(-c3noc(Cc4ccc5oc(=O)n(C6CCC(=O)NC6=O)c5c4)n3)c2)ccn1] | 553.50 | $^1$H NMR (400 MHz, DMSO-$d_6$) δ 11.21 (s, 1H), 8.68 (d, J = 5.2 Hz, 1H), 8.33 (s, 1H), 8.08 (t, J = 8.8 Hz, 2H), 7.89 (s, 1H), 7.84 (dd, J = 5.2, 1.2 Hz, 1H), 7.73 (t, J = 7.6 Hz, 1H), 7.43-7.40 (m, 2H), 7.23 (d, J = 9.2 Hz, 1H), 5.40 (dd, J = 12.8, 5.2 Hz, 1H), 4.50 (s, 2H), 3.04 (s, 3H), 2.97 (s, 3H), 2.94-2.86 (m, 1H), 2.74-2.62 (m, 2H), 2.18-2.12 (m, 1H). |
| 90 | 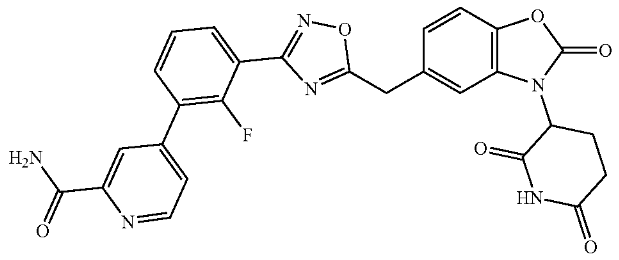 [SMILES: NC(=O)c1cc(-c2cccc(-c3noc(Cc4ccc5oc(=O)n(C6CCC(=O)NC6=O)c5c4)n3)c2F)ccn1] | 543.47 | $^1$H NMR (400 MHz, DMSO-$d_6$) δ 11.22 (s, 1H), 8.76 (d, J = 4.8 Hz, 1H), 8.23 (d, J = 8.0 Hz, 2H), 8.09 (t, J = 6.8 Hz, 1H), 7.92 (t, J = 6.0 Hz, 1H), 7.85 (d, J = 5.2 Hz, 1H), 7.75 (s, 1H), 7.56 (t, J = 7.6 Hz, 1H), 7.41 (d, J = 8.0 Hz, 2H), 7.23 (d, J = 8.4 Hz, 1H), 5.40 (dd, J = 12.8, 5.2 Hz, 1H), 4.51 (s, 2H), 2.90-2.85 (m, 1H), 2.73-2.63 (m, 2H), 2.20-2.16 (m, 1H) |
| 91 | 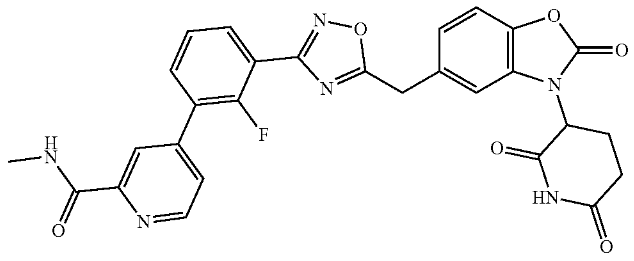 [SMILES: CNC(=O)c1cc(-c2cccc(-c3noc(Cc4ccc5oc(=O)n(C6CCC(=O)NC6=O)c5c4)n3)c2F)ccn1] | 557.49 | $^1$H NMR (400 MHz, DMSO-$d_6$) δ 11.21 (s, 1H), 8.87 (d, J = 4.8 Hz, 1H), 8.77 (d, J = 5.2 Hz, 1H), 8.22 (s, 1H), 8.09 (t, J = 6.4 Hz, 1H), 7.91 (t, J = 6.0 Hz, 1H), 7.85 (d, J = 5.2 Hz, 1H), 7.56 (t, J = 7.6 Hz, 1H), 7.41 (d, J = 7.6 Hz, 2H), 7.23 (d, J = 8.4 Hz, 1H), 5.40 (dd, J = 13.2, 4.8 Hz, 1H), 4.50 (s, 2H), 2.92-2.84 (m, 4H), 2.74-2.63 (m, 2H), 2.20-2.16 (m, 1H) |
| 92 | 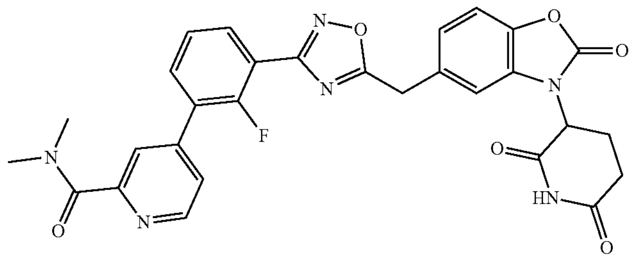 [SMILES: CN(C)C(=O)c1cc(-c2cccc(-c3noc(Cc4ccc5oc(=O)n(C6CCC(=O)NC6=O)c5c4)n3)c2F)ccn1] | 571.29 | $^1$H NMR (400 MHz, DMSO-$d_6$) δ 11.22 (s, 1H), 8.71 (d, J = 4.8 Hz, 1H), 8.08 (t, J = 6.8 Hz, 1H), 7.89 (t, J = 6.4 Hz, 1H), 7.77 (s, 1H), 7.72 (d, J = 5.2 Hz, 1H), 7.55 (t, J = 7.6 Hz, 1H), 7.41 (d, J = 8.0 Hz, 2H), 7.23 (d, J = 8.4 Hz, 1H), 5.40 (dd, J = 12.8, 5.2 Hz, 1H), 4.50 (s, 2H), 3.03 (s, 3H), 2.98 (s, 3H), 2.89-2.85 (m, 1H), 2.74-2.63 (m, 2H), 2.20-2.16 (m, 1H) |

3-(2-oxo-5-{[3-(pyrimidin-5-yl)-1,2,4-oxadiazol-5-yl]methyl}benzo[2,1-d][1,3]oxazol-3-yl)hexahydropyridine-2,6-dione (Compound 93)

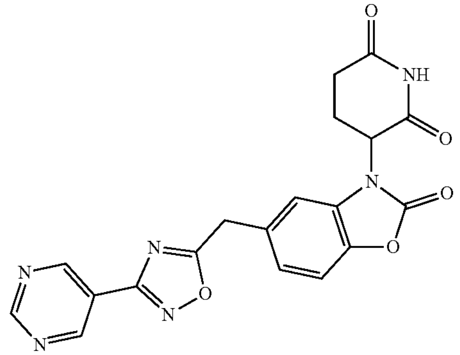 [SMILES: O=C1CCC(n2c(=O)oc3ccc(Cc4nc(-c5cncnc5)no4)cc32)C(=O)N1]

Step 1: [3-(2,6-dioxohexahydropyridin-3-yl)-2-oxobenzo[2,1-d][1,3]oxazol-5-yl]acetyl chloride

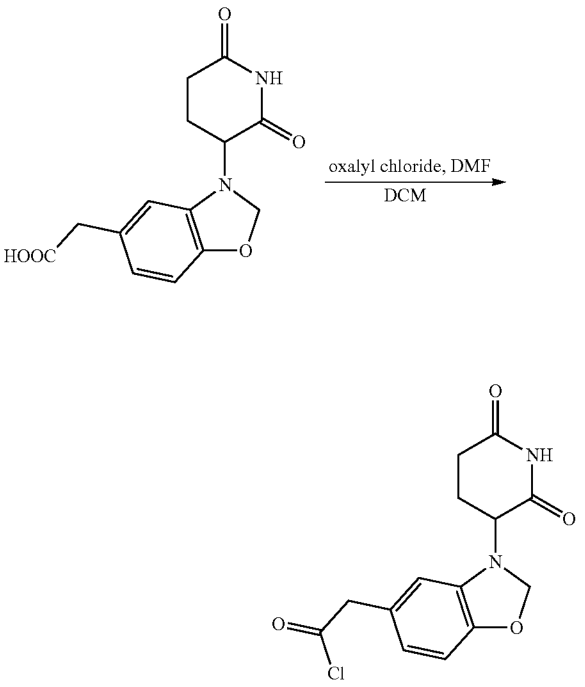 [SMILES: O=C(O)Cc1ccc2c(c1)N(C1CCC(=O)NC1=O)CO2 ; O=C(Cl)Cc1ccc2c(c1)N(C1CCC(=O)NC1=O)CO2]

To a solution of [3-(2,6-dioxohexahydropyridin-3-yl)-2-oxobenzo[2,1-d][1,3]oxazol-5-yl]acetic acid (100.0 mg, 0.33 mmol) in DCM (10 mL) was added $SOCl_2$ (117.3 mg, 0.99 mmol). The reaction was stirred at 50° C. for 1 h. TLC showed the reaction was complete. The reaction was concentrated under reduced pressure to give [3-(2,6-dioxohexahydropyridin-3-yl)-2-oxobenzo[2,1-d][1,3]oxazol-5-yl] acetyl chloride (60.00 mg, 0.19 mmol, 57%) as a brown oil. The crude product was used for next step without purification.

Step 2: 3-(2-oxo-5-{[3-(pyrimidin-5-yl)-1,2,4-oxadiazol-5-yl]methyl}benzo[2,1-d][1,3]oxazol-3-yl) hexahydropyridine-2,6-dione

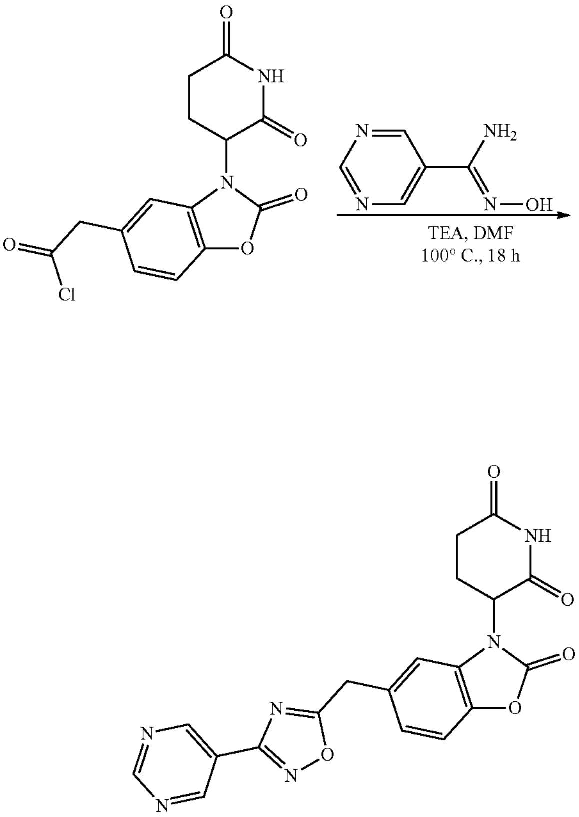

To a solution of [3-(2,6-dioxohexahydropyridin-3-yl)-2-oxobenzo[2,1-d][1,3]oxazol-5-yl]acetyl chloride (50.0 mg, 0.15 mmol) and (Z)—N'-hydroxypyrimidine-5-carboximidamide (21.4 mg, 0.15 mmol) in DMF (3 mL) was added TEA (0.02 mL, 0.15 mmol). The reaction was stirred at 90° C. for 18 hrs. LCMS showed the reaction was completed. The reaction was concentrated and purified by prep-HPLC (C18, Wave length: 220 nm/254 nm; phase A: $H_2O$, phase B: MeCN 5%-95%; 14 min/20 min) to give 3-(2-oxo-5-{[3-(pyrimidin-5-yl)-1,2,4-oxadiazol-5-yl]methyl}benzo[2,1-d][1,3]oxazol-3-yl)hexahydropyridine-2,6-dione (2.00 mg, 4.93 mol, 3%) as a white solid. LCMS (m/z): $[M]^+$ calcd: 406.10, found: 407.3. $^1H$ NMR (400 MHz, DMSO-$d_6$) δ 11.23 (s, 1H), 9.40 (s, 1H), 9.32 (s, 2H), 7.41 (d, J=8.3 Hz, 2H), 7.23 (d, J=8.1 Hz, 1H), 5.41-5.36 (m, 1H), 4.53 (s, 2H), 2.94-2.85 (m, 1H), 2.75-2.69 (m, 1H), 2.64 (d, J=2.4 Hz, 1H), 2.22-2.14 (m, 1H).

N-(2-(5-((3-(2,6-dioxopiperidin-3-yl)-2-oxo-2,3-dihydrobenzo[d]oxazol-5-yl)methyl)-1,2,4-oxadiazol-3-yl)phenyl)acetamide (Compound 94)

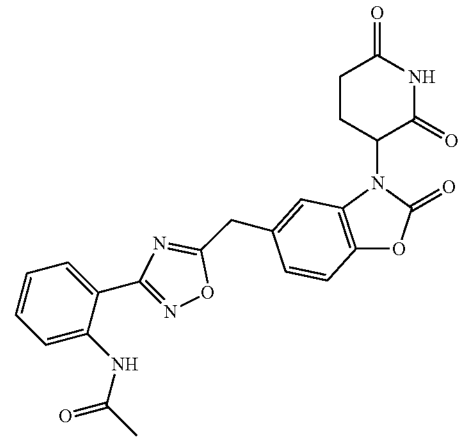 [SMILES: CC(=O)Nc1ccccc1-c1noc(Cc2ccc3oc(=O)n(C4CCC(=O)NC4=O)c3c2)n1]

Step 1. 3-(5-((3-(2-aminophenyl)-1,2,4-oxadiazol-5-yl)methyl)-2-oxobenzo[d]oxazol-3(2H)-yl)piperidine-2,6-dione

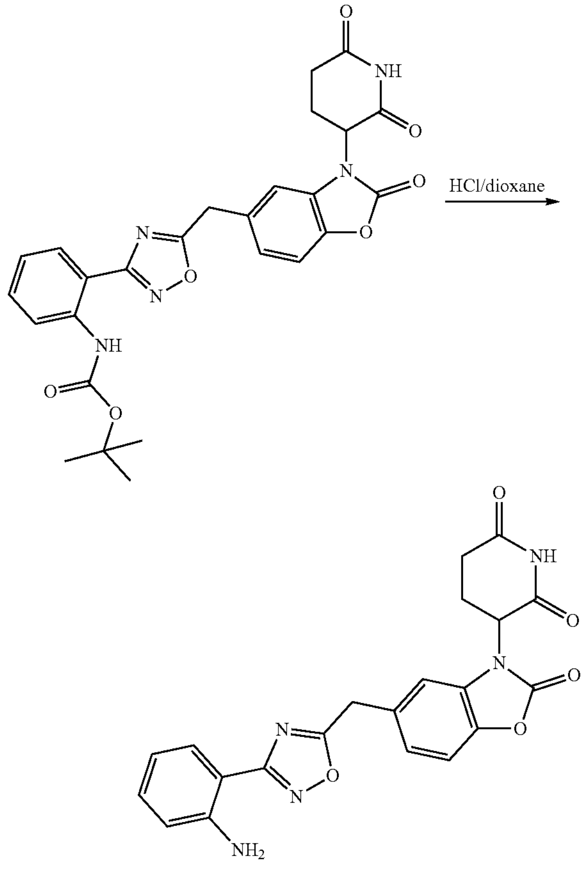

A solid of tert-butyl (2-(5-((3-(2,6-dioxopiperidin-3-yl)-2-oxo-2,3-dihydrobenzo[d]oxazol-5-yl)methyl)-1,2,4-oxadiazol-3-yl)phenyl)carbamate (200 mg, 0.38 mmol) was dissolved in 4M HCl/dioxane (10 mL). The mixture was stirred at rt for 2 hrs. LCMS showed the reaction was complete. The mixture was concentrated in vacuo to give a crude product of 3-(5-((3-(2-aminophenyl)-1,2,4-oxadiazol-5-yl)methyl)-2-oxobenzo[d]oxazol-3(2H)-yl)piperidine-2,6-dione (200 mg, 0.48 mmol, 123.87%). LCMS (m/z): $[M]^+$ calcd: 419.12, found: 420.3.

Step 2. N-(2-(5-((3-(2,6-dioxopiperidin-3-yl)-2-oxo-2,3-dihydrobenzo[d]oxazol-5-yl)methyl)-1,2,4-oxadiazol-3-yl)phenyl)acetamide

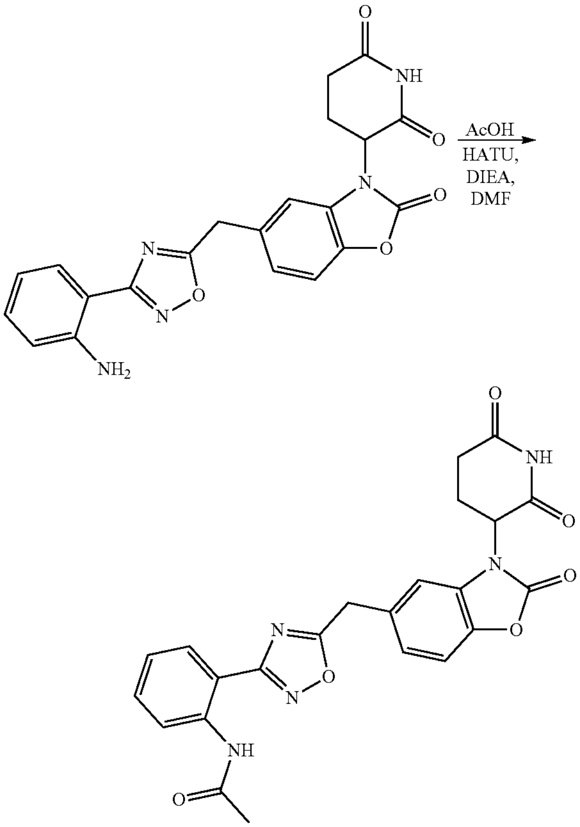

To a solution of 3-(5-((3-(2-aminophenyl)-1,2,4-oxadiazol-5-yl)methyl)-2-oxobenzo[d]oxazol-3(2H)-yl)piperidine-2,6-dione (100 mg, 0.24 mmol) in DMF (1 mL) were added acetic acid (0.01 mL, 0.24 mmol), HATU (99.7 mg, 0.26 mmol) and DIEA (92.5 mg, 0.72 mmol). The mixture was stirred at rt for 16 hr. LCMS showed the reaction was complete. The mixture was poured into water and extracted with EA. The organic phase was concentrated under reduced pressure and purified by CC (silica gel, PE:EA=80%) to get the crude DP (60 mg) which was purified by prep-HPLC (C18, Wave length: 205 nm/254 nm; phase A: $H_2O$ (FA 0.1%); phase B: MeCN 10%-95%, 18 min/22 min) to give N-(2-(5-((3-(2,6-dioxopiperidin-3-yl)-2-oxo-2,3-dihydrobenzo[d]oxazol-5-yl)methyl)-1,2,4-oxadiazol-3-yl)phenyl)acetamide (21.3 mg, 0.05 mmol, 19%). LCMS (m/z): [M]+ calcd: 461.13, found: 462.3. T NMR (400 MHz, DMSO) δ 11.23 (s, 1H), 9.90 (s, 1H), 8.08 (d, J=8.2 Hz, 1H), 7.95 (d, J=7.8 Hz, 1H), 7.54 (t, J=7.8 Hz, 1H), 7.44-7.36 (m, 2H), 7.26 (dd, J=16.3, 8.4 Hz, 2H), 5.39 (dd, J=12.7, 5.2 Hz, 1H), 4.49 (s, 2H), 2.90 (dd, J=23.7, 11.6 Hz, 1H), 2.75-2.57 (m, 2H), 2.21-2.09 (m, 1H), 2.01 (s, 3H).

General Method G: Compounds 142 and 143: 3-(5-((3-(2-fluoro-3-(pyridin-4-yl)phenyl)-1,2,4-oxadiazol-5-yl)methyl)-2-oxobenzo[d]oxazol-3(2H)-yl) piperidine-2,6-dione P1 and P2

P1

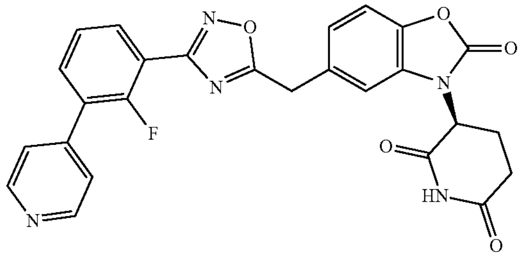

P2

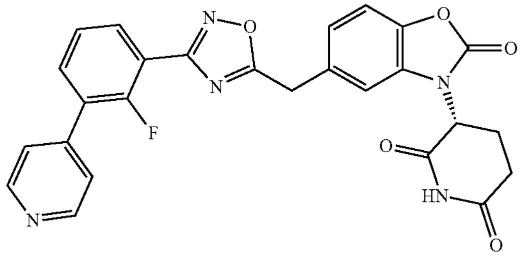

The 3-(5-((3-(2-fluoro-3-(pyridin-4-yl)phenyl)-1,2,4-oxadiazol-5-yl)methyl)-2-oxobenzo[d]oxazol-3(2H)-yl)piperidine-2,6-dione (8 mg, 0.016 mmol) was purified by SFC (IB-E-40, Wave length: 220 nm/254 nm phase A: $CO_2$; phase B: ETOH:MECN=2:1(V/V), 2.84 min&3.31 min/8 min) to give P1-3-(5-((3-(2-fluoro-3-(pyridin-4-yl)phenyl)-1,2,4-oxadiazol-5-yl)methyl)-2-oxobenzo[d]oxazol-3(2H)-yl)piperidine-2,6-dione (3.2 mg, 0.006 mmol, ee: 100%) and P2-3-(5-((3-(2-fluoro-3-(pyridin-4-yl)phenyl)-1,2,4-oxadiazol-5-yl)methyl)-2-oxobenzo[d]oxazol-3(2H)-yl)piperidine-2,6-dione (3.3 mg, 0.0067 mmol, ee: 92.64%) as white solids. LCMS (m/z): $[M]^+$ calcd, 499.13; found, 500.3. $^1H$ NMR (400 MHz, DMSO) δ 11.23 (s, 1H), 8.71 (d, J=5.9 Hz, 2H), 8.06 (t, J=6.4 Hz, 1H), 7.90-7.81 (m, 1H), 7.63 (d, J=4.7 Hz, 2H), 7.54 (t, J=7.8 Hz, 1H), 7.45-7.37 (m, 2H), 7.23 (d, J=8.5 Hz, 1H), 5.40 (dd, J=12.7, 5.2 Hz, 1H), 4.51 (s, 2H), 2.97-2.85 (m, 1H), 2.74-2.63 (m, 2H), 2.24-2.15 (m, 1H).

Compounds below may be synthesized utilizing General Method G

| Compound # | Structure | $[M + H]^+$ | $^1H$ NMR |
|---|---|---|---|
| 144 | 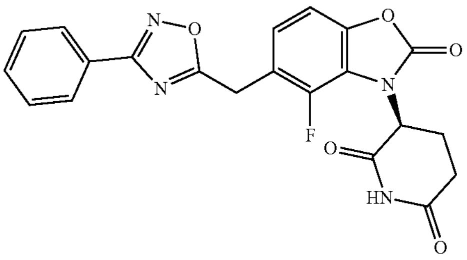 P1 | 423.1 | $^1H$ NMR (400 MHz, $CDCl_3$) δ 8.09-7.96 (m, 3H), 7.55-7.42 (m, 3H), 7.22-7.15 (m, 1H), 7.11 (d, J = 8.4 Hz, 1H), 5.21 (d, J = 8.3 Hz, 1H), 4.33 (dd, J = 43.8, 16.2 Hz, 2H), 2.98 (dd, J = 13.2, 2.4 Hz, 1H), 2.91-2.76 (m, 1H), 2.60 (s, 1H), 2.46-2.29 (m, 1H) |
| 145 | 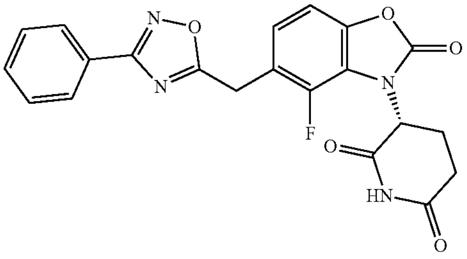 P2 | 423.1 | $^1H$ NMR (400 MHz, $CDCl_3$) δ 8.09-7.96 (m, 3H), 7.55-7.42 (m, 3H), 7.22-7.15 (m, 1H), 7.11 (d, J = 8.4 Hz, 1H), 5.21 (d, J = 8.3 Hz, 1H), 4.33 (dd, J = 43.8, 16.2 Hz, 2H), 2.98 (dd, J = 13.2, 2.4 Hz, 1H), 2.91-2.76 (m, 1H), 2.60 (s, 1H), 2.46-2.29 (m, 1H). |

-continued
| Compound # | Structure | [M + H]+ | $^{1}$H NMR |
|---|---|---|---|
| 146 | 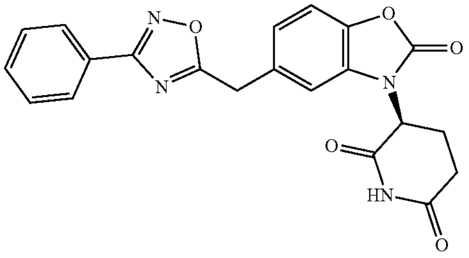 P1 | 405.3 | $^{1}$HNMR (400 MHz, DMSO-$d_6$) δ 11.21 (s, 1H), 8.04-7.90 (m, 2H), 7.64-7.49 (m, 3H), 7.40 (d, J = 8.6 Hz, 2H), 7.21 (d, J = 9.5 Hz, 1H), 5.38 (dd, J = 12.8, 5.3 Hz, 1H), 4.46 (s, 2H), 2.88 (dd, J = 11.5, 7.7 Hz, 1H), 2.76-2.57 (m, 2H), 2.23-2.12 (m, 1H) |
| 147 | 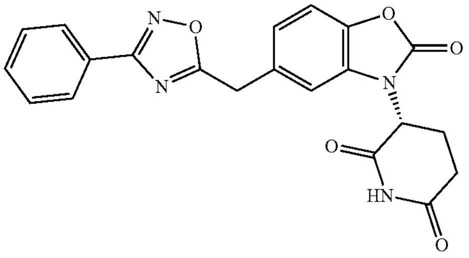 P2 | 405.3 | $^{1}$HNMR (400 MHz, DMSO-$d_6$) δ 11.21 (s, 1H), 8.04-7.90 (m, 2H), 7.64-7.49 (m, 3H), 7.40 (d, J = 8.6 Hz, 2H), 7.21 (d, J = 9.5 Hz, 1H), 5.38 (dd, J = 12.8, 5.3 Hz, 1H), 4.46 (s, 2H), 2.88 (dd, J = 11.5, 7.7 Hz, 1H), 2.76-2.57 (m, 2H), 2.23-2.12 (m, 1H) |
| 148 | 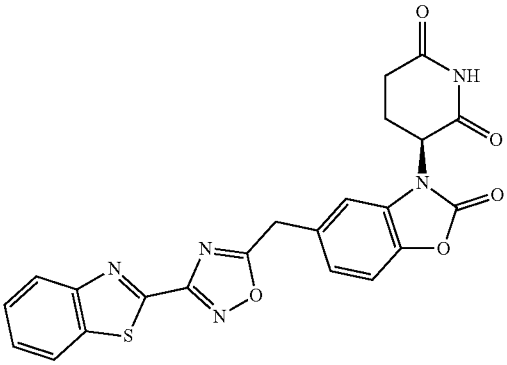 P1 | 462.3 | $^{1}$H NMR (400 MHz, DMSO-$d_6$) δ 11.23 (s, 1H), 8.24 (dd, J = 24.7, 7.9 Hz, 2H), 7.69-7.59 (m, 2H), 7.43 (d, J = 8.1 Hz, 2H), 7.26 (d, J = 8.3 Hz, 1H), 5.40 (dd, J = 12.7, 5.2 Hz, 1H), 4.55 (s, 2H), 2.98-2.83 (m, 1H), 2.76-2.62 (m, 2H), 2.24-2.14 (m, 1H) |
| 149 | 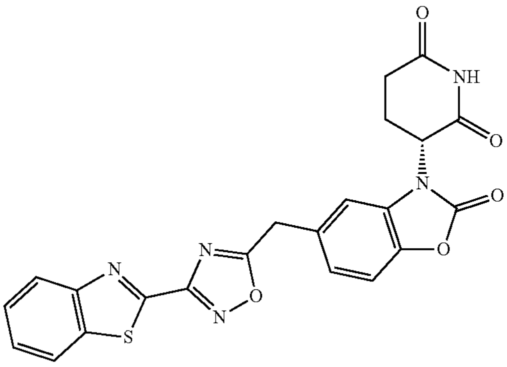 P2 | 462.3 | $^{1}$H NMR (400 MHz, DMSO-$d_6$) δ 11.23 (s, 1H), 8.24 (dd, J = 24.7, 7.9 Hz, 2H), 7.69-7.59 (m, 2H), 7.43 (d, J = 8.1 Hz, 2H), 7.26 (d, J = 8.3 Hz, 1H), 5.40 (dd, J = 12.7, 5.2 Hz, 1H), 4.55 (s, 2H), 2.98-2.83 (m, 1H), 2.76-2.62 (m, 2H), 2.24-2.14 (m, 1H) |

-continued
| Compound # | Structure | [M + H]$^+$ | $^1$H NMR |
|---|---|---|---|
| 150 | 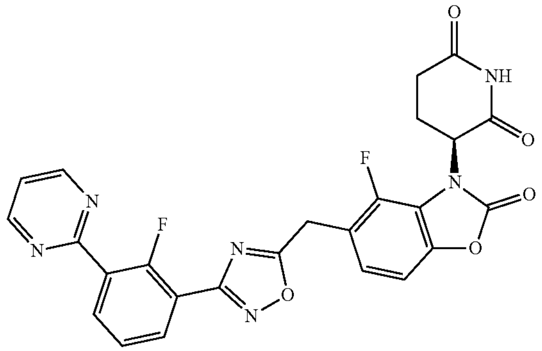 P1 | 519.4 | $^1$H NMR (400 MHz, DMSO-$d_6$) δ 11.24 (s, 1H), 8.99 (d, J = 4.9 Hz, 2H), 8.23-8.05 (m, 2H), 7.61-7.50 (m, 2H), 7.39-7.33 (m, 2H), 5.47 (s, 1H), 4.57 (s, 2H), 2.93 (d, J = 28.5 Hz, 1H), 2.68-2.61 (m, 1H), 2.36-2.13 (m, 2H) |
| 151 | 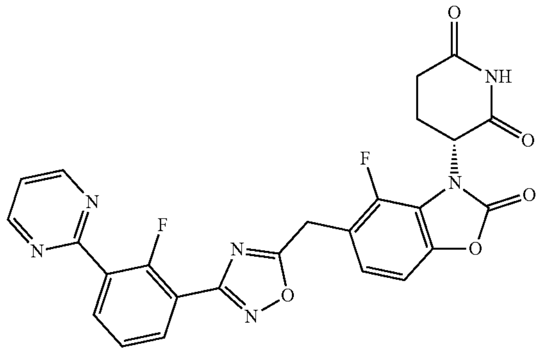 P2 | 519.4 | $^1$H NMR (400 MHz, DMSO-$d_6$) δ 11.24 (s, 1H), 8.99 (d, J = 4.9 Hz, 2H), 8.23-8.05 (m, 2H), 7.61-7.50 (m, 2H), 7.39-7.33 (m, 2H), 5.47 (s, 1H), 4.57 (s, 2H), 2.93 (d, J = 28.5 Hz, 1H), 2.68-2.61 (m, 1H), 2.36-2.13 (m, 2H) |
| 152 | 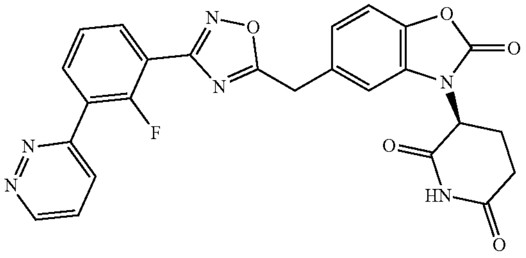 P2 | 501.3 | $^1$H NMR (400 MHz, DMSO) δ 11.22 (s, 1H), 9.52 (s, 1H), 9.38 (d, J = 5.4 Hz, 1H), 8.12 (t, J = 7.3 Hz, 1H), 7.97 (t, J = 7.7 Hz, 2H), 7.59 (t, J = 7.8 Hz, 1H), 7.41 (d, J = 8.0 Hz, 2H), 7.23 (d, J = 8.5 Hz, 1H), 5.39 (dd, J = 12.5, 4.7 Hz, 1H), 4.51 (s, 2H), 2.90 (s, 1H), 2.67 (s, 2H), 2.19 (s, 1H) |
| 153 | 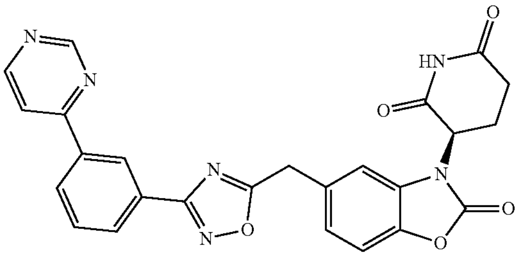 P1 | 482.13 | $^1$H NMR (400 MHz, DMSO) δ 11.22 (s, 1H), 9.31 (s, 1H), 8.92 (d, J = 5.3 Hz, 1H), 8.84 (s, 1H), 8.41 (d, J = 7.8 Hz, 1H), 8.18 (dd, J = 14.6, 6.5 Hz, 2H), 7.76 (t, J = 7.8 Hz, 1H), 7.46-7.38 (m, 2H), 7.24 (d, J = 8.5 Hz, 1H), 5.45-5.34 (m, 1H), 4.51 (s, 2H), 2.96-2.81 (m, 1H), 2.75-2.61 (m, 2H), 2.22-2.13 (m, 1H) |

-continued

| Compound # | Structure | [M + H]+ | $^1$H NMR |
|---|---|---|---|
| 154 | 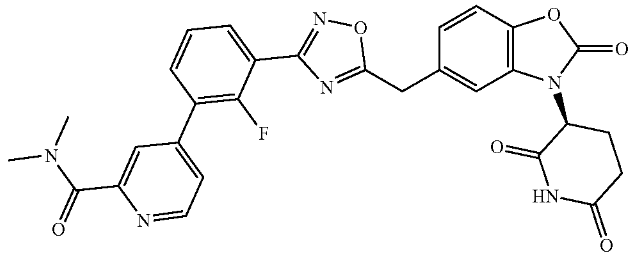 P1 | 571.1 | 1H NMR (400 MHz, DMSO-d6) δ 11.22 (s, 1H), 8.71 (d, J = 5.2 Hz, 1H), 8.08 (t, J = 7.0 Hz, 1H), 7.89 (t, J = 7.4 Hz, 1H), 7.77 (s, 1H), 7.72 (d, J = 5.3 Hz, 1H), 7.55 (t, J = 7.8 Hz, 1H), 7.42 (d, J = 6.3 Hz, 1H), 7.40 (s, 1H), 7.23 (d, J = 8.3 Hz, 1H), 5.39 (dd, J = 12.7, 5.2 Hz, 1H), 4.50 (s, 2H), 3.03 (s, 3H), 2.98 (s, 3H), 2.94-2.82 (m, 1H), 2.77-2.66 (m, 2H), 2.23-2.13 (m, 1H) |
| 155 | 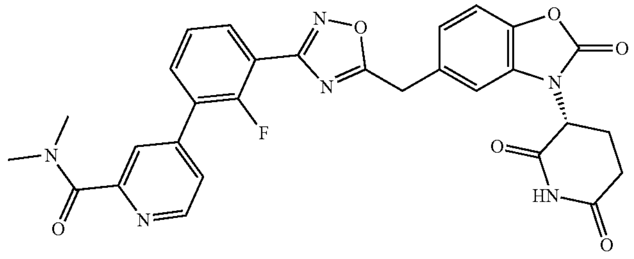 P2 | 571.1 | 1H NMR (400 MHz, DMSO-d6) δ 11.22 (s, 1H), 8.71 (d, J = 5.2 Hz, 1H), 8.08 (t, J = 7.0 Hz, 1H), 7.89 (t, J = 7.4 Hz, 1H), 7.77 (s, 1H), 7.72 (d, J = 5.3 Hz, 1H), 7.55 (t, J = 7.8 Hz, 1H), 7.42 (d, J = 6.3 Hz, 1H), 7.40 (s, 1H), 7.23 (d, J = 8.3 Hz, 1H), 5.39 (dd, J = 12.7, 5.2 Hz, 1H), 4.50 (s, 2H), 3.03 (s, 3H), 2.98 (s, 3H), 2.94-2.82 (m, 1H), 2.77-2.66 (m, 2H), 2.23-2.13 (m, 1H) |
| 156 | 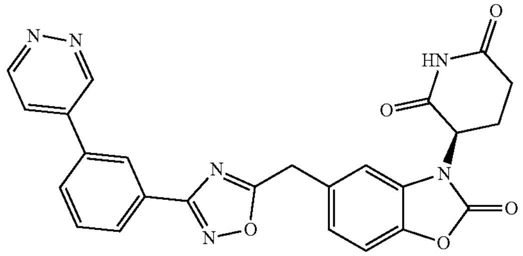 P1 | 483.5 | $^1$H NMR (400 MHz, DMSO-$d_6$) δ 11.23 (s, 1H), 9.69 (dd, J = 2.5, 1.2 Hz, 1H), 9.32 (dd, J = 5.5, 1.1 Hz, 1H), 8.40 (t, J = 1.8 Hz, 1H), 8.17-8.11 (m, 2H), 8.09 (dd, J = 5.5, 2.5 Hz, 1H), 7.77 (t, J = 7.8 Hz, 1H), 7.44-7.39 (m, 2H), 7.23 (dd, J = 8.2, 1.6 Hz, 1H), 5.40 (dd, J = 12.9, 5.2 Hz, 1H), 4.51 (s, 2H), 2.94-2.83 (m, 1H), 2.78-2.67 (m, 2H), 2.24-2.13 (m, 1H) |
| 157 | 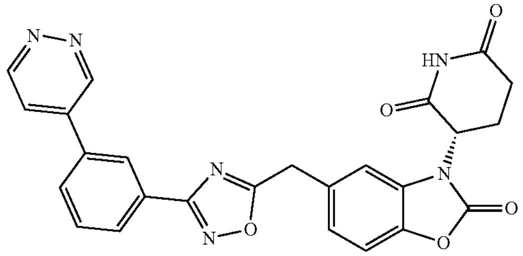 P2 | 483.5 | $^1$H NMR (400 MHz, DMSO-$d_6$) δ 11.23 (s, 1H), 9.69 (dd, J = 2.5, 1.2 Hz, 1H), 9.32 (dd, J = 5.5, 1.1 Hz, 1H), 8.40 (t, J = 1.8 Hz, 1H), 8.17-8.11 (m, 2H), 8.09 (dd, J = 5.5, 2.5 Hz, 1H), 7.77 (t, J = 7.8 Hz, 1H), 7.44-7.39 (m, 2H), 7.23 (dd, J = 8.2, 1.6 Hz, 1H), 5.40 (dd, J = 12.9, 5.2 Hz, 1H), 4.51 (s, 2H), 2.94-2.83 (m, 1H), 2.78-2.67 (m, 2H), 2.24-2.13 (m, 1H) |
| 158 | 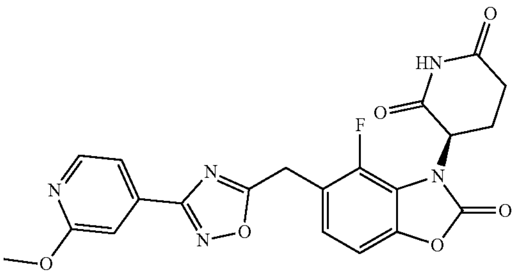 P1 | 454.3 | $^1$H NMR (400 MHz, DMSO) δ 11.22 (s, 1H), 8.36 (d, J = 5.3 Hz, 1H), 7.48 (dd, J = 5.3, 1.2 Hz, 1H), 7.37-7.31 (m, 2H), 7.25 (s, 1H), 5.45 (s, 1H), 4.56 (s, 2H), 3.91 (s, 3H), 3.03-2.88 (m, 1H), 2.65 (d, J = 17.0 Hz, 1H), 2.35-2.11 (m, 2H) |

-continued

| Compound # | Structure | [M + H]+ | $^1$H NMR |
|---|---|---|---|
| 159 | 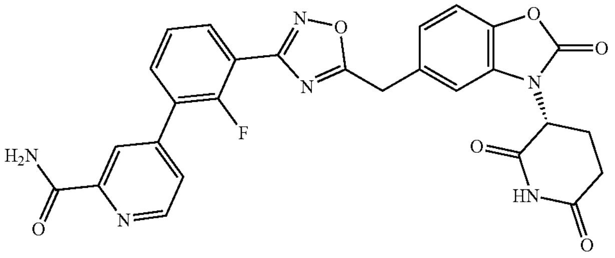 P1 | 543.1 | 1H NMR (400 MHz, DMSO) δ 8.76 (s, 1H), 8.24 (s, 2H), 8.09 (s, 1H), 7.86 (s, 1H), 7.76 (s, 1H), 7.56 (s, 1H), 7.40 (s, 3H), 7.25 (s, 2H), 5.32 (s, 1H), 4.51 (s, 2H), 2.89 (d, J = 7.2 Hz, 2H), 1.99 (s, 2H). |
| 160 | 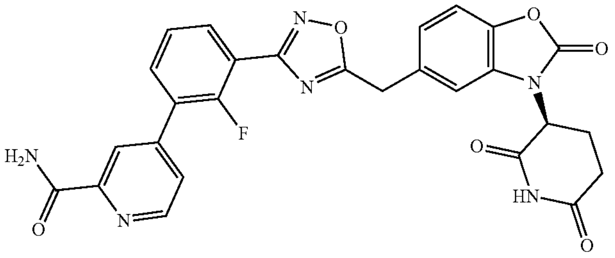 P2 | 543.1 | 1H NMR (400 MHz, DMSO) δ 11.22 (s, 1H), 9.52 (s, 1H), 9.38 (d, J = 5.4 Hz, 1H), 8.12 (t, J = 7.3 Hz, 1H), 7.97 (t, J = 7.7 Hz, 2H), 7.59 (t, J = 7.8 Hz, 1H), 7.41 (d, J = 8.0 Hz, 2H), 7.23 (d, J = 8.5 Hz, 1H), 5.39 (dd, J = 12.5, 4.7 Hz, 1H), 4.51 (s, 2H), 2.90 (s, 1H), 2.67 (s, 2H), 2.19 (s, 1H). |

Compound 161: 3-(4-fluoro-2-oxo-5-((1-phenyl-1H-1,2,3-triazol-4-yl)methyl)benzo[d]oxazol-3(2H)-yl)piperidine-2,6-dione

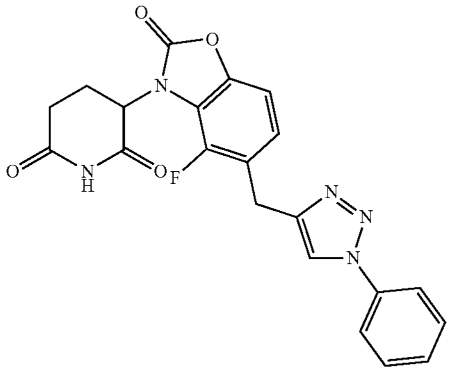 [SMILES: O=C1CCC(n2c(=O)oc3ccc(Cc4cn(-c5ccccc5)nn4)c(F)c32)C(=O)N1]

Step 1: 4-fluoro-5-((1-phenyl-1H-1,2,3-triazol-4-yl)methyl)-3-((2-(trimethylsilyl)ethoxy)methyl)benzo[d]oxazol-2(3H)-one

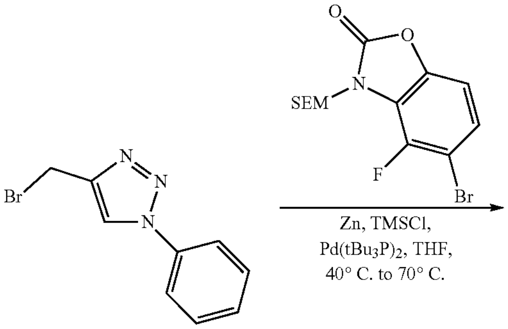

-continued

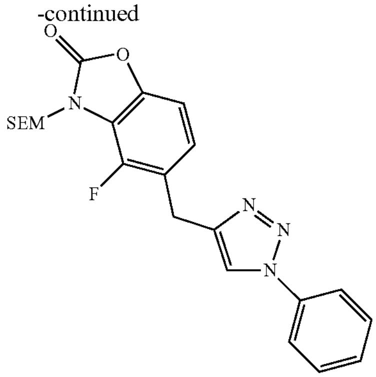

To a solution of Zn (208 mg, 3.2 mmol) in THF (5 mL) was added 1,2-dibromoethane (30 mg, 0.16 mmol). The resulting mixture was heated to 70° C. for 2 h. After the resulting mixture was added TMSCl (18 mg, 0.16 mmol) at 50° C. and stirred at 50° C. for 0.5 h. Then the resulting mixture was added 4-(bromomethyl)-1-phenyl-1H-1,2,3-triazole (380 mg, 1.60 mmol) at 40° C. and stirred at 40° C. for 40 mins. The mixture was added to a stirred mixture of 5-bromo-4-fluoro-3-((2-(trimethylsilyl)ethoxy)methyl)benzo[d]oxazol-2(3H)-one (580 mg, 1.60 mmol) and $Pd(tBu_3P)_2$ (82 mg, 0.16 mmol) at rt and stirred at 70° C. for 3 h. The reaction was concentrated and diluted with EA and $NH_4Cl$ solution, the organic layer was separated and extracted with $NH_4Cl$ solution twice, the organic layer was dried over $Na_2SO_4$, filtered and concentrated. The residue was purified by flash column chromatography (silica gel, 0~18% EA in PE) to afford 4-fluoro-5-((1-phenyl-1H-1,2,3-triazol-4-yl)methyl)-3-((2-(trimethylsilyl)ethoxy)methyl)benzo[d]oxazol-2(3H)-one (160 mg, 0.36 mmol, 22.5%) as a yellow oil. LCMS (m/z): $[M]^+$ calcd, 440.17; found, 441.2.

Step 2: 4-fluoro-5-((1-phenyl-1H-1,2,3-triazol-4-yl)methyl)benzo[d]oxazol-2(3H)-one

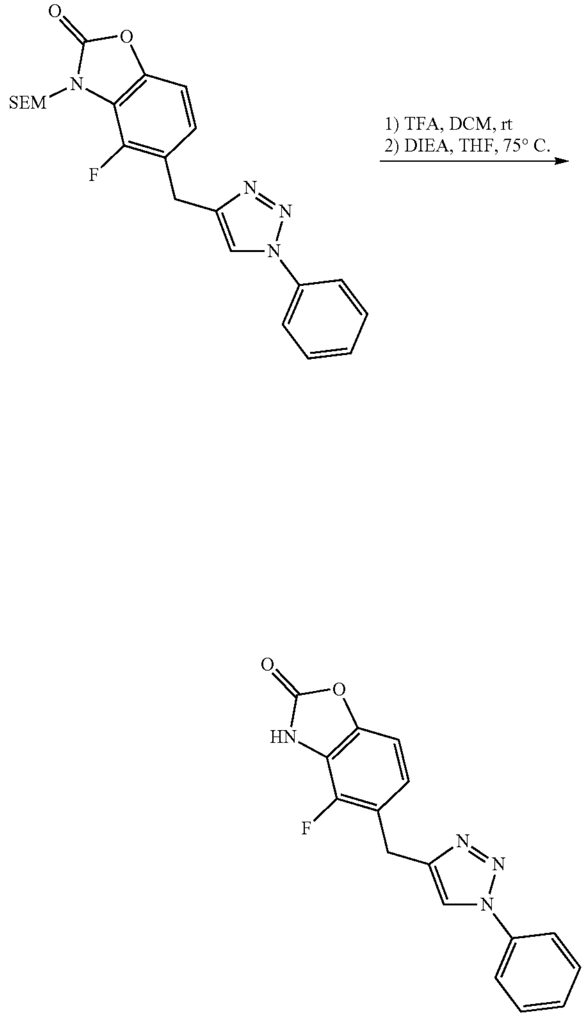

To a mixture of 4-fluoro-5-((1-phenyl-1H-1,2,3-triazol-4-yl)methyl)-3-((2-(trimethylsilyl)ethoxy)methyl)benzo[d]oxazol-2(3H)-one (160 mg, 0.36 mmol) in DCM (1.5 mL), TFA (1.5 mL). The reaction was stirred at rt for 2 h, removal of solvent. The residue was diluted with EtOAc, washed with $NaHCO_3$ (aq.), the organic layer was dried over $Na_2SO_4$, filtered and concentrated. The residue was added THF (1.5 mL), DIEA (1.5 mL), stirred at 75° C. for 2 h. After being cooled down to room temperature, removal of solvent. The residue was purified by flash column chromatography (silica gel, 0~4% MeOH in DCM) to afford 4-fluoro-5-((1-phenyl-1H-1,2,3-triazol-4-yl)methyl)benzo[d]oxazol-2(3H)-one (85 mg, 0.27 mmol, 75.0%) as a white solid. LCMS (m/z): $[M]^+$ calcd, 310.09; found, 311.1.

Step 3: 3-(4-fluoro-2-oxo-5-((1-phenyl-1H-1,2,3-triazol-4-yl)methyl)benzo[d]oxazol-3(2H)-yl)piperidine-2,6-dione

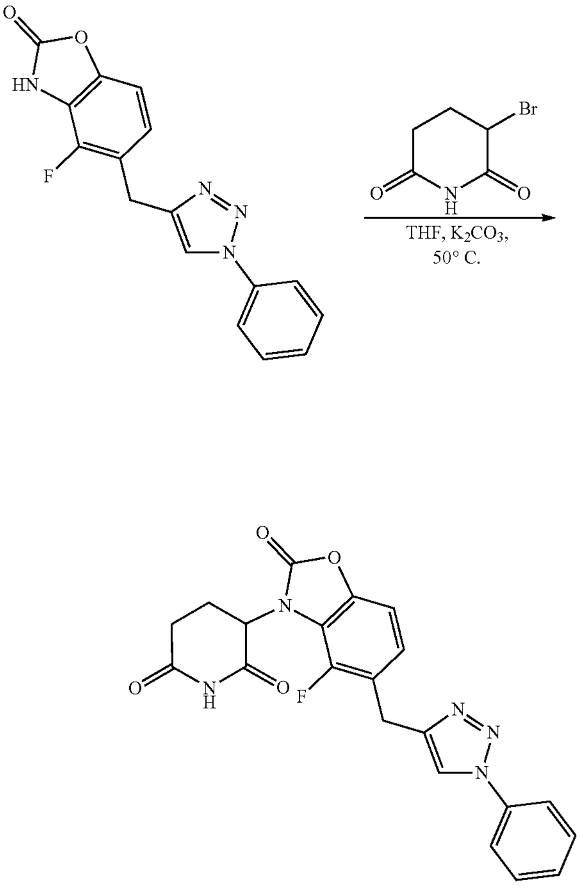

To a mixture of 4-fluoro-5-((1-phenyl-1H-1,2,3-triazol-4-yl)methyl)benzo[d]oxazol-2(3H)-one (85 mg, 0.27 mmol), $K_2CO_3$ (94 mg, 0.68 mmol) in THF (3 mL) were added 3-bromopiperidine-2,6-dione (79 mg, 0.41 mmol). The reaction was stirred at 50° C. for 16 h. After being cooled down to room temperature. The residue was purified by flash column chromatography (silica gel, 0~25% EA in DCM) and prep-HPLC (C18, Wave length: 220 nm/254 nm phase A: $H_2O$ (0.1% FA); phase B: MECN 5%-95%, 19 min/35 min) to afford 3-(4-fluoro-2-oxo-5-((1-phenyl-1H-1,2,3-triazol-4-yl)methyl)benzo[d]oxazol-3(2H)-yl)piperidine-2,6-dione (23.7 mg, 0.056 mmol, 20.7%) as a white solid. LCMS (m/z): $[M]^+$ calcd, 421.12; found, 422.3. $^1H$ NMR (400 MHz, DMSO) δ 11.24 (s, 1H), 8.60 (s, 1H), 7.93-7.81 (m, 2H), 7.58 (t, J=7.8 Hz, 2H), 7.47 (t, J=7.4 Hz, 1H), 7.28 (d, J=8.3 Hz, 1H), 7.22-7.13 (m, 1H), 5.46 (s, 1H), 4.14 (s, 2H), 2.93 (d, J=33.1 Hz, 1H), 2.66 (d, J=17.2 Hz, 1H), 2.18 (d, J=78.6 Hz, 2H).

Compound 162: 3-(4-fluoro-2-oxo-5-((4-phenyl-2H-1,2,3-triazol-2-yl)methyl)benzo[d]oxazol-3(2H)-yl) piperidine-2,6-dione

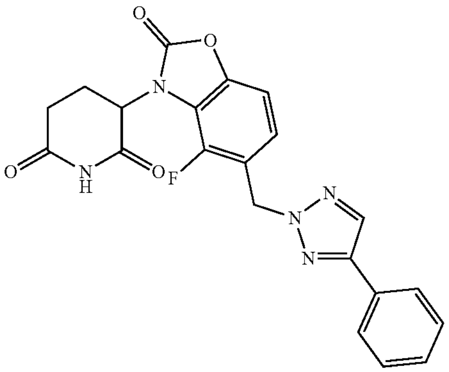 [SMILES: O=C1CCC(n2c(=O)oc3ccc(Cn4ncc(-c5ccccc5)n4)c(F)c32)C(=O)N1]

Step 1: Preparation of 5-bromo-3-(3,4-dimethylbenzyl)-4-fluorobenzo[d]oxazol-2(3H)-one

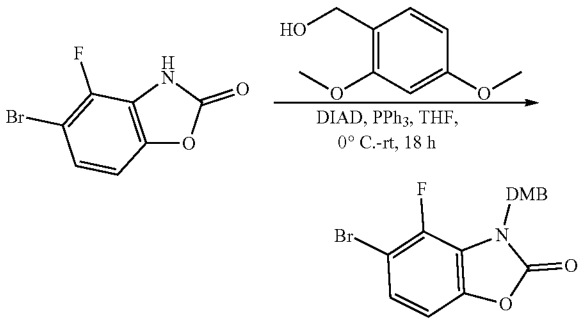

To the mixture of 5-bromo-4-fluoro-2,3-dihydrobenzo[2,1-d][1,3]oxazol-2-one (5 g, 21.55 mmol), triphenylphosphane (11.3 g, 43.10 mmol), (2,4-dimethoxyphenyl)methanol (3.62 g, 21.6 mmol) in THF (50 mL) was added DIAD (8.72 g, 43.10 mmol) at 0° C. The mixture was stirred at 25° C. under $N_2$ for 18 h. LCMS: SM consumed, DP found. The mixture was concentrated in vacuo. The residue was purified by FCC (silica gel, 0~33% DCM in PE) to give 5-bromo-3-[(2,4-dimethoxyphenyl)methyl]-4-fluoro-2,3-dihydrobenzo[2,1-d][1,3]oxazol-2-one (3 g, 7.85 mmol, 36%) as white solid. LCMS (m/z): [M]+ calcd: 382.19, found: 393.3.

Step 2: Preparation of 3-(3,4-dimethylbenzyl)-4-fluoro-5-(hydroxymethyl)benzo[d]oxazol-2(3H)-one

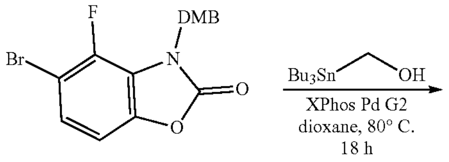

-continued

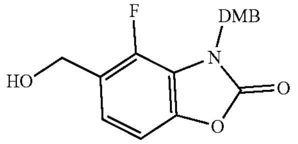

To the mixture of 5-bromo-3-[(2,4-dimethoxyphenyl)methyl]-4-fluoro-2,3-dihydrobenzo[d][1,3]oxazol-2-one (3 g, 7.85 mmol), (tributyl-λ[4]-stannanyl)methanol (3.02 g, 9.42 mmol) in dioxane (15 mL) was added XPhos Pd G2 (287.85 mg, 0.37 mmol). The mixture was stirred at 80° C. under $N_2$ for 18 h. LCMS: SM consumed; DP found. The mixture was quenched with water (20 mL), extracted with EA (30 mL*3). The organic phase was dried over $Na_2SO_4$, filtered and concentrated in vacuo. The residue was purified by FCC (silica gel, 0~33% EA in PE) to give 3-[(2,4-dimethoxyphenyl)methyl]-4-fluoro-5-(hydroxymethyl)-2,3-dihydrobenzo[d][1,3]oxazol-2-one (1.6 g, 4.80 mmol, 61.15%) as white solid. LCMS (m/z): [M]+ calcd: 333.32, found: 334.1.

Step 3: Preparation of 5-(bromomethyl)-3-(3,4-dimethylbenzyl)-4-fluorobenzo[d]oxazol-2(3H)-one

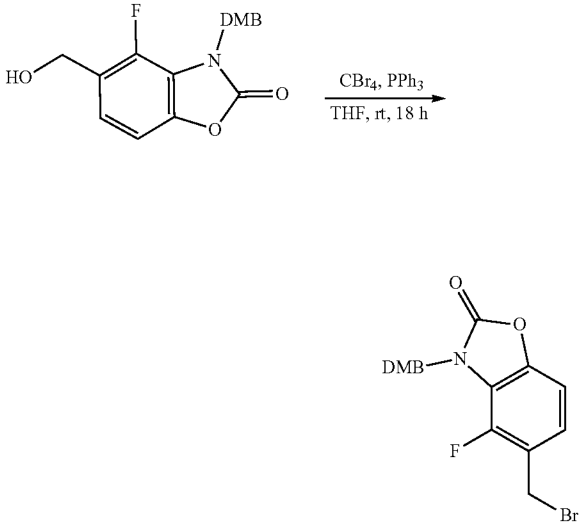

To the mixture of 4-fluoro-5-(hydroxymethyl)-2,3-dihydrobenzo[d][1,3]oxazol-2-one (1.6 mg, 4.80 mmol), $PPh_3$ (1.38 g, 5.28 mmol) in THF (20 mL) was added $CBr_4$ (1.75 g, 5.28 mmol). The mixture was stirred at 25° C. under $N_2$ for 2 h. LCMS: SM consumed; DP found. The mixture was concentrated in vacuo. The residue was purified by FCC (silica gel, 0~10% EA in PE) to give 5-(bromomethyl)-4-fluoro-2,3-dihydrobenzo[d][1,3]oxazol-2-one (1.7 g, 4.29 mmol, 89.38%) as white solid. LCMS (m/z): [M]+ calcd: 395.32, found: 396.

Step 4: Preparation of 3-(3,4-dimethylbenzyl)-4-fluoro-5-((4-phenyl-2H-1,2,3-triazol-2-yl)methyl) benzo[d]oxazol-2(3H)-one

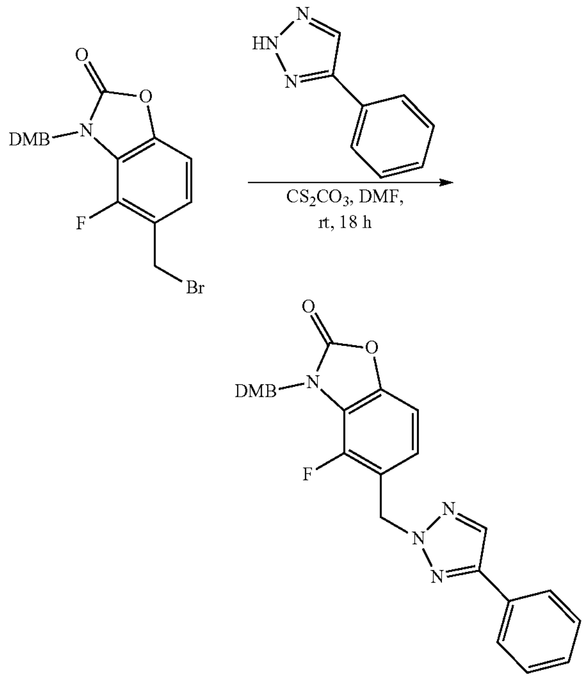

To the mixture of 5-(bromomethyl)-3-[(2,4-dimethoxyphenyl)methyl]-4-fluoro-2,3-dihydrobenzo[d][1,3]oxazol-2-one (1.7 g, 4.29 mmol), 4-phenyl-2H-1,2,3-triazole (0.62 g, 4.29 mmol) in DMF (20 mL) was added $Cs_2CO_3$ (2.80 g, 8.58 mmol). The mixture was stirred at 25° C. under $N_2$ for 3 h. LCMS: SM consumed, DP found. The mixture was quenched with water (10 mL) extracted with EA (10 mL*3). The organic phase was dried over $Na_2SO_4$, filtered and concentrated in vacuo. The residue was purified by FCC (silica gel, 0~20% EA in PE) to give 3-[(2,4-dimethoxyphenyl)methyl]-4-fluoro-5-[(4-phenyl-1,2,3-triazol-2-yl) methyl]-2,3-dihydrobenzo[d][1,3]oxazol-2-one (1.2 g, 2.61 mmol, 60.74%) as white solid. LCMS (m/z): [M]+ calcd: 460.47, found: 461.1.

Step 4: Preparation of 4-fluoro-5-((4-phenyl-2H-1,2,3-triazol-2-yl)methyl)benzo[d]oxazol-2(3H)-one

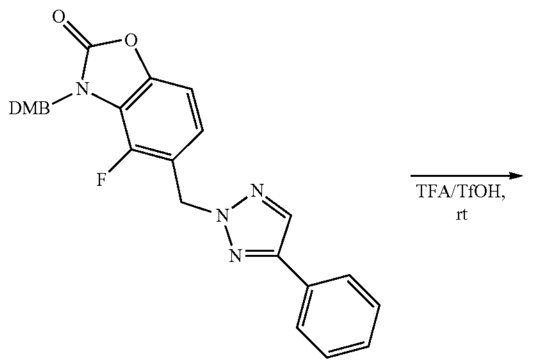

-continued

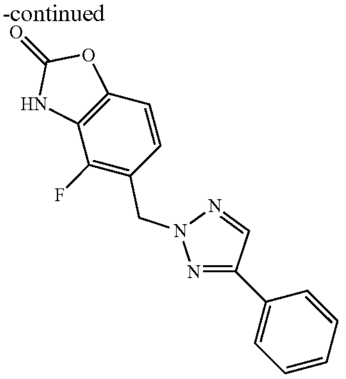

To the mixture of 3-[(2,4-dimethoxyphenyl)methyl]-4-fluoro-5-[(4-phenyl-1,2,3-triazol-2-yl)methyl]-2,3-dihydrobenzo[d][1,3]oxazol-2-one (1.2 g, 2.61 mmol) in TFA (10 mL) was added TfOH (1 mL, 1.13 mmol). The mixture was stirred at 50° C. under $N_2$ for 18 h. LCMS: SM consumed, DP found. The mixture was concentrated in vacuo, quenched with $NaHCO_3$ (10 mL) pH=7-8, extracted with EA (10 mL*3). The organic phase was dried over $Na_2SO_4$, filtered and concentrated in vacuo to give 4-fluoro-5-[(4-phenyl-1,2,3-triazol-2-yl)methyl]-2,3-dihydrobenzo[d][1,3]oxazol-2-one (0.8 g, 2.58 mmol, 98.93%) as white solid, which was used in the next step without further purification, which was used in the next step without further purification. LCMS (m/z): [M]+ calcd: 310.29 found: 311.3.

Step 5: Preparation of 3-(4-fluoro-2-oxo-5-((4-phenyl-2H-1,2,3-triazol-2-1 meth 1 benzo[d]oxazol-3 (2H)-yl)piperidine-2,6-dione

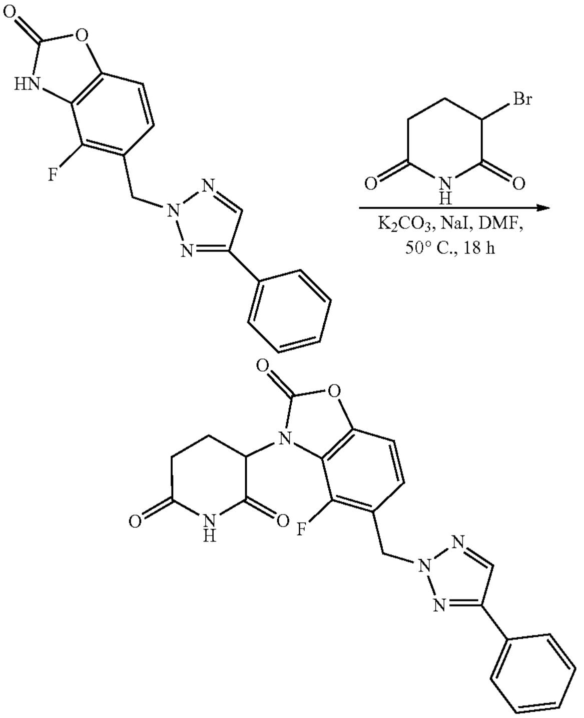

To the mixture of 4-fluoro-5-[(4-phenyl-1,2,3-triazol-2-yl)methyl]-2,3-dihydrobenzo[d][1,3]oxazol-2-one (120 mg, 0.39 mmol), 3-bromohexahydropyridine-2,6-dione (111.39 mg, 0.58 mmol) in THF (2 mL) was added potassium carbonate (106.90 mg, 0.77 mmol). The mixture was stirred at 50° C. under $N_2$ for 18 h. LCMS: SM remained, DP found. The mixture was quenched with water (10 mL), extracted with EA (10 mL*3). The organic phase was dried over $Na_2SO_4$, filtered and concentrated in vacuo. The residue was purified by prep-HPLC (C18, Wave length: 220 nm/254 nm phase A: $H_2O$ (0.1% FA); phase B: MECN 5%-95%, 22 min/24 min) to give 3-{4-fluoro-2-oxo-5-[(4-phenyl-1,2,3-triazol-2-yl)methyl]benzo[d][1,3]oxazol-3-yl}hexahydropyridine-2,6-dione (23.4 mg, 0.06 mmol, 14.36%) as white solid. LCMS (m/z): [M]+ calcd: 421.39, found: 422.1. $^1$H NMR (400 MHz, DMSO) δ 11.26 (s, 1H), 8.28 (s, 1H), 7.87-7.76 (m, 2H), 7.45 (t, J=7.5 Hz, 2H), 7.36 (dd, J=17.6, 7.8 Hz, 2H), 7.24 (d, J=7.1 Hz, 1H), 5.75 (s, 2H), 5.46 (s, 1H), 2.97 (s, 1H), 2.66 (d, J=16.7 Hz, 1H), 2.30 (dd, J=12.2, 6.3 Hz, 2H).

Compound 163: 3-(4-methyl-2-oxo-5-((3-phenyl-1,2,4-oxadiazol-5-yl)methyl)benzo[d]oxazol-3(2H)-yl)piperidine-2,6-dione

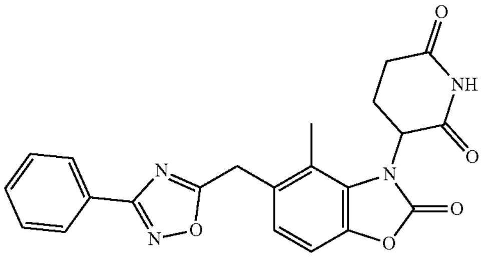 [SMILES: Cc1c(Cc2nc(-c3ccccc3)no2)ccc2oc(=O)n(C3CCC(=O)NC3=O)c12]

Step 1. 3-(4-methyl-2-oxo-5-((3-phenyl-1,2,4-oxadiazol-5-yl)methyl)benzo[d]oxazol-3(2H)-yl)piperidine-2,6-dione

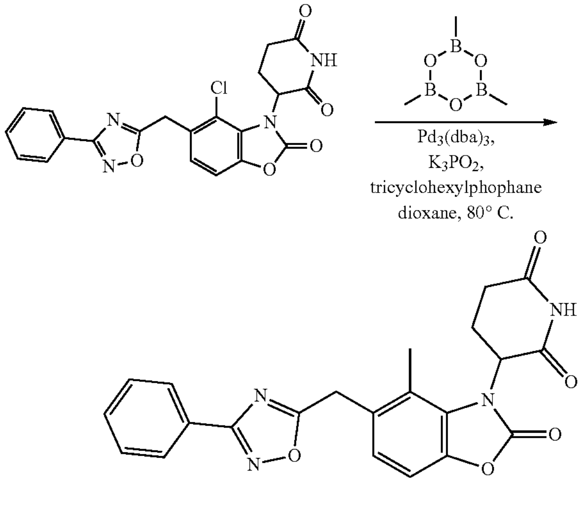

To a mixture of 3-(4-chloro-2-oxo-5-((3-phenyl-1,2,4-oxadiazol-5-yl)methyl)benzo[d]oxazol-3(2H)-yl)piperidine-2,6-dione (370 mg, 0.84 mmol), tricyclohexylphosphane (235 mg 0.84 mmol), $K_3PO_4$ (712 mg 3.36 mmol), $Pd_2(dba)_3$ (384 mg 0.42 mmol) in dioxane (10 mL) were added 2,4,6-trimethyl-1,3,5,2,4,6-trioxatriborinane (8.4 g, 67.2 mmol). The reaction was stirred at 80° C. for 20 h. Removal of solvent, the residue was purified by flash column chromatography (silica gel, 0~20% EA in DCM) and prep-HPLC (C18, Wave length: 220 nm/254 nm phase A: $H_2O$ (0.1% FA); phase B: MECN 20%-95%, 21 min/25 min) to afford 3-(4-methyl-2-oxo-5-((3-phenyl-1,2,4-oxadiazol-5-yl)methyl)benzo[d]oxazol-3(2H)-yl)piperidine-2,6-dione (9.4 mg, 0.0225 mmol, 2.7%) as a white solid. LCMS (m/z): $[M]^+$ calcd, 418.13; found, 419.3. $^1$H NMR (400 MHz, DMSO) δ 11.32-11.09 (m, 1H), 8.06-7.88 (m, 2H), 7.63-7.50 (m, 3H), 7.33-7.19 (m, 2H), 5.65-5.41 (m, 1H), 4.64-4.48 (m, 2H), 3.04-2.80 (m, 1H), 2.71-2.57 (m, 2H), 2.47 (s, 3H), 2.34 (dd, J=10.3, 5.2 Hz, 1H).

Biochemical Assays

In Vitro TR-FRET Ternary—ALK Mutant (Mut) CRBN:

A TR-FRET proximity assay was used to measure ternary complex formation induced by test compounds. Compounds dissolved in 100% DMSO were dispensed to a 384-well plate by an SPT Labtech Mosquito LV as duplicate 10-point dilution series to a total volume of 100 nanoliters of DMSO. One column of DMSO only and one column of 3-(3-{N-methyl[(3-phenyl-1,2,4-oxadiazol-5-yl)methyl]amino}-2,5-dioxo-3-pyrrolin-1-yl)-2,6-piperidinedione (final concentration 10 μM) served as negative and positive controls, respectively. To this plate was added 10 microliters of a reaction mixture containing 150 nM avi-tagged ALK, 75 nM ULight-Streptavidin (PerkinElmer), 50 nM 6×His-tagged CRBN/DDB1, and 0.5 nM Eu-W1024 Anti-6×His (PerkinElmer) in a buffer consisting of 50 mM Tris, 150 mM NaCl, 1 mM TCEP, 0.02% Tween-20, and 0.5 mg/mL BSA at pH 7.4. The plate was incubated at room temperature for 2 hours, then read on a BMG PHERAstar plate reader with a 337 nm excitation laser and 620 nm and 665 nm emission filters. The TR-FRET signal was calculated as the ratio of emission signals at 665 nm over 620 nm, and the compound-containing wells were normalized to negative controls (0% activity) and 3-(3-{N-methyl[(3-phenyl-1,2,4-oxadiazol-5-yl)methyl]amino}-2,5-dioxo-3-pyrrolin-1-yl)-2,6-piperidinedione (100% activity). Normalized data for each compound were then subjected to a 4-parameter logistic fit.

In Vitro TR-FRET Ternary—ALK Mutant (Mut) CRBN (v3):

A TR-FRET proximity assay was used to measure ternary complex formation induced by test compounds. Compounds dissolved in 100% DMSO were dispensed to a 384-well plate by an SPT Labtech Mosquito LV as duplicate 10-point dilution series to a total volume of 100 nanoliters of DMSO. One column of DMSO only and one column of 2-(2,6-dioxo-3-piperidyl)-4-[(3-phenyl-1,2,4-oxadiazol-5-yl)methyl]-2,4-diaza-4,5,6,7-tetrahydro-1H-indene-1,3(2H)-dione (final concentration 20 μM) served as negative and positive controls, respectively. To this plate was added 10 microliters of a reaction mixture containing 5 nM avi-tagged ALK, 0.5 nM Eu-W1024-Streptavidin (PerkinElmer), 5 nM 6×His-tagged CRBN/DDB1, and 30 nM ULight-Anti-6×His (PerkinElmer) in a buffer consisting of 50 mM Tris, 150 mM NaCl, 1 mM TCEP, 0.02% Tween-20, and 0.5 mg/mL BSA at pH 7.4. The plate was incubated at room temperature for 2 hours, then read on a BMG PHERAstar plate reader with a 337 nm excitation laser and 620 nm and 665 nm emission filters. The TR-FRET signal was calculated as the ratio of emission signals at 665 nm over 620 nm, and the compound-containing wells were normalized to negative controls (0% activity) and 2-(2,6-dioxo-3-piperidyl)-4-[(3-phenyl-1,2,4-oxadiazol-5-yl)methyl]-2,4-diaza-4,5,6,7-tetrahydro-1H-indene-1,3(2H)-dione (100% activity). Normalized data for each compound were then subjected to a 4-parameter logistic fit.

Results are shown in Table 1. The letter codes for EC50 include; A (<10 nM), B (10-100 nM), C (100-1000 nM), D (>1000 nM), The sign codes for Emax include; + (<50%), ++ (50-120), +++ (>120).

TABLE 1

| Cmpd. No. | TR-FRET ternary - ALK Mut CRBN: Mean EC50 | TR-FRET ternary - ALK Mut CRBN: Mean Emax | TR-FRET ternary - ALK Mut CRBN (v3): Mean EC50 | TR-FRET ternary - ALK Mut CRBN (v3): Mean Emax |
|---|---|---|---|---|
| 1 | a | +++ | b | +++ |
| 2 | b | +++ | b | +++ |
| 3 | c | + | d | + |
| 4 | a | +++ | a | +++ |
| 5 | a | +++ | b | +++ |
| 6 | b | +++ | b | ++ |
| 7 | a | +++ | b | ++ |
| 8 | a | +++ | b | ++ |
| 9 | a | +++ | b | +++ |
| 10 | a | +++ | b | ++ |
| 11 | b | +++ | b | ++ |
| 12 | b | +++ | b | ++ |
| 13 | b | +++ | a | +++ |
| 14 | a | +++ | a | +++ |
| 15 | a | +++ | a | +++ |
| 16 | b | +++ | b | +++ |
| 17 | b | +++ | b | +++ |
| 18 | | | a | +++ |
| 19 | | | a | +++ |
| 20 | | | a | +++ |
| 21 | | | a | +++ |
| 22 | | | a | +++ |
| 23 | | | c | ++ |
| 25 | | | b | +++ |
| 26 | | | b | ++ |
| 27 | | | c | + |
| 28 | | | b | ++ |
| 29 | | | b | +++ |
| 30 | | | c | ++ |
| 31 | | | b | +++ |
| 32 | | | d | ++ |
| 33 | | | b | ++ |
| 34 | a | +++ | a | +++ |
| 35 | | | b | +++ |
| 36 | | | b | ++ |
| 37 | | | c | ++ |
| 38 | | | b | +++ |
| 39 | | | c | + |
| 40 | | | c | + |
| 41 | | | c | + |
| 42 | | | d | ++ |
| 43 | | | b | +++ |
| 44 | | | c | + |
| 45 | | | c | + |
| 46 | | | b | ++ |
| 47 | | | b | ++ |
| 48 | | | c | + |
| 49 | | | c | + |
| 50 | | | c | + |
| 51 | | | c | + |
| 52 | | | c | + |
| 53 | | | c | ++ |
| 54 | | | c | + |
| 55 | | | c | + |
| 56 | | | c | + |
| 57 | | | c | + |
| 58 | | | b | +++ |
| 59 | | | b | +++ |
| 60 | | | b | +++ |
| 61 | | | b | +++ |
| 62 | | | C | + |
| 63 | | | b | ++ |
| 64 | | | c | + |
| 65 | | | b | +++ |

TABLE 1-continued

| Cmpd. No. | TR-FRET ternary - ALK Mut CRBN: Mean EC50 | TR-FRET ternary - ALK Mut CRBN: Mean Emax | TR-FRET ternary - ALK Mut CRBN (v3): Mean EC50 | TR-FRET ternary - ALK Mut CRBN (v3): Mean Emax |
|---|---|---|---|---|
| 66 | | | b | ++ |
| 67 | | | c | ++ |
| 68 | | | b | +++ |
| 69 | | | b | ++ |
| 70 | | | b | +++ |
| 71 | | | b | ++ |
| 72 | | | b | +++ |
| 73 | | | c | + |
| 74 | | | c | + |
| 75 | | | c | + |
| 77 | | | a | +++ |
| 78 | | | b | +++ |
| 79 | | | b | +++ |
| 80 | | | b | ++ |
| 81 | | | b | ++ |
| 82 | | | b | ++ |
| 83 | | | b | ++ |
| 84 | | | b | +++ |
| 85 | | | b | +++ |
| 86 | | | b | +++ |
| 87 | | | b | +++ |
| 88 | | | a | +++ |
| 89 | | | b | +++ |
| 90 | | | a | +++ |
| 91 | | | a | +++ |
| 92 | | | b | +++ |
| 93 | | | d | + |
| 94 | | | b | ++ |
| 95 | | | d | + |
| 96 | | | a | +++ |
| 97 | | | b | ++ |
| 98 | | | c | + |
| 99 | | | a | +++ |
| 100 | | | c | + |
| 101 | | | c | + |
| 102 | | | b | ++ |
| 103 | | | b | ++ |
| 104 | | | b | +++ |
| 105 | | | b | ++ |
| 106 | | | c | + |
| 107 | | | b | ++ |
| 108 | | | b | +++ |
| 109 | | | b | +++ |
| 110 | | | a | +++ |
| 111 | | | a | +++ |
| 112 | | | a | +++ |
| 113 | | | a | +++ |
| 114 | | | a | +++ |
| 115 | | | c | + |
| 116 | | | b | +++ |
| 117 | | | c | +++ |
| 118 | | | b | +++ |
| 119 | | | c | +++ |
| 120 | | | a | +++ |
| 121 | | | b | ++ |
| 122 | | | b | +++ |
| 123 | | | a | +++ |
| 124 | | | d | + |
| 125 | | | a | +++ |
| 126 | | | b | ++ |
| 127 | | | b | ++ |
| 128 | | | b | +++ |
| 129 | | | b | ++ |
| 130 | | | d | ++ |
| 131 | | | c | +++ |
| 132 | | | c | + |
| 133 | | | b | +++ |
| 134 | | | b | ++ |
| 135 | | | b | ++ |
| 136 | | | b | ++ |
| 137 | | | b | ++ |
| 138 | | | c | + |
| 139 | | | c | + |
| 140 | | | b | + |

TABLE 1-continued

| Cmpd. No. | TR-FRET ternary - ALK Mut CRBN: Mean EC50 | TR-FRET ternary - ALK Mut CRBN: Mean Emax | TR-FRET ternary - ALK Mut CRBN (v3): Mean EC50 | TR-FRET ternary - ALK Mut CRBN (v3): Mean Emax |
|---|---|---|---|---|
| 141 | | | b | ++ |
| 142 | | | a | +++ |
| 143 | | | b | +++ |
| 144 | | | a | +++ |
| 145 | | | c | +++ |
| 146 | | | a | +++ |
| 147 | | | b | +++ |
| 148 | | | b | +++ |
| 149 | | | b | +++ |
| 150 | | | b | +++ |
| 151 | | | a | +++ |
| 152 | | | b | +++ |
| 153 | | | b | +++ |
| 154 | | | b | +++ |
| 155 | | | b | +++ |
| 156 | | | b | +++ |
| 157 | | | b | +++ |
| 158 | | | b | +++ |
| 159 | | | b | +++ |
| 160 | | | b | +++ |
| 161 | | | c | + |
| 162 | | | b | + |
| 163 | | | c | ++ |

The invention claimed is:

1. A compound having the structural formula:

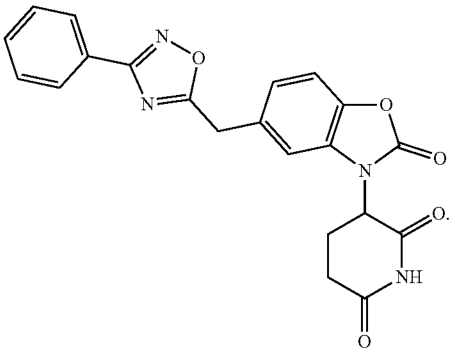 [SMILES: O=C1CCC(n2c(=O)oc3ccc(Cc4nc(-c5ccccc5)no4)cc32)C(=O)N1]

2. A compound having the structural formula:

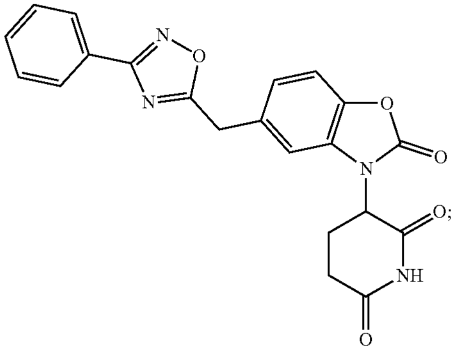 [SMILES: O=C1CCC(n2c(=O)oc3ccc(Cc4nc(-c5ccccc5)no4)cc32)C(=O)N1]

or a pharmaceutically acceptable salt thereof.

3. A pharmaceutical composition comprising a compound having the structural formula:

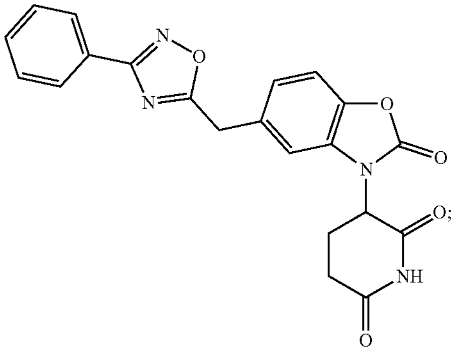 [SMILES: O=C1CCC(n2c(=O)oc3ccc(Cc4nc(-c5ccccc5)no4)cc32)C(=O)N1]

and a pharmaceutically acceptable carrier.

4. A pharmaceutical composition comprising a compound having the structural formula:

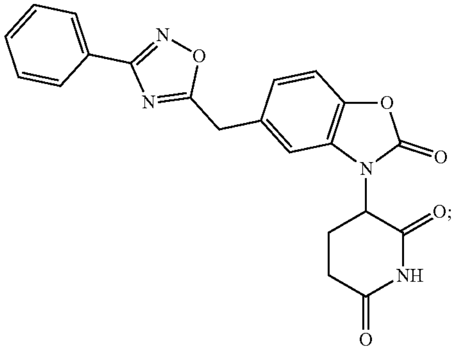 [SMILES: O=C1CCC(n2c(=O)oc3ccc(Cc4nc(-c5ccccc5)no4)cc32)C(=O)N1]

or a pharmaceutically acceptable salt thereof; and a pharmaceutically acceptable carrier.

* * * * *